United States Patent
Sauvageau et al.

(10) Patent No.: US 10,647,718 B2
(45) Date of Patent: May 12, 2020

(54) COMPOUNDS AND USE THEREOF IN THE EXPANSION OF HEMATOPOIETIC STEM CELLS AND/OR HEMATOPOIETIC PROGENITOR CELLS

(71) Applicant: UNIVERSITÉ DE MONTRÉAL, Montréal (CA)

(72) Inventors: Guy Sauvageau, Montréal (CA); Yves Gareau, Notre-Dame-de-l'Ile Perrot (CA); Stéphane Gingras, Montreal (CA)

(73) Assignee: UNIVERSITÉDE MONTRÉAL, Montréal (CA)

( * ) Notice: Subject to any disclaimer, the term of this patent is extended or adjusted under 35 U.S.C. 154(b) by 182 days.

(21) Appl. No.: 15/305,409

(22) PCT Filed: Apr. 21, 2015

(86) PCT No.: PCT/CA2015/050330
§ 371 (c)(1),
(2) Date: Oct. 20, 2016

(87) PCT Pub. No.: WO2015/161373
PCT Pub. Date: Oct. 29, 2015

(65) Prior Publication Data
US 2017/0037047 A1    Feb. 9, 2017

Related U.S. Application Data

(60) Provisional application No. 61/982,445, filed on Apr. 22, 2014.

(51) Int. Cl.

| | | |
|---|---|---|
| *C07D 471/14* | (2006.01) | |
| *A61K 35/28* | (2015.01) | |
| *C07D 471/04* | (2006.01) | |
| *A61K 31/5377* | (2006.01) | |
| *A61K 31/519* | (2006.01) | |
| *A61K 31/4545* | (2006.01) | |
| *A61K 45/06* | (2006.01) | |
| *A61K 31/444* | (2006.01) | |
| *A61P 43/00* | (2006.01) | |
| *A61P 35/00* | (2006.01) | |

(52) U.S. Cl.
CPC .......... *C07D 471/14* (2013.01); *A61K 31/444* (2013.01); *A61K 31/4545* (2013.01); *A61K 31/519* (2013.01); *A61K 31/5377* (2013.01); *A61K 35/28* (2013.01); *A61K 45/06* (2013.01); *A61P 35/00* (2018.01); *A61P 43/00* (2018.01); *C07D 471/04* (2013.01)

(58) Field of Classification Search
CPC ................................................... C07D 471/14
See application file for complete search history.

(56) References Cited

U.S. PATENT DOCUMENTS

| | | | |
|---|---|---|---|
| 4,835,160 A | 5/1989 | Bisagni et al. | |
| 9,409,906 B2 * | 8/2016 | Sauvageau | ........... C07D 487/04 |
| 2011/0287540 A1 | 11/2011 | Hirai et al. | |
| 2013/0303563 A1 | 11/2013 | Adler et al. | |
| 2014/0308747 A1 | 10/2014 | Zhang et al. | |
| 2014/0256706 A1 | 11/2014 | Wang et al. | |
| 2017/0334904 A1 * | 11/2017 | Sauvageau | ........... C07D 487/04 |

FOREIGN PATENT DOCUMENTS

| | | |
|---|---|---|
| CN | 101423517 A | 5/2009 |
| EP | 0239476 | 9/1987 |
| JP | 2008050355 A | 3/2008 |
| JP | 2010525836 A | 7/2010 |
| JP | 2010193879 A | 9/2010 |
| JP | 2016514134 A | 5/2016 |
| WO | 2000028987 | 5/2000 |
| WO | 2000035446 | 6/2000 |
| WO | 2000066112 | 11/2000 |
| WO | 2001017349 | 3/2001 |
| WO | 2001021180 | 3/2001 |
| WO | 2001034585 | 5/2001 |
| WO | 2001039773 | 6/2001 |
| WO | 2001089457 | 11/2001 |

(Continued)

OTHER PUBLICATIONS

Jantzen. Modern Pharmaceutics, p. 596. (Year: 1996).*

(Continued)

*Primary Examiner* — Noble E Jarrell
(74) *Attorney, Agent, or Firm* — Norton Rose Fulbright Canada LLP

(57) ABSTRACT

Compounds of general formula or salts or prodrugs thereof, are provided and described herein. The compounds are useful to expand hematopoietic stem cell and/or hematopoietic progenitor cell populations. Particularly, the hematopoietic cells are human cells. The compounds are also useful in the medical treatment of hematopoietic disorder/malignancy, an autoimmune disease and/or an inherited immune-deficient disease in a subject.

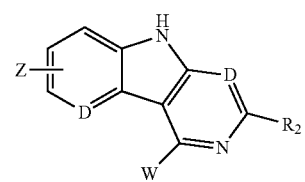

18 Claims, 6 Drawing Sheets

(56) References Cited

FOREIGN PATENT DOCUMENTS

| WO | 2002049413 | | 6/2002 | | |
|---|---|---|---|---|---|
| WO | 2002085343 | | 10/2002 | | |
| WO | WO 2003037898 | * | 5/2003 | ........... | C07D 487/04 |
| WO | 2003103686 | | 12/2003 | | |
| WO | 2004054515 | | 7/2004 | | |
| WO | 2007009120 | | 1/2007 | | |
| WO | 2007022269 | | 2/2007 | | |
| WO | 2007061764 | | 5/2007 | | |
| WO | 2007145227 | | 12/2007 | | |
| WO | 2008028645 | | 3/2008 | | |
| WO | 2008073748 | | 6/2008 | | |
| WO | 2009075830 | | 6/2009 | | |
| WO | 2011025685 | | 3/2011 | | |
| WO | 2011159857 | | 12/2011 | | |
| WO | 2013110198 | | 8/2013 | | |
| WO | 2013176698 A1 | | 11/2013 | | |
| WO | 2014164596 A1 | | 9/2014 | | |

OTHER PUBLICATIONS

Copelan. New England Journal of Medicine, 2006, 354:17, 1813-26 (Year: 2006).*
Harada. Heterocycles, 1994, 38(8), 1867-80 (Year: 1994).*
Gori, J.L. et al. "Effective Exapansion and Engraftment of Nonhuman Primate CD34+Hematopoietic Stem Cells After Co-Culture with the Small Molecule UM171". Blood Journal. vol. 122. Issue No. 21. Nov. 15, 2013. pp. 1-4, XP55400517. Retrieved from the Internet: URL: http://www.bloodjournal.org/content/122/21/1656?sso-checked=true [retrieved on Aug. 23, 2017] abstract.
Astori, G. Bone Marrow Transplant. 35: 1101. 2005.
Bisagni, E. et al. "Amino-Substituted 4-Methyl-BH-pyrido[4,3-b] indoles (7-Carbolines) as Tricyclic Analogues of Ellipticines: A New Class of Antineoplastic Agents". J. Med. Chem. 1988, 31. pp. 398-405.
Costache E. et al. "Amino-substituted 8-hydroxy-4,5-dimethyl-5H-pyrido[4,3-b]indoles with propyl—or methyl substituents at the 9-, and 7,9-positions: synthesis and biological evaluation". Anti-Cancer Drug Design (1998), 13, pp. 361-372.
Dubinsky, L. et al. "Diazirine based photoaffinity labeling". Bioorganic Med. Chem. 2012 (20), 554.
Engler, T.A. et al. "Lewis Acid-Directed Cyclocondensation of Piperidone Enol Ethers with 2-Methoxy-4-(N-phenylsulfonyl)-1,4-benzoquinoneimine: A New Regioselective Synthesis of Oxygenated Carbolines". J. Org. Chem. 2000, 65, pp. 2444-2457.
Greene, T. and Wuts, P. "Protecting Groups in Chemical Synthesis". 4th Ed. John Wiley & Sons, N.Y. 2007 (1082 pages).
Hannum, C. Nature. vol. 368. 1994. pp. 643-648.
Hansen, K.B. et al. Organic Letters. 7(22), 4935-4938. 2005.
Harada, K. et al. "New heterocyclic ring systems: the syntheses of of 2H,3H,7H-imidazo[1',2':1,2]pyrido[4,3-b]indoles and 2H,3H,4H,8H-pyrimido [1',2':1,2]pyrido[4,3-b]indoles". Heterocycles. vol. 38(8) 1994. pp. 1867-1880.
Kaushansky, K. N. Engl. J. Med. 354 (19): 2034-45. 2006.
Kishimoto, A. "Interleukin-6: From Basic Science to Medicine—40 Years in Immunology". Annu. Rev. Immunol. 23:1 2005.
Kolb et al. "Click Chemistry: Diverse Chemical Function from a Few Good Reactions". Angew. Chem. Int. Ed. Engl. 40. 2001. pp. 2004-2021.
Koller, M.R. Bone Marrow Transplant. 21 :653. 1998.
Koller, M.R. Blood, 82: 378. 1993.
Kraus, M. et al. "Efficacious Intermittent Dosing of a Novel JAK2 Inhibitor in Mouse Models of Polycythemia Vera". PloS ONE. vol. 7. Issue 5. 2012. pp. 1-10.
Lapinsky, D.J. "Tandem photoaffinity labeling-bioorthogonal conjugation in medicinal Chemistry". Bioorganic Med. Chem. 2012 (20), 6237-6247.
Lee, C-S. et al. "Some Reactions of PYRID0[4,3-b]INDOLE (y-CARBOLINE)". Heterocycles. vol. 16, No. 7, 1981. pp. 1081-1084.
Lewis et al. "Click Chemistry in Situ: Acetylcholinesterase as a Reaction Vessel for the Selective Assembly of a . . . ," Angew. Chem. Int. Ed. Engl. 41. 2002. pp. 1053-1057.
Li, J. et al. "Amidines for Versatile Ruthenium(II)—Catalyzed Oxidative C H Activations with Internal Alkynes and Acrylates". Chem. Eur. J. vol. 20. pp. 5403-5408. 2014.
Lim, J. et al. "Discovery of 1-Amino-5H-pyrido[4,3-b]indol-4-carboxamide Inhibitors of Janus Kinase 2 (JAK2) for the Treatment of Myeloproliferative Disordersr\". J. Med. Chem. vol. 54. 2011. pp. 7334-7349.
Maryanoff, B. et al. "Urotensin-II Receptor Modulators as Potential Drugs". J. Med. Chem. vol. 53. 2010. pp. 2695-2708.
Mcelroy, W.T. and Deshong, P. Tetrahedron. 62(29). pp. 6945-6954. 2006.
Nguyen, C.H. et al. "Synthesis and Antitumor Activity of I-[[ (Dialkylamino)alkyl]amino]-4-methyl-5H-pyrido[4,3-]~benzo[e 1- and -benzo[g])indoles. A New Class of Antineoplastic Agents". J. Med. Chem. 1990. pp. 1519-1528.
Nguyen, C.H. et al. "Synthese d'analogues tricycliques des ellipticines: Les methyl-4,5H-Pyrido [4,3-b] indoles ( y-carbolines) diversement substitués sur leurs sommets 1,5 et 8". Tetrahedron. vol. 43. No. 3. 1987. pp. 527-535.
Ohashi, T. et al. Bioorganic & Medicinal Chemistry. 20(18), pp. 5507-5517. 2012.
Pryde, D.C. et al. MedChemComm. 2(3) pp. 185-189. 2011.
Sathe, R.Y. et al. "Computational identification of JAK2 inhibitors: a combined pharmacophore mapping and molecular docking approach". Med Chem Res. 24. 2015. pp. 1449-1467.
Schwartz, R.M. Proc. Natl. Acad. Sci. U.S.A., 88:6760. 1991.
Smith, M.A. et al. ACTA Haematologica. 105, 3:143. 2001.
Wang, Y. et al. "N-Alkyl-5H-pyrido[4,3-b]indol-1-amines and derivatives as novel urotensin-II receptor antagonists". Bioorganic & Medicinal Chemistry Letters. 18. 2008. pp. 4936-4939.
Wu, X. et al. "Three Dimensional Quantitative Structure-Activity Relationship of 5H-Pyrido[4,3-b]indol-4-carboxamide JAK2 Inhibitors". Int. J. Mol. Sci. 2013. 14. pp. 12037-12053.
Fares, I. et al. "Pyrimidoindole derivatives are agonists of human hematopoietic stem cell self-renewal". Science. vol. 345, Issue 6203. 2014. pp. 1509-1512.
Chen, J. et al. "Design synthesis, and quantitative structure-activity relationship of cytotoxic y-carboline derivatives". Bioorganic & Medicinal Chemistry. (2009). 17. pp. 3324-3331.
Namirski, P.N. et al. "Synteza Karbolin Metoda Graebe-Ullmana: III. Synteza I Dzjalanie Hamujace Neiktorych Pochodnych y-Karboliny". Acta Poloniae Pharmaceutica. 1962, 19(3), pp. 229-242 (In Polish).
English Computer Translation—Abstract of CN101423517A.
English Computer Translation—Abstract of JP2008050355A.
1. Yeşilipek, Mehmet Akif. "Hematopoetic stem cell transplantation in children." Turkish Archives of Pediatrics/Türk Pediatri Arşivi 49.2 (2014): 91.
Wynn, Robert. "Stem cell transplantation in inherited metabolic disorders." ASH Education Program Book 2011.1 (2011): 285-291.
Gladstone, Douglas E., and Ephraim Fuchs. "Hematopoietic stem cell transplantation for chronic lymphocytic leukemia." Current opinion in oncology 24.2 (2012): 176.
Means, Robert T. Jr. "Pure red cell aplasia." Blood, 128 (2016): 2504-2509.
Palumbo, Antonio and Anderson, Kenneth. "Multiple Myeloma." NEJM 364 (2011): 1046-1060.
Suenaga, Kentaro, et al. "Successful application of nonmyeloablative transplantation for paroxysmal nocturnal nemoglobinuria." Experimental hematology 29.5 (2001): 639-642.
Collins, Erin, and Gary Gilkeson. "Hematopoetic and mesenchymal stem cell transplantation in the treatment of refractory systemic lupus erythematosus—where are we now?." Clinical immunology 148.3 (2013): 328-334.
McLornan, Donal P., et al. "Allogeneic stem cell transplantation for myelofibrosis in 2012." British journal of haematology 157.4 (2012): 413-425.

(56) References Cited

OTHER PUBLICATIONS

Salit, Rachel B., and H. Joachim Deeg. "Role of hematopoietic stem cell transplantation in patients with myeloproliferative disease." Hematology/Oncology Clinics 28.6 (2014): 1023-1035.

* cited by examiner

A)

| | \multicolumn{11}{c|}{Compound concentration (nM)} |
|---|---|---|---|---|---|---|---|---|---|---|---|
| | 9.766 | 19.53 | 39.06 | 78.13 | 156.3 | 312.5 | 625.0 | 1250 | 2500 | 5000 |
| Assay 1 | 0.887 | 0.979 | 0.883 | 1.049 | 1.040 | 1.405 | 1.625 | 1.502 | 1.321 | 0.655 |
| Assay 2 | 0.715 | 0.844 | 0.890 | 0.837 | 0.690 | 1.273 | 1.790 | 1.645 | 1.589 | 1.410 |
| Assay 3 | 0.976 | 0.819 | 0.961 | 0.745 | 0.831 | 0.864 | 1.453 | 1.661 | 1.280 | 0.655 |
| Average | 0.859 | 0.881 | 0.911 | 0.877 | 0.854 | 1.181 | 1.623 | 1.603 | 1.397 | 0.907 |
| SD | 0.133 | 0.086 | 0.043 | 0.156 | 0.176 | 0.282 | 0.169 | 0.088 | 0.168 | 0.436 |

B)

C)

A)

| | Compound concentration (nM) | | | | | | | | | |
|---|---|---|---|---|---|---|---|---|---|---|
| | 19.53 | 39.06 | 78.13 | 156.3 | 312.5 | 625 | 1250 | 2500 | 5000 | 10000 |
| Assay 1 | 0.813 | 0.862 | 0.813 | 0.757 | 1.009 | 1.566 | 1.355 | 1.196 | 1.045 | 0.297 |
| Assay 2 | 1.182 | 1.273 | 1.272 | 1.223 | | 1.636 | 1.505 | 1.522 | 1.346 | 0.735 |
| Assay 3 | 1.006 | 0.993 | 0.807 | 0.779 | 0.986 | 1.558 | 1.205 | 1.203 | 0.904 | 0.331 |
| Average | 1.000 | 1.043 | 0.964 | 0.920 | 0.998 | 1.587 | 1.355 | 1.307 | 1.098 | 0.454 |
| SD | 0.185 | 0.210 | 0.267 | 0.263 | 0.016 | 0.043 | 0.150 | 0.186 | 0.226 | 0.244 |

C)

B) Compound 3

A)

| | Compound concentration (nM) | | | | | | | | | |
|---|---|---|---|---|---|---|---|---|---|---|
| | 19.53 | 39.06 | 78.13 | 156.3 | 312.5 | 625 | 1250 | 2500 | 5000 | 10000 |
| Assay 1 | 1.066 | 0.967 | 1.068 | 1.273 | 1.166 | 1.941 | 1.471 | 1.014 | 1.000 | 0.104 |
| Assay 2 | 0.896 | 1.013 | 0.946 | 1.129 | 1.481 | 1.85 | 1.604 | 1.134 | 0.846 | 0.074 |
| Average | 0.981 | 0.990 | 1.007 | 1.201 | 1.324 | 1.896 | 1.538 | 1.074 | 0.923 | 0.089 |
| SD | 0.120 | 0.033 | 0.086 | 0.102 | 0.223 | 0.064 | 0.094 | 0.085 | 0.109 | 0.021 |

B)

C)

COMPOUNDS AND USE THEREOF IN THE EXPANSION OF HEMATOPOIETIC STEM CELLS AND/OR HEMATOPOIETIC PROGENITOR CELLS

CROSS-REFERENCE TO RELATED APPLICATIONS

The present application is the 371 National Phase entry of PCT/CA2015/050330 filed Apr. 21, 2015, the content of which is hereby incorporated in its entirety. The present application also claims priority from U.S. provisional patent application No. 61/982,445, filed Apr. 22, 2014 and entitled "COMPOUNDS AND USE THEREOF IN THE EXPANSION OF HEMATOPOIETIC STEM CELLS AND/OR HEMATOPOIETIC PROGENITOR CELLS", the disclosure of which is hereby incorporated by reference in its entirety.

FIELD OF THE INVENTION

The invention relates to certain compounds as described herein. Also, the invention relates to use of these compounds for expanding hematopoietic stem cells (HSCs), hematopoietic progenitor cells (HPCs), or both HSCs and HPCs. Moreover, the invention relates to the medical treatment of diseases involving HSCs and HPCs.

BACKGROUND OF THE INVENTION

The main sources of hematopoietic stem cells (HSCs) are the bone marrow and the umbilical cord blood (UCB). HSCs are used in the transplantation setting (autologous or allogeneic) which constitutes one of the most effective treatment strategies for achieving cures in patients with hematologic malignancies, bone marrow failure conditions, a variety of congenital diseases of global concern (e.g. sickle cell anemia and thalassemia) and autoimmune diseases such as lupus. However, this opportunity for life-saving or life-improving treatment is not available to many thousands of people worldwide due to an inability to amplify these cells ex vivo sufficiently to make the procedure safe and successful. More particularly, for every 3 patients, one will forego the opportunity for transplant because no human leucocyte antigen (HLA) identical donor can be found. Another proportion of patients will not have access to transplantation simply because too few HSCs are available in the graft (i.e. cord blood or autologous) for successful transplant. The safety and efficacy of marrow transplant is directly dependent on the number of HSCs and HPCs available for engrafting. The more that can be infused, the more rapidly is hematologic function restored, and the shorter is the window of risk for infection due to lack of granulocytes or of bleeding due to lack of platelets. The challenge in providing sufficient HSCs is further escalated where non-myeloablative conditioning is preferred such as in the context of gene therapy for major inherited blood disorders (the major genetic cause of morbidity and mortality worldwide).

In adults, HSCs mainly reside in the bone marrow and must be mobilized to enter the circulation prior to being collected by apheresis, either for autologous or allogeneic hematopoietic stem cell transplantation (HSCT). The collection of an adequate number of CD34+ cells, a surrogate marker of (HSCs), is paramount because the dose of CD34+ cells influences the success and rate of hematopoietic recovery. Several reports suggest that a higher infused CD34+ cell dose is independently predictive of improved survival.

The two most commonly used mobilizing regimens are granulocyte-colony stimulating factor (G-CSF) and G-CSF plus chemotherapy. Plerixafor, a CXCR4 antagonist approved by the United States Food and Drug Administration (FDA) in 2008 and in 2011 by Health Canada, enhances mobilization of HSCs when administered with G-CSF. However, Plerixafor is contraindicated in patients with leukemia because of mobilization of leukemic cells. Inability to obtain sufficient numbers of CD34+ cells/kg with currently used mobilization regimens is estimated to affect up to 15% of patients (varies between diseases). Use of autologous HSCT in hematological malignancies is often limited by the fact that both normal and cancer stem cells are present in the bone marrow and thus, likely to be mobilized.

Allogeneic HSCT with BM or mPBSC is another transplantation alternative. However, about one third to one fourth of the patients who are eligible for this type of transplant cannot find a suitable donor. For those who get transplanted, there is a high frequency of transplant related mortality due to graft-versus-host disease, relapse or graft rejection; and a risk of immunodeficiency for prolonged periods of time. Alternatively, umbilical cord blood has been shown as a valid option in allogeneic HSCT. However, a single CB unit typically provides insufficient HSCs for an adult patient for a rapid and efficient hematopoietic recovery.

There is thus a need for novel strategies for increasing the expansion of hematopoietic stem cells, hematopoietic progenitor cells, or both hematopoietic stem cells and hematopoietic progenitor cells.

SUMMARY OF THE INVENTION

The inventors have discovered certain compounds described herein. These compounds are useful to expand hematopoietic stem cell and/or hematopoietic progenitor cell populations. Particularly, the hematopoietic cells are human cells. The compounds are also useful in the medical treatment of diseases that involve HSCs and/or HPCs.

According to an aspect, the invention provides for compounds of the following general

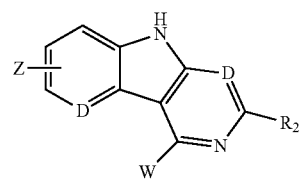

or formulas I, II, III, IV, V, VI, I', II', III', IV', V' and VI':

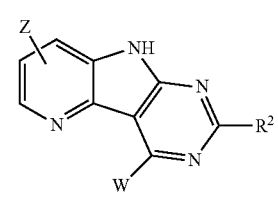

I

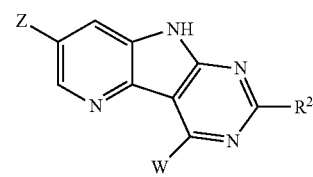

II

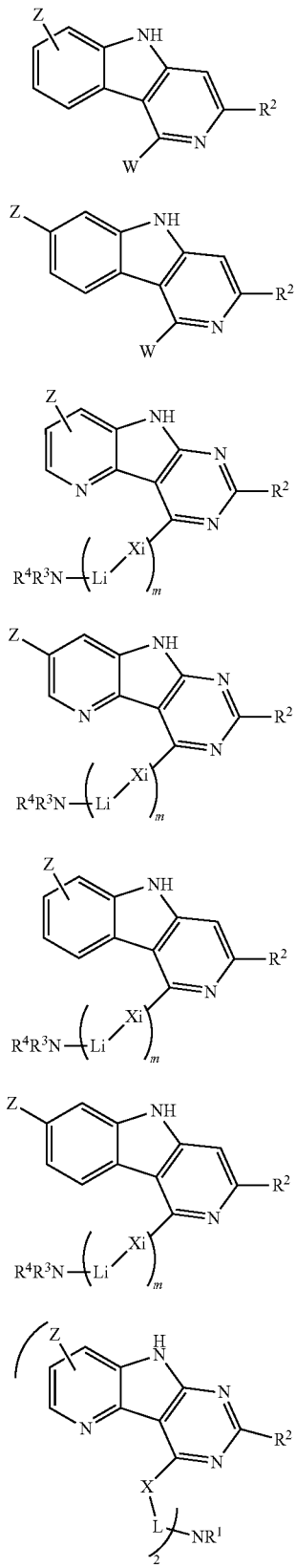
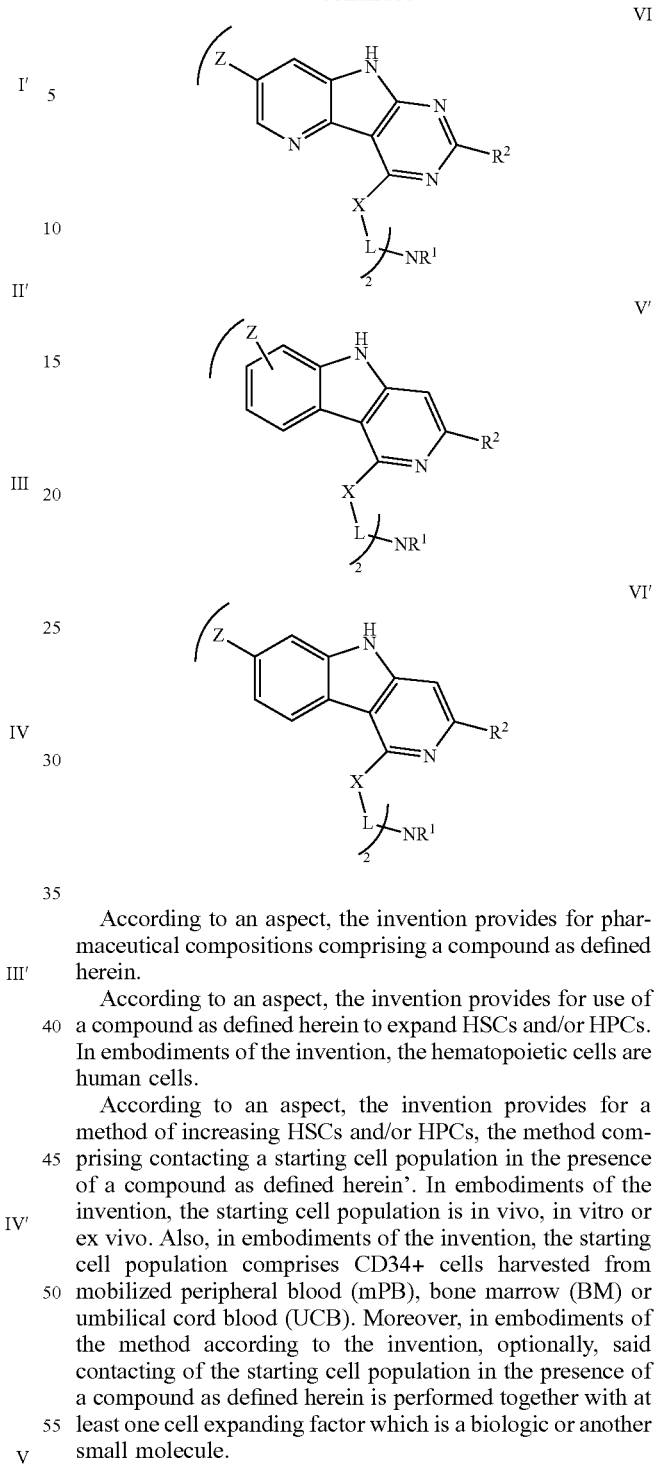

According to an aspect, the invention provides for pharmaceutical compositions comprising a compound as defined herein.

According to an aspect, the invention provides for use of a compound as defined herein to expand HSCs and/or HPCs. In embodiments of the invention, the hematopoietic cells are human cells.

According to an aspect, the invention provides for a method of increasing HSCs and/or HPCs, the method comprising contacting a starting cell population in the presence of a compound as defined herein'. In embodiments of the invention, the starting cell population is in vivo, in vitro or ex vivo. Also, in embodiments of the invention, the starting cell population comprises CD34+ cells harvested from mobilized peripheral blood (mPB), bone marrow (BM) or umbilical cord blood (UCB). Moreover, in embodiments of the method according to the invention, optionally, said contacting of the starting cell population in the presence of a compound as defined herein is performed together with at least one cell expanding factor which is a biologic or another small molecule.

According to an aspect, the invention provides for a cell population expanded according to the method of the invention, more specifically, a cell population expanded using a compound according to the invention. In embodiments, the invention provides for HSCs and/or HPCs expanded according to the method of the invention, more specifically, HSCs and/or HPCs expanded using a compound as defined herein.

According to an aspect, the invention provides for a method of treating a hematopoietic disorder/malignancy, an autoimmune disease and/or an inherited immunodeficient disease in a subject, the method comprising administering to the subject in need of such treatment HSCs expanded using a compound as defined herein.

In embodiments of the invention, the hematopoietic disorder/malignancy, the autoimmune disease and/or the inherited immunodeficient disease comprise bone marrow failure conditions, a variety of congenital diseases of global concern (e.g. sickle cell anemia and thalassemia), lupus, acute myeloid leukemia, acute lymphoblastic leukemia, chronic myeloid leukemia, chronic lymphocytic leukemia, myeloproliferative disorders, myelodysplastic syndromes, multiple myeloma, non-Hodgkin's lymphoma, Hodgkin's disease, aplastic anemia, pure red cell aplasia, hemoglobinuria, Fanconi anemia, thalassemia, sickle cell anemia, Wiskott-Aldrich syndrome, inborn errors of metabolism (such as Gaucher disease among others).

According to an aspect, the invention provides for a kit for use in increasing or expanding HSCs and/or HPCs, the kit comprising a compound as defined herein, and instructions for use. In embodiments of the invention, the kit comprises at least one cell expanding factor which is a biologic or another small molecule.

Other objects, advantages and features of the present invention will become more apparent upon reading of the following non-restrictive description of specific embodiments thereof, given by way of example only with reference to the accompanying drawings.

DETAILED DESCRIPTION OF THE INVENTION

Figure 1:
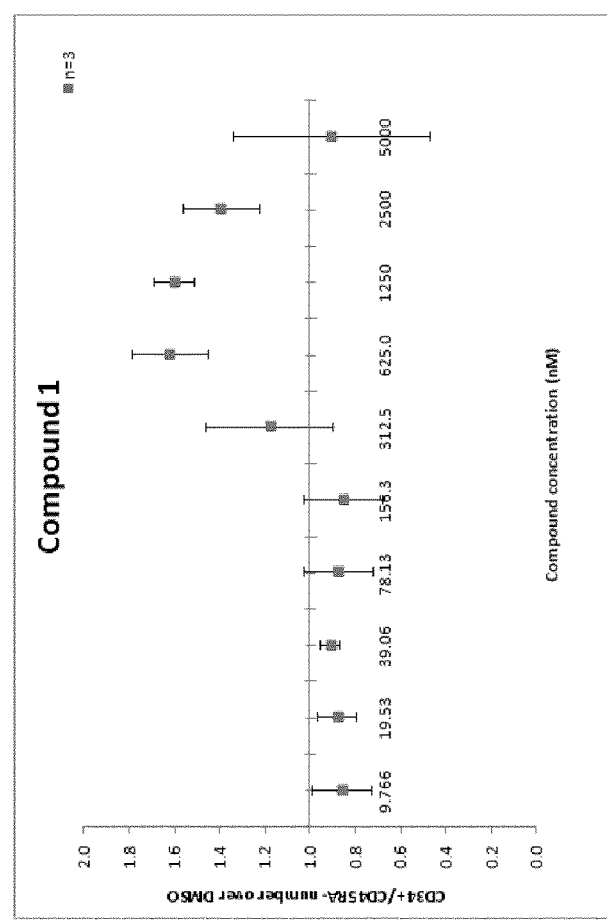
FIGS. 1 to 6 are tables of raw data and graphical representation of the ratio of CD34+/CD45RA− cell number in the presence of compounds disclosed herein over the CD34+/CD45RA− cell number in the presence of DMSO (negative control).
Figure 1:
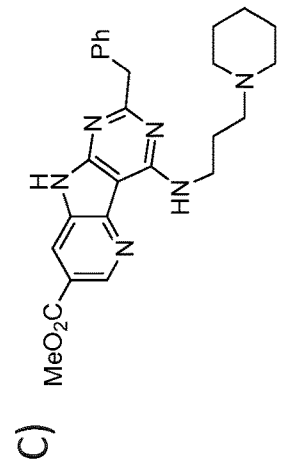

The inventors have discovered certain compounds described herein. These compounds are useful to expand hematopoietic stem cell and/or hematopoietic progenitor cell populations. Particularly, the hematopoietic cells are human cells. The compounds are also useful in the medical treatment of diseases that involve hematopoietic stem cells and/or hematopoietic progenitor cells.

In particular, the inventors have discovered that these compounds are useful as tool compounds. In one embodiment, the tool compound is comprised of a first reactant having a terminal alkyne moiety and a second reactant having a photoaffinity functional moiety such as a diazirine, azido and benzophenone, both moieties forming part of the tool compound. The tool compound can be used for "click chemistry" (Luba Dubinsky, Bastiaan P. Krom, Michael M. Meijler, "Diazirine based photoaffinity labeling" *Bioorganic Med. Chem.* 2012 (20), 554; David J. Lapinsky, Tandem photoaffinity labeling-bioorthogonal conjugation in medicinal Chemistry *Bioorganic Med. Chem.* 2012 (20), 6237; Kolb et al., "Click Chemistry: Diverse Chemical Function from a Few Good Reactions" *Angew. Chem. Int. Ed. Engl.* 40: 2004-2021 (2001); Lewis et al., "Click Chemistry in Situ: Acetylcholinesterase as a Reaction Vessel for the Selective Assembly of a . . . ," *Angew. Chem. Int. Ed. Engl.* 41: 1053-1057 (2002)). In another embodiment, the tool compound is comprised of a biotinylated moiety and a photoaffinity functional moiety.

Salts or prodrugs of the compounds as defined herein are also within the scope of the compounds according to the invention.

The substituents of the compounds as defined herein are defined as outlined below.

Z is: 1) —P(O)(OR$^1$)(OR$^1$), 2) —C(O)OR$^1$, 3) —C(O)NHR$^1$, 4) —C(O)N(R$^1$)R$^1$, 5) —C(O)R$^1$, 6) —CN, 7) —SR$^1$, 8) —S(O)$_2$NH$_2$, 9) —S(O)$_2$NHR$^1$, 10) —S(O)$_2$N(R$^1$)R$^1$, 11) —S(O)R$^1$, 12) —S(O)$_2$R$^1$, 13) -L, 14) -benzyl optionally substituted with 1, 2 or 3 R$^A$ or R$^1$ substituents, 15) -L-heteroaryl optionally substituted with one or more R$^A$ or R$^1$ substituents attached on either or both the L and the heteroaryl groups, 16) -L-heterocyclyl optionally substituted with one or more R$^A$ or R$^1$ substituents attached on either one or both the L and the heterocyclyl groups, 17) -L-aryl optionally substituted with one or more R$^A$ or R$^1$ substituents attached on either or both the L and the heteroaryl groups, 18) -heteroaryl optionally substituted with one or more R$^A$ or R$^1$ substituents, or 19) -aryl optionally substituted with one or more R$^A$ or R$^1$ substituents. In this list, each substituent is optionally attached to the L group if it is not already present; and, when (R$^1$) and R$^1$ are attached to a nitrogen atom, optionally they join together with the nitrogen atom to form a 3 to 7-membered ring which optionally includes one or more other heteroatom selected from N, O and S, optionally the ring is substituted with one or more R$^1$ or R$^A$.

W is H, a halogen or a group that is attached to the pyrimido indole core of the molecule through an atom which is N, O, S, or C. Optionally, W comprises at least one moiety which is saturated, unsaturated, linear, branched and/or cyclic alkyl and/or heteroalkyl having 1 to 20 carbon atoms. Also, optionally, the moiety comprises at least one other hetero atom which is N, O or S. As will be understood by a skilled person, W in the chemical structure of the compounds according to the invention can belong to various categories of chemical groups commonly used in the art.

More specifically, W is: 1) —H, 2) -halogen, 3) —OR$^1$, 4) -L-OH, 5) -L-OR$^1$, 6) —SR$^1$, 7) —CN, 8) —P(O)(OR$^1$)(OR$^1$), 9) —NHR$^1$, 10) —N(R$^1$)R$^1$, 11) -L-NH$_2$, 12) -L-NHR$^1$, 13) -L-N(R$^1$)R$^1$, 14) -L-SR$^1$, 15-L-S(O)R$^1$, 16) -L-S(O)$_2$R$^1$, 17) -L-P(O)(OR$^1$)(OR$^1$), 18) —C(O)OR$^1$, 19) —C(O)NH$_2$, 20) —C(O)NHR$^1$, 21) —C(O)N(R$^1$)R$^1$, 22) —NHC(O)R$^1$, 23) —NR$^1$C(O)R$^1$, 24) —NHC(O)OR$^1$, 25) —NR$^1$C(O)OR$^1$, 26) —OC(O)NH$_2$, 27) —OC(O)NHR$^1$, 28) —OC(O)N(R$^1$)R$^1$, 29) —OC(O)R$^1$, 30) —C(O)R$^1$, 31) —NHC(O)NH$_2$, 32) —NHC(O)NHR$^1$, 33) —NHC(O)N(R$^1$)R$^1$, 34) —NR$^1$C(O)NH$_2$, 35) —NR$^1$C(O)NHR$^1$, 36) —NR$^1$C(O)N(R$^1$)R$^1$, 37) —NHS(O)$_2$R$^1$, 38) —NR$^1$S(O)$_2$R$^1$, 39) —S(O)$_2$NH$_2$, 40) —S(O)$_2$NHR$^1$, 41) —S(O)$_2$N(R$^1$)R$^1$, 42) —S(O)R$^1$, 43) —S(O)$_2$R$^1$, 44) —OS(O)$_2$R$^1$, 45) —S(O)$_2$OR$^1$, 46) -benzyl optionally substituted with 1, 2 or 3 R$^A$ or R$^1$ substituents, 47) -L-heteroaryl optionally substituted with one or more R$^A$ or R$^1$ substituents attached on either or both the L and the heteroaryl groups, 48) -L-heterocyclyl optionally substituted with one or more R$^A$ or R$^1$ substituents attached on either or both the L and the heterocyclyl groups, 49) -L-aryl optionally substituted with one or more R$^A$ or R$^1$ substituents attached on either or both the L and aryl groups, 50) -L-NR$^1$(R$^1$), 51) -L-)$_2$NR$^1$, 52) -L-(N(R$^1$)-L)$_n$-N(R$^1$)R$^1$, 53) -L-(N(R$^1$)-L)$_n$-(N(R$^1$)R$^1$)$_n$, 54) -L-(N(R$^1$)-L)$_n$-heteroaryl optionally substituted with one or more R$^A$ or R$^1$ substituents attached on either or both the L and heteroaryl groups, 55) -L-(N(R$^1$)-L)$_n$-heterocyclyl optionally substituted with one or more R$^A$ or R$^1$ substituents attached on either or both the L and heterocyclyl groups, 56) -L-(N(R$^1$)-L)$_n$-aryl optionally substituted with one or more $R^A$ or $R^1$ substituents attached on either or both the L and aryl groups, 57) —O-L-N($R^1$)$R^1$, 58) —O-L-heteroaryl optionally substituted with one or more $R^A$ or $R^1$ substituents attached on either or both the L and heteroaryl groups, 59) —O-L-heterocyclyl optionally substituted with one or more $R^A$ or $R^1$ substituents attached on either or both the L and heterocyclyl groups, 60) —O-L-aryl optionally substituted with one or more $R^A$ or $R^1$ substituents attached on either or both the L and aryl groups, 61) —O-L)$_2$-N$R^1$, 62) —O-L-(N($R^1$)-L)$_n$-N($R^1$)$R^1$, 63) —O-L-(N($R^1$)-L)$_n$-(N($R^1$)$R^1$)$_n$, 64) —O-L-(N($R^1$)-L)$_n$-heteroaryl optionally substituted with one or more $R^A$ or $R^1$ substituents attached on either or both the L and heteroaryl groups, 65) —O-L-(N($R^1$)-L)$_n$-heterocyclyl optionally substituted with one or more $R^A$ or $R^1$ substituents attached on either or both the L and heterocyclyl groups, 66) —O-L-(N($R^1$)-L)$_n$-aryl optionally substituted with one or more $R^A$ or $R^1$ substituents, 67) —S-L-heteroaryl optionally substituted with one or more $R^A$ or $R^1$ substituents, 68) —S-L-heterocyclyl optionally substituted with one or more $R^A$ or $R^1$ substituents, 69) —S-L-aryl optionally substituted with one or more $R^A$ or $R^1$ substituents attached on either or both the L and aryl groups, 70) —S-L)$_2$N$R^1$, 71) —S-L-(N($R^1$)-L)$_n$-N($R^1$)$R^1$, 72) —S-L-(N($R^1$)-L)$_n$-(N($R^1$)$R^1$)$_n$, 73) —S-L-(N($R^1$)-L)$_n$-heteroaryl optionally substituted with one or more $R^A$ substituents, 74) —S-L-(N($R^1$)-L)$_n$-heterocyclyl optionally substituted with one or more $R^A$ substituents, 75) —S-L-(N($R^1$)-L)$_n$-aryl optionally substituted with one or more $R^A$ substituents, 76) —N$R^1$($R^1$), 77) —(N($R^1$)-L)$_n$-N($R^1$)$R^1$, 78) —(N($R^1$)-L)$_n$-(N($R^1$)$R^1$)$_n$, 79) —N($R^1$)L)$_2$-N$R^1$, 80) —(N($R^1$)-L)$_n$-N($R^1$)$R^A$, 81) —(N($R^1$)-L)$_n$-heteroaryl optionally substituted with one or more $R^A$ or $R^1$ substituents, 82) —(N($R^1$)-L)$_n$-heterocyclyl optionally substituted with one or more $R^A$ or $R^1$ substituents, 83) —(N($R^1$)-L)$_n$-aryl optionally substituted with one or more $R^A$ or $R^1$ substituents, 84) -heteroaryl optionally substituted with one or more $R^A$ substituents, or 85) -aryl optionally substituted with one or more $R^A$ substituents, 86) —X(C$R^1$C$R^1$)$_m$—C(O)—(C$R^1$C$R^1$)$_n$—X($R^1R^1$)-[L-N($R^1R^1$)]$_p$, 87) —X(C$R^1$C$R^1$)$_m$—C$R^1$(O$R^1$)—(C$R^1$C$R^1$)$_n$—X($R^1R^1$)-[L-N($R^1R^1$)], 88) —X($R^1$)-L-N($R^1$)-(LX)$_n$—$R^A$, 89) —X($R^1$)-L-N($R^1$)-(LX)$_n$—H. In this list, each substituent is optionally attached to the L group if it is not already present; and when two $R^1$ substituents are present on the same nitrogen atom, then each $R^1$ substituent is independently selected from the list of $R^1$ values described thereafter; and n is an integer equal to either 0, 1, 2, 3, 4, or 5; and, when ($R^1$) and $R^1$ are attached to a nitrogen atom, optionally they join together with the nitrogen atom to form a 3 to 7-membered ring which optionally includes one or more other heteroatom selected from N, O and S, optionally the ring is substituted with one or more $R^1$ or $R^A$.

L is: 1) —$C_{1-6}$ alkyl, 2) —$C_{2-6}$ alkenyl, 3) —$C_{2-6}$ alkynyl, 4) —$C_{3-7}$ cycloalkyl, 5) —$C_{3-7}$ cycloalkenyl, 6) heterocyclyl, 7) —$C_{1-6}$ alkyl-$C_{3-7}$ cycloalkyl, 8) —$C_{1-6}$ alkyl-heterocyclyl, 9) aryl, or 10) heteroaryl. In this list, the alkyl, the alkenyl, the alkynyl, the cycloalkyl, the cycloalkenyl, the heterocyclyl, the aryl and the heteroaryl groups are each independently optionally substituted with one or two $R^A$ or $R^1$ substituent.

$R^1$ is: 1) —H, 2) —$C_{1-6}$ alkyl, 3) —$C_{2-6}$ alkenyl, 4) —$C_{2-6}$ alkynyl, 5) —$C_{3-7}$ cycloalkyl, 6) —$C_{3-7}$ cycloalkenyl, 7) —$C_{1-5}$ fluorinated including one or more fluorine atoms, 8) -heterocyclyl, 9) -aryl, 10) -heteroaryl, 11) -benzyl, or 12) 5-[(3aS,4S,6aR)-2-oxohexahydro-1H-thieno[3,4-d]imidazol-4-yl]pentanoyl. In this list, the alkyl, the alkenyl, the alkynyl, the cycloalkenyl, the perfluorinated alkyl, the heterocyclyl, the aryl, the heteroaryl and the benzyl groups are each independently optionally substituted with 1, 2 or 3 $R^A$ or $R^1$ substituents and wherein, when ($R^1$) and $R^1$ are attached to a nitrogen atom, optionally they join together with the nitrogen atom to form a 3 to 7-membered ring which optionally includes one or more other heteroatom selected from N, O and S, optionally the ring is substituted with one or more $R^1$ or $R^A$.

$R^2$ is: 1) —H, 2) —$C_{1-6}$ alkyl, 3) —S$R^1$, 4) —C(O)$R^1$, 5) —S(O)$R^1$, 6) —S(O)$_2R^1$, 7)-benzyl optionally substituted with 1, 2 or 3 $R^A$ or $R^1$ substituents, 8) -L-heteroaryl optionally substituted with one or more $R^A$ or R1 substituents attached on either one or both the L and the heteroaryl groups, 9) -L-heterocyclyl optionally substituted with one or more $R^A$ or $R^1$ substituents attached on either one or both the L and the heterocyclyl groups, 10) -L-aryl optionally substituted with one or more $R^A$ or $R^1$ substituents attached on either one or both the L and the aryl groups, 11) -heteroaryl optionally substituted with one or more $R^A$ or $R^1$ substituents, or 12) -aryl optionally substituted with one or more $R^A$ or $R^1$ substituents. In this list, each substituent is optionally attached to the L group if it is not already present.

$R^A$ is: 1) -halogen, 2) —CF$_3$, 3) —OH, 4) —O$R^1$, 5) -L-OH, 6) -L-O$R^1$, 7) —OCF$_3$, 8) —SH, 9) —S$R^1$, 10) —CN 11) —NO$_2$, 12) —NH$_2$, 13) —NH$R^1$, 14) —N$R^1R^1$, 15) -L-NH$_2$, 16) -L-NH$R^1$, 17) -L-N$R^1R^1$, 18) -L-S$R^1$, 19) -L-S(O)$R^1$, 20) -L-S(O)$_2R^1$, 21) —C(O)OH, 22) —C(O)O$R^1$, 23) —C(O)NH$_2$, 24) —C(O)NH$R^1$, 25) —C(O)N($R^1$)$R^1$, 26) —NHC(O)$R^1$, 27) —N$R^1$C(O)$R^1$, 28) —NHC(O)O$R^1$, 29) —N$R^1$C(O)O$R^1$, 30) —OC(O)NH$_2$, 31) —OC(O)NH$R^1$, 32) —OC(O)N($R^1$)$R^1$, 33) —OC(O)$R^1$, 34) —C(O)$R^1$, 35) —NHC(O)NH$_2$, 36) —NHC(O)NH$R^1$, 37) —NHC(O)N($R^1$)$R^1$, 38) —N$R^1$C(O)NH$_2$, 39) —N$R^1$C(O)NH$R^1$, 40) —N$R^1$C(O)N($R^1$)$R^1$, 41) —NHS(O)$_2R^1$, 42) —N$R^1$S(O)$_2R^1$, 43) —S(O)$_2$NH$_2$, 44) —S(O)$_2$NH$R^1$, 45) —S(O)$_2$N($R^1$)$R^1$, 46) —S(O)$R^1$, 47) —S(O)$_2R^1$, 48) —OS(O)$_2R^1$, 49) —S(O)$_2$O$R^1$, 50) -benzyl, 51) —N$_3$, or 52) —C(═N═N—)(CF$_3$). In this list, the benzyl group is optionally substituted with 1, 2 or 3 $R^A$ or $R^1$ substituents, optionally, at least one hydrogen atom in the compound is replaced by a deuterium, optionally, the compound is attached to a solid support which is a resin, a polymer or a cellulose including polystyrene cross-linked, polyamide resin, agarose beads.

In one embodiment, in the compounds described herein:
D is CH or N;
Z is —CN; —C(O)OR1; —C(O)N(R1)R3; —C(O)R1, or -heteroaryl optionally substituted with one or more RA or R4 substituents,
wherein, when (R1) and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;
W is —CN; —N(R1)R3, —C(O)OR1, —C(O)N(R1)R3, —NR1C(O)R1, —NR1C(O)OR1, —OC(O)N(R1)R3, —OC(O)R1, —C(O)R1, —NR1C(O)N(R1)R3, —NR1S(O)$_2$R1, -benzyl optionally substituted with 1, 2 or 3 RA or R1 substituents, —X-L-(X-L)n-N(R1)R3, —X-L-(X-L)n-heteroaryl optionally substituted with one or more RA or R4 substituents attached on either or both the L and heteroaryl groups, —X-L-(X-L)n-heterocyclyl optionally substituted with one or more RA or R4 substituents attached on either or both the L and heterocyclyl groups, —X-L-(X-L)n-aryl optionally substituted with one or more RA or R4 substituents, —X-L-(X-L)$_n$-NR1RA or —(N(R1)-L)$_n$-N$^+$R1R3R5 R6$^-$: wherein n is an integer equal to either 0, 1, 2, 3, 4, or 5, and wherein, when R1 and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;

each X is independently selected from O, S, and NR1;

each L is independently —$C_{1-6}$ alkylene, —$C_{2-6}$ alkenylene, —$C_{2-6}$ alkynylene, —$C_{3-7}$cycloalkylene, which optionally includes one or more other heteroatom selected from N, O and S or —C3-7 cycloalkenylene, which optionally includes one or more other heteroatom selected from N, O and S wherein the alkylene, the alkenylene, the alkynylene the cycloalkylene and the cycloalkenylene groups are each independently optionally substituted with one or two R4 or RA substituent;

R1 is each independently —H, —$C_{1-6}$ alkyl, —$C_{2-6}$ alkenyl, —$C_{2-6}$ alkynyl, —$C_{3-7}$ cycloalkyl, —$C_{3-7}$ cycloalkenyl, —$C_{1-5}$ perfluorinated, -heterocyclyl, -aryl, -heteroaryl, or -benzyl, wherein the alkyl, the alkenyl, the alkynyl, the cycloalkyl, the perfluorinated alkyl, the heterocyclyl, the aryl, the heteroaryl and the benzyl groups are each independently optionally substituted with 1, 2 or 3 RA or Rd substituents;

R2 is —H, —$C_{1-6}$ alkyl, optionally substituted with one more more RA substituents, —C(O)R4, -L-heteroaryl optionally substituted with one or more RA or R4 substituents, -L-heterocyclyl optionally substituted with one or more RA or R4, or -L-aryl optionally substituted with one or more RA or R4 substituents;

R3 is each independently —H, —$C_{1-6}$ alkyl, —$C_{2-6}$ alkenyl, —$C_{2-6}$ alkynyl, —$C_{3-7}$ cycloalkyl, —$C_{3-7}$ cycloalkenyl, —$C_{1-5}$ perfluorinated, -heterocyclyl, -aryl, -heteroaryl, or -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

R4 is each independently —H, —$C_{1-6}$ alkyl, —$C_{2-6}$ alkenyl, —$C_{2-6}$ alkynyl, —$C_{3-7}$ cycloalkyl, —$C_{3-7}$ cycloalkenyl, —$C_{1-5}$ perfluorinated, -heterocyclyl, -aryl, -heteroaryl, or -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

R5 is each independently —$C_{1-6}$ alkyl, —$C_{1-6}$ alkylene-$C_{2-6}$ alkenyl which optionally includes one or more other heteroatom selected from N, O and S, —$C_{1-6}$ alkylene-$C_{2-6}$ alkynyl which optionally includes one or more other heteroatom selected from N, O and S; -L-aryl which optionally includes one or more RA or R4 substituents; -L-heteroaryl which optionally includes one or more RA or R4 substituents; —$C_{1-6}$ alkylene-C(O)O—, —$C_{1-6}$ alkylene-C(O)OR1, —$C_{1-6}$ alkylene-CN, —$C_{1-6}$ alkylene-C(O)NR1R3, wherein R1 and R3 optionally they join together with the nitrogen atom to form a 3 to 7-membered ring which optionally includes one or more other heteroatom selected from N, O and S; or —$C_{1-6}$ alkylene-OH;

R6 is halogen, OC(O)CF$_3$ or OC(O)R1;

RA is each independently -halogen, —CF$_3$, —OR1, -L-OR1, —OCF$_3$, —SR1, —CN, —NO$_2$, —NR1R3, -L-NR1R1, —C(O)OR1, S(O)$_2$R4, —C(O)N(R1)R3, —NR1C(O)R1, —NR1C(O)OR1, OC(O)N(R1)R3, —OC(O)R1, —C(O)R4, —NHC(O)N(R1)R3, —NR1C(O)N(R1)R3, or —N$_3$; and Rd is each independently —H, —$C_{1-6}$ alkyl, —$C_{2-6}$ alkenyl, —$C_{2-6}$ alkynyl, —$C_{3-7}$ cycloalkyl, —$C_{3-7}$ cycloalkenyl, —$C_{1-5}$ perfluorinated -benzyl or -heterocyclyl.

In one embodiment, in the compounds described herein:

Z is —CN, —C(O)OR1, —C(O)N(R1)R3, or -heteroaryl optionally substituted with one or more RA or R4 substituents, W is —CN, —N(R1)R3, -benzyl optionally substituted with 1, 2 or 3 RA or R1 substituents, —X-L-(X-L)n-N(R1)R3, —X-L-(X-L)$_n$-NR1RA or —(N(R1)-L)$_n$-N$^+$R1R3R5 R6$^-$ wherein n is an integer equal to either 0, 1, 2, or 3 and wherein, when R1 and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;

each X is independently O, S, or NR1,

L is each independently —$C_{1-6}$ alkylene, —$C_{2-6}$ alkenylene, —$C_{2-6}$ alkynylene, —C3-7 cycloalkylene, which optionally includes one or more other heteroatom selected from N, O and S or —C3-7 cycloalkenylene, which optionally includes one or more other heteroatom selected from N, O and S wherein the alkylene, the alkenylene, the alkynylene the cycloalkylene and the cycloalkenylene are each independently optionally substituted with one or two R4 or RA substituent;

R1 is each independently —H, —$C_{1-6}$ alkyl, —$C_{2-6}$ alkenyl, —$C_{2-6}$ alkynyl, —$C_{3-7}$ cycloalkyl, —$C_{3-7}$ cycloalkenyl, —$C_{1-5}$ perfluorinated, -heterocyclyl, -heteroaryl, or -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

R2 is —H, —$C_{1-6}$ alkyl, optionally substituted with one more more RA substituents, —C(O)R4, -L-heteroaryl optionally substituted with one or more RA or R4 substituents, -L-heterocyclyl optionally substituted with one or more RA or R4, or -L-aryl optionally substituted with one or more RA or R4 substituents R3 is each independently —H, —$C_{1-6}$ alkyl, —$C_{2-6}$ alkenyl, —$C_{2-6}$ alkynyl, or —$C_{1-5}$ perfluorinated, wherein the alkyl, the alkenyl, the alkynyl, the perfluorinated alkyl groups are each independently optionally substituted with 1, 2 or 3 RA or Rd substituents;

R4 is each independently —H, —$C_{1-6}$ alkyl, —$C_{2-6}$ alkenyl, —$C_{2-6}$ alkynyl, —$C_{3-7}$ cycloalkyl, —$C_{3-7}$ cycloalkenyl, —$C_{1-5}$ perfluorinated, -heterocyclyl, -aryl, -heteroaryl, or -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

R5 is each independently —$C_{1-6}$ alkyl, -L-aryl which optionally includes one or more RA or R4 substituents, -L-heteroaryl which optionally includes one or more RA or R4 substituents, —$C_{1-6}$ alkylene-C(O)O—, —$C_{1-6}$ alkylene-C(O)OR1, —$C_{1-6}$ alkylene-CN, —$C_{1-6}$ alkylene-C(O)NR1R3, or —$C_{1-6}$ alkylene-OH;

R6 is halogen, OC(O)CF$_3$ or OC(O)R1;

RA is each independently -halogen, —CF$_3$, —OR1, -L-OR1, —OCF$_3$, —SR1, —CN, —NO$_2$, —NR1R3, -L-NR1R1, —C(O)OR1, S(O)$_2$R4, —C(O)N(R1)R3, —NR1C(O)R1, —NR1C(O)OR1, —OC(O)N(R1)R3, —OC(O)R1, —C(O)R4, —NHC(O)N(R1)R3, —NR1C(O)N(R1)R3, or —N$_3$;

Rd is each independently —H, —$C_{1-6}$ alkyl, —$C_{2-6}$ alkenyl, —$C_{2-6}$ alkynyl, —$C_{3-7}$ cycloalkyl, —$C_{3-7}$ cycloalkenyl, —$C_{1-5}$ perfluorinated, -benzyl or -heterocyclyl.

In embodiments of the invention, the compounds have the general Formula IIA, IIB, IIA', or IIB', shown below. Salts or prodrugs of such compounds are also within the scope of the compounds according to the invention.

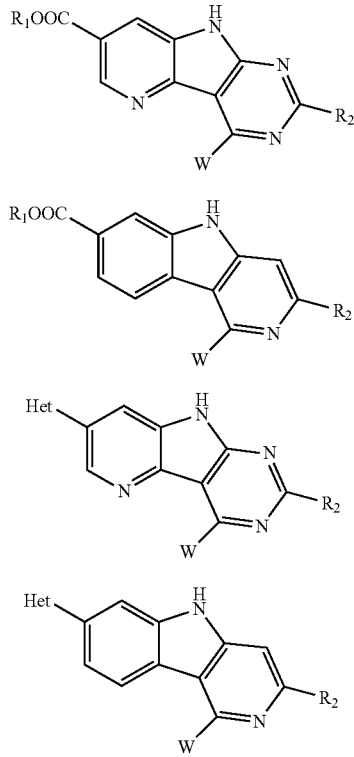

In embodiments of the invention according to compounds of general formula IIA or IIA' above, $R^1$, W and $R^2$ are each as defined herein above.

In embodiments of the invention according to compounds of general formula IIB or IIB' above, W and $R^2$ are each as defined herein above, and Het is a heteroaryl, optionally substituted with one or more $R^1$ or $R^4$ as defined herein above.

In embodiments of the invention according to compounds of general formula IVA or IVA' above, W, L, $R^1$ and $R^2$ are each as defined herein above. Also, m, Li, $R^3$ and $R^4$ are each as defined herein above.

In embodiments of the invention according to compounds of general formula VIA or VIA' above, Z is $CO_2Me$ or 2-methyl-2H-tetrazol-5-yl; $R^2$ is benzyl optionally substituted with OMe, 3-thienylmethyl or 3-pyridinyl methyl; and W is NH-L-N($R^1$)$R^1$ wherein L is $C_{2-4}$ alkyl and $R^1$ is $C_{1-4}$ alkyl or ($R^1$) and $R^1$ join together with the nitrogen atom to which they are attached to form a 3 to 7-membered ring, which optionally includes one or more other heteroatom selected from N, O and S, optionally the ring is substituted with one or more $R^1$ or $R^4$.

In one embodiment, there is provided a compound wherein
D is CH or N
Z is -heteroaryl optionally substituted with one or more RA or $R^1$ substituents; or —C(O)O$R^1$, wherein $R^1$ is —C1-6 alkyl;
W is —(N($R^1$)-L)$_n$-N($R^1$)$R^1$, wherein n=1, and L is —C3-7 cycloalkyl or —C1-6 alkyl; or
-L-N$R^1$($R^1$) wherein L is heterocyclyl optionally substituted with one or two $R^4$ or $R^1$ substituent, provided that said —N$R^1$($R^1$) is not bound to a heteroatom atom of said heterocyclyl, and wherein each $R^1$ is independently H, or —C1-6 alkyl, or N($R^1$)$R^1$ join together with the nitrogen atom to form a 3 to 7-membered heterocyclic ring optionally substituted with one or more $R^1$ or $R^4$
R2 is —H; -L-heteroaryl optionally substituted with one or more $R^4$ or $R^1$ substituents on either or both the L and the heteroaryl groups, wherein L is $C_{1-6}$ alkyl, or -L-aryl optionally substituted with one or more $R^4$ or $R^1$ substituents on either or both the L and aryl groups, wherein L is $C_{1-6}$ alkyl.

In one embodiment, Z is -heteroaryl optionally substituted with one or more RA or $R^1$ substituents, preferably the heteroaryl is a 5-membered ring, such as a tetrazolyl including 2-methyl-2H-tetrazol-5-yl.

In a further embodiment, Z is —C(O)O$R^1$, wherein $R^1$ is —C1-6 alkyl, preferably $R^1$ is —C1-3 alkyl such as methyl, ethyl, propyl and i-propyl.

In one embodiment, R2 is H.

In one embodiment, R2 is -L-heteroaryl optionally substituted with one or more RA or R1 substituents on either or both the L and the heteroaryl groups, wherein L is $C_{1-6}$ alkyl. Preferably, heteroaryl is a 5-6 membered heteroaryl. Preferably, -L-heteroaryl is —$CH_2$-heteroaryl such as —$CH_2$-pyridinyl or —$CH_2$-thienyl.

In one embodiment, R2 is -L-aryl optionally substituted with one or more RA or R1 substituents on either or both the L and aryl groups, wherein L is $C_{1-6}$ alkyl. Preferably, -L-aryl is —$CH_2$-aryl such as —$CH_2$-phenyl substituted with one or more RA or R1 substituents.

In one embodiment, W is —(N($R^1$)-L)$_n$-N($R^1$)$R^1$, wherein n=1, and L is —C3-7 cycloalkyl or —C1-6 alkyl; wherein each $R^1$ is independently H, or —C1-6 alkyl, or N($R^1$)$R^1$ join together with the nitrogen atom to form a 3 to 7-membered heterocyclic ring optionally substituted with one or more $R^1$ or $R^4$.

In one embodiment, W is —N($R^1$)-L-N($R^1$)$R^1$, wherein —N($R^1$)— is —N(H)— or —N(C1-2alkyl)-; L is —C5-6 cycloalkyl or —C2-4 alkyl; and —N($R^1$)$R^1$ is —N(H)C1-2alkyl, —N(C1-2alkyl)C1-2alkyl or N($R^1$)$R^1$ join together with the nitrogen atom to form a 5 or 6-membered heterocyclic ring such as pyperidyn-1yl or pyrrolidyn-1yl.

In one embodiment, W is -L-N$R^1$($R^1$) wherein L is heterocyclyl optionally substituted with one or two $R^4$ or $R^1$ substituent, provided that said —N$R^1$($R^1$) is not bound to a heteroatom atom of said heterocyclyl, and wherein each $R^1$ is independently H, or —C1-6 alkyl, or —N$R^1$($R^1$) join together with the nitrogen atom to form a 3 to 7-membered heterocyclic ring optionally substituted with one or more $R^1$ or $R^4$ In one embodiment, W is -L-N$R^1$($R^1$) wherein L is 6-membered heterocyclyl such as pyperidyn-1yl wherein each $R^1$ is independently H, or —C1-6 alkyl, or —N$R^1$($R^1$) join together with the nitrogen atom to form a 5 or 6-membered heterocyclic ring such as pyperidyn-1yl or pyrrolidyn-1yl.

In one embodiment, W is

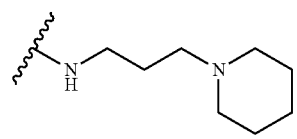

W1

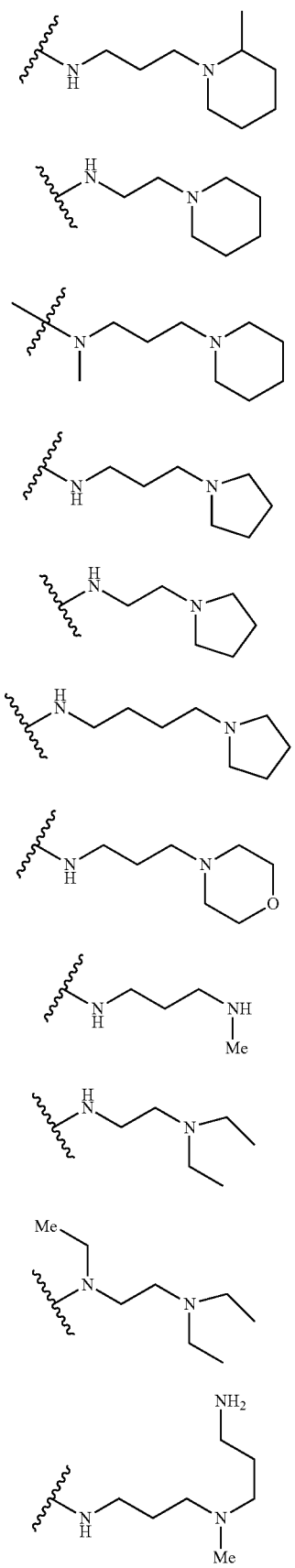
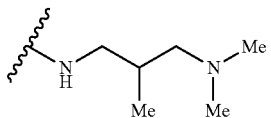
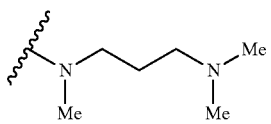
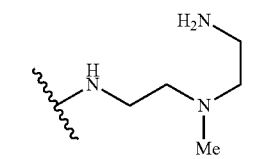
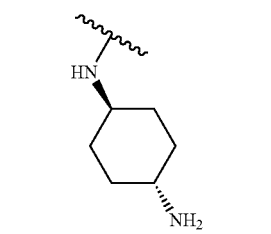
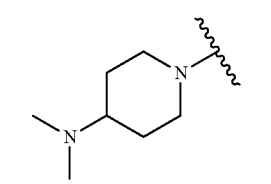
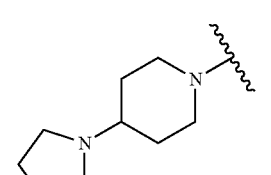
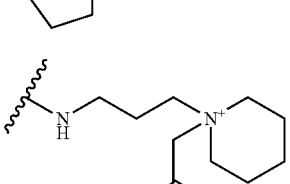
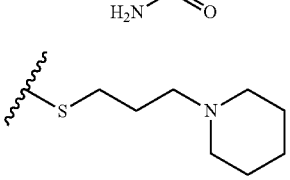
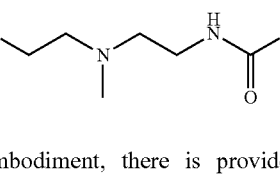
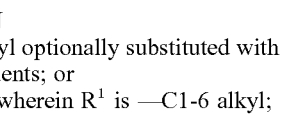
In one embodiment, there is provided a compound wherein
D is CH or N
Z is -heteroaryl optionally substituted with one or more RA or R¹ substituents; or
—C(O)OR¹, wherein R¹ is —C1-6 alkyl;

W is

—(N(R$^1$)-L)$_n$-N(R$^1$)R$^1$, wherein n=1, and L is —C3-7 cycloalkyl or —C1-6 alkyl;

-L-NR$^1$(R$^1$) wherein L is heterocyclyl optionally substituted with one or two R$^4$ or R$^1$ substituent, provided that said —NR$^1$(R$^1$) is not bound to a heteroatom atom of said heterocyclyl, and wherein each R$^1$ is independently H, or —C1-6 alkyl, or (R$^1$) and R$^1$ join together with the nitrogen atom to form a 3 to 7-membered heterocyclic ring optionally substituted with one or more R$^1$ or R$^4$;

—(N(R1)-L)$_n$-N$^+$R1R3R5 R6$^-$ wherein n=1, and L is —C1-6 alkyl; wherein R1 and R3 join together with the nitrogen atom to form a 5 to 6-membered ring R5 is —C$_{1-6}$ alkyl and R6 is halogen, OC(O)CF$_3$ or OC(O)R1;

-L-aryl which optionally includes one or more RA or R4 substituents;

-L-heteroaryl which optionally includes one or more RA or R4 substituents,

—C$_{1-6}$ alkylene-C(O)O—,

—C$_{1-6}$ alkylene-C(O)OR1,

—C$_{1-6}$ alkylene-CN,

—C$_{1-6}$ alkylene-C(O)NR1R3, or

—C$_{1-6}$ alkylene-OH;

R2 is —H; -L-heteroaryl optionally substituted with one or more RA or R1 substituents on either or both the L and the heteroaryl groups, wherein L is C$_{1-6}$ alkyl, or -L-aryl optionally substituted with one or more RA or R1 substituents on either or both the L and aryl groups, wherein L is C$_{1-6}$ alkyl; and when R1 and Ra are substituents, said R1 and Ra are preferably selected as follows:

R1, is each independently —H, —C$_{1-6}$ alkyl, —C$_{2-6}$ alkenyl, —C$_{2-6}$ alkynyl, —C$_{3-7}$ cycloalkyl, —C$_{3-7}$ cycloalkenyl, —C$_{1-5}$ perfluorinated, -heterocyclyl, -heteroaryl, or -benzyl RA is each independently -halogen, —CF$_3$, —OR1, -L-OR1, —OCF$_3$, —SR1, —CN, —NO$_2$, —NR1R3, -L-NR1R1, —C(O)OR1, S(O)$_2$R4, —C(O)N(R1)R3, —NR1C(O)R1, —NR1C(O)OR1, —OC(O)N(R1)R3, —OC(O)R1, —C(O)R4, —NHC(O)N(R1)R3, —NR1C(O)N(R1)R3, or —N$_3$ wherein R3 and R4 are each independently —H, —C$_{1-6}$ alkyl, —C$_{2-6}$ alkenyl, —C$_{2-6}$ alkynyl, —C$_{3-7}$ cycloalkyl, —C$_{3-7}$ cycloalkenyl, —C$_{1-5}$ perfluorinated, -heterocyclyl, -heteroaryl, or -benzyl.

In one embodiment, there is provided a compound wherein

D is CH or N

Z is -heteroaryl optionally substituted with one or more RA or R$^1$ substituents; or —C(O)OR$^1$, wherein R$^1$ is —C1-6 alkyl;

W is

—(N(R$^1$)-L)$_n$-N(R$^1$)R$^1$, wherein n=1, and L is —C3-7 cycloalkyl or —C1-6 alkyl;

-L-NR$^1$(R$^1$) wherein L is heterocyclyl optionally substituted with one or two R$^4$ or R$^1$ substituent, provided that said —NR$^1$(R$^1$) is not bound to a heteroatom atom of said heterocyclyl, and wherein each R$^1$ is independently H, or —C1-6 alkyl, or (R$^1$) and R$^1$ join together with the nitrogen atom to form a 3 to 7-membered heterocyclic ring optionally substituted with one or more R$^1$ or R$^4$ —(N(R1)-L)$_n$-N$^+$R1R3R5 R6$^-$ wherein n=1, and L is —C1-6 alkyl; wherein R1 and R3 join together with the nitrogen atom to form a 5 to 6-membered ring, R5 is —C$_{1-6}$ alkyl, —C$_{1-6}$ alkylene-C(O)OR1, and R6 is halogen, OC(O)CF$_3$ or OC(O)R1;

R2 is —H; -L-heteroaryl optionally substituted with one or more RA or R1 substituents on either or both the L and the heteroaryl groups, wherein L is C$_{1-6}$ alkyl, or -L-aryl optionally substituted with one or more RA or R1 substituents on either or both the L and aryl groups, wherein L is C$_{1-6}$ alkyl; and when R1 and Ra are substituents, said R1 and Ra are preferably selected as follows:

R1 is each independently —H, —C$_{1-6}$ alkyl, or —C$_{3-7}$ cycloalkyl,

RA is each independently -halogen, —CF$_3$, —C$_{1-6}$ alkoxy, —CN, —NO$_2$.

In one embodiment, there is provided a compound wherein

D is CH or N

Z is -heteroaryl optionally substituted with one or more RA or R$^1$ substituents; or —C(O)OR$^1$, wherein R$^1$ is —C1-6 alkyl;

W is

—(N(R$^1$)-L)$_n$-N(R$^1$)R$^1$, wherein n=1, and L is —C3-7 cycloalkyl or —C1-6 alkyl; or -L-NR$^1$(R$^1$) wherein L is heterocyclyl optionally substituted with one or two R$^4$ or R$^1$ substituent, provided that said —NR$^1$(R$^1$) is not bound to a heteroatom atom of said heterocyclyl, and wherein each R$^1$ is independently —H, or —C1-6 alkyl, or (R$^1$) and R$^1$ join together with the nitrogen atom to form a 3 to 7-membered heterocyclic ring optionally substituted with one or more R$^1$ or R$^4$;

R2 is —H; -L-heteroaryl optionally substituted with one or more RA or R1 substituents on either or both the L and the heteroaryl groups, wherein L is C$_{1-6}$ alkyl, or -L-aryl optionally substituted with one or more RA or R1 substituents on either or both the L and aryl groups, wherein L is C$_{1-6}$ alkyl; and when R1 and Ra are substituents, said R1 and Ra are preferably selected as follows:

R1, is each independently —H, —C$_{1-6}$ alkyl, —C$_{2-6}$ alkenyl, —C$_{2-6}$ alkynyl, —C$_{3-7}$ cycloalkyl, —C$_{3-7}$ cycloalkenyl, —C$_{1-5}$ perfluorinated, -heterocyclyl, -heteroaryl, or -benzyl RA is each independently -halogen, —CF$_3$, —OR1, -L-OR1, —OCF$_3$, —SR1, —CN, —NO$_2$, —NR1R3, -L-NR1R1, —C(O)OR1, S(O)$_2$R4, —C(O)N(R1)R3, —NR1C(O)R1, —NR1C(O)OR1, —OC(O)N(R1)R3, —OC(O)R1, —C(O)R4, —NHC(O)N(R1)R3, —NR1C(O)N(R1)R3, or —N$_3$ wherein R3 and R4 are each independently —H, —C$_{1-6}$ alkyl, —C$_{2-6}$ alkenyl, —C$_{2-6}$ alkynyl, —C$_{3-7}$ cycloalkyl, —C$_{3-7}$ cycloalkenyl, —C$_{1-5}$ perfluorinated, -heterocyclyl, -heteroaryl, or -benzyl.

In one embodiment, there is provided a compound wherein

D is CH;

Z is -heteroaryl optionally substituted with one or more RA or R$^1$ substituents; or —C(O)OR$^1$, wherein R$^1$ is —C1-6 alkyl;

W is —(N(R$^1$)-L)$_n$-N(R$^1$)R$^1$, wherein n=1, and L is —C3-7 cycloalkyl or —C1-6 alkyl; or -L-NR$^1$(R$^1$) wherein L is heterocyclyl optionally substituted with one or two R$^4$ or R$^1$ substituent, provided that said —NR$^1$(R$^1$) is not bound to a heteroatom atom of said heterocyclyl, and wherein each R$^1$ is independently H, or —C1-6 alkyl, or N(R$^1$)R$^1$ join together with the nitrogen atom to form a 3 to 7-membered heterocyclic ring optionally substituted with one or more R$^1$ or R$^4$ R2 is —H; -L-heteroaryl optionally substituted with one or more RA or R1 substituents on either or both the L and the heteroaryl groups, wherein L is C$_{1-6}$ alkyl, or -L-aryl optionally substituted with one or more RA or R1 substituents on either or both the L and aryl groups, wherein L is C$_{1-6}$ alkyl.

In one embodiment, there is provided a compound wherein
D is N
Z is -heteroaryl optionally substituted with one or more RA or $R^1$ substituents; or
—C(O)OR$^1$, wherein $R^1$ is —C1-6 alkyl;
W is —(N(R$^1$)-L)$_n$-N(R$^1$)R$^1$, wherein n=1, and L is —C3-7 cycloalkyl or —C1-6 alkyl; or
-L-NR$^1$(R$^1$) wherein L is heterocyclyl optionally substituted with one or two R$^A$ or R$^1$ substituent, provided that said —NR$^1$(R$^1$) is not bound to a heteroatom atom of said heterocyclyl, and wherein each R$^1$ is independently H, or —C1-6 alkyl, or N(R$^1$)R$^1$ join together with the nitrogen atom to form a 3 to 7-membered heterocyclic ring optionally substituted with one or more R$^1$ or R$^A$
R2 is —H; -L-heteroaryl optionally substituted with one or more RA or R1 substituents on either or both the L and the heteroaryl groups, wherein L is $C_{1-6}$ alkyl, or -L-aryl optionally substituted with one or more RA or R1 substituents on either or both the L and aryl groups, wherein L is $C_{1-6}$ alkyl.

In one embodiment, there is provided a compound wherein
D is CH or N
Z is -heteroaryl, preferably a heteroaryl of 5-membered ring, such as a tetrazolyl, optionally substituted with one or more RA or R$^1$ substituents; or —C(O)OR$^1$, wherein R$^1$ is —C1-6 alkyl, preferably R$^1$ is —C1-3 alkyl such as methyl, ethyl, propyl and i-propyl and preferably methyl;
W is N(R$^1$)-L-N(R$^1$)R$^1$, wherein —N(R$^1$)— is —N(H)— or —N(C1-2alkyl)-; L is —C5-6 cycloalkyl or —C2-4 alkyl; and —N(R$^1$)R$^1$ is —N(H)C1-2alkyl, —N(C1-2alkyl)C1-2alkyl or N(R$^1$)R$^1$ join together with the nitrogen atom to form a 5 or 6-membered heterocyclic ring such as pyperidyn-1yl or pyrrolidyn-1yl; or
-L-NR$^1$(R$^1$) wherein L is 6-membered heterocyclyl such as pyperidyn-1yl wherein each R$^1$ is independently H, or —C1-6 alkyl, or —NR$^1$(R$^1$) join together with the nitrogen atom to form a 5 or 6-membered heterocyclic ring such as pyperidyn-1yl or pyrrolidyn-1yl;
R2 is —H; -L-heteroaryl optionally substituted with one or more RA or R1 substituents on either or both the L and the heteroaryl groups, wherein the heteroaryl is a 5-6 membered heteroaryl such as pyridinyl or thienyl and L is $C_{1-3}$ alkyl, or -L-aryl optionally substituted with one or more RA or R1 substituents on either or both the L and aryl groups, wherein said aryl is phenyl and L is $C_{1-3}$ alkyl.

In one embodiment, there is provided a compound wherein
D is CH or N
Z is a heteroaryl of 5-membered ring, such as a tetrazolyl, optionally substituted with —$C_{1-6}$ alkyl such as methyl; or —C(O)OR$^1$, preferably R$^1$ is —C1-3 alkyl and preferably methyl;
W is selected from W1-W21 and preferably W1 and W16;
R2 is —CH$_2$-heteroaryl such as —CH$_2$-pyridinyl or —CH$_2$-thienyl or —CH2-aryl such as —CH2-phenyl; each of said heteroaryl and aryl is optionally substituted by one RA.

In one embodiment, there is provided a compound wherein
D is CH or N
Z is a heteroaryl of 5-membered tetrazolyl ring, optionally substituted with methyl; or
—C(O)OR$^1$, wherein R$^1$ methyl;
W is selected from W1 and W16
R2 is —CH2-heteroaryl such as —CH2-pyridinyl or —CH2-thienyl or —CH2-aryl such as —CH2-phenyl; each of said heteroaryl and aryl is optionally substituted by one RA, preferably selected from -halogen, C1-6alkoxy-such as methoxy, hydroxyl or C1-6alkyl such as methyl.

one embodiment, there is provided a compound wherein
D is CH or N
Z is a heteroaryl of 5-membered tetrazolyl ring, optionally substituted with methyl; or
—C(O)OR$^1$, wherein R$^1$ methyl;
W is selected from W1 and W16
R2 is —CH2-heteroaryl such as —CH2-pyridinyl or —CH2-thienyl or —CH2-aryl such as —CH2-phenyl; each of said heteroaryl and aryl is optionally substituted by one RA, preferably selected from -halogen, C1-6alkoxy-such as methoxy, hydroxyl or C1-6alkyl such as methyl.

In one embodiment, there is provided a compound wherein
D is CH
Z is a heteroaryl of 5-membered ring, such as a tetrazolyl, optionally substituted with —$C_{1-6}$ alkyl such as methyl; or —C(O)OR$^1$, preferably R$^1$ is —C1-3 alkyl and preferably methyl;
W is selected from W1-W21 and preferably W1 and W16
R2 is —CH2-heteroaryl such as —CH2-pyridinyl or —CH2-thienyl or —CH2-aryl such as —CH2-phenyl; each of said heteroaryl and aryl is optionally substituted with one or more RA or R1 substituents and preferably unsubstituted or substituted by one RA selected from -halogen, C1-6alkoxy- such as methoxy, hydroxyl or C1-6alkyl such as methyl.

In one embodiment, there is provided a compound wherein
D is N
Z is a heteroaryl of 5-membered ring, such as a tetrazolyl, optionally substituted with —$C_{1-6}$ alkyl such as methyl; or —C(O)OR$^1$, preferably R$^1$ is —C1-3 alkyl and preferably methyl;
W is selected from W1-W21 and preferably W1 and W16
R2 is —CH$_2$-heteroaryl such as —CH$_2$-pyridinyl or —CH$_2$-thienyl or —CH$_2$-aryl such as —CH$_2$-phenyl; each of said heteroaryl and aryl is optionally substituted with one or more RA or R1 substituents and preferably unsubstituted or substituted by one RA selected from -halogen, C1-6alkoxy-such as methoxy, hydroxyl or C1-6alkyl such as methyl.

In one embodiment, there is provided a compound wherein
D is CH
Z is —C(O)OR$^1$, wherein R$^1$ is —C1-3 alkyl and preferably methyl;
W is selected from W1-W21 and preferably W1 and W16;
R2 is —CH$_2$-heteroaryl such as —CH$_2$-pyridinyl or —CH$_2$-thienyl or —CH$_2$-aryl such as —CH$_2$-phenyl; each of said heteroaryl and aryl is unsubstituted or substituted by one RA selected from halogen, C1-6alkoxy- such as methoxy, hydroxyl or C1-6alkyl such as methyl.

In one embodiment, there is provided a compound wherein
D is N
Z is —C(O)OR$^1$, wherein R$^1$ is —C1-3 alkyl and preferably methyl;
W is selected from W1-W21 and preferably W1 and W16;
R2 is —CH$_2$-heteroaryl such as —CH$_2$-pyridinyl or —CH$_2$-thienyl or —CH$_2$-aryl such as —CH$_2$-phenyl; each of said heteroaryl and aryl is unsubstituted or substituted by one RA selected from -halogen, C1-6alkoxy- such as methoxy, hydroxyl or C1-6alkyl such as methyl.

In embodiments of the invention, the compounds of the invention are the compounds depicted in Table 1 herein below and the compounds depicted in Table 1' herein below.

Salts or prodrugs of such compounds are also within the scope of the compounds according to the invention.

Definitions:

Unless otherwise specified, the following definitions apply:

The singular forms "a", "an" and "the" include corresponding plural references unless the context clearly dictates otherwise.

As used herein, the term "comprising" is intended to mean that the list of elements following the word "comprising" are required or mandatory but that other elements are optional and may or may not be present.

As used herein, the term "consisting of" is intended to mean including and limited to whatever follows the phrase "consisting of." Thus the phrase "consisting of" indicates that the listed elements are required or mandatory and that no other elements may be present.

As used herein, the term "alkyl" is intended to include both branched and straight chain saturated aliphatic hydrocarbon groups having the specified number of carbon atoms, for example, $C_1$-$C_6$ in $C_1$-$C_6$ alkyl is defined as including groups having 1, 2, 3, 4, 5 or 6 carbons in a linear or branched saturated arrangement. Examples of $C_1$-$C_6$ alkyl as defined above include, but are not limited to, methyl, ethyl, n-propyl, i-propyl, n-butyl, t-butyl, i-butyl, pentyl, and hexyl.

As used herein, the term "cycloalkyl" is intended to mean a monocyclic saturated aliphatic hydrocarbon group having the specified number of carbon atoms therein, for example, $C_3$-$C_7$ in $C_3$-$C_7$ cycloalkyl is defined as including groups having 3, 4, 5, 6 or 7 carbons in a monocyclic saturated arrangement. Examples of $C_3$-$C_7$ cycloalkyl as defined above include, but are not limited to, cyclopropyl, cyclobutyl, cyclopentyl, cyclohexyl and cycloheptyl.

As used herein, the term, "alkenyl" is intended to mean unsaturated straight or branched chain hydrocarbon groups having the specified number of carbon atoms therein, and in which at least two of the carbon atoms are bonded to each other by a double bond, and having either E or Z regiochemistry and combinations thereof. For example, $C_2$-$C_6$ in $C_2$-$C_6$ alkenyl is defined as including groups having 2, 3, 4, 5 or 6 carbons in a linear or branched arrangement, at least two of the carbon atoms being bonded together by a double bond. Examples of $C_2$-$C_6$ alkenyl include, but are not limited to, ethenyl (vinyl), 1-propenyl, 2-propenyl, 1-butenyl and the like.

As used herein, the term "alkynyl" is intended to mean unsaturated, straight chain hydrocarbon groups having the specified number of carbon atoms therein and in which at least two carbon atoms are bonded together by a triple bond. For example $C_2$-$C_4$ alkynyl is defined as including groups having 2, 3 or 4 carbon atoms in a chain, at least two of the carbon atoms being bonded together by a triple bond. Examples of such alkynyl include, but are not limited to, ethynyl, 1-propynyl, 2-propynyl and the like.

As used herein, the term "cycloalkenyl" is intended to mean a monocyclic saturated aliphatic hydrocarbon group having the specified number of carbon atoms therein, for example, $C_3$-$C_7$ in $C_3$-$C_7$ cycloalkenyl is defined as including groups having 3, 4, 5, 6 or 7 carbons in a monocyclic arrangement. Examples of $C_3$-$C_7$ cycloalkenyl as defined above include, but are not limited to, cyclopentenyl, cyclohexenyl and the like.

As used herein, the term "halo" or "halogen" is intended to mean fluorine, chlorine, bromine or iodine.

As used herein, the term "haloalkyl" is intended to mean an alkyl as defined above, in which each hydrogen atom may be successively replaced by a halogen atom. Examples of haloalkyl include, but are not limited to, $CH_2F$, $CHF_2$ and $CF_3$.

As used herein, the term "aryl," either alone or in combination with another radical, means a carbocyclic aromatic monocyclic group containing 6 carbon atoms which may be further fused to a second 5- or 6-membered carbocyclic group which may be aromatic, saturated or unsaturated. Examples of aryl include, but are not limited to, phenyl, indanyl, 1-naphthyl, 2-naphthyl, tetrahydronaphthyl and the like. The aryl may be connected to another group either at a suitable position on the cycloalkyl ring or the aromatic ring.

As used herein, the term "heteroaryl" is intended to mean a monocyclic or bicyclic ring system of up to 10 atoms, wherein at least one ring is aromatic, and contains from 1 to 4 hetero atoms selected from the group consisting of O, N, and S. The heteroaryl may be attached either via a ring carbon atom or one of the heteroatoms. Examples of heteroaryl include, but are not limited to, thienyl, benzimidazolyl, benzo[b]thienyl, furyl, benzofuranyl, pyranyl, isobenzofuranyl, chromenyl, xanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, napthyridinyl, quinoxalinyl, quinazolinyl, cinnolinyl, pteridinyl, isothiazolyl, isochromanyl, chromanyl, isoxazolyl, furazanyl, indolinyl, isoindolinyl, thiazolo[4,5-b]-pyridine, tetrazolyl, oxadiazolyl, thiadiazolyl, thienyl and fluoroscein derivatives.

As used herein, the term "heterocycle," "heterocyclic" or "heterocyclyl" is intended to mean a 3, 4, 5, 6, or 7 membered non-aromatic ring system containing from 1 to 4 heteroatoms selected from the group consisting of O, N and S. Examples of heterocycles include, but are not limited to, pyrrolidinyl, tetrahydrofuranyl, piperidyl, 3,5-dimethylpiperidyl, pyrrolinyl, piperazinyl, imidazolidinyl, morpholinyl, imidazolinyl, pyrazolidinyl, pyrazolinyl, and the like, where the attachment to the ring can be on either the nitrogen atom or a carbon atom of the ring such as described hereafter:

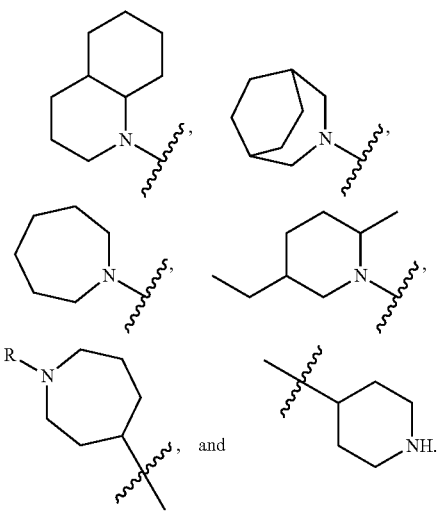

As used herein, the term "optionally substituted with one or more substituents" or its equivalent term "optionally substituted with at least one substituent" is intended to mean that the subsequently described event of circumstances may or may not occur, and that the description includes instances where the event or circumstance occurs and instances in which it does not. The definition is intended to mean from zero to five substituents.

As used herein, the term "subject" or "patient" is intended to mean humans and non-human mammals such as primates, cats, dogs, swine, cattle, sheep, goats, horses, rabbits, rats, mice and the like.

If the substituents themselves are incompatible with the synthetic methods described herein, the substituent may be protected with a suitable protecting group (PG) that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, "Protecting Groups in Chemical Synthesis" (4th ed.), John Wiley & Sons, NY (2007), which is incorporated herein by reference in its entirety. Examples of protecting groups used throughout include, but are not limited to, Fmoc, Bn, Boc and CBz. In some instances, a substituent may be specifically selected to be reactive under the reaction conditions used in the methods described herein. Under these circumstances, the reaction conditions convert the selected substituent into another substituent that is either useful in an intermediate compound in the methods described herein or is a desired substituent in a target compound.

The "salts" of the compounds referred to herein are preferably pharmaceutically acceptable salts. As used herein, the term "pharmaceutically acceptable salt" is intended to mean both acid and base addition salts.

As used herein, the term "pharmaceutically acceptable acid addition salt" is intended to mean those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

As used herein, the term "pharmaceutically acceptable base addition salt" is intended to mean those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

The compounds according to the invention or their pharmaceutically acceptable salts may contain one or more asymmetric centers, chiral axes and chiral planes and may thus give rise to enantiomers, diastereomers, and other stereoisomeric forms and may be defined in terms of absolute stereochemistry, such as (R)- or (S)- or, as (D)- or (L)- for amino acids. The present is intended to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, selective reaction of one enantiomer with an enantiomer specific reagent. It will also be appreciated by those skilled in the art that where the desired enantiomer is converted into another chemical entity by a separation technique, an additional step is then required to form the desired enantiomeric form. Alternatively specific enantiomers may be synthesized by asymmetric synthesis using optically active reagents, substrates, catalysts, or solvents or by converting one enantiomer to another by asymmetric transformation.

Certain compounds according to the invention may exist as a mix of epimers. Epimers means diastereoisomers that have the opposite configuration at only one of two or more stereogenic centers present in the respective compound.

Compounds according to the invention may exist in Zwitterionic form and the present includes Zwitterionic forms of these compounds and mixtures thereof.

In addition, the compounds according to the invention also may exist in hydrated and anhydrous forms. Hydrates of the compound of any of the formulas described herein are included. In a further embodiment, the compound according to any of the formulas described herein is a monohydrate. In embodiments of the invention, the compounds described herein comprise about 10% or less, about 9% or less, about 8% or less, about 7% or less, about 6% or less, about 5% or less, about 4% or less, about 3% or less, about 2% or less, about 1% or less, about 0.5% or less, about 0.1% or less by weight of water. In others embodiments, the compounds described herein comprise, about 0.1% or more, about 0.5% or more, about 1% or more, about 2% or more, about 3% or more, about 4% or more, about 5% or more, or about 6% or more by weight of water.

It may be convenient or desirable to prepare, purify, and/or handle the compound in the form of a prodrug. Thus, the term "prodrug", as used herein, pertains to a compound which, when metabolized (e.g., in vivo), yields the desired active compound. Typically, the prodrug is inactive, or less active than the desired active compound, but may provide advantageous handling, administration, or metabolic properties. Unless otherwise specified, a reference to a particular compound also includes prodrugs thereof.

As used herein, the term "$EC_{50}$" is intended to mean the concentration that results in a 50% increase in CD34+ CD45RA− cell count compared to vehicle cultures (DMSO).

As used herein, the term "hematopoietic stem cells" or "HSCs" is intended to mean cells having both pluripotency which allows them to differentiate into functional mature cells such as granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g., monocytes, macrophages), and the ability to regenerate while maintaining their pluripotency (self-renewal).

As used herein, the term "hematopoietic progenitor cells" or "HPCs" is intended to mean cells having the potential to differentiate into functional mature cells such as granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g., monocytes, macrophages).

HSCs and/or HPCs are part of the starting cell population. These cells are optionally obtained from the body or an organ of the body containing cells of hematopoietic origin. Such sources include un-fractionated bone marrow, umbilical cord, peripheral blood, liver, thymus, lymph and spleen. All of the aforementioned crude or un-fractionated blood products can be enriched for cells having hematopoietic stem cell characteristics in ways known to those of skill in the art.

As used herein, the term "starting cell population" is meant to identify a cell population comprising HSCs and/or HPCs harvested from one of various sources mentioned above, as known in the art. The starting cell population can be enriched in CD34+ cells meaning a cell population selected based on the presence of the cell surface marker CD34+. CD34+ cells can be detected and counted using for example flow cytometry and fluorescently labeled anti-CD34 antibodies. Moreover, the starting cell population may be used directly for expansion or frozen and stored for use at a later point in time.

During hematopoiesis, HSCs first diverge into the progenitor stage into the myeloid lineage and the lymphoid lineage, then differentiate into myeloid stem cells (mixed colony forming cells, CFU-GEMM) and into lymphoid stem cells, respectively. Further, myeloid stem cells differentiate into erythrocytes via erythroid burst forming cells (BFU-E) and erythroid colony forming cells (CFU-E), into thrombocytes via megakaryocyte colony forming cells (CFU-MEG), into monocytes, neutrophils and basophils via granulocyte-macrophage colony forming cells (CFU-GM), and into eosinophils via eosinophil colony forming cells (CFU-Eo), while lymphoid stem cells differentiate into T cells via T lymphoid progenitor cells and into B cells via B lymphoid progenitor cells. These myeloid stem cells and various hematopoietic progenitor cells derived from them are identified by the properties of colonies they form on soft agar, semisolid methylcellulose media or the like in the presence of various cytokines.

The present invention also includes use of a compound according to the invention and as defined herein, or a salt thereof, in the preparation of a medicament for the treatment of a subject (or patient) suffering from the following non-limiting list of disorders: autologous or allogeneic transplantation or treatment of a subject (or patient) suffering from the above-mentioned disorders or from auto-immune disorders. Examples of hematological malignancies/disorders and congenital diseases may include, without limitation, acute myeloid leukemia, acute lymphoblastic leukemia, chronic myeloid leukemia, chronic lymphocytic leukemia, myeloproliferative disorders, myelodysplastic syndromes, multiple myeloma, non-Hodgkin's lymphoma, Hodgkin's disease, aplastic anemia, pure red cell aplasia, hemoglobinuria, Fanconi anemia, thalassemia, sickle cell anemia, Wiskott-Aldrich syndrome, inborn errors of metabolism (such as Gaucher disease among others). Examples of immunological disorders that may benefit from transplantation are numerous and include multiple sclerosis, lupus, certain forms or arthritis, severe combined immunodeficiencies, and the like.

Thus, the present invention encompasses administration, to a patient suffering from any one of the above-mentioned disorders/malignancies, HSCs and/or HPCs that are expanded using a compound according to the invention.

Furthermore, the compounds and compositions as described can be used in the following non-limiting settings: autologous or allogeneic transplantation or treatment of a subject (or patient) suffering from the above-mentioned disorders or from auto-immune disorders. Examples of hematological malignancies/disorders and congenital diseases may include, without limitation, acute myeloid leukemia, acute lymphoblastic leukemia, chronic myeloid leukemia, chronic lymphocytic leukemia, myeloproliferative disorders, myelodysplastic syndromes, multiple myeloma, non-Hodgkin's lymphoma, Hodgkin's disease, aplastic anemia, pure red cell aplasia, hemoglobinuria, Fanconi anemia, thalassemia, sickle cell anemia, Wiskott-Aldrich syndrome, inborn errors of metabolism (such as Gaucher disease among others). Examples of immunological disorders that may benefit from transplantation are numerous and include multiple sclerosis, lupus, certain forms or arthritis, severe combined immunodeficiencies, and the like.

Thus, the present invention encompasses administration, to a patient suffering from any one of the above-mentioned disorders/malignancies, HSCs and/or HPCs that are expanded using a compound according to the invention.

Also encompassed within the present invention is a cell population obtained after expansion using the method according to the invention and as described herein. Both hematopoietic stem cells and hematopoietic progenitor cells can be harvested from adult, umbilical cord blood, fetal or embryonic sources. Cell expansion using the method of the present invention can lead to an increase in the number of progenitor cells which is useful in hastening the time to neutrophil or platelet engraftment, for example. Such method comprises: contacting a starting population comprising HSCs and/or HPCs with an agent capable of increasing the number of HSCs and/or HPCs. The starting population may be enriched in the cell surface marker of interest or a combination thereof (for example CD34+, CD34+ CD45RA+/−)

Methods for Expanding HSCs and/or HPCs

The invention therefore relates to a method for expanding HCSs and/or HPCs, comprising (a) providing a starting cell population comprising HCSs and/or HPCs and (b) contacting said starting cell population ex vivo under suitable conditions for expanding HCSs and/or HPCs.

In an embodiment, the method for expanding HSCs and/or HPCs comprises (a) providing a starting cell population comprising HSCs and/or HPCs and (b) contacting said starting cell population ex vivo in the presence of the compound or composition of the present invention.

The cell population may first be subjected to enrichment or purification steps, including negative and/or positive selection of cells based on specific cellular markers in order to provide the starting cell population. Methods for isolating said starting cell population based on specific cellular markers may use fluorescent activated cell sorting (FACS) technology also called flow cytometry or solid or insoluble substrate to which is bound antibodies or ligands that interact with specific cell surface markers. For example, cells may be contacted with a solid substrate (e.g., column of beads, flasks, magnetic particles) containing the antibodies and any unbound cells are removed. When a solid substrate comprising magnetic or paramagnetic beads is used, cells bound to the beads can be readily isolated by a magnetic separator.

In one embodiment, said starting cell population is enriched in CD34+ cells. Methods for enriching blood cell population in CD34+ cells include kits commercialized by Miltenyi Biotec (CD34+ direct isolation kit, Miltenyi Biotec, Bergisch, Gladbach, Germany) or by Baxter (lsolex 3000).

The amount of cord blood from a single birth is often inadequate to treat an adult or an older child. One advantage of the expansion method using the compound or composition of the invention is that it enables the production of a sufficient amount of HCSs and/or HPCs from only one cord blood unit.

Accordingly, in one embodiment, the starting cell population is derived from neonatal umbilical cord blood cells which have been enriched in CD34+ cells. In one related embodiment, said starting cell population is derived from one or two umbilical cord blood units.

In another embodiment, the starting cell population is derived from human mobilized peripheral blood cells which have been enriched in CD34+ cells. In one related embodiment, said starting cell population is derived from human mobilized peripheral blood cells isolated from only one patient.

Said starting cell population may preferably contain at least 50% CD34+ cells, in some embodiments, more than 90% of CD34+ cells.

Culture conditions of the starting cell population for the expansion will vary depending on the starting cell population, the desired final number of cells, and desired final proportion of HSCs and/or HPCs.

In an embodiment, in particular, using a starting cell population from umbilical cord blood cells enriched in CD34+ cells, the culturing conditions comprise the use of other cell expanding factors like cytokines and growth factors, generally known in the art for HSC/HPC expansion. Such cytokines and growth factors can be biologics or small molecules and they include without limitation IL-1, IL-3, IL-6, IL-11, G-CSF, GM-CSF, SCF, FIT3-L, thrombopoietin (TPO), erythropoietin, and analogs thereof. As used herein, "analogs" include any structural variants of the cytokines and growth factors having the biological activity as the naturally occurring forms, including without limitation, variants with enhanced or decreased biological activity when compared to the naturally occurring forms or cytokine receptor agonists such as an agonist antibody against the TPO receptor (for example, VB22B sc(Fv)2 as detailed in patent publication WO 2007/145227, and the like). Cytokine and growth factor combinations are chosen to expand HSC and progenitor cells while limiting the production of terminally differentiated cells. In one specific embodiment, one or more cytokines and growth factors are selected from the group consisting of SCF, Flt3-L and TPO.

Human IL6 or interleukin-6, also known as B-cell stimulatory factor 2 has been described by (Kishimoto, *Ann. review of* 1 *mm.* 23:1 2005) and is commercially available. Human SCF or stem cell factor, also known as c-kit ligand, mast cell growth factor or Steel factor has been described (Smith, M A et al., *ACTA Haematologica*, 105, 3:143, 2001) and is commercially available. Flt3-L or FLT-3 Ligand, also referred as FL is a factor that binds to flt3-receptor. It has been described (Hannum C, *Nature* 368 (6472): 643-8) and is commercially available. TPO or thrombopoietin, also known as megakaryocyte growth factor (MGDF) or c-Mpl ligand has been described (Kaushansky K (2006). *N. Engl. J. Med.* 354 (19): 2034-45) and is commercially available.

In another specific embodiment, one or more cytokines and growth factors are selected from the group consisting of SCF, Flt3-L, TPO and IL6. In a further specific embodiment, one or more cytokines and growth factors are selected from the group consisting of SCF, Flt3-L, TPO, IL6 and IL3.

The chemical components and biological components mentioned above may be used not only by adding them to the medium but also by immobilizing them onto the surface of the substrate or support used for the culture, specifically speaking, by dissolving a component to be used in an appropriate solvent, coating the substrate or support with the resulting solution and then washing away an excess of the component. Such a component to be used may be added to the substrate or support preliminarily coated with a substance which binds to the component.

The expansion of HSCs may be carried out in natural medium, a semi-synthetic medium or a synthetic medium in terms of composition, and may be a solid medium, a semisolid medium or a liquid medium in terms of shape, and any nutrient medium used for hematopoietic stem cell and/or hematopoietic progenitor cell culture, which is supplemented with the mixtures of cell expanding factors described above. Such medium typically comprises sodium, potassium, calcium, magnesium, phosphorus, chlorine, amino acids, vitamins, cytokines, hormones, antibiotics, serum, fatty acids, saccharides or the like. In the culture, other chemical components or biological components may be incorporated singly or in combination, as the case requires. Such components to be incorporated in the medium may be fetal calf serum, human serum, horse serum, insulin, transferin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, methylcellulose, various cytokines, various growth factors or the like. Examples of such basal medium appropriate for a method of expanding HSCs include, without limitation, StemSpan™ Serum-Free Expansion Medium (SFEM) (StemCell Technologies, Vancouver, Canada), StemSpan™ H3000-Defined Medium (StemCell Technologies, Vancouver, Canada), CellGro™, SCGM (CellGenix, Freiburg Germany), StemPro™-34 SFM (Invitrogen), Dulbecco's Modified Eagles's Medium (DMEM), Ham's Nutrient Mixture H12 Mixture F12, McCoy's 5A medium, Eagles's Minimum Essential Medium (EMEM), αMEM medium (alpha Modified Eagles's Minimum Essential Medium), RPMI1640 medium, lsocove's Modified Dulbecco's Medium (IMDM), StemPro34 (lnvitrogen), X-VIVO 10 (Cambrex), X-VIVO 15 (Cambrex) and Stemline II (Sigma-Aldrich).

In one embodiment, the compound or the composition of the invention is administered during the expansion method of said starting cell population under a concentration appropriate for HSC and/or HPC expansion. In one specific embodiment, said compound or composition is administered at a concentration comprised between 1 and 3000 nmol or for example between 1 and 100 nmol.

In one specific embodiment where the starting cell population essentially consists of CD34+ enriched cells from one or two cord blood units, or from mobilized PB cells or from harvested bone marrow, the cells are grown under conditions for HSC and/or HPC expansion, for example between 2 and 21 days and/or until the indicated fold expansion and the characteristic cell populations are obtained. In one specific embodiment, the cells are grown ex vivo under conditions for HSC and/or HPC expansion not more than 21 days, 12 days, 10 days or 7 days.

The cell population may then be washed to remove the compound or composition of invention and/or any other component of the cell culture and re-suspended in an appropriate cell suspension medium for short term use or in a long-term storage medium, for example a medium suitable for cryopreservation.

The HSCs and/or HPCs can be cultured in a culture vessel generally used for animal cell culture such as a Petri dish, a flask, a plastic bag, a Teflon™ bag, optionally after preliminary coating with an extracellular matrix or a cell adhesion molecule. The material for such a coating may be collagens Ito XIX, fibronectin, vitronectin, laminins 1 to 12, nitrogen, tenascin, thrombospondin, von Willebrand factor, osteoponin, fibrinogen, various elastins, various proteoglycans, various cadherins, desmocolin, desmoglein, various integrins, E-selectin, P-selectin, L-selectin, immunoglobulin superfamily, Matrigel, poly-D-lysine, poly-L-lysine, chitin, chitosan, Sepharose, alginic acid gel, hydrogel or a fragment thereof. Such a coating material may be a recombinant material having an artificially modified amino acid sequence. The hematopoietic stem cells and/or hematopoietic progenitor cells may be cultured by using a bioreactor which can mechanically control the medium composition, pH and the like and obtain high density culture (Schwartz R M, *Proc. Natl. Acad. Sci. U.S.A.*, 88:6760, 1991; Koller M R, *Bone Marrow Transplant*, 21:653, 1998; Koller, M R, *Blood*, 82: 378, 1993; Astori G, *Bone Marrow Transplant*, 35: 1101, 2005).

The invention further provides a cell population with expanded HSCs and/or HPCs, obtainable or obtained by the expansion method described above. In one specific embodiment, such cell population is re-suspended in a pharmaceutically acceptable medium suitable for administration to a mammalian host, thereby providing a therapeutic composition.

The invention further provides the cell population with expanded HSCs and/or HPCs or its composition for use in allogeneic or autologous stem cell transplantation in a mammalian subject.

The subject referred to herein is, for example, a bone marrow donor or an individual with or at risk for depleted or limited blood cell levels. Optionally, the subject is a bone marrow donor prior to bone marrow harvesting or a bone marrow donor after bone marrow harvesting. The subject is optionally a recipient of a bone marrow transplant. The methods described herein are particularly useful in subjects that have limited bone marrow reserve such as elderly subjects or subjects previously exposed to an immune depleting treatment or myeloablative treatment such as chemotherapy, e.g., for treating leukemia or lymphomas. The subject, optionally, has a decreased blood cell level or is at risk for developing a decreased blood cell level as compared to a control blood cell level. As used herein the term "control blood cell level" refers to an average level of blood cells in a subject prior to or in the substantial absence of an event that changes blood cell levels in the subject. An event that changes blood cell levels in a subject includes, for example, anemia, trauma, chemotherapy, bone marrow transplant and radiation therapy. For example, the subject has anemia or blood loss due to, for example, trauma.

The transplant may be a composition containing a buffer solution, an antibiotic, a pharmaceutical in addition to HCSs and/or HPCs expanded by the method of the present invention.

The expanded HSC and/or HPC population or the composition comprising the cell population with expanded HSCs and/or HPCs is administered to the subject, for example, before, at the same time, or after chemotherapy, radiation therapy or a bone marrow transplant. The subject optionally has depleted bone marrow related to, for example, congenital, genetic or acquired syndrome characterized by bone marrow loss or depleted bone marrow. Thus, the subject is optionally a subject in need of hematopoiesis. Optionally, the subject is a bone marrow donor or is a subject with or at risk for depleted bone marrow.

Hematopoietic stem cell manipulation is useful as a supplemental treatment to chemotherapy or radiation therapy. For example, HSCs are localized into the peripheral blood and then isolated from a subject that will undergo chemotherapy, and after the therapy the cells are returned. Thus, the subject is a subject undergoing or expected to undergo an immune cell depleting treatment such as chemotherapy, radiation therapy or serving as a donor for a bone marrow transplant. Bone marrow is one of the most prolific tissues in the body and is therefore often the organ that is initially damaged by chemotherapy drugs and radiation. The result is that blood cell production is rapidly destroyed during chemotherapy or radiation treatment, and chemotherapy or radiation must be terminated to allow the hematopoietic system to replenish the blood cell supplies before a patient is re-treated with chemotherapy. Therefore, as described herein, HSCs, HPCs or blood cells made by the methods described herein are optionally administered to such subjects in need of additional blood cells.

Provided are HSCs and/or HPCs expanded by a compound or a composition of the invention as described above in combination with a therapeutic capable of enhancing the proliferation of HSCs and/or HPCs in vivo, in vitro, or ex vivo (for example, a small molecule, an antibody, or the like) and optionally at least one pharmaceutically acceptable excipient or carrier. By a therapeutic capable of enhancing HSC and/or HPC proliferation is meant, without being limited thereto, an agonist antibody against the TPO receptor (for example, VB22B sc(Fv)2 as detailed in patent publication WO 2007/145227, and the like); a cytokine such as SCF, IL-6, Flt-3 ligand, TPO or a TPO mimetic (for example, such as described in WO/2007/022269; WO/2007/009120; WO/2004/054515; WO/2003/103686; WO/2002/085343; WO/2002/049413; WO/2001/089457; WO/2001/039773; WO/2001/034585; WO/2001/021180; WO/2001/021180; WO/2001/017349; WO/2000/066112; WO/2000/035446; WO/2000/028987; WO/2008/028645; and the like); granulocyte colony stimulating factor (G-CSF); granulocyte macrophage colony stimulating factor (GM-CSF); a prostaglandin or a prostaglandin receptor agonist (for example, prostaglandin E2 receptor-1 (EP-I) agonist, prostaglandin E2 receptor-2 (EP-2) agonist, prostaglandin E2 receptor-3 (EP-3) agonist and prostaglandin E2 receptor-4 (EP-4) agonists, as detailed in patent publication WO/2008/073748); tetraethylenepentamine (TEPA); Notch-ligands (Delta-1); and/or a WNT agonist. In addition, culturing stem cells with mesenchymal stem cells (MSCs) prevents graft-versus-host disease (GvHD) and may help stem cell expansion.

By "pharmaceutically acceptable" is meant a material that is not biologically or otherwise undesirable, i.e., the material may be administered to a subject or cell, without causing undesirable biological effects or interacting in a deleterious manner with the other components of the pharmaceutical composition in which it is contained. The carrier or excipient is selected to minimize degradation of the active ingredient and to minimize adverse side effects in the subject or cell.

The compositions are formulated in any conventional manner for use in the methods described herein. In embodiments, the composition according to the invention comprises a compound as defined herein. In other embodiments, the composition according to the invention comprises a HSC and/or HPC population expanded using a compound as defined herein. The composition according to the invention may also comprise a pharmaceutically acceptable carrier. Administration of the composition is via any route known to be effective by one of ordinary skill. For example, the composition is administered orally, parenterally (e.g., intravenously), by intramuscular injection, by intraperitoneal injection, transdermally, extracorporeally, intranasally or topically.

The preferred method of administration is intravenous infusion. The number of cells transfused will take into consideration factors such as sex, age, weight, the types of disease or disorder, stage of the disorder, the percentage of the desired cells in the cell population and the amount of cells needed to produce a therapeutic benefit. In one particular embodiment, the composition is administered by intravenous infusion and comprises at least ≥0.3×10$^5$ CD34$^+$/kg or >2×10$^6$ CD34$^+$ for cord blood and 2.5×10$^5$ CD34$^+$/kg or more for bone marrow or mobilized peripheral blood cells. In one specific embodiment, the infused cells are all deriving from expanded cord blood cells from a single birth.

Expanded HCSs and/or HPCs may be infused by drip, for example, in the case of treatment of leukemia, into patients pretreated with an anticancer drug, total body irradiation or an immunosuppressive drug for eradication of cancer cells or for facilitation of donor cell engraftment. The disease to be treated, the pretreatment and the cell transplantation method are selected appropriately by the person in charge. The engraftment of so transplanted HCSs and/or HPCs in the recipient, the recovery of hematopoiesis, the presence of side effects of the transplantation and the therapeutic effect of the transplantation can be judged by an ordinary assay used in transplantation therapy.

As described above, the present invention makes it possible to expand HCSs and/or HPCs and to carry out transplantation therapy safely and easily in a short term by using the expanded HSCs and/or HPCs.

Also provided herein is a kit comprising one or more containers filled with one or more of the ingredients described herein. Such kits optionally comprise solutions and buffers as needed or desired. The kit optionally includes an expanded population of stem cells made by the methods described above or can comprise containers or compositions for making an expanded population of HSCs and/or HPCs. In particular, the invention provides a kit for expanding ex vivo hematopoietic stem cells, comprising a compound of the invention as defined herein and instructions for use of such compound in a method for HSC and/or HPC expansion and, optionally, one or more cell expanding factors, or media for cell growth, in particular media for HSC and/or HPC growth as described above. The kit may further comprise antibodies for monitoring production of the cells, such as anti-CD34, anti-CD38 and/or anti-CD45RA antibodies. In one specific embodiment, such kit further includes one or more cell expanding factors selected from the group consisting of IL6, FLT3-L, SCF and TPO. Optionally associated with such pack(s) or kit(s) are instructions for use.

Also provided is a kit for providing an effective amount of a compound of the invention to increase HSCs and/or HPCs in a subject comprising one or more doses of the compound for use over a period of time, wherein the total number of doses of the compound of the invention in the kit equals the effective amount sufficient to increase HSCs and/or HPCs in a subject. The period of time is from about one to several days or weeks or months. Thus, the period of time is from at least about 5, 6, 7, 8, 10, 12, 14, 20, 21, 30 or 60 days or more or any number of days between one and 180.

Biological Assays

Screening Assay: screening assays were conducted as described in the inventors' previous patent application, WO 2013/110198.

Figure 2:
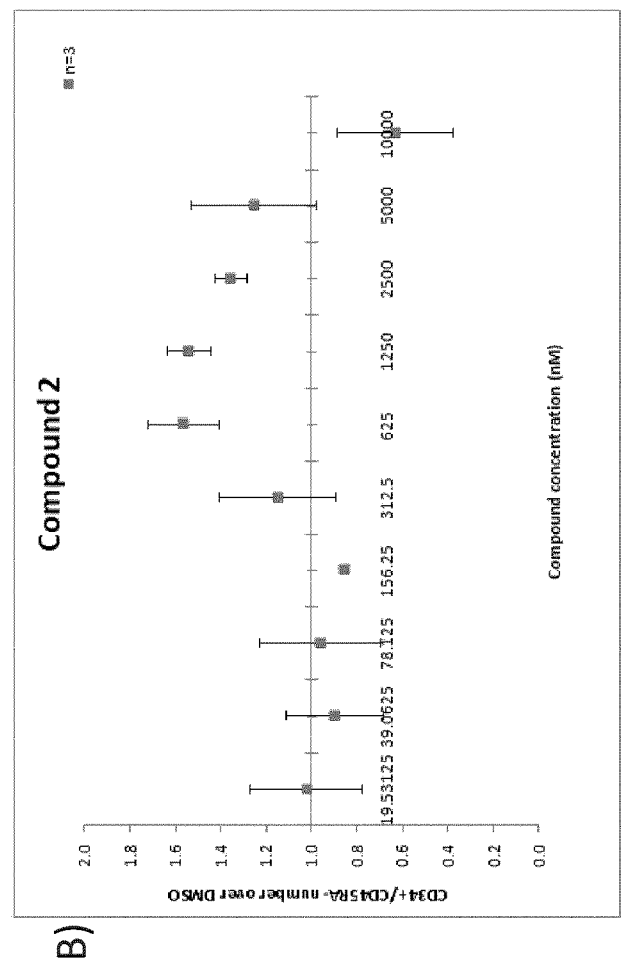
Figure 2:
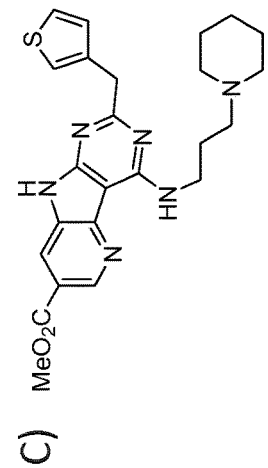
Figure 3:
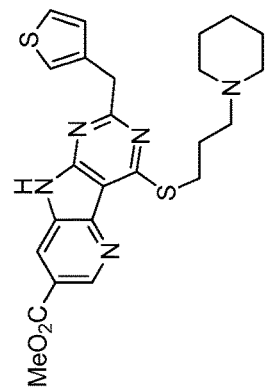
Figure 3:
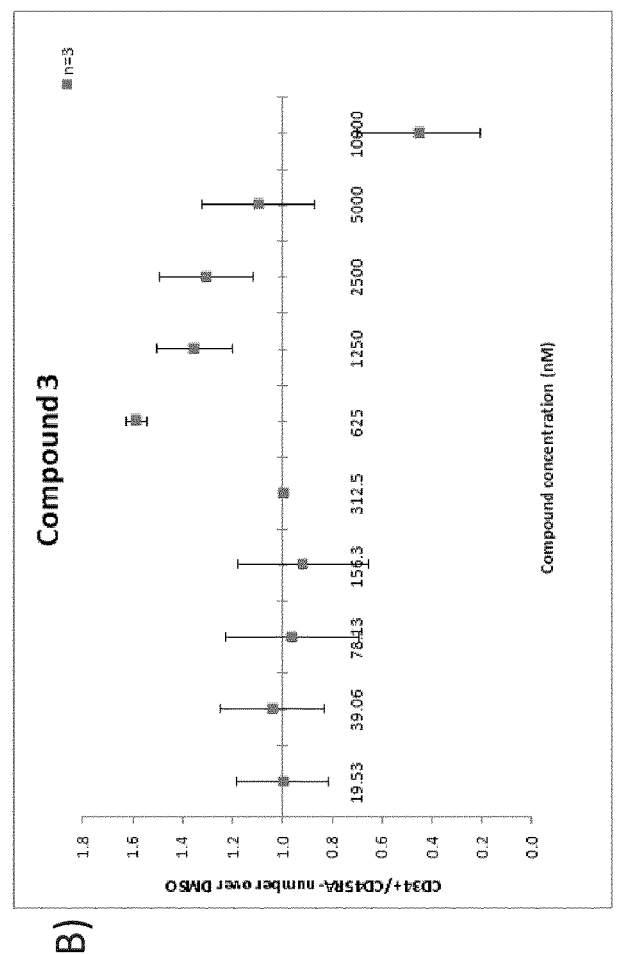
Figure 4:
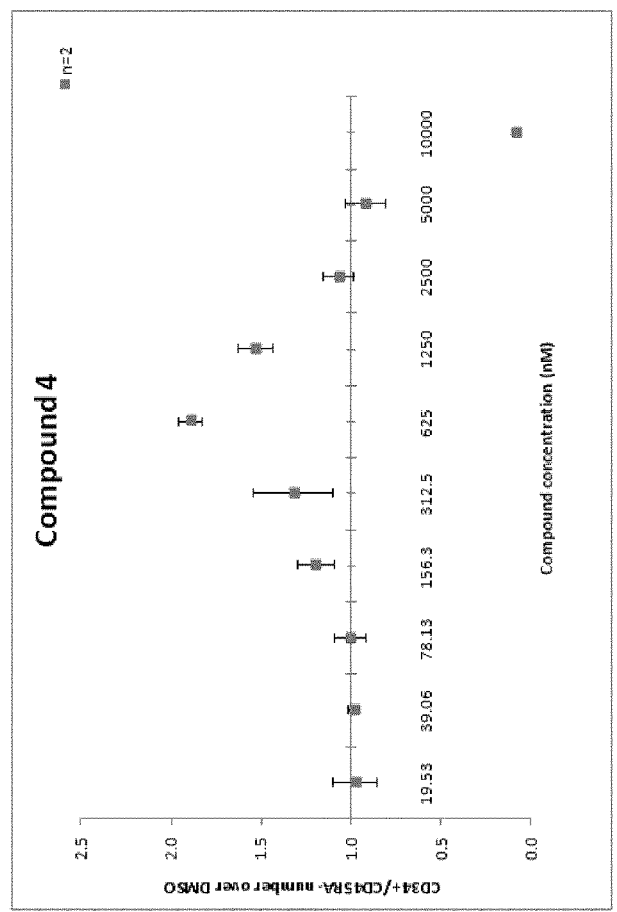
Figure 4:
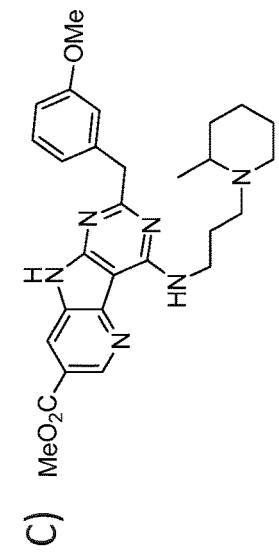
Figure 5:
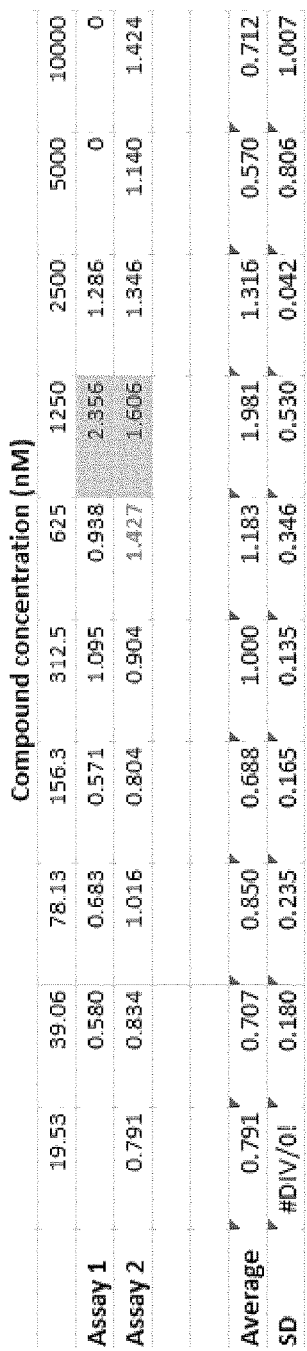
Figure 5:
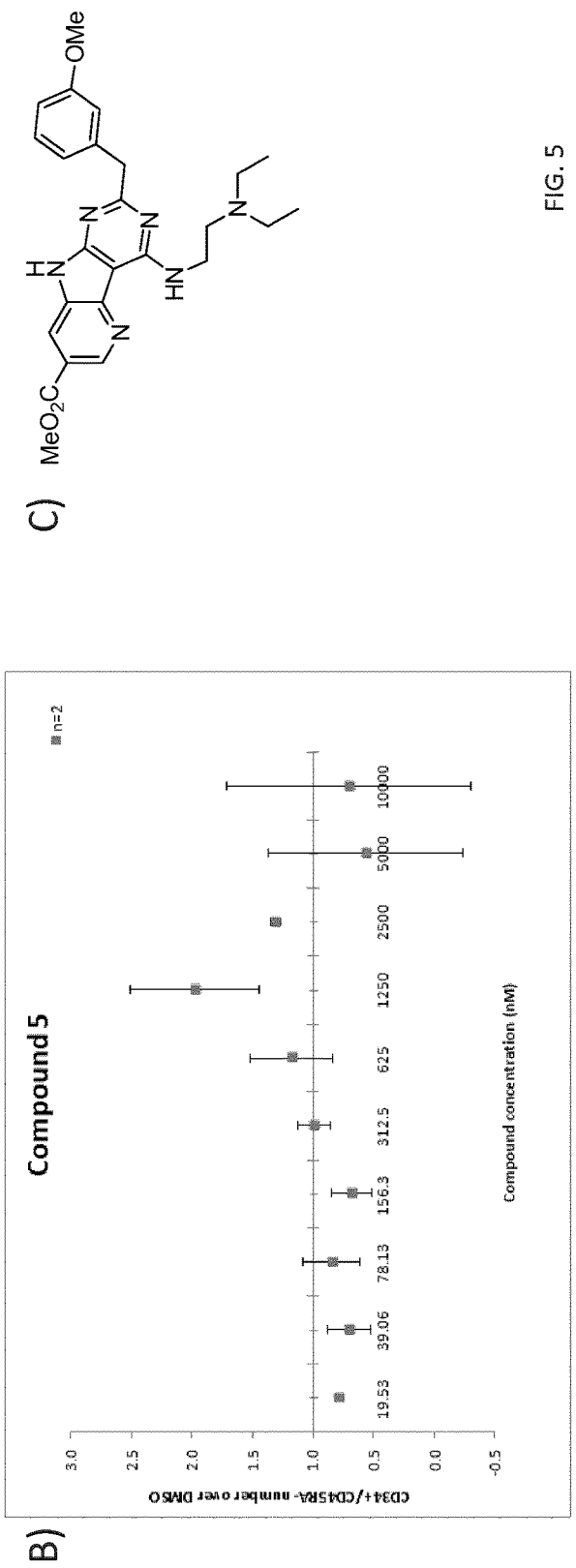
Figure 6:
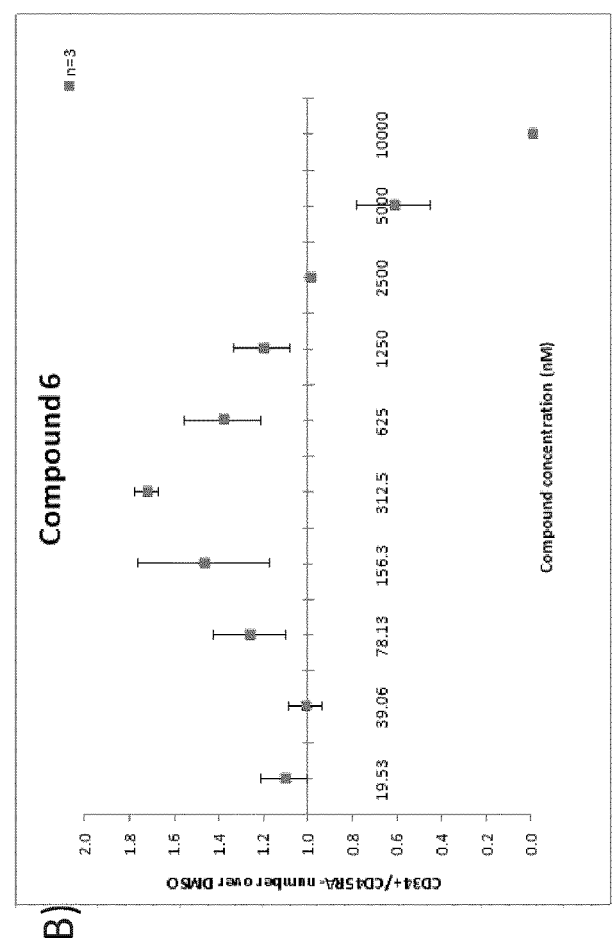

The following biological assays were used to assess the effect of the compounds of the invention on hematopoietic stem cell expansion The results are illustrated in FIGS. 1 to 6. Culture medium: The culture medium used consisted of serum-free medium supplemented with the following recombinant cytokines: interleukin-6, thrombopoietin, Flt-3 ligand, and stem cell factor, each at a final concentration of 100 ng/ml, in the presence of vehicle (DMSO), positive control (SR1), or compound of the invention or a combination of compounds. Cell Culture: CD34+ cell purity of initial harvests was higher than 90%, as determined by flow cytometry. The CD34+ CD45RA− subpopulation reached purity levels higher than 70%. Cells were plated at 40,000 cells/ml and incubated for 7 to 12-days at 37° C. in 5% CO$_2$. For long term cultures, 200,000 CD34+cells/ml from mobilized PB were plated with serum free media supplemented with interleukin-6, thrombopoietin, Flt3 ligand, and stem cell factor, each at a final concentration of 100 ng/ml, in the presence of vehicle (DMSO), positive control, or a compound of the invention at 500 nM.

Synthetic Methodology of Pyridopyrrolo Pirimidinyl Compounds

The synthetic methodology outlined below relates to embodiments of the invention wherein. As will be understood by a skilled person, a similar synthetic methodology can be performed, with variations that are apparent to such person.

Scheme 1

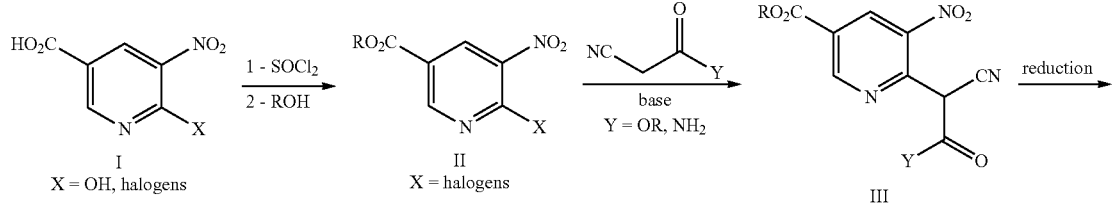

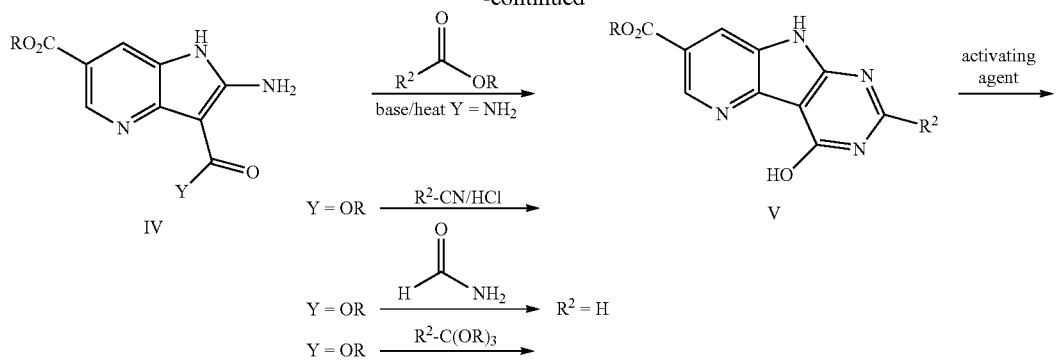
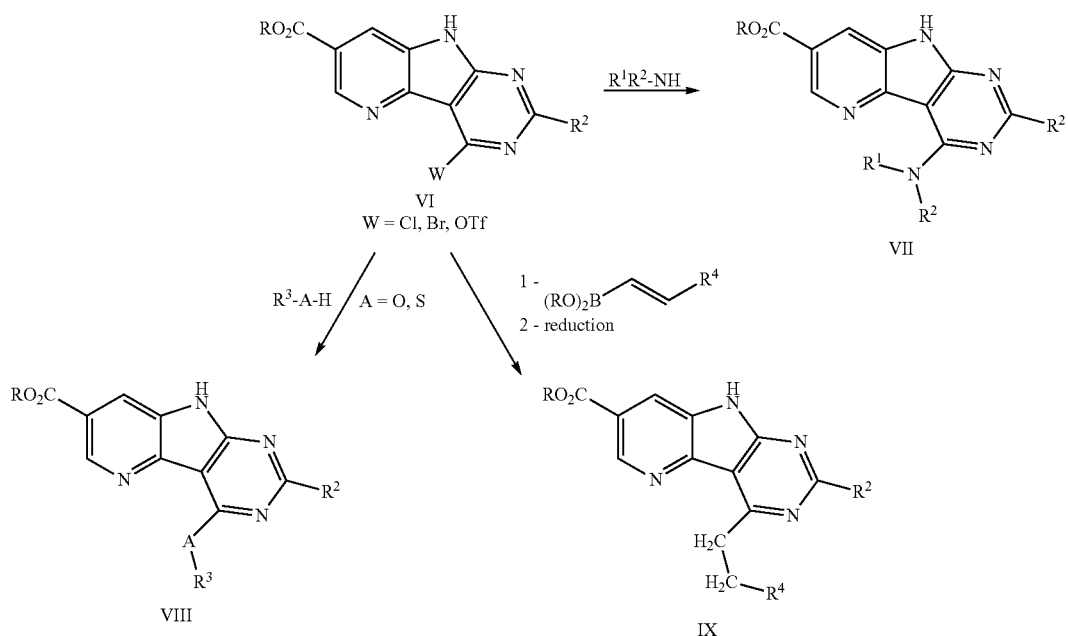
Scheme 2
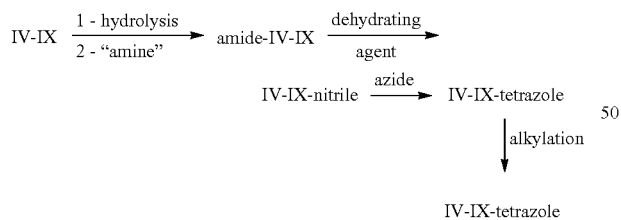
Scheme 3
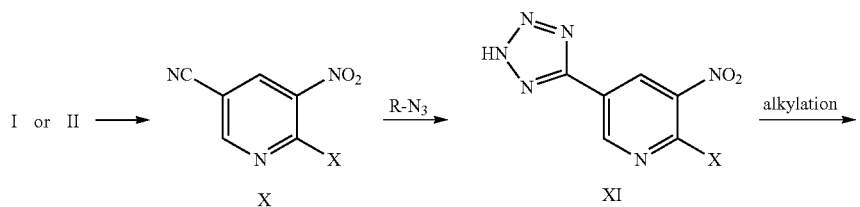

-continued

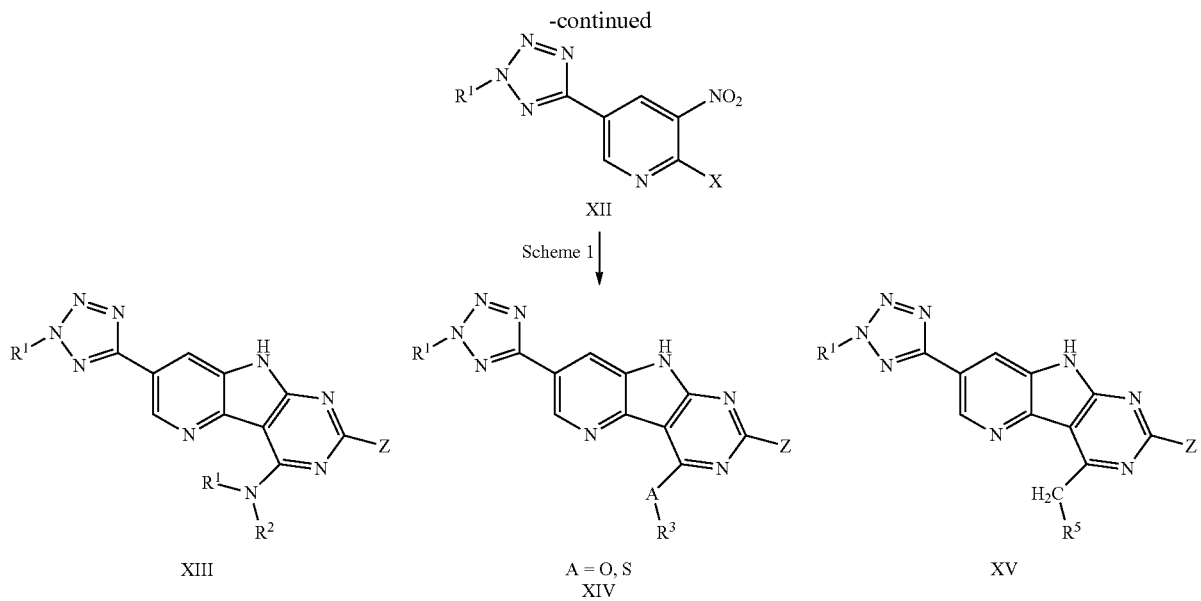

Scheme 1: Starting from 6-hydroxy-5-nitronicotinic acid, the OH is converted to the halide with and activating agent such as SOCl$_2$ and the carboxylic acid as an acyl halide which can then react with an alcohol to form an ester (II). The ester could also be prepared in the first step via the numerous ways to prepare ester such as the Fisher esterification. Displacement of the halide (or mesylate for example if the OH was selected) by the anion of 2-cyanoacetamide generated by a base such as NaH, MeONa or potassium t-butoxide yield the Intermediate III. The same procedure could be applied with a cyanoacetate such as an alkyl cyanoacetate. Reduction of the nitro group followed by cyclization can be accomplish with various metals such as iron/ammonium chloride in a polar solvent such as dimethyl formamide and heat, with zinc/acetic acid and heat, palladium or tin dichloride to name a few. This reduction-cyclization formed the Intermediate IV which can be converted to the Intermediate V (when Y=NH$_2$) by heating with an ester in a polar solvent such as methanol and N-methyl pyrrolidine at high temperature (80-140° C.) with a base such as sodium methoxide. When Y=OR, the intermediate can be treated with a cyanide derivative with HCl followed by basic conditions such as potassium carbonate and sodium methoxide. Alternatively, IV (Y=OR) can be converted with an orthoformate derivative or with formamide by heating (80-200° C.) to the Intermediate V. Conversion of the phenol (or the isomeric amide) to a leaving group such as triflate, chloride or bromide (VI) can be done with triflic anhydride with a base such as triethylamine in an inert solvent such as dichloromethane or by halogenation with reagents such as phosphorus oxychloride (or bromide). Intermediate VI can be heated (60-160° C.) with and amine (with or without a base such as triethylamine) to furnish the compound VII. Intermediate VIII could be obtained by heating (80-160° C.) intermediate VI with an excess (5-25 eq.) of the desired alcohol followed by treatment with an alkoxide (23-140° C.) such as methanol to get back the ester in the 7-position. Similarly, a mixture of Intermediate VI with an appropriate thiolate generated from a hydride such as NaH or a base such as sodium methoxide or a carbonate or from the deprotection of a silyl group with a fluoride source in DMF (N-methyl pyrrolidine) yielded the desired intermediate VIII. An appropriate vinyl boronate (usually prepared from an alkyne and a dialkoxyborane) and intermediate VI in the presence of a metal catalyst such as palladium (ex. PdCl$_2$(PPh$_3$)$_2$-CuI-Et$_3$N) in a solvent such as dimethyl formamide with heat (30-140° C.) furnished the corresponding alkene. This alkene could be reduced by numerous ways such as hydrogen with palladium on charcoal to give compound IX.

Scheme 2: The ester at the 7-position could be converted to the amide either directly by heating a solution of amine in an alcohol at high temperature or in a two-step manner by first hydrolysis of the ester followed by amide formation according to standard procedures. The corresponding nitrile could be obtained by dehydration of the previous amide with thionyl chloride or trifluoroacetic anhydride, for example. The intermediate tetrazole could be obtained by heating the previous nitrile with trimethylsilyl or tributyltin azide in hot toluene. Alkylation could be performed with a alkyl halide with a base such as potassium carbonate in an inert solvent such as acetonitrile and numerous ways are well known to perform this type of transformation.

Scheme 3: According to Scheme 2, Intermediate I or II could be converted to the nitrile X, then to Intermediate XI with an azide and finally to Intermediate XII after alkylation. Final compounds XIII-XV could be obtained following Scheme 1.

The sequences of the schemes could be interchange in function of the availability of some starting materials or by the type of functionalities on the intermediates.

EXAMPLES

General

Reported HPLC retention time are for reverse-phase HPLC (Agilent, 1200 series) using the following conditions Solvent A: MeOH:H$_2$O:TFA (5:95:0.05); Solvent B: MeOH:H$_2$O:TFA (95:5:0.05); flow: 3.0 mL/min; gradient 0 to 100% B in 2.0 minutes; column: ZorbaxC18, 3.5 microns, 4.6×30 mm: wavelength 220 nm.

Mass spectra were recorded on a 6210 G1969A LC/MSD TOF spectrometer from Agilent Technologies or on a Qua- Experimental Procedures Example 1

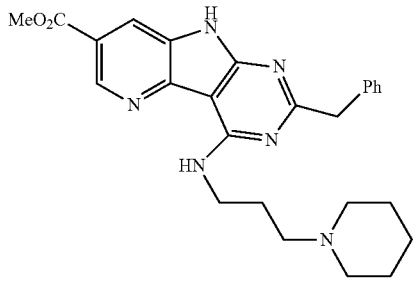 [SMILES: COC(=O)c1cnc2c(c1)[nH]c1nc(Cc3ccccc3)nc(NCCCN3CCCCC3)c12]

methyl 2-benzyl-4-((3-(piperidin-1-yl)propyl)amino)-9H-pyrido[2',3':4,5]pyrrolo[2,3-d]pyrimidine-7-carboxylate Intermediate 1A

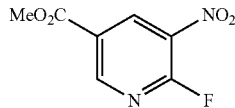

methyl 6-fluoro-5-nitronicotinate

A mixture of 6-hydroxy-5-nitronicotinic acid (5.00 g, 27.2 mmol), SOCl$_2$ (29.7 ml, 407 mmol) and DMF (0.315 ml, 4.07 mmol) was refluxed overnight. The volatiles were removed and the residue taken in DCM. Removal of the solvent under reduced pressure got rid of the last trace of reagent. The residue was diluted in DCM (50 mL), brought to −40° C. under N$_2$ and MeOH (54.4 mmol) was added slowly. The solution was brought to r.t. and 1 h later the solvent was removed to give 5.2 g (88%) of crude ester. $^1$H NMR (400 MHz, CDCl$_3$) δ ppm 4.03 (s, 3H) 8.77 (d, J=1.9 Hz, 1H) 9.18 (d, J=2.3 Hz, 1H).

Intermediate 1B

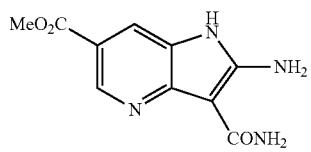

methyl 2-amino-3-carbamoyl-1H-pyrrolo[3,2-b]pyridine-6-carboxylate

NaH (0.776 g, 19.39 mmol, 60% weight) was added to a 5° C. solution of 2-cyanoacetamide (0.815 g, 9.70 mmol) in DMF (12 ml). The mixture was brought to it for 15 min then back to 5° C. Methyl 6-chloro-5-nitronicotinate (2.00 g, 9.23 mmol) in THF (6 ml) was added slowly to the previous solution and then brought to rt. After 3 h of stirring, the solution was cooled to 5° C. and quenched with 24 ml of water followed 10 min later by HCl$_{conc}$ (0.81 ml, 9.7 mmol). The solid obtained was filtered and dried overnight under vacuum to give 0.80 g of methyl 6-(2-amino-1-cyano-2-oxoethyl)-5-nitronicotinate. LCMS m/z 263.2 (M−H); $^1$H NMR (400 MHz, DMSO-d$_6$) δ ppm 3.95 (s, 3H) 5.99 (s, 1H) 7.81 (s, 1H), 8.15 (s, 1H) 8.86 (d, J=2.0 Hz, 1H) 9.38 (d, J=2.0 Hz, 1H) with some of the regioisomer (Z)-methyl 6-(2-amino-1-cyano-2-oxoethylidene)-5-nitro-1,6-dihydro-pyridine-3-carboxylate.

A mixture of iron (1.522 g, 27.3 mmol) and saturated ammonium chloride (0.348 g, 7.57 mmol) in DMF (9 ml) was brought to 85° C. and methyl 6-(2-amino-1-cyano-2-oxoethyl)-5-nitronicotinate (0.800 g, 3.03 mmol) in DMF (6 ml) was added dropwise. After 4 h of stirring, the mixture was diluted with more DMF (6 ml), filtered hot and the solvent removed under vacuum. Purification on ISCO using a RediSep column with DCM-MeOH (0-20%) gave 290 mg of the desired product. $^1$H NMR (400 MHz, DMSO-d$_6$) δ ppm 3.84 (s, 3H) 7.04 (br. s, 1H) 7.40 (br. s, 2H) 7.80 (br. s, 1H) 7.83 (d, J=1.5 Hz, 1H) 8.67 (d, J=1.6 Hz, 1H) 10.90 (br. s, 1H).

Intermediate 1C

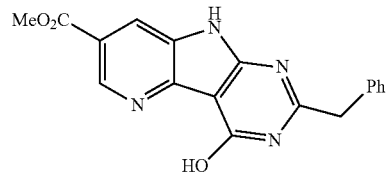 [SMILES: COC(=O)c1cnc2c(c1)[nH]c1nc(Cc3ccccc3)nc(O)c12]

methyl 2-benzyl-4-hydroxy-9H-pyrido[2',3':4,5]pyrrolo[2,3-d]pyrimidine-7-carboxylate A mixture of methyl 2-amino-3-carbamoyl-1H-pyrrolo[3,2-b]pyridine-6-carboxylate (0.100 g, 0.42 mmol), sodium methoxide (0.248 ml, 1.71 mmol) and methyl 2-phenylacetate (0.280 g, 1.70 mmol) in MeOH (1.3 ml) was heated in a microwave apparatus for 80 min. The solution was cooled to it and quenched with acetic acid (0.100 ml, 1.75 mmol). The solid obtained was filtered and rinsed with a minimum of methanol and dried under vacuum to yield 0.095 g of the title compound; $^1$H NMR (400 MHz, DMSO-d6) δ ppm 3.89 (s, 3H) 4.04 (s, 2H) 7.23-7.29 (m, 1H) 7.34 (t, J=7.4 Hz, 2H) 7.39 (d, J=7.8 Hz, 2H) 8.17 (d, J=1.9 Hz, 1H) 8.98 (d, J=1.9 Hz, 1H) 12.59 (br. s, 2H); LCMS m/z 333.2 (M−H)$^-$.

Intermediate 1D

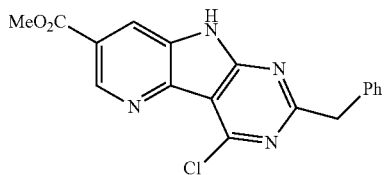 [SMILES: COC(=O)c1cnc2c(c1)[nH]c1nc(Cc3ccccc3)nc(Cl)c12]

methyl 2-benzyl-4-chloro-9H-pyrido[2',3':4,5]pyrrolo[2,3-d]pyrimidine-7-carboxylate A mixture of Intermediate 10 (0.092 g; 0.27 mmol) in POCl$_3$ (2.0 ml) and dioxane (2.0 ml) was heated at 90° C. for 2.5 h. The solvent was then removed under vacuum and the residue partitioned between EA and NaHCO$_{3(sol)}$. The organic phase was separated, dried over MgSO$_4$, filtered and the solvent removed under vacuum to give 0.096 g of the intermediate methyl 2-benzyl-4-chloro-9H-pyrido[2',3':4,5] pyrrolo[2,3-d]pyrimidine-7-carboxylate which was use directly for the next step.

Intermediate 1E

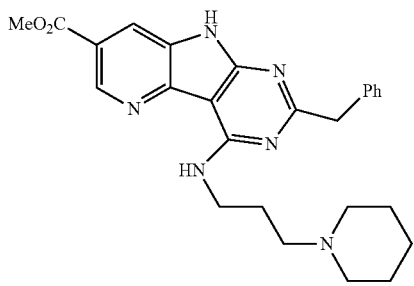 [SMILES: COC(=O)c1cnc2c(c1)[nH]c1nc(Cc3ccccc3)nc(NCCCN3CCCCC3)c12]

methyl 2-benzyl-4-((3-(piperidin-1-yl)propyl)amino)-9H-pyrido[2',3':4,5]pyrrolo[2,3-d]pyrimidine-7-carboxylate The intermediate 1D was heated with 3-(piperidin-1-yl) propan-1-amine (0.047 ml, 0.28 mmol) and Et$_3$N (0.020 ml, 0.14 mmol) in a microwave apparatus for 40 min at 140° C. The solvent was removed under vacuum and the residue purified on preparative HPLC using a Zorbax SB-018 column 21.2×150 mm with water (0.05% TFA)-MeOH (0.05% TFA) from 30 to 100%. The desired fractions were combined and the solvent was removed under vacuum. The residue obtained was lyophilized to yield 16 mg of the title compound as the TFA salt. Characteristic peaks are: $^1$H NMR (400 MHz, DMSO-d$_6$) δ ppm 1.19-1.42 (m, 1H) 1.51-1.72 (m, 3H) 1.79 (d, J=14.9 Hz, 2H) 1.98-2.08 (m, 2H) 2.80 (q, J=11.7 Hz, 2H) 3.03-3.11 (m, 2H) 3.72 (q, J=6.3 Hz, 2H) 3.92 (s, 3H) 4.09 (s, 2H) 7.21 (t, J=7.4 Hz, 1H) 7.30 (t, J=7.6 Hz, 2H) 7.38 (d, J=7.2 Hz, 2H) 7.62 (t, J=6.2 Hz, 1H) 8.21 (d, J=1.5 Hz, 1H) 8.91 (br. s., 1H) 9.01 (d, J=1.6 Hz, 1H) 12.30 (s, 1H); HRMS m/z 459.2531 (M+H)$^+$.

Example 2

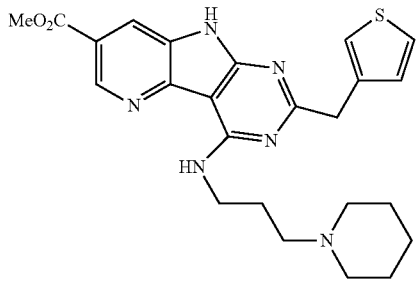 [SMILES: COC(=O)c1cnc2c(c1)[nH]c1nc(Cc3ccsc3)nc(NCCCN3CCCCC3)c12]

methyl 4-((3-(piperidin-1-yl)propyl)amino)-2-(thiophen-3-ylmethyl)-9H-pyrido[2',3':4,5]pyrrolo[2,3-d]pyrimidine-7-carboxylate

Intermediate 2A

methyl 4-hydroxy-2-(thiophen-3-ylmethyl)-9H-pyrido[2',3':4,5]pyrrolo[2,3-d]pyrimidine-7-carboxylate Starting from ethyl 2-(thiophen-3-yl)acetate (0.257 ml, 1.71 mmol) the Intermediate 2A (0.108 g) was obtained according to the procedure described in example 10. $^1$H NMR (400 MHz, DMSO-d$_6$) δ ppm 3.90 (s, 3H) 4.04 (s, 2H) 7.13 (dd, J=4.9, 1.4 Hz, 1H) 7.40 (d, J=1.9 Hz, 1H) 7.50 (dd, J=4.9, 2.9 Hz, 1H) 8.18 (d, J=1.9 Hz, 1H) 8.99 (d, J=1.9 Hz, 1H) 12.53 (br. s, 2H) 12.53-12.53 (m, 1H); LCMS m/z 341.2 (M+H)$^+$.

Intermediate 2B

methyl 4-chloro-2-(thiophen-3-ylmethyl)-9H-pyrido[2',3':4,5]pyrrolo[2,3-d]pyrimidine-7-carboxylate Starting from the intermediate 2A, the title compound was obtained according to the procedure described in 1D. LCMS m/z 359.0 (M+H)$^+$.

Intermediate 2C

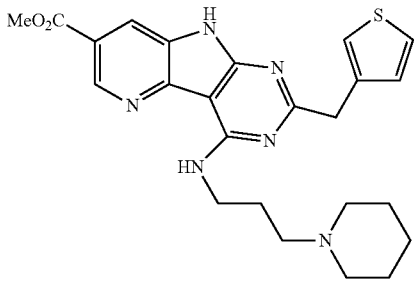 [SMILES: COC(=O)c1cnc2c(c1)[nH]c1nc(Cc3ccsc3)nc(NCCCN3CCCCC3)c12]

methyl 4-((3-(piperidin-1-yl)propyl)amino)-2-(thiophen-3-ylmethyl)-9H-pyrido[2',3':4,5]pyrrolo[2,3-d]pyrimidine-7-carboxylate Starting from the Intermediate 2B, the title compound was obtained according to the procedure described in Example 1 as the TFA salt. $^1$H NMR (400 MHz, DMSO-$d_6$) δ ppm 1.29-1.42 (m, 1H) 1.51-1.72 (m, 3H) 1.74-1.84 (m, 2H) 1.97-2.10 (m, 2H) 2.83 (q, J=12.1 Hz, 2H) 3.04-3.13 (m, 2H) 3.73 (q, J=6.3 Hz, 2H) 3.92 (s, 3H) 4.10 (s, 2H) 7.14 (dd, J=4.7, 1.2 Hz, 1H) 7.31 (d, J=1.9 Hz, 1H) 7.46 (dd, J=4.9, 2.9 Hz, 1H) 7.62 (t, J=5.8 Hz, 1H) 8.22 (d, J=1.5 Hz, 1H) 8.91 (br. s, 1H) 9.01 (d, J=1.5 Hz, 1H) 12.29 (s, 1H); HRMS m/z 465.2064 (M+H)$^+$.

Example 3

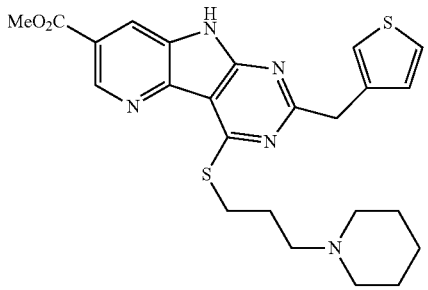 [SMILES: COC(=O)c1cnc2c(c1)[nH]c1nc(Cc3ccsc3)nc(SCCCN3CCCCC3)c12]

methyl 4-((3-(piperidin-1-yl)propyl)thio)-2-(thiophen-3-ylmethyl)-9H-pyrido[2',3':4,5]pyrrolo[2,3-d]pyrimidine-7-carboxylate

Intermediate 3A

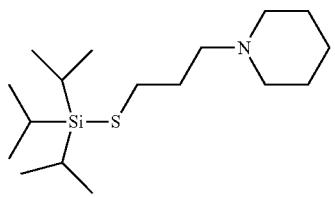 [SMILES: CC(C)[Si](SCCCN1CCCCC1)(C(C)C)C(C)C]

1-(3-((triisopropylsilyl)thio)propyl)piperidine

To a mixture of 1-(3-chloropropyl)piperidine.HCl (0.500 g, 2.52 mmol) in THF (14.8 ml, 18 mmol) under $N_2$ was added triisopropylsilanethiol (1.09 ml, 5.0 mmol) and tetrabutylammoniun iodide (0.093 g, 0.25 mmol). Then NaH (0.252 g, 6.3 mmol; 60% weight) was added portion-wise and the mixture was heated at 50° C. for 19 h. The reaction was cooled to rt, diluted with water (15 ml) and extracted with EtOAc (4×15 mL). The organic phases were combined and washed with water (2×15 ml) then with brine (15 ml). The organic layer was dried over $MgSO_4$, filtered and the solvent removed under vacuum. Purification on ISCO using a RediSep column ($CH_2Cl_2$-MeOH) from 20 to 100% afforded 0.71 g of the title compound. $^1$H NMR (400 MHz, DMSO-$d_6$) δ ppm 1.06 (d, J=7.0 Hz, 18H) 1.14-1.29 (m, 3H) 1.36 (m, J=5.1 Hz, 2H) 1.46 (quin, J=5.4 Hz, 4H) 1.65 (quin, J=7.0 Hz, 2H) 2.29 (m, J=6.7 Hz, 6H) 2.53 (t, J=7.3 Hz, 2H).

Intermediate 3B

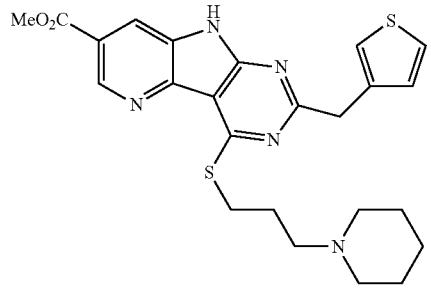

methyl 4-((3-(piperidin-1-yl)propyl)thio)-2-(thiophen-3-ylmethyl)-9H-pyrido[2',3':4,5]pyrrolo[2,3-d]pyrimidine-7-carboxylate Tetrabutylammonium fluoride (0.223 ml, 0.22 mmol) was added to a solution of Intermediate 2B (0.040 g, 0.11 mmol) and Intermediate 3A (0.074 g, 0.23 mmol) in N-methyl pyrrolidine (0.5 ml) and heated at 35° C. overnight. The reaction mixture was directly purified on preparative HPLC. The desired fractions were combined and the solvent was removed under vacuum. The residue obtained was lyophilized to yield 10 mg of the title compound as the TFA. Characteristic peaks are: $^1$H NMR (400 MHz, DMSO-$d_6$) δ ppm 1.29-1.42 (m, 1H) 1.51-1.72 (m, 3H) 1.74-1.84 (m, 2H) 1.97-2.10 (m, 2H) 2.83 (q, J=12.1 Hz, 2H) 3.04-3.13 (m, 2H) 3.73 (q, J=6.3 Hz, 2H) 3.92 (s, 3H) 4.10 (s, 2H) 7.14 (dd, J=4.7, 1.2 Hz, 1H) 7.31 (d, J=1.9 Hz, 1H) 7.46 (dd, J=4.9, 2.9 Hz, 1H) 7.62 (t, J=5.8 Hz, 1H) 8.22 (d, J=1.6 Hz, 1H) 8.91 (br. s, 1H) 9.01 (d, J=1.6 Hz, 1H) 12.29 (s, 1H). HRMS m/z 482.1683 (M+H)$^+$.

Example 4

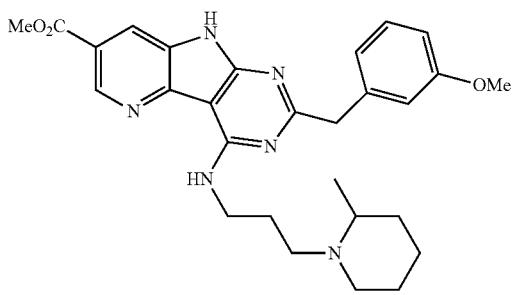 [SMILES: COC(=O)c1cnc2c(c1)[nH]c1nc(Cc3cccc(OC)c3)nc(NCCCN3CCCCC3C)c12]

methyl 2-(3-methoxybenzyl)-4-((3-(2-methylpiperi-din-1-yl)propyl)amino)-9H-pyrido[2',3':4,5]pyrrolo[2,3-d]pyrimidine-7-carboxylate

Intermediate 4A

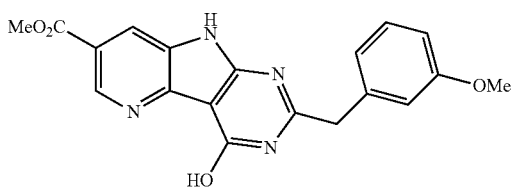

methyl 4-hydroxy-2-(3-methoxybenzyl)-9H-pyrido[2',3':4,5]pyrrolo[2,3-d]pyrimidine-7-carboxylate Following the procedure for the preparation of Intermediate 1C, methyl 2-(3-methoxyphenyl)acetate (0.246 g, 1.36 mmol) afforded 0.062 g of the title compound. $^1$H NMR (400 MHz, DMSO-d$_6$) δ ppm 3.74 (s, 3H) 3.90 (s, 3H) 3.99 (s, 2H) 6.83 (d, J=7.04 Hz, 1H) 6.91-7.03 (m, 3H) 7.25 (t, J=7.8 Hz, 1H) 8.17 (s, 1H) 8.97 (s, 1H) 12.37 (br. s, 2H);

Intermediate 4B

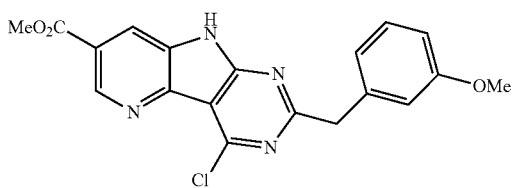 [SMILES: COC(=O)c1cnc2c(c1)[nH]c1nc(Cc3cccc(OC)c3)nc(Cl)c12]

methyl 4-chloro-2-(3-methoxybenzyl)-9H-pyrido[2',3':4,5]pyrrolo[2,3-d]pyrimidine-7-carboxylate Intermediate 4A (0.062 g, 0.17 mmol) in POCl$_3$ (2.0 ml) was heated 1 h at 100° C. The mixture was cooled to it and the solvent removed under vacuum. The residue was partitioned between EA and NaHCO$_3$(sol) and the organic phase was separated, dried over MgSO$_4$, filtered and the solvent removed under vacuum to give 0.027 g of crude 4B; LCMS m/z 383.2 (M+H)$^+$.

Intermediate 4C

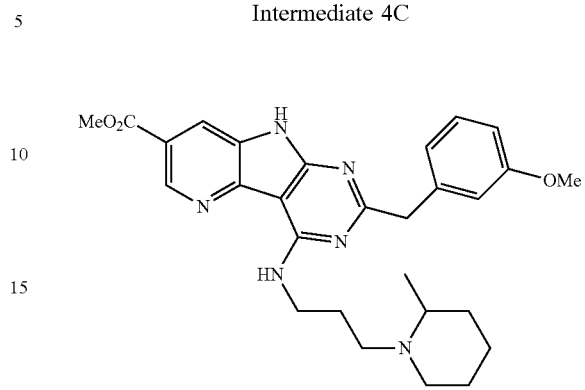

methyl 2-(3-methoxybenzyl)-4-((3-(2-methylpiperi-din-1-yl)propyl)amino)-9H-pyrido[2',3':4,5]pyrrolo[2,3-d]pyrimidine-7-carboxylate A mixture of intermediate 4B (0.060 g, 0.15 mmol), 3-(2-methylpiperidin-1-yl)propan-1-amine (0.073 g, 0.47 mmol) and Et$_3$N (0.044 ml, 0.31 mmol) in methanol (0.7 ml) was heated at 140° C. for 45 min in a microwave apparatus. The solvent was removed under vacuum and the residue purified on ISCO with a RediSep column using DCM-MeOH—NH$_4$OH (80-20-2.5%) to furnish 0.024 g of the title compound. $^1$H NMR (400 MHz, DMSO-d$_6$) δ ppm 0.97 (d, J=6.3 Hz, 3H) 1.23-1.36 (m, 2H) 1.49-1.64 (m, 4H) 1.70-1.85 (m, 2H) 1.95-2.08 (m, 1H) 2.16-2.31 (m, 2H) 2.70-2.91 (m, 2H) 3.65-3.71 (m, 2H) 3.72 (s, 3H) 3.91 (s, 3H) 4.03 (s, 2H) 6.77 (dd, J=8.2, 1.9 Hz, 1H) 6.92-6.99 (m, 2H) 7.19 (t, J=7.8 Hz, 1H) 7.6 (t, J=5.6 Hz, 1H) 8.18 (d, J=1.6 Hz, 1H) 8.96 (d, J=1.6 Hz, 1H) 12.21 (br. s., 1H). HRMS m/z 503.2771 (M+H)$^+$.

Example 5

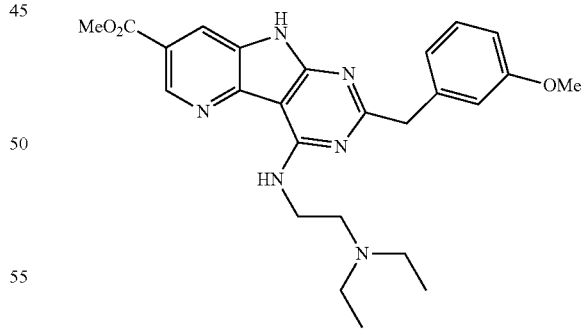

methyl 4-((2-(diethylamino)ethyl)amino)-2-(3-methoxybenzyl)-9H-pyrido[2',3':4,5]pyrrolo[2,3-d]pyrimidine-7-carboxylate

Intermediate 5A

Following the procedure of Example 4, a mixture of Intermediate 4B (0.060 g, 0.15 mmol), N—N-diethylethane- 1,2-diamine (0.055 g, 0.47 mmol) and Et₃N (0.022 ml, 0.157 mmol) afforded 0.025 g of the title compound as the TFA salt after purification on preparative HPLC. ¹H NMR (400 MHz, DMSO-d₆) δ ppm 1.17 (t, J=7.04 Hz, 6H) 3.13-3.22 (m, 4H) 3.35 (q, J=5.1 Hz, 2H) 3.73 (s, 3H) 3.93 (s, 3H) 3.94-3.98 (m, 2H) 4.08 (s, 2H) 6.80 (dd, J=8.2, 1.9 Hz, 1H) 6.89-6.94 (m, 2H) 7.22 (t, J=8. Hz, 1H) 7.75 (t, J=5.8 Hz, 1H) 8.24 (d, J=1.5 Hz, 1H) 9.03 (d, J=1.5 Hz, 1H) 12.39 (s, 1H).

Example 6

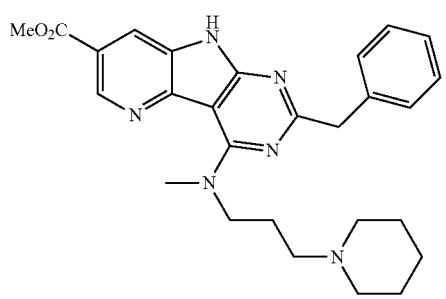 [SMILES: COC(=O)c1cnc2c(c1)[nH]c1nc(Cc3ccccc3)nc(N(C)CCCN3CCCCC3)c12]

methyl 2-benzyl-4-(methyl(3-(piperidin-1-yl)propyl)amino)-9H-pyrido[2',3':4,5]pyrrolo[2,3-d]pyrimidine-7-carboxylate A mixture of Intermediate 1C (0.092 g, 0.27 mmol) in POCl₃ (2.0 ml, 21.4 mmol) and dioxane (2.0 ml) was heated at 90° C. for 2.5 h. The mixture was brought to rt and the solvent removed under vacuum. The residue obtained was partitioned between EA and NaHCO₃-sol and the organic phase was separated, dried over MgSO₄, filtered and the solvent removed under vacuum to afford 0.096 g of the crude chloro analogue.

The previous crude (0.096 g, 0.27 mmol) was heated with N-methyl-3-(piperidin-1-yl)propan-1-amine (0.128 g, 0.81 mmol) and Et₃N (0.038 ml, 0.27 mmol) in methanol (1.08 ml) in a microwave apparatus for 50 min at 140° C. The solvent was then removed and the crude oil purified on preparative HPLC. The desired fractions were combined and the solvent was removed under vacuum. The residue obtained was lyophilized to yield 16 mg of the title compound as the TFA salt. Characteristic peaks are: ¹H NMR (400 MHz, DMSO-d₆) δ ppm 1.26-1.43 (m, 1H) 1.50-1.71 (m, 3H) 1.79 (br. s., 2H) 2.00-2.13 (m, 2H) 2.85 (q, J=13.7 Hz, 2H) 3.05-3.16 (m, 2H) 3.92 (s, 3H) 4.06 (s, 2H) 4.33 (br. s, 2H) 7.21 (t, J=7.4 Hz, 1H) 7.30 (t, J=7.4 Hz, 2H) 7.38 (d, J=7.0 Hz, 2H) 8.17 (d, J=1.9 Hz, 1H) 8.95 (br. s, 1H) 9.03 (d, J=1.9 Hz, 1H) 12.43 (s, 1H). HRMS m/z 473.2658 (M+H)⁺.

Example 7

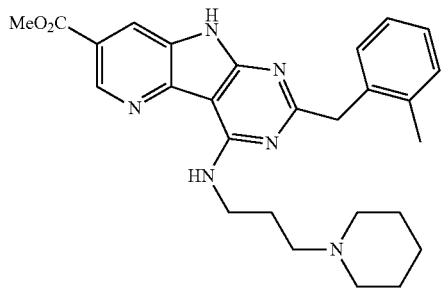

methyl 2-(2-methylbenzyl)-4-((3-(piperidin-1-yl)propyl)amino)-9H-pyrido[2',3':4,5]pyrrolo[2,3-d]pyrimidine-7-carboxylate Intermediate 7A

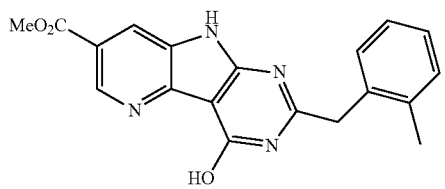 [SMILES: COC(=O)c1cnc2c(c1)[nH]c1nc(Cc3ccccc3C)nc(Cl)c12]

methyl 4-hydroxy-2-(2-methylbenzyl)-9H-pyrido[2',3':4,5]pyrrolo[2,3-d]pyrimidine-7-carboxylate Following the procedure for the preparation on 1C, methyl 2-(o-tolyl)acetate (0.240 g, 1.34 mmol) afforded 0.105 g of the title compound. ¹H NMR (400 MHz, DMSO-d₆) δ ppm 2.35 (s, 3H) 3.84 (s, 3H) 3.89 (s, 2H) 7.07-7.20 (m, 4H) 7.21-7.27 (m, 1H) 8.00 (br. s., 1H) 8.71 (br. s, 1H) 11.06 (br. s, 1H);

Intermediate 7B

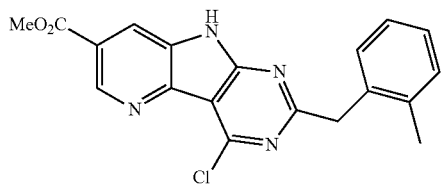

methyl 4-chloro-2-(2-methylbenzyl)-9H-pyrido[2',3':4,5]pyrrolo[2,3-d]pyrimidine-7-carboxylate To intermediate 7A (0.090 g, 0.25 mmol) in dichloethane (2 ml) was added TFA (0.4 ml) to get a solution. Then the solvent was removed and the residue in POCl₃ (2.0 ml) was heated in a microwave apparatus for 10 min at 160° C. According to the procedure of intermediate 1D, 0.095 g of intermediate 7B was obtained. LCMS m/z 367.1 (M+H)⁺.

Intermediate 7C

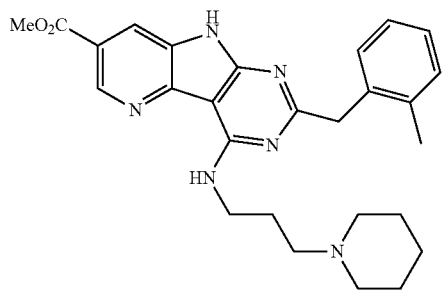 [SMILES: COC(=O)c1cnc2c(c1)[nH]c1nc(Cc3ccccc3C)nc(NCCCN3CCCCC3)c12]

methyl 2-(2-methylbenzyl)-4-((3-(piperidin-1-yl)propyl)amino)-9H-pyrido[2',3':4,5]pyrrolo[2,3-d]pyrimidine-7-carboxylate A mixture of intermediate 7B (0.020 g, 0.055 mmol), 3-(piperidin-1-yl)propan-1-amine (0.039 g, 0.27 mmol) in methanol (0.5 ml) was heated in a microwave according to the procedure described for intermediate 40 to furnish 0.005 mg of the title compound. 1H NMR (400 MHz, DMSO-$d_6$) ☐ ppm 1.31-1.44 (m, 2H) 1.50-1.61 (m, 4H) 1.77 (quin, J=6.70 Hz, 2H) 2.23-2.44 (m, 9H) 3.67 (q, J=6.13 Hz, 2H) 3.91 (s, 3H) 4.09 (s, 2H) 7.06-7.18 (m, 3H) 7.21-7.30 (m, 1H) 7.64 (t, J=5.48 Hz, 1H) 8.08-8.20 (m, 1H) 8.86-9.00 (m, 1H) 12.24 (br. s., 1H).

Example 8

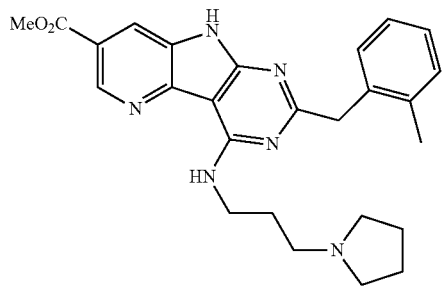 [SMILES: COC(=O)c1cnc2c(c1)[nH]c1nc(Cc3ccccc3C)nc(NCCCN3CCCC3)c12]

methyl 2-(2-methylbenzyl)-4-((3-(pyrrolidin-1-yl)propyl)amino)-9H-pyrido[2',3':4,5]pyrrolo[2,3-d]pyrimidine-7-carboxylate Intermediate 8A Following the procedure of example 7, intermediate 7B (0.045 g, 0.12 mmol) and 3-(pyrrolidin-1-yl)propan-1-amine (3 equivalent) furnished 0.010 mg of the title compound. Characteristics peaks are: $^1$H NMR (400 MHz, DMSO-$d_6$) δ ppm 1.70-1.87 (m, 6H) 2.64 (br. s., 6H) 3.69 (q, J=5.90 Hz, 2H) 3.91 (s, 3H) 4.10 (s, 2H) 7.06-7.18 (m, 3H) 7.21-7.30 (m, 1H) 7.70 (t, J=6.30 Hz, 1H) 8.16 (d, J=1.56 Hz, 1H) 8.97 (d, J=1.56 Hz, 1H) 12.26 (br. s., 1H).

Example 9

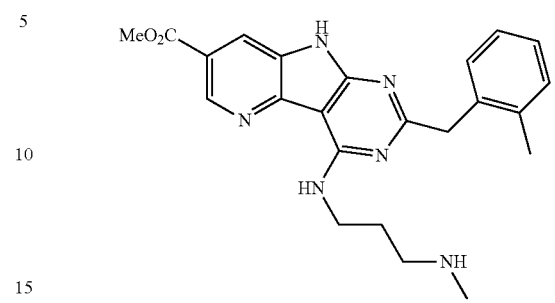

methyl 4-((3-(methylamino)propyl)amino)-2-(2-methylbenzyl)-9H-pyrido[2',3':4,5]pyrrolo[2,3-d]pyrimidine-7-carboxylate Intermediate 9A Following the procedure of example 7, intermediate 7B (0.045 g, 0.12 mmol), tert-butyl (3-aminopropyl)(methyl)carbamate hydrochloride (0.046 g, 0.24 mmol) and triethylamine (0.037 g, 0.37 mmol) was heated in a microwave apparatus according to the procedure described for intermediate 40 to furnish the title compound as the BOC-protected amine. This crude material was then treated with a mixture of DCM-trifluoroacetic acid for 45 min to furnished 0.009 g of the title compounds as the trifluoroacetic salt. Characteristic peaks are: $^1$H NMR (400 MHz, DMSO-$d_6$) δ ppm 1.93 (quint, J=7.00, 7.00, 7.00, 7.00, 7.00, 7.00 Hz, 1H) 2.36 (s, 3H) 2.54-2.56 (m, 3H) 2.84-2.93 (m, 2H) 3.66-3.71 (m, 2H) 3.92 (s, 3H) 4.12 (s, 2H) 7.09-7.19 (m, 3H) 7.22-7.29 (m, 1H) 7.61 (t, J=6.06 Hz, 1H) 8.19 (d, J=1.56 Hz, 1H) 8.27 (br. s., 2H) 9.01 (d, J=1.56 Hz, 1H) 12.33 (s, 1H).

Example 10

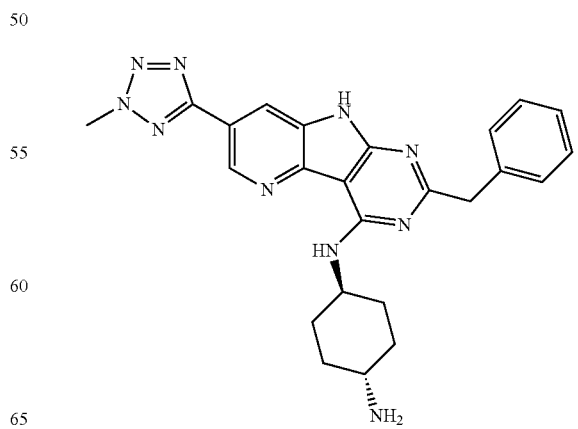

(1R,4R)—N¹-(2-benzyl-7-(2-methyl-2H-tetrazol-5-yl)-9H-pyrido[2',3':4,5]pyrrolo[2,3-d]pyrimidin-4-yl)cyclohexane-1,4-diamine Intermediate 10A

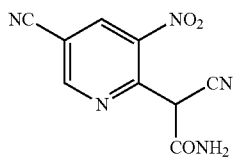

2-cyano-2-(5-cyano-3-nitropyridin-2-yl)acetamide

To a 0° C. suspensiom of sodium hydride 60% (1.77 g, 44.4 mmol) in DMF (22 ml) was added 2-cyanoacetamide (1.86 g, 22.2 mmol) portionwise. After stirring 15 min at it the temperature was brought to 0° C. and a solution of 6-Chloro-5-nitronicotinonitrile (3.88 g, 21.1 mmol) in THF was added slowly over 10 min. After 1 h, the temperature was brought to rt for 5 h. The mixture was cooled back to 0° C., quenched with water (55 ml) and HCl$_{conc}$ (1.8 ml) and left in the fridge overnight. The slurry was filtered and the cake washed with water, hexane and dried to furnished 4.32 g of the title compound. Characteristic peaks are: ¹H NMR (400 MHz, DMSO-d$_6$) δ ppm 3.06 (s, 1H) 7.31 (br. s., 2H) 7.76 (s, 1H) 8.23 (s, 1H).

Intermediate 10B

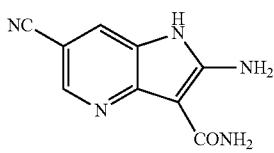

2-amino-6-cyano-1H-pyrrolo[3,2-b]pyridine-3-carboxamide

To a 85° C. suspension of iron (8.6 g, 154 mmol) and a saturated solution of ammonium chloride (11 ml) was added a solution of the intermediate 10A (4.32 g, 17.1 mmol) in DMF (34 ml). After 3 h, the reaction mixture was filtered over celite and the cake washed with DMF (three times). The solvent was removed and the dark oil absorbed on silica gel. Purification on ISCO with a RediSep column using DCM-MeOH (0-25%) furnished 0.229 g of the title compound. LCMS m/z 200.1 (M–H)⁻.

Intermediate 10C

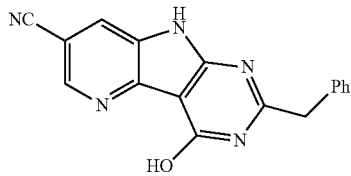 [SMILES: N#Cc1cnc2c(c1)[nH]c1nc(Cc3ccccc3)nc(O)c12]

2-benzyl-4-hydroxy-9H-pyrido[2',3':4,5]pyrrolo[2,3-d]pyrimidine-7-carbonitrile

A mixture of intermediate 10B (0.229 g, 1.14 mmol), potassium t-butoxide (0.513 g, 4.57 mmol) and methyl 2-phenylacetate (0.644 ml, 4.57 mmol) in dioxane was heated to reflux for 2 h. The reaction mixture was cooled to 45° C. and water (2.94 ml, 163 mmol) was added. Continued stirring at 60° C. and after 30 minutes, water (5.88 ml) was added. The mixture was cooled and stirred for 2 more hours. The solids were collected on Buchner and the cake was washed with 1,4-Dioxane/Water (1:3, 2×1 ml) then with MeOH (2×0.5 ml) to furnish 0.121 g of the title compound; LCMS m/z 302.2 (M+H)⁺.

Intermediate 10D

2-benzyl-4-chloro-9H-pyrido[2',3':4,5]pyrrolo[2,3-d]pyrimidine-7-carbonitrile

A mixture of intermediate 10C (0.050 g, 0.17 mmol) in phosphorus oxychloride (1.0 ml) was heated in a microwave apparatus at 175° C. for 15 min. The reaction mixture was concentrated to dryness and the residue suspended in water (4 ml). A saturated solution of NaHCO$_3$ (5 mL) was added and the resulting suspension stirred for 1 hour. The solids were collected on Buchner and the cake was washed with water twice and dried to furnish 0.039 g of the title compound; LCMS m/z 320.1 (M+H)⁺.

Intermediate 10E

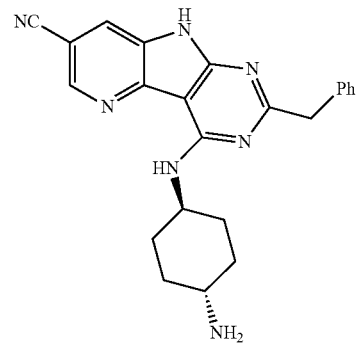 [SMILES: N#Cc1cnc2c(c1)[nH]c1nc(Cc3ccccc3)nc(N[C@H]3CC[C@H](N)CC3)c12]

4-(((1R,4R)-4-aminocyclohexyl)amino)-2-benzyl-9H-pyrido[2',3':4,5]pyrrolo[2,3-d]pyrimidine-7-carbonitrile A mixture of intermediate 10D (0.091 g, 0.29 mmol) and (1R,4R)-cyclohexane-1,4-diamine (0.227 g, 1.99 mmol) in MeOH (3.00 ml) was heated in a microwave apparatus at 140° C. for 30 min. The reaction mixture was concentrated to dryness and purification of the residue on ISCO with a RediSep column using DCM-MeOH/NH₄OH furnished 0.113 g of the title compound; Characteristic peaks are: ¹H NMR (400 MHz, DMSO-d₆) δ ppm 1.14-1.30 (m, 2H) 1.38-1.55 (m, 2H) 1.83 (m, J=11.30 Hz, 2H) 2.00 (m, J=9.80 Hz, 2H) 2.58-2.72 (m, 1H) 4.08 (s, 2H) 4.00-4.22 (m, 1H) 6.71 (d, J=8.22 Hz, 1H) 7.15-7.23 (m, 1H) 7.29 (t, J=7.43 Hz, 2H) 7.38 (d, J=7.43 Hz, 2H) 8.24 (d, J=1.80 Hz, 1H) 8.80 (d, J=1.80 Hz, 1H).

Intermediate 10F

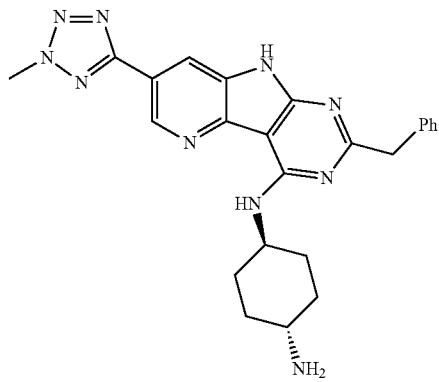 [SMILES: Cn1nnc(-c2cnc3c(c2)[nH]c2nc(Cc4ccccc4)nc(N[C@H]4CC[C@H](N)CC4)c23)n1]

(1R,4R)—N¹-(2-benzyl-7-(2-methyl-2H-tetrazol-5-yl)-9H-pyrido[2',3':4,5]pyrrolo[2,3-d]pyrimidin-4-yl)cyclohexane-1,4-diamine A mixture of intermediate 10E (0.059 g, 0.15 mmol) and azidotributyltin (0.43 ml, 1.57 mmol) in (trifluoromethyl)benzene (2.1 ml) was heated to 180° C. for 30 min in a microwave. After 30 minutes the mixture was concentrated to dryness and MeOH (3.6 ml), HCl 4M in dioxane (1.1 ml) ane Et₂O (3.6 ml) were added. After ca. 2 minutes, the crystallization started and let stirred overnight. The solids were collected and washed with Et₂O (3×0.5 mL) and then with hexane (3×0.5 mL) to furnish 0.074 g of (1R,4R)—N1-(2-benzyl-7-(2H-tetrazol-5-yl)-9H-pyrido[2',3':4,5]pyrrolo[2,3-d]pyrimidin-4-yl)cyclohexane-1,4-diamine; LCMS m/z 441.2 (M+H)⁺.

Trimethylsilyldiazomethane 2M in hexane (0.52 ml, 1.04 mmol) was added to a suspension of the previous intermediate in THF (4.8 ml) and MeOH (1.2 ml). After 5 minutes the same amount of trimethylsilyldiazomethane followed 5 min later by the same amount again. The reaction was quenched with 10 drops of acetic acid and concentrated to dryness. The residue was purified on ISCO using a RediSep column (DCM/MeOH/NH₄OH) to furnish 0.004 g of the title compound; Characteristic peaks are: ¹H NMR (400 MHz, DMSO-d₆) δ ppm 1.14-1.31 (m, 2H) 1.40-1.57 (m, 2H) 1.84 (d, J=10.96 Hz, 2H) 2.02 (d, J=10.56 Hz, 2H) 2.65 (m, J=10.80, 10.80 Hz, 1H) 4.09 (s, 2H) 4.11-4.20 (m, 1H) 4.46 (s, 3H) 6.66 (d, J=7.83 Hz, 1H) 7.16-7.24 (m, 1H) 7.29 (t, J=7.43 Hz, 2H) 7.35-7.43 (m, 2H) 8.29 (d, J=1.57 Hz, 1H) 9.11 (d, J=1.57 Hz, 1H); HRMS m/z 455.2406 (M+H)⁺.

Example 11

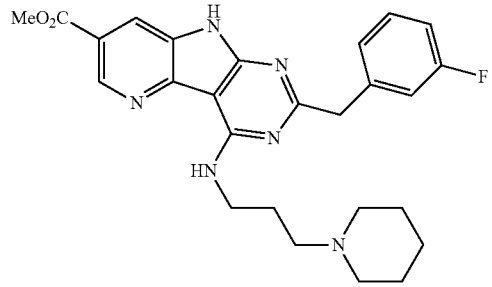 [SMILES: COC(=O)c1cnc2c(c1)[nH]c1nc(Cc3cccc(F)c3)nc(NCCCN3CCCCC3)c12]

methyl 2-(3-fluorobenzyl)-4-((3-(piperidin-1-yl)propyl)amino)-9H-pyrido[2',3':4,5]pyrrolo[2,3-d]pyrimidine-7-carboxylate Intermediate 11A

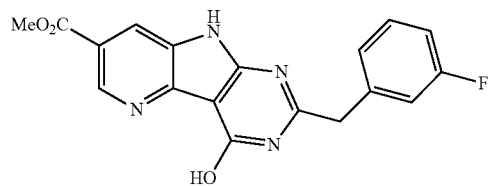 [SMILES: COC(=O)c1cnc2c(c1)[nH]c1nc(Cc3cccc(F)c3)nc(O)c12]

methyl 2-(3-fluorobenzyl)-4-hydroxy-9H-pyrido[2',3':4,5]pyrrolo[2,3-d]pyrimidine-7-carboxylate Starting from the intermediate 1B (0.090 g, 0.38 mmol) and 4.0 equivalents of methyl 2-(3-fluorophenyl)acetate, 0.110 g of the title compound was obtained according to the procedure described in example 1. ¹H NMR (400 MHz, DMSO-d₆) δ ppm 3.91 (s, 3H) 4.08 (s, 2H) 7.11 (t, J=9.40 Hz, 1H) 7.20-7.28 (m, 2H) 7.39 (s, 1H) 8.17 (s, 1H) 8.99 (s, 1H) 12.56 (br. s, 2H).

Intermediate 11C

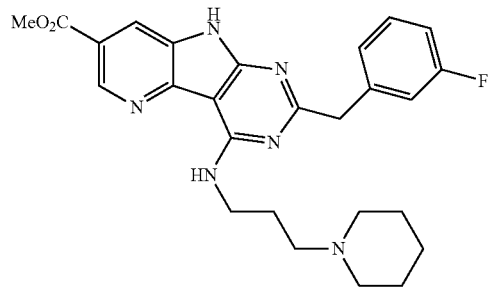 [SMILES: COC(=O)c1cnc2c(c1)[nH]c1nc(Cc3cccc(F)c3)nc(NCCCN3CCCCC3)c12]

methyl 2-(3-fluorobenzyl)-4-((3-(piperidin-1-yl)propyl)amino)-9H-pyrido[2',3':4,5]pyrrolo[2,3-d]pyrimidine-7-carboxylate A mixture of intermediate 11A (0.108 g, 0.31 mmol) and phosphorus oxychloride (0.2 ml) in dichloroethane-dioxane (0.5 ml-1.5 ml) was heated in a microwave apparatus at a 155° C. for 10 min. The solvent was removed and the residue taken in ethyl acetate and NaHCO₃. The organic phase was separated, dried over Na₂SO₄, filtered and the solvent removed to furnish the 0.095 g of methyl 4-chloro-2-(3-fluorobenzyl)-9H-pyrido[2',3':4,5]pyrrolo[2,3-d]pyrimidine-7-carboxylate (Intermediate 11B).

This intermediate 11B (0.030 g, 0.081 mmol) was treated with 3-(piperidin-1-yl)propan-1-amine according to example 4 to furnish 0.017 g of the title compound. Characteristic peaks are: $^1$H NMR (400 MHz, DMSO-d$_6$) δ ppm 1.34-1.43 (m, 2H) 1.49-1.60 (m, 4H) 1.78 (quin, J=6.70 Hz, 2H) 2.25-2.40 (m, 6H) 3.70 (q, J=6.26 Hz, 2H) 3.91 (s, 3H) 4.10 (s, 2H) 7.03 (t, J=9.70 Hz, 1H) 7.20 (d, J=7.43 Hz, 2H) 7.27-7.38 (m, 1H) 7.69 (t, J=5.67 Hz, 1H) 8.18 (d, J=1.96 Hz, 1H) 8.97 (d, J=1.96 Hz, 1H) 12.23 (br. s., 1H); HRMS m/z 477.2411 (M+H)⁺.

Example 12

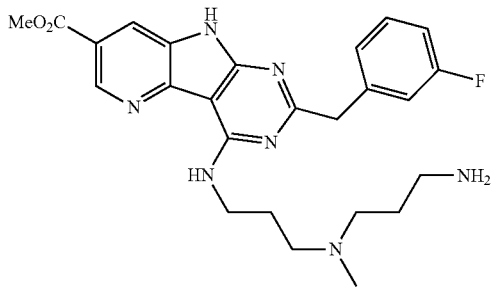 [SMILES: COC(=O)c1cnc2c(c1)[nH]c1nc(Cc3cccc(F)c3)nc(NCCCN(C)CCCN)c12]

methyl 4-((3-((3-aminopropyl)(methyl)amino)propyl)amino)-2-(3-fluorobenzyl)-9H-pyrido[2',3':4,5]pyrrolo[2,3-d]pyrimidine-7-carboxylate Intermediate 12A The intermediate 11B (0.030 g; 0.65 mmol) was treated with N1-(3-aminopropyl)-N1-methylpropane-1,3-diamine (0.094 g; 0.081 mmol) and triethylamine (0.066 g; 0.65 mmol) according to example 4 to furnish 0.007 g of the title compound after purification on ISCO with a RediSep column using DCM/MeOH—NH₄OH (80-20-2.5%). Characteristic peaks are: $^1$H NMR (400 MHz, DMSO-d$_6$) δ ppm 1.34-1.43 (m, 2H) 1.49-1.60 (m, 4H) 1.78 (quin, J=6.70 Hz, 2H) 2.25-2.40 (m, 6H) 3.70 (q, J=6.26 Hz, 2H) 3.91 (s, 3H) 4.10 (s, 2H) 7.03 (t, J=9.70 Hz, 1H) 7.20 (d, J=7.43 Hz, 2H) 7.27-7.38 (m, 1H) 7.69 (t, J=5.67 Hz, 1H) 8.18 (d, J=1.96 Hz, 1H) 8.97 (d, J=1.96 Hz, 1H) 12.23 (br. s., 1H); HRMS m/z 480.2570 (M+H)⁺.

Example 13

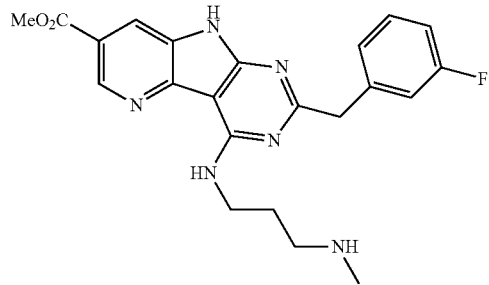 [SMILES: CNCCCNc1nc(Cc2cccc(F)c2)nc2[nH]c3cc(C(=O)OC)cnc3c12]

methyl 2-(3-fluorobenzyl)-4-(3-(methylamino)propyl)amino)-9H-pyrido[2',3':4,5]pyrrolo[2,3-d]pyrimidine-7-carboxylate Intermediate 13A

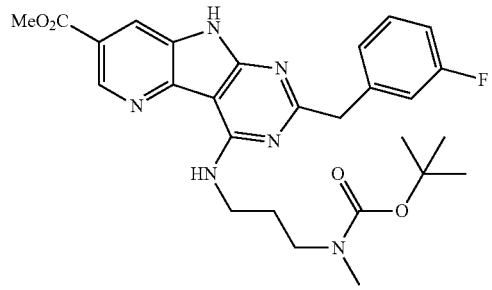 [SMILES: COC(=O)c1cnc2c(c1)[nH]c1nc(Cc3cccc(F)c3)nc(NCCCN(C)C(=O)OC(C)(C)C)c12]

methyl 4-((3-((tert-butoxycarbonyl)(methyl)amino)propyl)amino)-2-(3-fluorobenzyl)-9H-pyrido[2',3':4,5]pyrrolo[2,3-d]pyrimidine-7-carboxylate Intermediate 11B (0.030 g; 0.08 mmol) was treated with tert-butyl (3-aminopropyl)(methyl)carbamate hydrochloride (0.091 g; 0.41 mmol) and triethylamine (0.090 ml; 0.65 mmol) in methanol (0.6 ml) according to the example 4 to furnish 0.013 g of the title compound. Characteristic peaks are: $^1$H NMR (400 MHz, DMSO-d$_6$) δ ppm 1.23-1.41 (m, 9H) 1.83 (br. s., 2H) 2.77 (br. s., 3H) 3.23 (t, J=6.85 Hz, 2H) 3.62 (q, J=6.70 Hz, 2H) 3.91 (s, 3H) 4.10 (s, 2H) 6.99-7.06 (m, 1H) 7.20 (s, 2H) 7.27-7.36 (m, 1H) 7.44 (br. s, 1H) 8.19 (d, J=1.56 Hz, 1H) 8.99 (d, J=1.56 Hz, 1H) 12.25 (s, 1H).

Intermediate 13B

To a solution intermediate 13A (0.010 g, 0.019 mmol) in DCM (1.0 ml) was added TFA (0.5 ml). After 30 min of stirring the solvent was removed ans the residue purified on ISCO with a RediSep column using DCM/MeOH—NH₄OH (80-20-2.5%) to furnish 0.008 g of the title compound. Characteristic peaks are: $^1$H NMR (400 MHz, DMSO-d$_6$) δ ppm 1.77 (quin, J=6.70 Hz, 2H) 2.29 (s, 3H) 2.57 (t, J=6.65 Hz, 2H) 3.69 (quin, J=5.90 Hz, 2H) 3.91 (s, 3H) 4.10 (s, 2H) 7.03 (td, J=9.40, 2.30 Hz, 1H) 7.18-7.24 (m, 2H) 7.29-7.37 (m, 1H) 7.67 (t, J=5.10 Hz, 0H) 8.18 (d, J=1.56 Hz, 1H) 8.99 (d, J=1.57 Hz, 1H); HRMS m/z 423.1968 (M+H)⁺.

Example 14

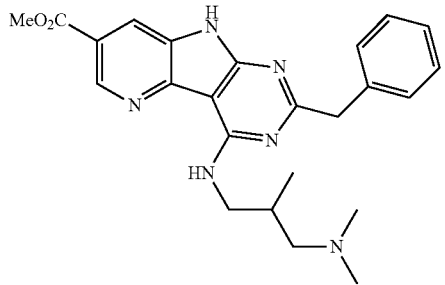 [SMILES: COC(=O)c1cnc2c(c1)[nH]c1nc(Cc3ccccc3)nc(NCC(C)CN(C)C)c12]

methyl 2-benzyl-4-((3-(dimethylamino)-2-methyl-propyl)amino)-9H-pyrido[2',3':4,5]pyrrolo[2,3-d]pyrimidine-7-carboxylate Intermediate 14A Intermediate 1D (0.029 g, 0.08 mmol) and N1,N1,2-trimethylpropane-1,3-diamine (0.048 g, 0.41 mmol furnished 0.013 g of the title compound according to the procedure described in example 4. Characteristic peaks are: $^1$H NMR (400 MHz, DMSO-d$_6$) δ ppm 0.89 (d, J=6.65 Hz, 3H) 2.05-2.18 (m, 2H) 2.22 (s, 6H) 2.28-2.37 (m, 1H) 3.46-3.53 (m, 1H) 3.68-3.75 (m, 1H) 3.91 (s, 3H) 4.06 (s, 2H) 7.19 (m, J=7.04 Hz, 1H) 7.28 (t, J=7.63 Hz, 2H) 7.33-7.40 (m, 2H) 8.17 (d, J=1.56 Hz, 1H) 8.31 (br. s., 1H) 9.00 (d, J=1.57 Hz, 1H) 12.19 (s, 1H); HRMS m/z 433.2387 (M+H)$^+$.

Example 15

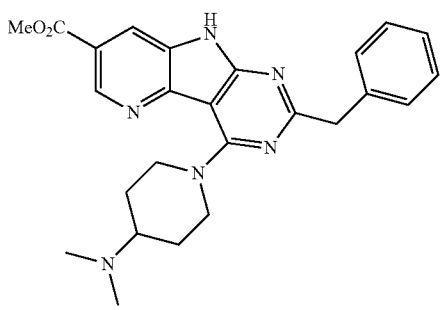 [SMILES: COC(=O)c1cnc2c(c1)[nH]c1nc(Cc3ccccc3)nc(N3CCC(N(C)C)CC3)c12]

methyl 2-benzyl-4-(4-(dimethylamino)piperidin-1-yl)-9H-pyrido[2',3':4,5]pyrrolo[2,3-d]pyrimidine-7-carboxylate Intermediate 15A Intermediate 1D (0.029 g, 0.08 mmol) and N,N-dimethylpiperidin-2-amine (0.053 g, 0.42 mmol) furnished 0.014 g of the title compound according to the procedure described in example 4. Characteristic peaks are: $^1$H NMR (400 MHz, DMSO-d$_6$) δ ppm 1.40 (qd, J=11.93, 3.72 Hz, 2H) 1.83-1.93 (m, 2H) 2.17 (s, 6H) 3.15 (t, J=12.13 Hz, 2H) 3.83-3.94 (m, 4H) 4.04 (s, 2H) 7.14-7.21 (m, 1H) 7.27 (t, J=7.43 Hz, 2H) 7.36 (d, J=7.43 Hz, 2H) 8.13 (d, J=1.96 Hz, 1H) 8.95 (d, J=1.56 Hz, 1H) 12.35 (br. s, 1H); HRMS m/z 445.2363 (M+H)$^+$.

Example 16

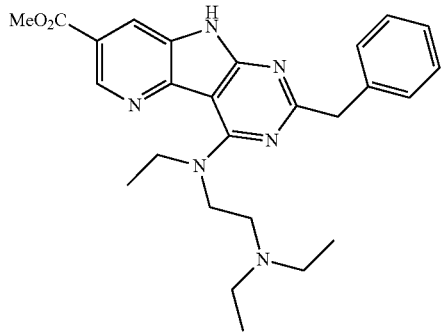 [SMILES: CCN(CC)CCN(CC)c1nc(Cc2ccccc2)nc2[nH]c3cc(C(=O)OC)cnc3c12]

methyl 2-benzyl-4-((2-(diethylamino)ethyl)(ethyl)amino)-9H-pyrido[2',3':4,5]pyrrolo[2,3-d]pyrimidine-7-carboxylate Intermediate 16A Intermediate 1D (0.029 g, 0.08 mmol) and N1,N1,N2-triethylethane-1,2-diamine (0.059 g, 0.41 mmol) furnished 0.008 g of the title compound according to the procedure described in example 4. Characteristic peaks are: $^1$H NMR (400 MHz, DMSO-d$_6$) δ ppm 0.93 (br. s., 6H) 1.17 (t, J=6.85 Hz, 3H) 2.67 (br. s., 2H) 3.32 (br. s, 10H) 3.91 (s, 3H) 4.02 (s, 2H) 7.15-7.22 (m, 1H) 7.28 (t, J=7.63 Hz, 2H) 7.32-7.38 (m, 2H) 8.13 (d, J=1.96 Hz, 1H) 8.93 (d, J=1.96 Hz, 1H) 12.35 (br. s., 1H); HRMS m/z 461.2685 (M+H)$^+$.

Reported HPLC retention time are for reverse-phase HPLC (Agilent, 1200 series) using the following conditions Solvent A: MeOH:H$_2$O:TFA (5:95:0.05); Solvent B: MeOH:H$_2$O:TFA (95:5:0.05); flow: 2.0 mL/min.; gradient 0 to 100% B in 1.5 min; run time: 3.5 min; column: Kinetex C18, 2.6 μm, 100 Å, 4.6×30 mm; wavelength 254 nm.

TABLE 1

| Compound number | Structure | HPLC R$_T$ (min) analytical | MS m/z (M + H)+ | Biological data EC$_{50}$ |
|---|---|---|---|---|
| 1 | 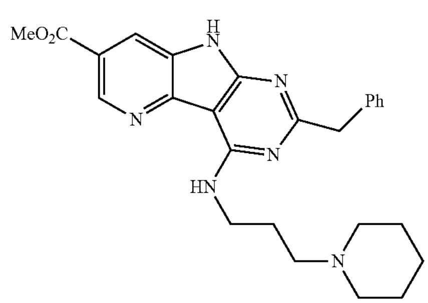 [SMILES: COC(=O)c1cnc2c(c1)[nH]c1nc(Cc3ccccc3)nc(NCCCN3CCCCC3)c12] | 1.74 | 459.2 | C |

TABLE 1-continued

| Compound number | Structure | HPLC R_T (min) analytical | MS m/z (M + H)+ | Biological data EC$_{50}$ |
|---|---|---|---|---|
| 2 | 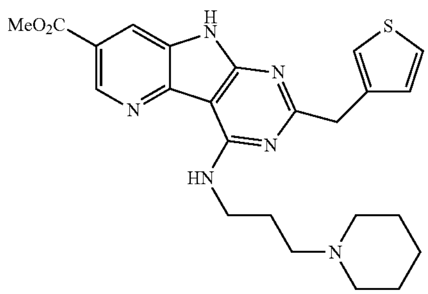 [SMILES: COC(=O)c1cnc2c(c1)[nH]c1nc(Cc3ccsc3)nc(NCCCN3CCCCC3)c12] | 1.71 | 465.2 | C |
| 3 | 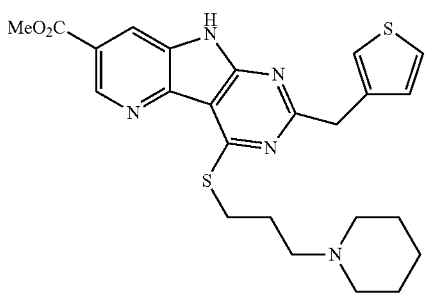 [SMILES: COC(=O)c1cnc2c(c1)[nH]c1nc(Cc3ccsc3)nc(SCCCN3CCCCC3)c12] | 1.82 | 482.2 | B |
| 4 | 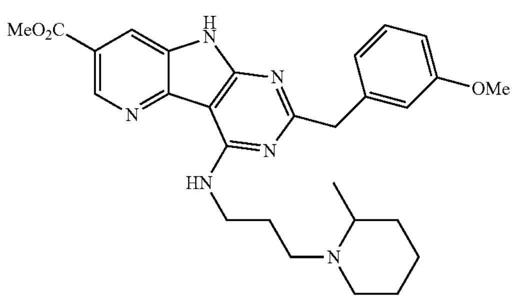 [SMILES: COC(=O)c1cnc2c(c1)[nH]c1nc(Cc3cccc(OC)c3)nc(NCCCN3CCCCC3C)c12] | 1.81 | 503.3 | C |
| 5 | 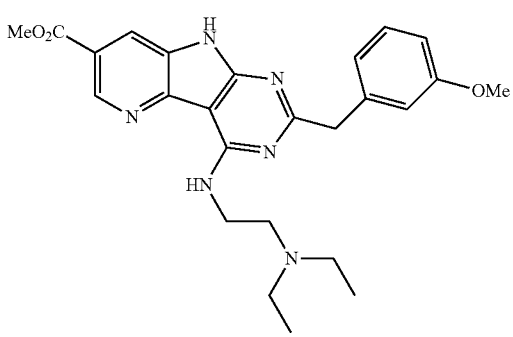 [SMILES: CCN(CC)CCNc1nc(Cc2cccc(OC)c2)nc2[nH]c3cc(C(=O)OC)cnc3c12] | 1.77 | 463.2 | B |
| 6 | 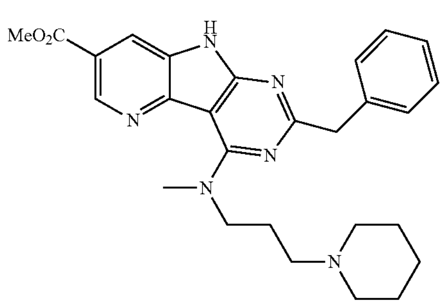 [SMILES: COC(=O)c1cnc2c(c1)[nH]c1nc(Cc3ccccc3)nc(N(C)CCCN3CCCCC3)c12] | 1.78 | 473.3 | E |

TABLE 1-continued
| Compound number | Structure | HPLC $R_T$ (min) analytical | MS m/z (M + H)+ | Biological data $EC_{50}$ |
|---|---|---|---|---|
| 7 | 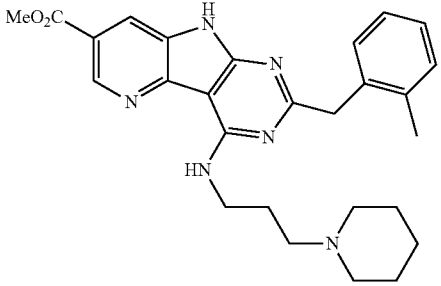 [SMILES: COC(=O)c1cnc2c(c1)[nH]c1nc(Cc3ccccc3C)nc(NCCCN3CCCCC3)c12] | 1.82 | 473.4 | C |
| 8 | 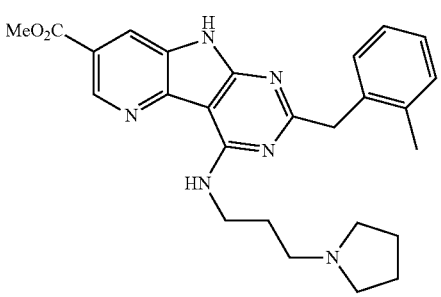 [SMILES: COC(=O)c1cnc2c(c1)[nH]c1nc(Cc3ccccc3C)nc(NCCCN3CCCC3)c12] | 1.78 | 459.3 | C |
| 9 | 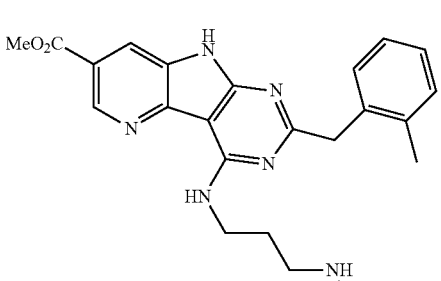 | 1.81 | 419.3 | B |
| 10 | 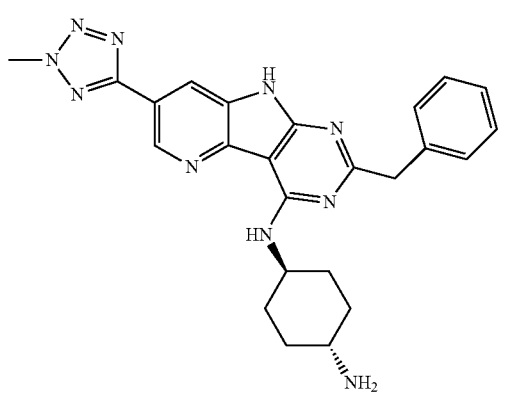 [SMILES: Cn1nnc(-c2cnc3c(c2)[nH]c2nc(Cc4ccccc4)nc(N[C@H]4CC[C@H](N)CC4)c23)n1] | 1.78 | 455.3 | C |
| 11 | 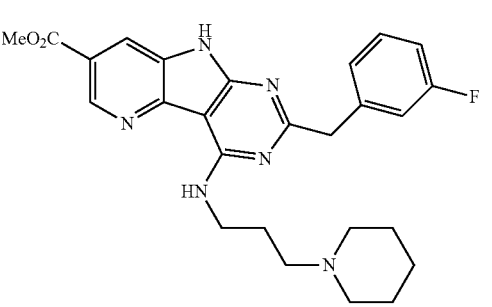 [SMILES: COC(=O)c1cnc2c(c1)[nH]c1nc(Cc3cccc(F)c3)nc(NCCCN3CCCCC3)c12] | 1.83 | 477.3 | A |

TABLE 1-continued

| Compound number | Structure | HPLC R$_T$ (min) analytical | MS m/z (M + H)+ | Biological data EC$_{50}$ |
|---|---|---|---|---|
| 12 | (structure) | 1.64 | 480.2 | C |
| 13 | (structure) | 1.78 | 423.2 | A |
| 14 | (structure) | 1.77 | 433.3 | B |
| 15 | (structure) | 1.76 | 445.3 | D |
| 16 | (structure) | 1.89 | 461.3 | C |

TABLE 1-continued

| Compound number | Structure | HPLC $R_T$ (min) analytical | MS m/z (M + H)+ | Biological data $EC_{50}$ |
|---|---|---|---|---|

The $EC_{50}$ is defined as the concentration that results in a 50% increase in $CD34^+CD45RA^-$ cell count compared to vehicle cultures (DMSO).

\* $EC_{50}$:
A >1000 nM;
B: >500-1000 nM;
C: >250-500 nM;
D = 100-250;
E = <100 nM.

Synthetic Methodology of Pyrido[4,3,B]Indolyl Compounds

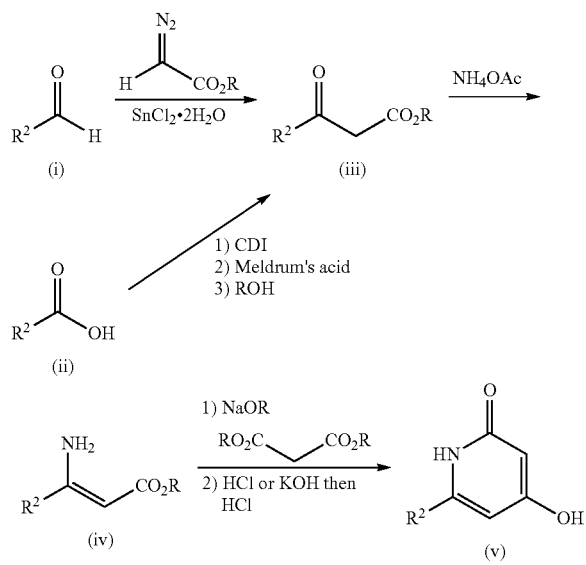

In order to prepare the 5H-pyrido[4,3-b]indoles, commercially available starting material (v) can be used or prepared according to known procedure (McElroy, William T. and DeShong, Philip. *Tetrahedron* 2006, 62(29), 6945-6954; Pryde, David C. et al. *MedChemComm.* 2011, 2(3), 185-189; Ohashi, Tomohiro et al. *Bioorganic & Medicinal Chemistry* 2012, 20(18), 5507-5517; Hansen, Karl B. et al. *Organic Letters* 2005, 7(22), 4935-4938). These compounds (v) are prepared by a method illustrated in Scheme 1. The aldehyde (i) is treated with tin chloride dihydrate and ethyl diazoacetate, for example, in methylene chloride to give compound (iii). Alternatively, this compound (iii) can be obtained by treating an acid (ii) with 1,1'-carbonyldiimidazole in a solvent such as methylene chloride and then treated with Meldrum's acid (2,2-Dimethyl-1,3-dioxane-4,6-dione). The isolated intermediate is reflux in an alcohol to give compound (iii). This product is then reacted with ammonium acetate in ethanol, for example, to give compound (iv). This product is then cyclized and decarboxylated by reacting with sodium ethoxide and diethyl malonate, for example, in a mixture of ethanol and toluene followed by heating in acid, for example, HCl in dioxane at 100° C. to give compound (v) or heating in base, for example KOH in water at 100° C. followed by acidification with HCl in water to give compound (v).

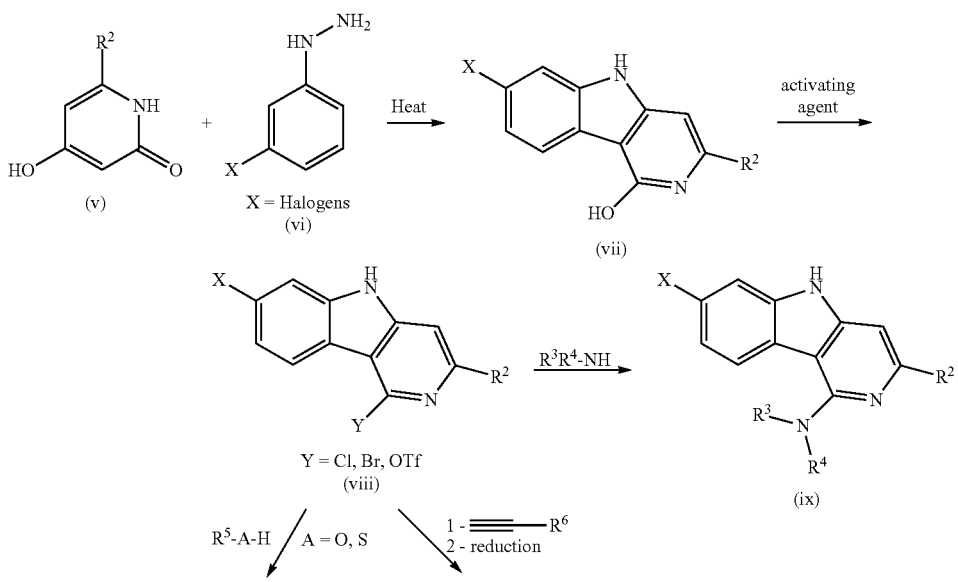

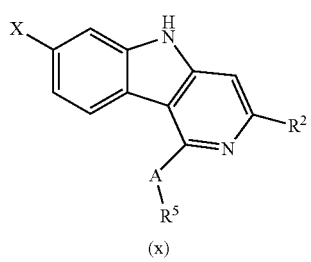

(x)

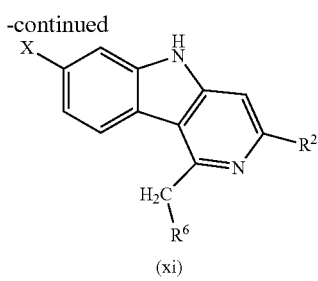

(xi)

The general approach to prepare 5H-pyrido[4,3-b]indoles cores (ix, x and xi) is illustrated in Scheme 2. The 4-hydroxypyridin-2(1H)-one (v) is heated with an hydrazine (vi) to 175 to 220° C. in an organic non-polar solvent, such as diphenyl ether. For the preparation of compound (viii), conversion of the phenol (or the isomeric amide) to a leaving group such as triflate, chloride or bromide can be done with triflic anhydride with a base such as triethylamine in an inert solvent such as dichloromethane or by halogenation with reagents such as phosphorus oxychloride (or phosphorus oxybromide) neat or in a polar organic solvent such as 1,4-dioxane. The intermediate (viii) can be heated (60-160° C.) with and amine (with or without a base such as triethylamine) to furnish the compound (ix). Intermediate (x) could be obtained by heating (80-160° C.) intermediate (viii) with an excess (5-25 eq.) of the desired alcohol. Similarly, a mixture of intermediate (viii) with an appropriate thiolate generated from a hydride such as NaH or a base such as sodium methoxide or a carbonate or from the deprotection of a silyl group with a fluorine source in DMF (N-methyl pyrrolidine) can yield the desire intermediate (x). An appropriate vinyl boronate (usually prepared from an alkyne and a dialkoxyborane) and intermediate (viii) in the presence of a metal catalyst such as palladium (ex. $PdCl_2.(PPh_3)_2$-CuI-$Et_3N$) in a solvent such as dimethyl formamide with heat (30-140° C.) can give the corresponding alkene. This alkene could be reduced by numerous ways such as hydrogen with palladium on charcoal to give compound (xi).

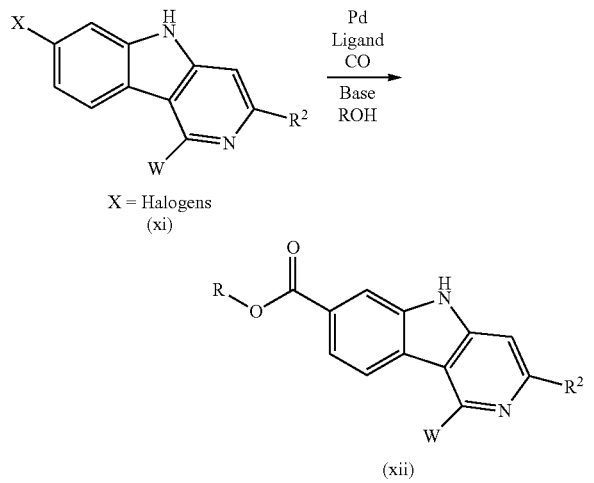

Compound (xii) can be obtained according to the approach described in Scheme 3. The intermediate (xi) can be carbonylated in the presence of a metal catalyst, such as palladium (ex. $Pd(OAc)_2$-Xantphos or $Pd(OAc)_2$-dppf) with an organic base such as triethylamine and in the presence of an alcohol such as methanol. The reaction is carried at 70-85° C. under an atmosphere of carbon monoxide. A polar aprotic solvent such as dimethylsulfoxide can also be used.

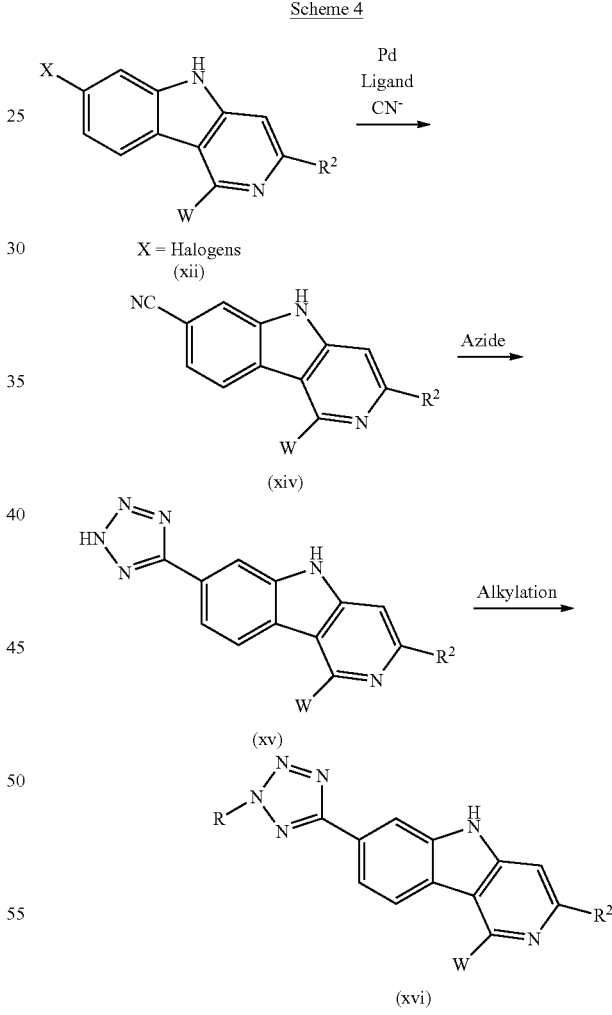

Compound (xvi) can be obtained according to the approach described in Scheme 4. The intermediate (xii) can be cyanated in the presence of a metal catalyst, such as palladium (ex. $Pd(PPh_3)_4$) in the presence of cyanide source such as zinc cyanide in a polar aprotic solvent such as N,N-dimethylformamide at high temperature (ex. 160° C.). The nitrile group of product (xiv) is then converted into a tetrazole (xv). This conversion can be done using azidotributyltin in a non-polar solvent such as (trifluoromethyl)benzene at 180° C. followed by acidic hydrolysis using HCl in methanol. This transformation can also be performed using other know methods such as sodium azide and an acid or trimethylsilyl azide and dibutyltin oxide in a non-polar aprotic solvent such as benzene or toluene at high temperature (80-100° C.). The tetrazole (xv) can then be alkylated to product (xvi) using diazomethane or trimethylsilyldiazomethane in a polar aprotic solvent such as tetrahydrofuran in the presence of methanol. The alkylation can also be performed using a base, such as sodium hydride or a carbonate (sodium/potassium or cesium) and an alkyl halide in a polar aprotic solvent such as tetrahydrofuran, 1,4-dioxane, acetonitrile, N,N-dimethylformamide or N,N-dimethylacetamide.

The sequences of the schemes could be interchange in function of the availability of some starting materials or by the type of functionalities on the intermediates.

Experimental Procedure

Example 1

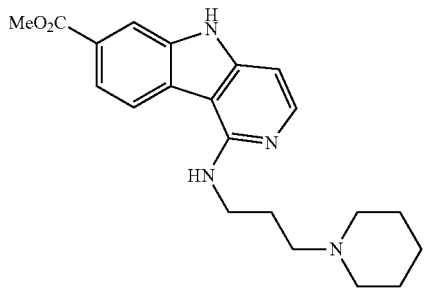 [SMILES: COC(=O)c1ccc2c(c1)[nH]c1ccnc(NCCCN3CCCCC3)c12]

methyl 1-((3-(piperidin-1-yl)propyl)amino)-5H-pyrido[4,3-b]indole-7-carboxylate

Intermediate 1A

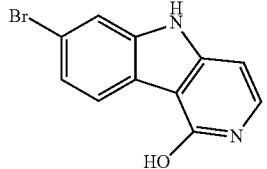 [SMILES: Oc1nccc2[nH]c3cc(Br)ccc3c12]

7-bromo-5H-pyrido[4,3-b]indol-1-ol

In a 50 mL round-bottomed flask equipped with a Dean-Stark were added (3-bromophenyl)hydrazine free-base (3.20 g, 17.11 mmol) and pyridine-2,4-diol (1 g, 9.00 mmol) in diphenyl ether (15.75 ml) under $N_2$ (3 cycles vacuum then refill with $N_2$). The mixture was heated to 175° C. for ca. 20 minutes, then gradually to 230° C. and stirred for 3 hours. The biphasic mixture was cooled to 100° C. and toluene (25 ml) was added. The resulting slurry was stirred at 20° C. for 1 hour and the solids were collected on Buchner. The cake was washed with toluene (3×5 mL) and the product dried at 20° C. under high vacuum to give 2.05 g as a tan solid containing two isomers. The solids were ground to a fine solid and sonicated in MeOH (5 mL) for 15 minutes and collected again on Buchner. This furnished 761 mg of the product containing ca. 10% of the 9-bromo isomer. This sequence was repeated to give 7-bromo-5H-pyrido[4,3-b]indol-1-ol (642 mg, 2.4 mmol, 27.1% yield) as a tan solid. $^1$H NMR (400 MHz, DMSO-d6) δ ppm 6.52 (d, J=7.0 Hz, 1H) 7.29-7.37 (m, 2H) 7.67 (d, J=1.6 Hz, 1H) 8.00 (d, J=8.6 Hz, 1H) 11.13-11.23 (m, 1H) 11.82 (s, 1H).

Intermediate 1B

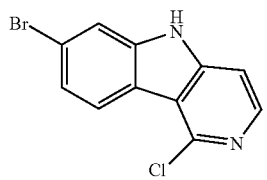 [SMILES: Clc1nccc2[nH]c3cc(Br)ccc3c12]

7-bromo-1-chloro-5H-pyrido[4,3-b]indole

A mixture of 7-bromo-5H-pyrido[4,3-b]indol-1-ol (0.205 g, 0.78 mmol) in $POCl_3$ (2.18 ml, 23.38 mmol) was heated to 175° C. in a microwave apparatus for 15 minutes. The reaction mixture was cooled to 20° C. and poured onto ice (50 g). The mixture was basified with NaOH 50% wt. in water (6.14 ml, 117 mmol) and the aqueous layer was extracted with EtOAc (2×50 mL). The organic layer was dried over anhydrous $MgSO_4$, filtered and concentrated to dryness to give crude 7-bromo-1-chloro-5H-pyrido[4,3-b]indole (93 mg, 0.33 mmol, 42.4% yield) as a tan solid that was used as-is in the next step. LCMS m/z 280.9, 282.9 (M+H)$^+$.

Intermediate 1C

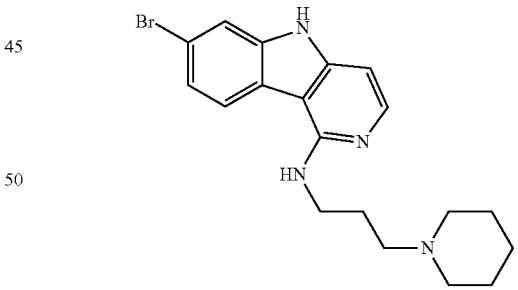

7-bromo-N-(3-(piperidin-1-yl)propyl)-5H-pyrido[4,3-b]indol-1-amine

A mixture of 7-bromo-1-chloro-5H-pyrido[4,3-b]indole (0.093 g, 0.33 mmol) in 3-(Piperidin-1-yl)propan-1-amine (2.00 ml, 12.59 mmol) was heated to 150° C. for 19 hours. The reaction mixture was cooled to 20° C., poured into water (10 mL) and extracted with EtOAc (3×10 mL). The combined organic layers were washed with water (8×10 mL) and then with brine (10 mL). The organic layer was dried over anhydrous $MgSO_4$, filtered and concentrated. The residue was purified on ISCO using a RediSep 24 g column (CH₂Cl₂/MeOH/NH₄OH) to give 94 mg as a red foam which was suspended in Et₂O (2 mL) and stirred for 30 minutes. The solids were collected on Buchner, washed with Et₂O (2×0.5 mL) and dried at 40° C. under high vacuum to give 7-bromo-N-(3-(piperidin-1-yl)propyl)-5H-pyrido[4,3-b]indol-1-amine (56 mg, 0.14 mmol, 43.8% yield) as a pink solid. ¹H NMR (400 MHz, DMSO-d6) δ ppm 1.33-1.45 (m, 2H) 1.46-1.58 (m, 4H) 1.76-1.91 (m, 2H) 2.19-2.48 (m, 6H) 3.53-3.64 (m, 2H) 6.45 (br. s., 1H) 6.74 (d, J=5.8 Hz, 1H) 7.33 (dd, J=8.2, 1.8 Hz, 1H) 7.64 (d, J=1.8 Hz, 1H) 7.93 (d, J=5.8 Hz, 1H) 8.22 (d, J=8.2 Hz, 1H) 11.60 (s, 1H). LCMS m/z (M+H)±=387.1, 389.1.

Intermediate 1D

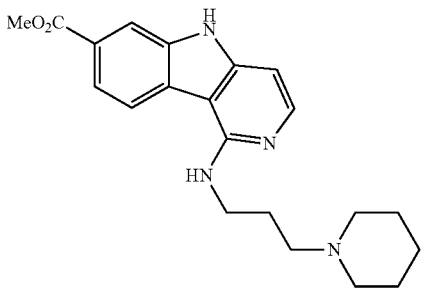 [SMILES: COC(=O)c1ccc2c(c1)[nH]c1ccnc(NCCCN3CCCCC3)c12]

methyl 1-((3-(piperidin-1-yl)propyl)amino)-5H-pyrido[4,3-b]indole-7-carboxylate

A mixture of 7-bromo-N-(3-(piperidin-1-yl)propyl)-5H-pyrido[4,3-b]indol-1-amine (0.05 g, 0.13 mmol), Pd(OAc)₂ (1.44 mg, 6.45 μmol) and 4,5-bis(diphenylphosphino)-9,9-dimethylxanthene (7.47 mg, 0.013 mmol) were placed in a vial under N2. Methanol (0.104 ml, 2.58 mmol) and triethylamine (0.45 ml, 3.23 mmol) were added and carbon monoxide was bubbled through the pink suspension for 1 minute and the mixture was heated to 70° C. for 18 hours. The reaction mixture was diluted with EtOAc (3 mL) and MeOH (2 mL) and then filtered over 0.45 μm filter. The flask and filter were rinsed with EtOAc (2 mL) and MeOH (2 mL). Concentrated to dryness gave 67 mg of an orange oil. The crude material was purified on preparative HPLC with water (0.05% TFA)-MeOH (0.05% TFA) from 20 to 100%. The desired fractions were combined and the solvent was removed under vacuum. The solid obtained was suspended in EtOAc (5 mL) and saturated NaHCO₃ (3 mL) was added. The mixture was stirred vigorously for 10 minutes after which the aqueous layer was extracted with EtOAc (5 mL). The combined organic layers were dried over anhydrous MgSO₄, filtered and concentrated to give 33 mg of an oil that was lyophilized from CH₃CN to give methyl 1-((3-(piperidin-1-yl)propyl)amino)-5H-pyrido[4,3-b]indole-7-carboxylate (29 mg, 0.079 mmol, 61.3% yield) as a white solid. ¹H NMR (400 MHz, DMSO-d6) δ ppm 1.38-1.47 (m, 2H) 1.47-1.61 (m, 4H) 1.79-1.94 (m, 2H) 2.24-2.48 (m, 6H) 3.61 (q, J=6.7 Hz, 2H) 3.89 (s, 3H) 6.63 (br. s., 1H) 6.78 (d, J=5.9 Hz, 1H) 7.81 (dd, J=8.2, 1.5 Hz, 1H) 7.97 (d, J=5.9 Hz, 1H) 8.07 (d, J=1.5 Hz, 1H) 8.37 (d, J=8.2 Hz, 1H) 11.76 (s, 1H). LCMS m/z (M+H)⁺=367.2.

Example 2

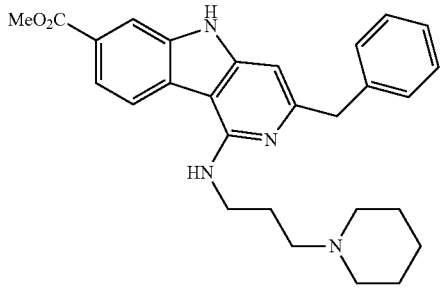

methyl 3-benzyl-1-((3-(piperidin-1-yl)propyl)amino)-5H-pyrido[4,3-b]indole-7-carboxylate Intermediate 2A

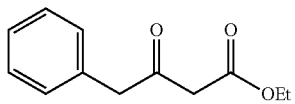 [SMILES: CCOC(=O)CC(=O)Cc1ccccc1]

ethyl 3-oxo-4-phenylbutanoate

To a suspension of SnCl₂.2H₂O (1.409 g, 6.2 mmol) and ethyl 2-diazoacetate (8.55 g, 74.9 mmol) in DCM (80 ml) was added dropwise 2-phenylacetaldehyde (7.5 g, 62.4 mmol). After 2 h of stirring, the suspension was filtered and diluted with a brine solution. The organic phase was separated, dried over anhydrous MgSO₄, filtered and the solvent removed under vacuum. The residue was purified on ISCO with a RediSep column using Hex-EA (0-40%) to yield 6.00 g of the title compound. ¹H NMR (400 MHz, CDCl₃) δ ppm 1.26 (t, J=7.04 Hz, 3H) 3.44 (s, 2H) 3.83 (s, 2H) 4.17 (q, J=7.30 Hz, 2H) 7.10-7.38 (m, 5H).

Intermediate 2B

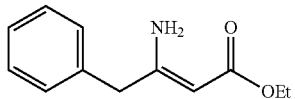 [SMILES: CCOC(=O)/C=C(\N)Cc1ccccc1]

ethyl 3-amino-4-phenylbut-2-enoate

A mixture of ethyl 3-oxo-4-phenylbutanoate (0.200 g, 0.97 mmol) and ammonium acetate (0.374 g, 4.8 mmol) in ethanol (2.0 ml) was heated to 75° C. After 3 h of stirring the temperature was cooled to 20° C. and the solvent removed under vacuum. The residue was taken in Et₂O and washed with a saturated solution of NaHCO₃. The organic phase was separated, dried over anhydrous MgSO₄, filtered and the solvent removed under vacuum to yield 180 mg of the title compound. ¹H NMR (400 MHz, DMSO-d₆) ☐☐ ppm 1.12

(t, J=7.04 Hz, 3H) 3.38 (s, 2H) 3.94 (q, J=7.30 Hz, 2H) 4.29 (s, 1H) 7.04 (br. s., 1H) 7.19-7.34 (m, 5H) 7.72 (br. s., 1H).

Intermediate 2C

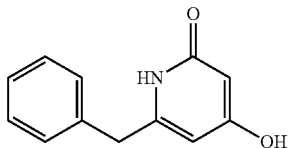 [SMILES: O=c1cc(O)cc(Cc2ccccc2)[nH]1]

6-benzyl-4-hydroxypyridin-2(1H)-one

A mixture of ethyl 3-amino-4-phenylbut-2-enoate (5.45 g, 26.6 mmol), sodium ethoxide (10.88 ml, 29.2 mmol) and diethyl malonate (4.46 ml, 29.2 mmol) in a mixture of ethanol (20 mL) and toluene (20 ml) was heated to 80° C. for 30 min and then at 110° C. overnight. Most of the solvent was removed under vacuum and the solid filtered, rinsed with a mixture of toluene:ethanol (4:1) to furnish 3.2 g of the intermediate ester. This ester was heated overnight at 100° C. in 4M HCl-dioxane (60 ml). The solvent was removed under vacuum and the residue taken in methanol and filtered. The solid obtained was absorbed on $SiO_2$ and purified on ISCO with a RediSep column using DCM-MeOH (0-15%) to yield 1.00 g of the title compound. $^1$H NMR (400 MHz, DMSO-d$_6$) δ ppm 3.71 (s, 2H) 5.37 (d, J=1.96 Hz, 1H) 5.56 (d, J=1.96 Hz, 1H) 7.11-7.37 (m, 5H) 10.41 (br. s., 1H) 11.14 (br. s., 1H).

Intermediate 2D

3-benzyl-7-bromo-5H-pyrido[4,3-b]indol-1-ol

In a 50 mL round-bottomed flask equipped with a Dean-Stark were added (3-bromophenyl)hydrazine free-base (1.76 g, 9.44 mmol) and 6-benzyl-4-hydroxypyridin-2(1H)-one (1 g, 4.97 mmol) in degassed diphenyl ether (9.25 ml). The flask and Dean-Stark were flushed with $N_2$ (3 cycles, vacuum then fill with $N_2$) and heated to 175° C. for 1 hour and gradually increasing to 230° C. After 3 hours the mixture was cooled to 100° C. and toluene (14 ml) was added. The resulting suspension was stirred at 20° C. for 1 hour and the solids were collected on Buchner, washed with toluene (3×3 mL) and dried at 20° C. under high vacuum to give 1.17 g of a tan solid containing the two isomers. The solid obtained was adsorbed on $SiO_2$ and was purified on ISCO using a RediSep 40 g column DCM-MeOH (0-20%) to yield 3-benzyl-7-bromo-5H-pyrido[4,3-b]indol-1-ol (534 mg, 1.512 mmol, 30.4% yield) as a tan solid. LCMS m/z 353.0, 355.0 (M+H)$^+$.

Intermediate 2E

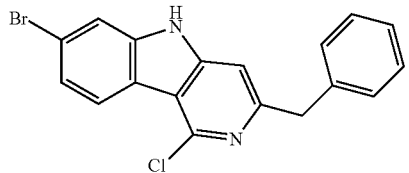 [SMILES: Clc1nc(Cc2ccccc2)cc2[nH]c3cc(Br)ccc3c12]

3-benzyl-7-bromo-1-chloro-5H-pyrido[4,3-b]indole

A mixture of 3-benzyl-7-bromo-5H-pyrido[4,3-b]indol-1-ol (0.205 g, 0.58 mmol) in phosphorus oxychloride (3.00 ml, 32.2 mmol) was heated to 175° C. in a microwave apparatus for 15 minutes and the reaction mixture was concentrated to dryness on rotovap. Water (12.00 ml) was added and the pH was brought to 8-10 by adding potassium hydroxide 45% wt. in water (13.4 ml, 157 mmol). The resulting suspension was stirred for 30 minutes and the solids were collected on Buchner followed by a wash with water (2×1.5 mL) to give 196 mg of a brown solid (crude). The residue was purified on ISCO using a RediSep 12 g column with Hex-EtOAc (0-100%) to give 3-benzyl-7-bromo-1-chloro-5H-pyrido[4,3-b]indole (61 mg, 0.16 mmol, 28.3% yield) as a pink solid. $^1$H NMR (400 MHz, DMSO-d6) δ ppm 4.19 (s, 2H) 7.18-7.26 (m, 1H) 7.26-7.35 (m, 4H) 7.38 (s, 1H) 7.48 (dd, J=8.20, 1.60 Hz, 1H) 7.79 (d, J=1.60 Hz, 1H) 8.22 (d, J=8.22 Hz, 1H) 12.11 (br. s., 1H); LCMS m/z 371.0, 373.0 (M+H)$^+$.

Intermediate 2F

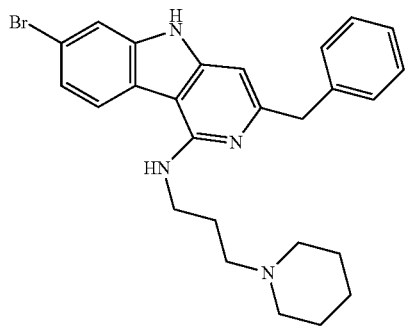 [SMILES: Brc1ccc2c(c1)[nH]c1cc(Cc3ccccc3)nc(NCCCN3CCCCC3)c12]

3-benzyl-7-bromo-N-(3-(piperidin-1-yl)propyl)-5H-pyrido[4,3-b]indol-1-amine

A mixture of crude 3-benzyl-7-bromo-1-chloro-5H-pyrido[4,3-b]indole (0.170 g, 0.45 mmol) in 3-(piperidin-1-yl)propan-1-amine (1.00 ml, 6.29 mmol) was heated to 150° C. for 16 hours. The reaction mixture was cooled to 20° C. and poured into water (20 mL). The aqueous layer was extracted with EtOAc (3×20 mL) and the combined organic layers were washed with water (3×20 mL) and then brine (10 mL). The organic layer was dried over anhydrous $MgSO_4$, filtered and concentrated to give 253 mg of a red oil. The residue was purified on ISCO using a RediSep 40 g column with DCM—2% $NH_4OH$/MeOH (0-20%) to give 169 mg of a red oil. The red oil was dissolved in MeOH (3.4 ml) and HCl 4M in 1,4-dioxane (0.266 ml, 1.06 mmol) was added. To the resulting red solution was added EtOAc (6.80 ml) and the suspension was stirred for 2 hours. The solids were collected on Buchner and washed with MeOH:EtOAc (1:4, 3×0.5 mL). The solid (75 mg) was re-suspended in EtOAc (15 mL)-NaHCO$_3$ (saturated) (7.5 mL) and stirred vigorously for 10 minutes. The layers were separated and the aqueous layer was back extracted with EtOAc (5 mL). The combined organic layers were dried over anhydrous MgSO$_4$, filtered and concentrated to give 3-benzyl-7-bromo-N-(3-(piperidin-1-yl)propyl)-5H-pyrido[4,3-b]indol-1-amine (70 mg, 0.147 mmol, 32.1% yield) as a red foam. $^1$H NMR (400 MHz, DMSO-d6) δ ppm 1.31-1.43 (m, 2H) 1.50 (quin, J=5.5 Hz, 4H) 1.80 (quin, J=6.9 Hz, 2H) 2.21-2.44 (m, 6H) 3.51-3.65 (m, 2H) 3.96 (s, 2H) 6.42 (t, J=5.5 Hz, 1H) 6.55 (s, 1H) 7.12-7.21 (m, 1H) 7.23-7.31 (m, 3H) 7.32-7.39 (m, 2H) 7.57 (d, J=1.6 Hz, 1H) 8.15 (d, J=8.6 Hz, 1H) 11.44 (s, 1H); LCMS m/z 477.2, 479.2 (M+H)$^+$.

Intermediate 2G

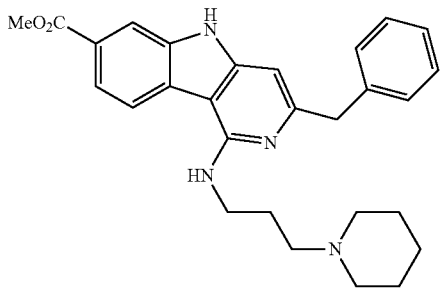 [SMILES: COC(=O)c1ccc2c(c1)[nH]c1cc(Cc3ccccc3)nc(NCCCN3CCCCC3)c12]

methyl 3-benzyl-1-((3-(piperidin-1-yl)propyl) amino)-5H-pyrido[4,3-b]indole-7-carboxylate To a mixture of 3-benzyl-7-bromo-N-(3-(piperidin-1-yl) propyl)-5H-pyrido[4,3-b]indol-1-amine (0.035 g, 0.07 mmol) in MeOH (0.73 ml), triethylamine (0.051 ml, 0.37 mmol) and DMSO (1.45 ml) was added DPPF (4.06 mg, 7.3 µmol) and Pd(OAc)$_2$ (1.646 mg, 7.3 µmol). The flask was evacuated with carbon monoxide (3 vacuum+carbon monoxide refill cycles) and carbon monoxide was bubbled through the red suspension for 1 minute. Under a carbon monoxide atmosphere (balloon), the mixture was heated to 85° C. for 21.5 hours. The reaction mixture was diluted with EtOAc (10 mL)-water (10 mL) and the layers were separated. The aqueous layer was back extracted with EtOAc (2×10 mL) and the combined organic layers were washed with water (4×10 mL) then with brine (10 mL). The organic layer was dried over anhydrous MgSO$_4$, filtered and concentrated to give 40 mg of a red oil. The residue was purified on ISCO using a RediSep 12 g column with DCM—2% NH$_4$OH/MeOH (0-20%) to yield 32 mg of a red oil. The residue was purified on preparative HPLC with water (0.05% TFA)-MeOH (0.05% TFA) from 20 to 100%. The desired fractions were combined and the solvent was removed under vacuum. The residue obtained was lyophilized from acetonitrile to give methyl 3-benzyl-1-((3-(piperidin-1-yl)propyl)amino)-5H-pyrido[4,3-b]indole-7-carboxylate 2,2,2-trifluoroacetate (18.4 mg, 0.032 mmol, 44.0% yield) as a white solid. $^1$H NMR on free base (TFA salt in DMSO treated with solid Na$_2$CO$_3$ then filtered) (400 MHz, DMSO-d$_6$) δ ppm 1.39 (m, J=5.1 Hz, 2H) 1.51 (quin, J=5.5 Hz, 4H) 1.82 (quin, J=6.9 Hz, 2H) 2.18-2.46 (m, 6H) 3.61 (q, J=6.7 Hz, 2H) 3.88 (s, 3H) 3.98 (s, 2H) 6.57 (s, 1H) 6.59 (t, J=5.5 Hz, 1H) 7.13-7.22 (m, 1H) 7.27 (t, J=7.4 Hz, 2H) 7.36 (m, J=7.0 Hz, 2H) 7.77 (dd, J=8.2, 1.4 Hz, 1H) 8.00 (d, J=1.4 Hz, 1H) 8.30 (d, J=8.2 Hz, 1H) 11.59 (s, 1H); HRMS m/z 457.2596 (M+H)$^+$.

Example 3

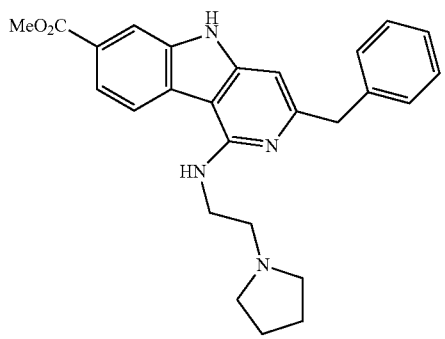

methyl 3-benzyl-1-((2-(pyrrolidin-1-yl)ethyl) amino)-5H-pyrido[4,3-b]indole-7-carboxylate Intermediate 3A

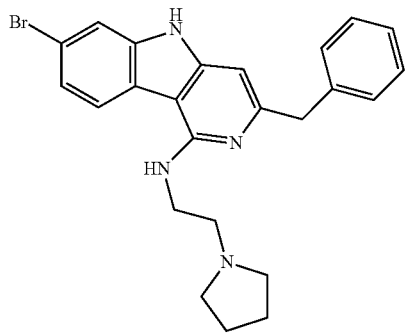 [SMILES: Brc1ccc2c(c1)[nH]c1cc(Cc3ccccc3)nc(NCCN3CCCC3)c12]

3-benzyl-7-bromo-N-(2-(pyrrolidin-1-yl)ethyl)-5H-pyrido[4,3-b]indol-1-amine

Following the procedure for the preparation of Intermediate 2F using the purified Intermediate 2E (30 mg, 0.081 mmol) and 2-(pyrrolidin-1-yl)ethanamine (0.512 ml, 4.04 mmol) afforded 3-benzyl-7-bromo-N-(2-(pyrrolidin-1-yl) ethyl)-5H-pyrido[4,3-b]indol-1-amine (21 mg, 0.047 mmol, 57.9% yield) as a red oil. LCMS m/z 449.2, 451.2 (M+H)$^+$.

Example 3

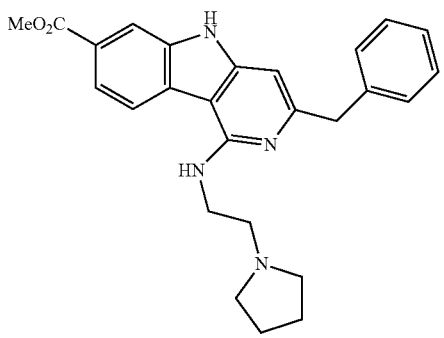 [SMILES: COC(=O)c1ccc2c(c1)[nH]c1cc(Cc3ccccc3)nc(NCCN3CCCC3)c12]

methyl 3-benzyl-1-((2-(pyrrolidin-1-yl)ethyl)amino)-5H-pyrido[4,3-b]indole-7-carboxylate Following the procedure for the preparation of example 1 using 3-benzyl-7-bromo-N-(2-(pyrrolidin-1-yl)ethyl)-5H-pyrido[4,3-b]indol-1-amine (21 mg, 0.047 mmol), Pd(OAc)$_2$ (1.049 mg, 4.6 µmol), 4,5-bis(diphenylphosphino)-9,9-dimethylxanthene (5.41 mg, 9.3 µmol), MeOH (76 µl, 1.86 mmol) and triethylamine (326 µl, 2.3 mmol) afforded methyl 3-benzyl-1-((2-(pyrrolidin-1-yl)ethyl)amino)-5H-pyrido[4,3-b]indole-7-carboxylate (10.2 mg, 0.024 mmol, 50.9% yield) as a white solid. $^1$H NMR (400 MHz, DMSO-d6) δ ppm 1.60-1.87 (m, 4H) 2.57-3.03 (m, 6H) 3.66-3.82 (m, 2H) 3.88 (s, 3H) 4.00 (s, 2H) 6.64 (s, 1H) 6.61 (br. s., 1H) 7.14-7.23 (m, 1H) 7.29 (t, J=7.63 Hz, 2H) 7.32-7.39 (m, 2H) 7.80 (d, J=8.22 Hz, 1H) 8.02 (s, 1H) 8.28 (d, J=8.22 Hz, 1H) 11.65 (br. s., 1H); HRMS m/z 429.2293 (M+H)$^+$.

Example 4

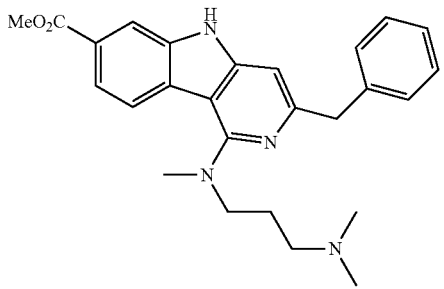 [SMILES: COC(=O)c1ccc2c(c1)[nH]c1cc(Cc3ccccc3)nc(N(C)CCCN(C)C)c12]

methyl 3-benzyl-1-((3-(dimethylamino)propyl)(methyl)amino)-5H-pyrido[4,3-b]indole-7-carboxylate

Intermediate 4A

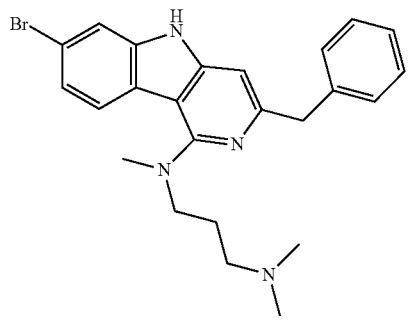 [SMILES: CN(C)CCCN(C)c1nc(Cc2ccccc2)cc2[nH]c3cc(Br)ccc3c12]

$N^1$-(3-benzyl-7-bromo-5H-pyrido[4,3-b]indol-1-yl)-$N^1$,$N^3$,$N^3$-trimethylpropane-1,3-diamine Following the procedure for the preparation of Intermediate 2F using the purified Intermediate 2E (30 mg, 0.08 mmol) and $N^1$,$N^1$,$N^3$-trimethylpropane-1,3-diamine (0.591 ml, 4.04 mmol) afforded $N^1$-(3-benzyl-7-bromo-5H-pyrido[4,3-b]indol-1-yl)-$N^1$,$N^3$,$N^3$-trimethylpropane-1,3-diamine (22 mg, 0.049 mmol, 60.4% yield) as a yellow oil. LCMS m/z 451.2, 453.2 (M+H)$^+$.

Example 4

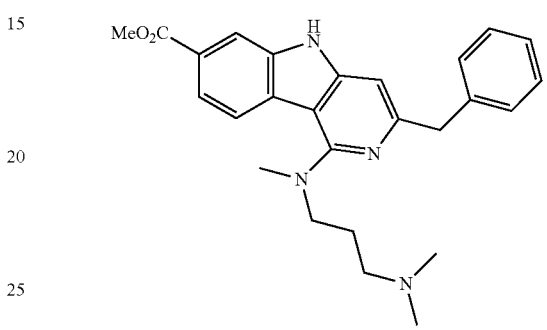

methyl 3-benzyl-1-((3-(dimethylamino)propyl)(methyl)amino)-5H-pyrido[4,3-b]indole-7-carboxylate Following the procedure for the preparation of Example 1 using $N^1$-(3-benzyl-7-bromo-5H-pyrido[4,3-b]indol-1-yl)-$N^1$,$N^3$,$N^3$-trimethylpropane-1,3-diamine (22 mg, 0.05 mmol), Pd(OAc)$_2$ (1.6 mg, 7.3 µmol), 4,5-bis(diphenylphosphino)-9,9-dimethylxanthene (8.5 mg, 0.015 mmol), MeOH (79 µl, 1.95 mmol) and triethylamine (340 µl, 2.43 mmol) afforded methyl 3-benzyl-1-((3-(dimethylamino)propyl)(methyl)amino)-5H-pyrido[4,3-b]indole-7-carboxylate (12.7 mg, 0.029 mmol, 60.5% yield) as a white solid. $^1$H NMR (400 MHz, DMSO-d6) δ ppm 1.75 (quin, J=7.24 Hz, 2H) 2.06 (s, 6H) 2.20 (t, J=6.06 Hz, 2H) 3.03 (s, 3H) 3.42-3.52 (m, 2H) 3.89 (s, 3H) 4.07 (s, 2H) 6.86 (s, 1H) 7.15-7.22 (m, 1H) 7.28 (t, J=7.43 Hz, 2H) 7.32-7.39 (m, 2H) 7.84 (dd, J=8.41, 1.20 Hz, 1H) 7.94 (d, J=8.40 Hz, 1H) 8.05 (d, J=1.20 Hz, 1H) 11.76 (s, 1H); HRMS m/z 431.2453 (M+H)$^+$.

Example 5

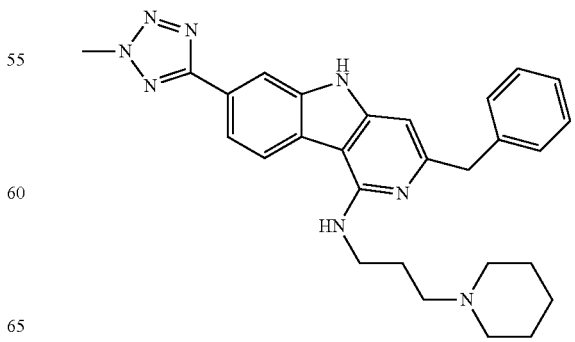

3-benzyl-7-(2-methyl-2H-tetrazol-5-yl)-N-(3-(piperi-din-1-yl)propyl)-5H-pyrido[4,3-b]indol-1-amine Intermediate 5A

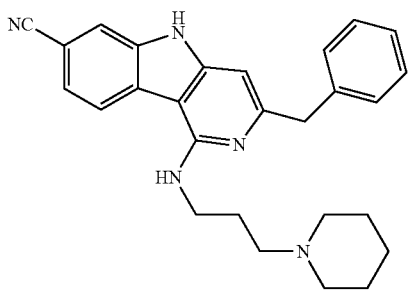 [SMILES: N#Cc1ccc2c(c1)[nH]c1cc(Cc3ccccc3)nc(NCCCN3CCCCC3)c12]

3-benzyl-1-((3-(piperidin-1-yl)propyl)amino)-5H-pyrido[4,3-b]indole-7-carbonitrile A mixture of 3-benzyl-7-bromo-N-(3-(piperidin-1-yl)propyl)-5H-pyrido[4,3-b]indol-1-amine (0.022 g, 0.046 mmol), zinc cyanide (10.8 mg, 0.09 mmol) and tetrakis(triphenylphosphine) palladium (0) (10.6 mg, 9.2 µmol) in DMF (0.70 ml, 9.04 mmol) was flushed with nitrogen (3 vacuum+ nitrogen refill cycles). The mixture was heated to 160° C. in a microwave apparatus for 1.5 hour. The reaction mixture was poured into EtOAc (30 mL) and washed with water (2×10 mL) then with brine (10 mL). The organic layer was dried over anhydrous MgSO$_4$, filtered and concentrated to give 35 mg of a red oil. The residue was purified on ISCO using a RediSep 4 g column with DCM—2% NH$_4$OH/MeOH (0-20%) and the solid obtained was lyophilized from acetonitrile to give 3-benzyl-1-((3-(piperidin-1-yl)propyl)amino)-5H-pyrido[4,3-b]indole-7-carbonitrile (14.3 mg, 0.03 mmol, 73.3% yield) as a pink solid. $^1$H NMR (400 MHz, DMSO-d6) δ ppm 1.31-1.45 (m, 2H) 1.50 (s, 4H) 1.81 (s, 2H) 2.20-2.46 (m, 6H) 3.54-3.65 (m, 2H) 3.98 (s, 2H) 6.59 (s, 1H) 6.65 (t, J=5.48 Hz, 1H) 7.13-7.22 (m, 1H) 7.27 (t, J=7.43 Hz, 2H) 7.36 (d, J=7.43 Hz, 2H) 7.56 (d, J=8.22 Hz, 1H) 7.85 (s, 1H) 8.39 (d, J=8.22 Hz, 1H) 11.76 (s, 1H); HRMS m/z 424.2485 (M+H)$^+$.

Intermediate 5B

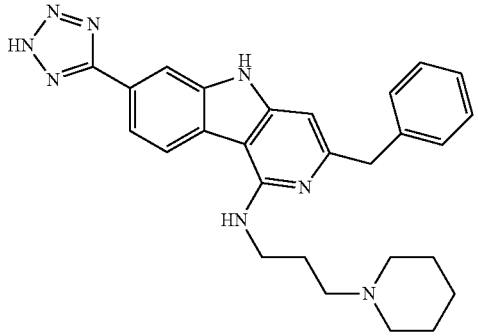 [SMILES: c1ccc(Cc2cc3[nH]c4cc(-c5nn[nH]n5)ccc4c3c(NCCCN3CCCCC3)n2)cc1]

3-benzyl-N-(3-(piperidin-1-yl)propyl)-7-(2H-tetrazol-5-yl)-5H-pyrido[4,3-b]indol-1-amine A mixture of 3-benzyl-1-((3-(piperidin-1-yl)propyl)amino)-5H-pyrido[4,3-b]indole-7-carbonitrile (13.1 mg, 0.03 mmol) and azidotributyltin (89 µl, 0.32 mmol) in (trifluoromethyl)benzene (750 µl) was heated to 180° C. in a microwave apparatus for 30 minutes. The mixture was concentrated to dryness to give a red oil to which was added MeOH (750 µl) and HCl 4M in 1,4-dioxane (232 µl, 0.928 mmol). Et$_2$O (1.4 mL) was added and the resulting suspension was stirred for 1 hour. The solids were collected on Buchner and washed with Et$_2$O (3×0.5 mL) and then with hexane (3×0.5 mL). The solid was dried at 20° C. under high vacuum to give 3-benzyl-N-(3-(piperidin-1-yl)propyl)-7-(2H-tetrazol-5-yl)-5H-pyrido[4,3-b]indol-1-amine hydrochloride (16 mg, 0.032 mmol, 103% yield) as a tan solid. LCMS m/z 451.2, 467.4 (M+H)$^+$.

Example 5

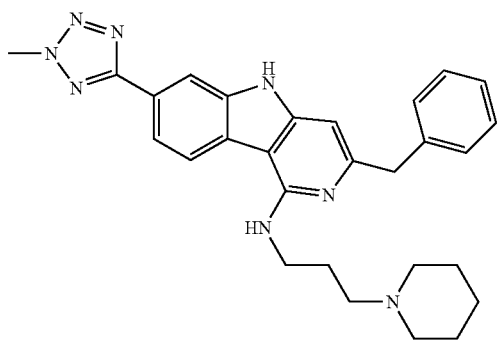 [SMILES: Cn1nnc(-c2ccc3c(c2)[nH]c2cc(Cc4ccccc4)nc(NCCCN4CCCCC4)c23)n1]

3-benzyl-7-(2-methyl-2H-tetrazol-5-yl)-N-(3-(piperi-din-1-yl)propyl)-5H-pyrido[4,3-b]indol-1-amine To a mixture of 3-benzyl-N-(3-(piperidin-1-yl)propyl)-7-(2H-tetrazol-5-yl)-5H-pyrido[4,3-b]indol-1-amine hydrochloride (16 mg, 0.032 mmol) and DIPEA (23.76 µl, 0.136 mmol) in THF (1 mL) and MeOH (0.25 ml) was added diazomethane 0.5M in Et$_2$O (372 µl, 0.18 mmol). At completion, the reaction was quenched with acetic acid (3 drops) and concentrated to dryness on rotovap. The residue was purified on preparative HPLC with water (0.05% TFA)-MeOH (0.05% TFA) from 20 to 100%. The desired fractions were combined and the solvent was removed under vacuum. The residue obtained was lyophilized from acetonitrile to give 3-benzyl-7-(2-methyl-2H-tetrazol-5-yl)-N-(3-(piperi-din-1-yl)propyl)-5H-pyrido[4,3-b]indol-1-amine 2,2,2-trifluoroacetate (10.4 mg, 0.017 mmol, 56.5% yield) as a white solid. $^1$H NMR on free base (TFA salt in DMSO treated with solid Na$_2$CO$_3$ then filtered) (400 MHz, DMSO-d6) δ ppm 1.40 (m, J=5.09 Hz, 2H) 1.52 (dt, J=10.86, 5.33 Hz, 4H) 1.83 (dt, J=13.89, 6.75 Hz, 2H) 2.25-2.42 (m, 6H) 3.56-3.66 (m, 2H) 3.98 (s, 2H) 4.43 (s, 3H) 6.53 (t, J=5.28 Hz, 1H) 6.58 (s, 1H) 7.14-7.22 (m, 1H) 7.28 (t, J=7.63 Hz, 2H) 7.37 (d, J=7.04 Hz, 2H) 7.86 (dd, J=8.20, 1.20 Hz, 1H) 8.08 (s, 1H) 8.35 (d, J=8.22 Hz, 1H) 11.57 (br. s., 1H); HRMS m/z 481.2823 (M+H)$^+$.

Example 6

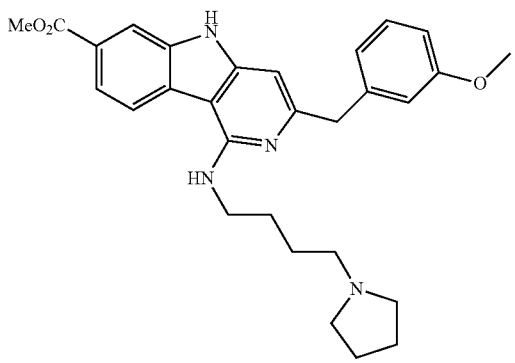 [SMILES: COC(=O)c1ccc2c(c1)[nH]c1cc(Cc3cccc(OC)c3)nc(NCCCCN3CCCC3)c12]

methyl 3-(3-methoxybenzyl)-1-((4-(pyrrolidin-1-yl)butyl)amino)-5H-pyrido[4,3-b]indole-7-carboxylate

Intermediate 6A

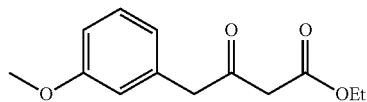 [SMILES: CCOC(=O)CC(=O)Cc1cccc(OC)c1]

ethyl 4-(3-methoxyphenyl)-3-oxobutanoate

To a solution of 2-(3-methoxyphenyl)acetic acid (5 g, 30.1 mmol) in $CH_2Cl_2$ (50 mL) was added CDI (5.28 g, 32.6 mmol) in portions over 5 minutes. Stirred the mixture at 20° C. for 30 minutes. Meldrum's acid (4.70 g, 32.6 mmol) was added and stirred at 20° C. for 16 hours. At completion, the reaction mixture was poured into HCl 5% (175 mL, 245 mmol). Stirred vigorously and separated layers. The aqueous layers was extracted with —$CH_2Cl_2$ (3×50 mL). The combined organic layers were washed with HCl 5% (125 mL) then with water (125 mL). The organic layer was dried over anhydrous $MgSO_4$, filtered and concentrated to give 9.56 g as a light orange oil. The oil was placed into a 100 mL round-bottomed flask and dissolved in anhydrous EtOH (25 mL, 429 mmol). The reaction mixture was heated to reflux for 1 hour then was concentrated to dryness on rotovap. Poured the resulting oil in a solution of $NaHCO_3$ 5% wt. in water (175 mL). Extracted the mixture with EtOAc (3×50 mL). The combined organic layers were washed with water (125 mL) and then with brine (50 mL). The organic layer was dried over anhydrous $MgSO_4$, filtered and concentrated to give 6.55 g as a light orange oil. The residue was purified on ISCO using a RediSep Gold 120 g column (Hex/EtOAc) to yield ethyl 4-(3-methoxyphenyl)-3-oxobutanoate (6.1 g, 25.8 mmol, 86% yield) as a colorless oil. $^1$H NMR (400 MHz, DMSO-d6) δ ppm 1.17 (t, J=7.20 Hz, 3H) 3.64 (s, 2H) 3.73 (s, 3H) 3.83 (s, 2H) 4.07 (q, J=7.20 Hz, 2H) 6.73-6.78 (m, 2H) 6.80-6.86 (m, 1H) 7.19-7.27 (m, 1H); LCMS m/z 237.2 (M+H)$^+$.

Intermediate 6B

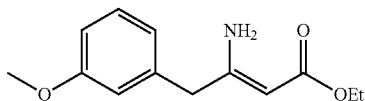 [SMILES: CCOC(=O)/C=C(\N)Cc1cccc(OC)c1]

ethyl 3-amino-4-(3-methoxyphenyl)but-2-enoate

A mixture of ethyl 4-(3-methoxyphenyl)-3-oxobutanoate (6.1 g, 25.8 mmol) and ammonium acetate (9.95 g, 129 mmol) in anhydrous EtOH (103 mL) was heated to reflux for 5 hours. The mixture was concentrated to dryness on rotovap and diluted with EtOAc (129 mL). The organic layer was washed with water (2×129 mL) then with brine (30 mL). The organic layer was dried over anhydrous $MgSO_4$, filtered and concentrated to dryness to yield ethyl 3-amino-4-(3-methoxyphenyl)but-2-enoate (6.07 g, 25.8 mmol, 100% yield) as a yellow oil. $^1$H NMR (400 MHz, DMSO-d6) δ ppm 1.12 (t, J=7.04 Hz, 3H) 3.34 (s, 2H) 3.73 (s, 3H) 3.94 (q, J=7.04 Hz, 2H) 4.31 (s, 1H) 6.77-6.83 (m, 1H) 6.83-6.89 (m, 2H) 7.02 (br. s., 1H) 7.21 (t, J=8.02 Hz, 1H) 7.71 (br. s., 1H); LCMS m/z 236.2 (M+H)$^+$.

Intermediate 6C

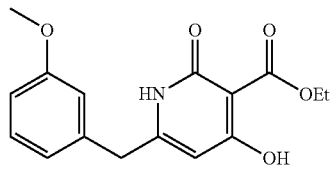 [SMILES: CCOC(=O)c1c(O)cc(Cc2cccc(OC)c2)[nH]c1=O]

ethyl 4-hydroxy-6-(3-methoxybenzyl)-2-oxo-1,2-dihydropyridine-3-carboxylate

A mixture of ethyl 3-amino-4-(3-methoxyphenyl)but-2-enoate (6.07 g, 25.8 mmol), diethyl malonate (4.13 mL, 27.1 mmol) and sodium ethoxide 21% wt. in ethanol (11.56 mL, 31.0 mmol) was heated to 150° C. and stirred for 43 hours. The suspension was cooled to 20° C. and poured into a mixture of water:ice (1:1) (65 g). Acidified the mixture to pH 1.5 with HCl 2N in water (21.93 mL, 43.9 mmol). Heated to 45° C. and slowly cooled to 20° C. The resulting white suspension was stirred for 2 hours. The solids were collected on Buchner and solids were washed with water (2×15 mL). Dried the product at 20° C. under high vacuum until constant weight to give ethyl 4-hydroxy-6-(3-methoxybenzyl)-2-oxo-1,2-dihydropyridine-3-carboxylate (6.92 g, 22.81 mmol, 88% yield) as a white solid. $^1$H NMR (400 MHz, DMSO-d6) δ ppm 1.24 (t, J=7.04 Hz, 3H) 3.72 (s, 2H) 3.74 (s, 3H) 4.23 (q, J=7.04 Hz, 2H) 5.73 (s, 1H) 6.80-6.86 (m, 1H) 6.88 (d, J=7.83 Hz, 1H) 6.91-6.95 (m, 1H) 7.20-7.28 (m, 1H) 11.53 (br. s., 1H) 12.39 (s, 1H); LCMS m/z 304.1 (M+H)$^+$.

Intermediate 6D

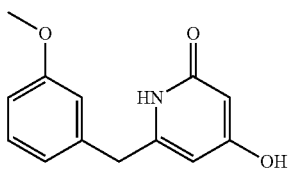 [SMILES: COc1cccc(Cc2cc(O)cc(=O)[nH]2)c1]

4-hydroxy-6-(3-methoxybenzyl)pyridin-2(1H)-one

A mixture of ethyl 4-hydroxy-6-(3-methoxybenzyl)-2-oxo-1,2-dihydropyridine-3-carboxylate (6.67 g, 21.99 mmol) in a solution of potassium hydroxide (7.26 g, 110 mmol) in water (53.5 mL) was heated to reflux for 2.5 hours. The mixture was cooled to 20° C. and acidified to pH 2 with HCl 4M in water (29.4 mL). The resulting white suspension was stirred for 30 minutes. The solids were collected on Buchner and solids were washed with water (3×25 mL). Dried the product at 20° C. under high vacuum until constant weight to give 4-hydroxy-6-(3-methoxybenzyl)pyridin-2(1H)-one (4.36 g, 18.85 mmol, 86% yield) as an off-white solid. $^1$H NMR (400 MHz, DMSO-d6) δ ppm 3.66 (s, 2H) 3.73 (s, 3H) 5.33 (d, J=2.35 Hz, 1H) 5.56 (d, J=2.35 Hz, 1H) 6.79-6.84 (m, 1H) 6.86 (d, J=7.43 Hz, 1H) 6.88-6.92 (m, 1H) 7.23 (t, J=8.02 Hz, 1H) 10.32 (s, 1H) 11.03 (br. s., 1H); LCMS m/z 232.1 (M+H)$^+$.

Intermediate 6E

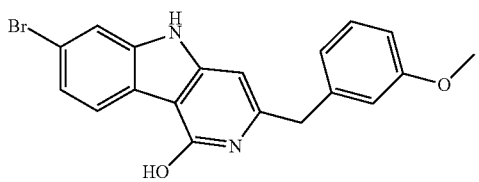 [SMILES: COc1cccc(Cc2cc3[nH]c4cc(Br)ccc4c3c(O)n2)c1]

7-bromo-3-(3-methoxybenzyl)-5H-pyrido[4,3-b]indol-1-ol

Following the procedure for the preparation of Intermediate 2D using (3-bromophenyl)hydrazine free base (6.51 g, 34.81 mmol) and intermediate 6D (4.00 g, 17.3 mmol) afforded 7-bromo-3-(3-methoxybenzyl)-5H-pyrido[4,3-b]indol-1-ol (4.70 g, 12.26 mmol, 70.9% yield) as a gray solid containing a mixture of 7-bromo and 9-bromo isomers (2.6:1 ratio). This intermediate was not purified by flash chromatography. LCMS m/z 383.1, 385.1 (M+H)$^+$.

Intermediate 6F

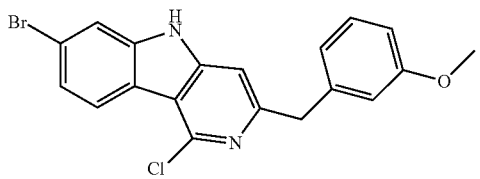 [SMILES: COc1cccc(Cc2cc3[nH]c4cc(Br)ccc4c3c(Cl)n2)c1]

7-bromo-1-chloro-3-(3-methoxybenzyl)-5H-pyrido[4,3-b]indole

Following the procedure for the preparation of Intermediate 2E using 7-bromo-3-(3-methoxybenzyl)-5H-pyrido[4,3-b]indol-1-ol (4.2 g, 10.95 mmol) and phosphorus oxychloride (45.0 mL, 483 mmol) afforded 7-bromo-1-chloro-3-(3-methoxybenzyl)-5H-pyrido[4,3-b]indole (4.90 g, 12.20 mmol, 111% yield) as a gray solid containing a mixture of 7-bromo and 9-bromo isomers (2.3:1 ratio). This intermediate was not purified. LCMS m/z 401.1, 403.1 (M+H)$^+$.

Intermediate 6G

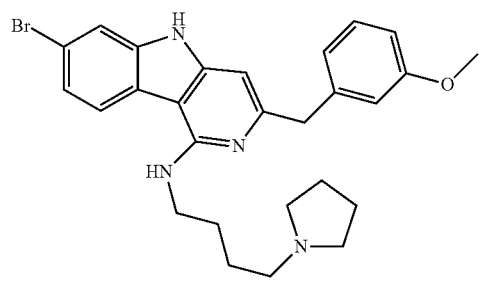 [SMILES: COc1cccc(Cc2cc3[nH]c4cc(Br)ccc4c3c(NCCCCN3CCCC3)n2)c1]

7-bromo-3-(3-methoxybenzyl)-N-(4-(pyrrolidin-1-yl)butyl)-5H-pyrido[4,3-b]indol-1-amine Following the procedure for the preparation of Intermediate 2F using the Intermediate 6F (500 mg, 1.245 mmol) and 4-(pyrrolidin-1-yl)butan-1-amine (0.959 ml, 6.22 mmol) afforded 7-bromo-3-(3-methoxybenzyl)-N-(4-(pyrrolidin-1-yl)butyl)-5H-pyrido[4,3-b]indol-1-amine (214 mg, 0.422 mmol, 33.9% yield) as a pink solid. $^1$H NMR (400 MHz, DMSO-d6) δ ppm 1.48-1.62 (m, 2H) 1.62-1.81 (m, 6H) 2.52-2.86 (m, 6H) 3.58 (q, J=6.65 Hz, 2H) 3.72 (s, 3H) 3.93 (s, 2H) 6.39 (t, J=5.67 Hz, 1H) 6.56 (s, 1H) 6.75 (dd, J=8.22, 1.57 Hz, 1H) 6.89-6.96 (m, 2H) 7.19 (t, J=7.83 Hz, 1H) 7.30 (dd, J=8.20, 2.00 Hz, 1H) 7.57 (d, J=1.96 Hz, 1H) 8.18 (d, J=8.22 Hz, 1H) 11.44 (s, 1H); LCMS m/z 507.2, 509.2 (M+H)$^+$.

Intermediate 6H

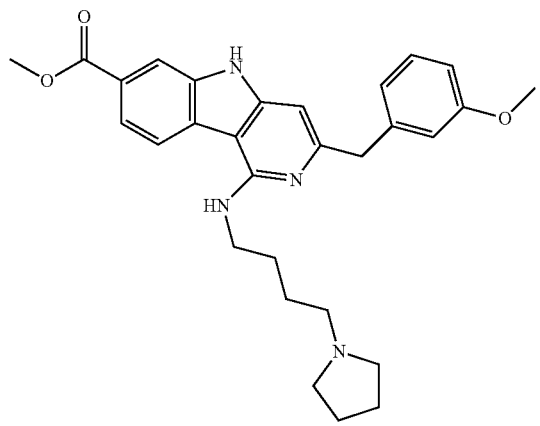

methyl 3-(3-methoxybenzyl)-1-((4-(pyrrolidin-1-yl)butyl)amino)-5H-pyrido[4,3-b]indole-7-carboxylate Following the procedure for the preparation of Example 1 using 7-bromo-3-(3-methoxybenzyl)-N-(4-(pyrrolidin-1-yl)butyl)-5H-pyrido[4,3-b]indol-1-amine (120 mg, 0.236 mmol), Pd(OAc)$_2$ (7.96 mg, 0.035 mmol), 4,5-bis(diphenylphosphino)-9,9-dimethylxanthene (41 mg, 0.071 mmol), MeOH (383 µl, 9.46 mmol) and triethylamine (1.65 mL, 11.8 mmol) afforded methyl 3-(3-methoxybenzyl)-1-((4-(pyrrolidin-1-yl)butyl)amino)-5H-pyrido[4,3-b]indole-7-carboxylate (53 mg, 0.109 mmol, 46.1% yield) as a white solid. $^1$H NMR (400 MHz, DMSO-d6) δ ppm 1.63-1.78 (m, 4H) 1.91 (br. s., 4H) 2.99 (br. s., 2H) 3.09-3.21 (m, 2H) 3.46 (br. s., 2H) 3.58-3.68 (m, 2H) 3.73 (s, 3H) 3.88 (s, 3H) 3.96 (s, 2H) 6.55-6.64 (m, 2H) 6.78 (m, J=8.20, 1.60 Hz, 1H) 6.89-6.98 (m, 2H) 7.21 (t, J=7.83 Hz, 1H) 7.79 (dd, J=8.20, 1.37 Hz, 1H) 8.01 (d, J=1.40 Hz, 1H) 8.34 (d, J=8.22 Hz, 1H) 11.62 (s, 1H); HRMS m/z 487.2701 (M+H)$^+$.

Example 7

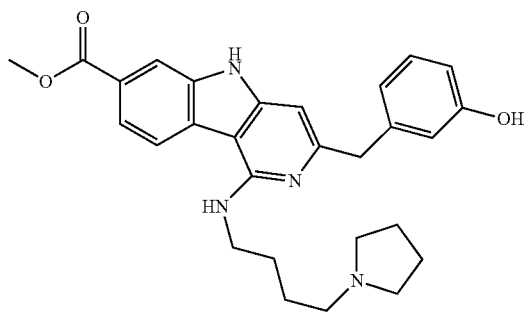 [SMILES: COC(=O)c1ccc2c(c1)[nH]c1cc(Cc3cccc(O)c3)nc(NCCCCN3CCCC3)c12]

methyl 3-(3-hydroxybenzyl)-1-((4-(pyrrolidin-1-yl)butyl)amino)-5H-pyrido[4,3-b]indole-7-carboxylate A mixture of methyl 3-(3-methoxybenzyl)-1-((4-(pyrrolidin-1-yl)butyl)amino)-5H-pyrido[4,3-b]indole-7-carboxylate (0.045 g, 0.092 mmol) in CH$_2$Cl$_2$ (7 mL) was cooled to −78° C. Boron tribromide 1M in CH$_2$Cl$_2$ (0.555 mL, 0.555 mmol) was added. The resulting suspension was stirred for 30 minutes and then slowly warmed to 20° C. and stirred for an additional 21 hours. MeOH (4.00 ml, 99 mmol) was added and the mixture was stirred for 1 hour at 20° C. and then heated to reflux for 7 hours. The mixture was concentrated to dryness on rotovap. The residue was purified two times on ISCO using a RediSep 4 g column (CH$_2$Cl$_2$/MeOH) to give 15 mg as an off-white sticky solid. The solid was suspended in Et$_2$O (2 mL) and stirred for 30 minutes. The solids were collected on Buchner and solids were washed with Et$_2$O (2×0.5 mL). Dried the product at 40° C. under high vacuum until constant weight to give methyl 3-(3-hydroxybenzyl)-1-((4-(pyrrolidin-1-yl)butyl)amino)-5H-pyrido[4,3-b]indole-7-carboxylate (13 mg, 0.028 mmol, 29.7% yield) as a tan solid. $^1$H NMR (400 MHz, DMSO-d6) δ ppm 1.60-1.79 (m, 4H) 1.80-2.08 (m, 4H) 2.80-3.06 (m, 2H) 3.08-3.21 (m, 2H) 3.41-3.55 (m, 2H) 3.57-3.69 (m, 2H) 3.82-3.96 (m, 5H) 6.49-6.66 (m, 3H) 6.71-6.82 (m, 2H) 7.08 (t, J=7.63 Hz, 1H) 7.79 (d, J=7.43 Hz, 1H) 8.01 (br. s., 1H) 8.34 (d, J=8.22 Hz, 1H) 9.23 (br. s., 1H) 11.62 (br. s., 1H); HRMS m/z 473.2568 (M+H)$^+$.

Example 8

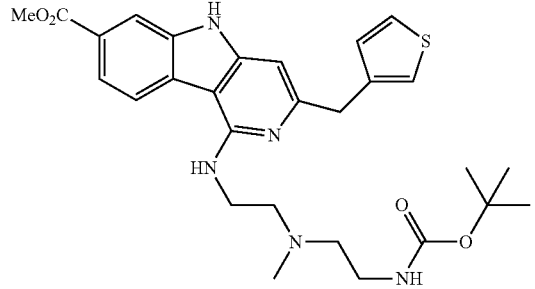 [SMILES: COC(=O)c1ccc2c(c1)[nH]c1cc(Cc3ccsc3)nc(NCCN(C)CCNC(=O)OC(C)(C)C)c12]

methyl 1-((2-((2-((tert-butoxycarbonyl)amino)ethyl)(methyl)amino)ethyl)amino)-3-(thiophen-3-ylmethyl)-5H-pyrido[4,3-b]indole-7-carboxylate Intermediate 8A

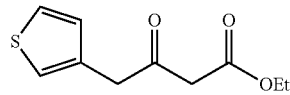 [SMILES: CCOC(=O)CC(=O)Cc1ccsc1]

ethyl 3-oxo-4-(thiophen-3-yl)butanoate

Following the procedure for the preparation of Intermediate 6A using 2-(thiophen-3-yl)acetic acid (6 g, 42.2 mmol), —CH$_2$Cl$_2$ (70 mL), CDI (7.41 g, 45.7 mmol) and Meldrum's acid (6.59 g, 45.7 mmol) for the first reaction and anhydrous EtOH (50 mL) for the second reaction afforded ethyl 3-oxo-4-(thiophen-3-yl)butanoate (8.23 g, 38.8 mmol, 92% yield) as a light orange oil. $^1$H NMR (400 MHz, DMSO-d6) δ ppm 1.18 (t, J=7.24 Hz, 3H) 3.63 (s, 2H) 3.88 (s, 2H) 4.08 (q, J=7.20 Hz, 2H) 6.96 (dd, J=4.89, 1.37 Hz, 1H) 7.29 (m, J=1.76, 0.98 Hz, 1H) 7.49 (dd, J=4.89, 2.93 Hz, 1H); LCMS m/z 213.0 (M+H)$^+$.

Intermediate 8B

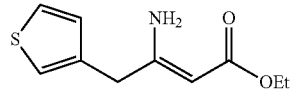 [SMILES: CCOC(=O)/C=C(\N)Cc1ccsc1]

ethyl 3-amino-4-(thiophen-3-yl)but-2-enoate

Following the procedure for the preparation of Intermediate 6B using ethyl 3-oxo-4-(thiophen-3-yl)butanoate (8.23 g, 38.8 mmol), ammonium acetate (14.94 g, 194 mmol) and anhydrous EtOH (155 mL) afforded ethyl 3-amino-4-(thiophen-3-yl)but-2-enoate (8.10 g, 38.3 mmol, 99% yield) as an orange oil. $^1$H NMR (400 MHz, DMSO-d6) δ ppm 1.12 (t, J=7.04 Hz, 3H) 3.40 (s, 2H) 3.94 (q, J=7.04 Hz, 2H) 4.30 (s, 1H) 7.04 (br. s, 1H) 7.02 (dd, J=4.70, 1.17 Hz, 1H) 7.30 (m, J=1.96, 1.17 Hz, 1H) 7.46 (dd, J=4.89, 2.93 Hz, 1H) 7.70 (br. s., 1H); LCMS m/z 212.1 (M+H)$^+$.

Intermediate 8C

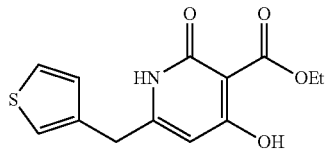 [SMILES: CCOC(=O)c1c(O)cc(Cc2ccsc2)[nH]c1=O]

ethyl 4-hydroxy-2-oxo-6-(thiophen-3-ylmethyl)-1,2-dihydropyridine-3-carboxylate

Following the procedure for the preparation of Intermediate 6C using ethyl 3-amino-4-(thiophen-3-yl)but-2-enoate (8.10 g, 38.3 mmol), diethyl malonate (7.31 mL, 47.9 mmol) and sodium ethoxide 21% wt. in ethanol (20.04 ml, 53.7 mmol) afforded ethyl 4-hydroxy-2-oxo-6-(thiophen-3-ylmethyl)-1,2-dihydropyridine-3-carboxylate (6.59 g, 23.59 mmol, 61.5% yield) as a tan solid. $^1$H NMR (400 MHz, DMSO-d6) δ ppm 1.25 (t, J=7.20 Hz, 3H) 3.77 (s, 2H) 4.23 (q, J=7.20 Hz, 2H) 5.71 (s, 1H) 7.06 (dd, J=5.09, 1.17 Hz, 1H) 7.36 (dd, J=2.74, 1.17 Hz, 1H) 7.51 (dd, J=5.10, 2.70 Hz, 1H) 11.53 (br. s., 1H) 12.42 (s, 1H); LCMS m/z 280.1 (M+H)$^+$.

Intermediate 8D

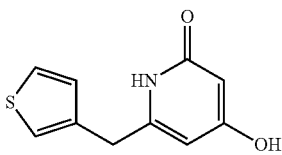 [SMILES: O=c1cc(O)cc(Cc2ccsc2)[nH]1]

4-hydroxy-6-(thiophen-3-ylmethyl)pyridin-2(1H)-one

Following the procedure for the preparation of Intermediate 6D using ethyl 4-hydroxy-2-oxo-6-(thiophen-3-ylmethyl)-1,2-dihydropyridine-3-carboxylate (6.59 g, 23.59 mmol), potassium hydroxide (7.79 g, 118 mmol) and water (57.4 mL) afforded 4-hydroxy-6-(thiophen-3-ylmethyl)pyridin-2(1H)-one (4.62 g, 22.29 mmol, 94% yield) as an off-white solid. $^1$H NMR (400 MHz, DMSO-d6) δ ppm 3.71 (s, 2H) 5.34 (d, J=2.20 Hz, 1H) 5.55 (d, J=2.20 Hz, 1H) 7.04 (dd, J=4.89, 1.37 Hz, 1H) 7.32 (m, J=1.76, 0.98 Hz, 1H) 7.49 (dd, J=4.89, 2.93 Hz, 1H) 10.34 (s, 1H) 11.04 (br. s., 1H); LCMS m/z 208.2 (M+H)$^+$.

Intermediate 8E

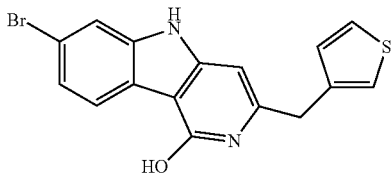 [SMILES: Oc1nc(Cc2ccsc2)cc2[nH]c3cc(Br)ccc3c12]

7-bromo-3-(thiophen-3-ylmethyl)-5H-pyrido[4,3-b]indol-1-ol

Following the procedure for the preparation of Intermediate 2D using (3-bromophenyl)hydrazine free base (8.12 g, 43.4 mmol) and intermediate 8D (4.50 g, 21.7 mmol) afforded 7-bromo-3-(thiophen-3-ylmethyl)-5H-pyrido[4,3-b]indol-1-ol (6.69 g, 18.62 mmol, 86% yield) as a gray solid containing a mixture of 7-bromo and 9-bromo isomers (2:1 ratio). This intermediate was not purified by flash chromatography. LCMS m/z 359.0, 361.0 (M+H)$^+$.

Intermediate 8F

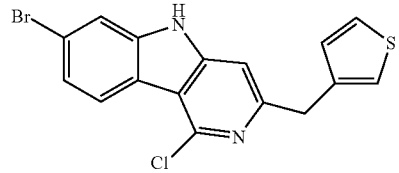 [SMILES: Clc1nc(Cc2ccsc2)cc2[nH]c3cc(Br)ccc3c12]

7-bromo-1-chloro-3-(thiophen-3-ylmethyl)-5H-pyrido[4,3-b]indole

Following the procedure for the preparation of Intermediate 2E using 7-bromo-3-(thiophen-3-ylmethyl)-5H-pyrido[4,3-b]indol-1-ol (6.69 g, 18.63 mmol) and phosphorus oxychloride (52.1 mL, 558 mmol) afforded 7.85 g as a crude dark gray solid. The residue (2.15 g) was purified on ISCO using a RediSep 80 g column and (5.70 g) was purified on ISCO using a RediSep Gold 220 g column (Hexane/CH2Cl2/MeOH) to give 7.15 g as a dark solid. The solid was suspended in 1,4-dioxane (220 mL) and heated to reflux for 1 hour. Cooled to 20° C. and stirred for 16 hours. The solids were filtered over Buchner and the solids were washed with 1,4-dioxane (2×12.5 mL). The filtrate was concentrated to dryness to give 3.38 g as a brown foam. The foam was divided into two portions and each portions were purified on ISCO using a RediSep 120 g column (Hex/EtOAc) to give 7-bromo-1-chloro-3-(thiophen-3-ylmethyl)-5H-pyrido[4,3-b]indole (1.54 g, 4.08 mmol, 21.90% yield) as a light orange solid. LCMS m/z 377.0, 379.0 (M+H)$^+$.

Intermediate 8G

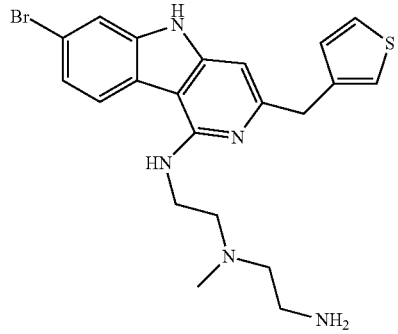 [SMILES: CN(CCN)CCNc1nc(Cc2ccsc2)cc2[nH]c3cc(Br)ccc3c12]

N[1]-(2-aminoethyl)-N[2]-(7-bromo-3-(thiophen-3-ylmethyl)-5H-pyrido[4,3-b]indol-1-yl)-N[1]-methylethane-1,2-diamine Following the procedure for the preparation of Intermediate 2F using the Intermediate 8F (100 mg, 0.265 mmol) and N[1]-(2-aminoethyl)-N[1]-methylethane-1,2-diamine (1.023 ml, 7.94 mmol) afforded N[1]-(2-aminoethyl)-N[2]-(7-bromo-3-(thiophen-3-ylmethyl)-5H-pyrido[4,3-b]indol-1-yl)-N[1]-methylethane-1,2-diamine (107 mg, 0.233 mmol, 88% yield) as a yellow foam. $^1$H NMR (400 MHz, DMSO-d6) δ ppm 1.54 (br. s., 2H) 2.26 (s, 3H) 2.40 (t, J=6.46 Hz, 2H) 2.62 (t, J=6.46 Hz, 4H) 3.66 (q, J=6.26 Hz, 2H) 3.98 (s, 2H) 6.29 (t, J=5.67 Hz, 1H) 6.56 (s, 1H) 7.11 (dd, J=4.89, 0.98 Hz, 1H) 7.27 (d, J=1.96 Hz, 1H) 7.31 (dd, J=8.41, 1.76 Hz, 1H) 7.44 (dd, J=5.09, 3.13 Hz, 1H) 7.58 (d, J=1.96 Hz, 1H) 8.08 (d, J=8.22 Hz, 1H) 11.46 (br. s., 1H); LCMS m/z 458.1, 460.1 (M+H)+.

Intermediate 8H

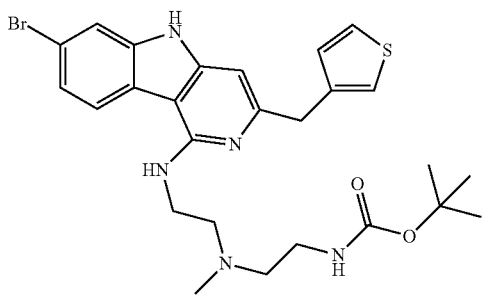 [SMILES: CN(CCNC(=O)OC(C)(C)C)CCNc1nc(Cc2ccsc2)cc2[nH]c3cc(Br)ccc3c12]

tert-butyl (2-((2-((7-bromo-3-(thiophen-3-ylmethyl)-5H-pyrido[4,3-b]indol-1-yl)amino)ethyl)(methyl)amino)ethyl)carbamate To a mixture of N[1]-(2-aminoethyl)-N[2]-(7-bromo-3-(thiophen-3-ylmethyl)-5H-pyrido[4,3-b]indol-1-yl)-N[1]-methylethane-1,2-diamine (0.099 g, 0.216 mmol) and triethylamine (0.060 ml, 0.432 mmol) in CH$_2$Cl$_2$ (4.6 mL) was added a solution of di-tert-butyl dicarbonate (0.070 mL, 0.302 mmol) in CH$_2$Cl$_2$ (0.46 mL). Stirred at 20° C. for 15 minutes. The mixture was concentrated to dryness on rotovap. The residue was purified on ISCO using a RediSep 12 g column (CH$_2$Cl$_2$/MeOH/NH$_4$OH) to give tert-butyl (2-((2-((7-bromo-3-(thiophen-3-ylmethyl)-5H-pyrido[4,3-b]indol-1-yl)amino)ethyl)(methyl)amino)ethyl)carbamate (107 mg, 0.192 mmol, 89% yield) as a white foam. $^1$H NMR (400 MHz, DMSO-d6) δ ppm 1.33 (s, 9H) 2.27 (br. s., 3H) 2.46 (br. s., 2H) 2.64 (br. s., 2H) 3.06 (br. s., 2H) 3.65 (br. s., 2H) 3.99 (s, 2H) 6.27 (br. s., 1H) 6.56 (br. s., 1H) 6.62 (br. s., 1H) 7.10 (d, J=4.70 Hz, 1H) 7.26 (d, J=2.35 Hz, 1H) 7.32 (d, J=8.22 Hz, 1H) 7.43 (dd, J=4.70, 3.13 Hz, 1H) 7.58 (s, 1H) 8.08 (d, J=7.83 Hz, 1H) 11.47 (br. s., 1H); LCMS m/z 558.2, 560.2 (M+H)+.

Example 8

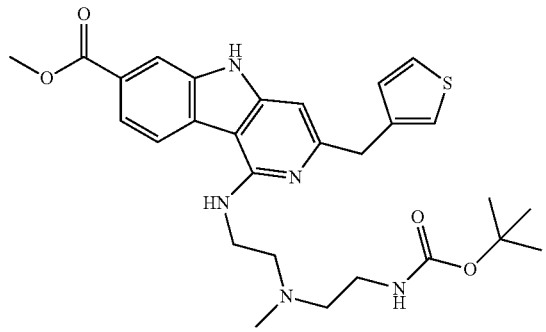 [SMILES: COC(=O)c1ccc2c(c1)[nH]c1cc(Cc3ccsc3)nc(NCCN(C)CCNC(=O)OC(C)(C)C)c12]

methyl 1-((2-((2-((tert-butoxycarbonyl)amino)ethyl)(methyl)amino)ethyl)amino)-3-(thiophen-3-ylmethyl)-5H-pyrido[4,3-b]indole-7-carboxylate Following the procedure for the preparation of Example 1 using tert-butyl (2-((2-((7-bromo-3-(thiophen-3-ylmethyl)-5H-pyrido[4,3-b]indol-1-yl)amino)ethyl)(methyl)amino)ethyl)carbamate (88 mg, 0.158 mmol), Pd(OAc)$_2$ (5.31 mg, 0.024 mmol), 4,5-bis(diphenylphosphino)-9,9-dimethylxanthene (27.3 mg, 0.047 mmol), MeOH (255 μl, 6.30 mmol) and triethylamine (1.1 mL, 7.88 mmol) afforded methyl 1-((2-((2-((tert-butoxycarbonyl)amino)ethyl)(methyl)amino)ethyl)amino)-3-(thiophen-3-ylmethyl)-5H-pyrido[4,3-b]indole-7-carboxylate (46 mg, 0.086 mmol, 54.3% yield) as a white foam. $^1$H NMR (400 MHz, DMSO-d6) δ ppm 1.33 (s, 9H) 2.20-2.34 (m, 3H) 2.43 (br. s, 2H) 2.65 (br. s., 2H) 3.07 (br. s., 2H) 3.67 (br. s., 2H) 3.88 (s, 3H) 4.01 (s, 2H) 6.43 (br. s., 1H) 6.58 (s, 1H) 6.63 (br. s., 1H) 7.11 (d, J=4.70 Hz, 1H) 7.27 (d, J=1.57 Hz, 1H) 7.44 (dd, J=4.70, 3.13 Hz, 1H) 7.81 (d, J=8.22 Hz, 1H) 8.01 (s, 1H) 8.22 (d, J=8.22 Hz, 1H) 11.62 (br. s., 1H); HRMS m/z 538.2485 (M+H)+.

Example 9

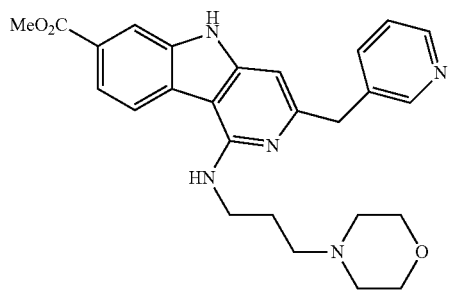 [SMILES: COC(=O)c1ccc2c(c1)[nH]c1cc(Cc3cccnc3)nc(NCCCN3CCOCC3)c12]

methyl 1-((3-morpholinopropyl)amino)-3-(pyridin-3-ylmethyl)-5H-pyrido[4,3-b]indole-7-carboxylate Intermediate 9A

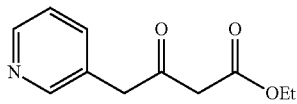

ethyl 3-oxo-4-(pyridin-3-yl)butanoate

To a mixture of 2-(pyridin-3-yl)acetic acid hydrochloride (15 g, 86 mmol) and triethylamine (12.04 mL, 86 mmol) in $CH_2Cl_2$ (144 mL) was added CDI (15.17 g, 94 mmol) in one portion. Stirred at 20° C. for 45 minutes and then added Meldrum's acid (13.49 g, 94 mmol). The reaction mixture was stirred at 20° C. for 19 hours. The mixture was concentrated to dryness on rotovap. The resulting oil was dissolved in EtOAc (225 mL). Extracted the organic layer with saturated $NaHCO_3$ (2×110 mL) then with water-saturated $NaHCO_3$ (1:1, 110 mL). To the combined aqueous layers was added water (110 mL). The aqueous layer was washed with EtOAc (3×110 mL). The aqueous layer was acidified to pH 4 with concentrated HCl (44 mL). Stirred the resulting suspension for 30 minutes. The solids were collected on Buchner and solids were washed with water (2×15 mL). Dried the product at 20° C. under high vacuum until constant weight. To the filtrate was added NaCl (50 g) and stirred until dissolution. The filtrate was extracted with $CH_2Cl_2$ (5×175 mL). The organic layer was dried over anhydrous $MgSO_4$, filtered and concentrated to dryness. The combined intermediates (21.42 g) were dissolved in anhydrous EtOH (202 mL) and heated to reflux for 5 hours. The mixture was concentrated to dryness on rotovap. The resulting oil was added to a solution of sodium bicarbonate 5% wt. in water (300 mL). Extracted the mixture with EtOAc (3×150 mL). The combined organic layers were washed with water (200 mL) then with brine (200 mL). The water and brine washes were combined and back-extracted with EtOAc (150 mL). The combined organic layers were dried over anhydrous $MgSO_4$, filtered and concentrated to dryness to give ethyl 3-oxo-4-(pyridin-3-yl)butanoate (15.21 g, 73.4 mmol, 85% yield) as an orange oil. $^1$H NMR (400 MHz, DMSO-d6) δ ppm 1.18 (t, J=7.24 Hz, 3H) 3.72 (s, 2H) 3.95 (s, 2H) 4.09 (q, J=7.17 Hz, 2H) 7.35 (dd, J=7.63, 4.80 Hz, 1H) 7.59 (d, J=7.60 Hz, 1H) 8.38 (s, 1H) 8.46 (d, J=4.80 Hz, 1H); LCMS m/z 208.1 (M+H)$^+$.

Intermediate 9B

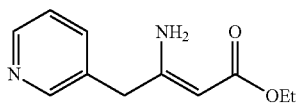 [SMILES: CCOC(=O)/C=C(\N)Cc1cccnc1]

ethyl 3-amino-4-(pyridin-3-yl)but-2-enoate

Following the procedure for the preparation of Intermediate 6B using ethyl 3-oxo-4-(pyridin-3-yl)butanoate (15.21 g, 73.4 mmol), ammonium acetate (28.3 g, 367 mmol) and EtOH (294 mL) afforded ethyl 3-amino-4-(pyridin-3-yl)but-2-enoate (12.52 g, 60.7 mmol, 83% yield) as a light yellow solid. $^1$H NMR (400 MHz, DMSO-d6) δ ppm 1.12 (t, J=7.04 Hz, 3H) 3.41 (s, 2H) 3.95 (q, J=7.04 Hz, 2H) 4.32 (s, 1H) 7.13 (br. s., 1H) 7.30-7.37 (m, 1H) 7.71 (dt, J=7.83, 1.96 Hz, 2H) 8.44 (dd, J=4.70, 1.57 Hz, 1H) 8.52 (d, J=1.96 Hz, 1H); LCMS m/z 207.2 (M+H)$^+$.

Intermediate 9C

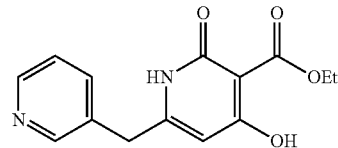 [SMILES: CCOC(=O)c1c(O)cc(Cc2cccnc2)[nH]c1=O]

ethyl 4-hydroxy-2-oxo-6-(pyridin-3-ylmethyl)-1,2-dihydropyridine-3-carboxylate

Following the procedure for the preparation of Intermediate 60 using ethyl 3-amino-4-(pyridin-3-yl)but-2-enoate (12.52 g, 60.7 mmol), diethyl malonate (13.89 mL, 91 mmol) and sodium ethoxide 21% wt. in ethanol (37.4 ml, 100 mmol) afforded ethyl 4-hydroxy-2-oxo-6-(pyridin-3-ylmethyl)-1,2-dihydropyridine-3-carboxylate (10.72 g, 39.1 mmol, 64.4% yield) as a tan solid. $^1$H NMR (400 MHz, DMSO-d6) δ ppm 1.24 (t, J=7.04 Hz, 3H) 3.80 (s, 2H) 4.23 (q, J=7.04 Hz, 2H) 5.75 (s, 1H) 7.32-7.41 (m, 1H) 7.73 (dt, J=7.83, 1.96 Hz, 1H) 8.48 (dd, J=4.70, 1.56 Hz, 1H) 8.55 (d, J=1.56 Hz, 1H) 11.60 (br. s., 1H) 12.38 (s, 1H); LCMS m/z 275.2 (M+H)$^+$.

Intermediate 9D

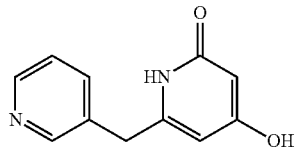 [SMILES: O=c1cc(O)cc(Cc2cccnc2)[nH]1]

4-hydroxy-6-(pyridin-3-ylmethyl)pyridin-2(1H)-one

A mixture of ethyl 4-hydroxy-2-oxo-6-(pyridin-3-ylmethyl)-1,2-dihydropyridine-3-carboxylate (10.72 g, 39.1 mmol) in HCl 6M in water (78 mL, 469 mmol) was heated to reflux for 22.5 hours. The mixture was cooled to 20° C. and slowly basified to pH 8-9 with ammonium hydroxide 28% $NH_3$ (38.0 ml, 563 mmol). To the resulting solution was added very slowly acetic acid (7.68 mL, 134 mmol). The resulting suspension was stirred for 1 hour and the solids were collected on Buchner. The solids were washed with water (3×20 mL). Dried the product at 20° C. under high vacuum until constant weight to give 4-hydroxy-6-(pyridin-3-ylmethyl)pyridin-2(1H)-one (7.56 g, 37.4 mmol, 96% yield) as a tan solid. $^1$H NMR (400 MHz, DMSO-d6) δ ppm 3.73 (s, 2H) 5.35 (d, J=2.20 Hz, 1H) 5.56 (d, J=2.20 Hz, 1H) 7.32-7.38 (m, 1H) 7.70 (dt, J=7.83, 1.96 Hz, 1H) 8.46 (dd, J=4.70, 1.57 Hz, 1H) 8.53 (d, J=1.57 Hz, 1H) 10.36 (br. s., 1H) 11.11 (br. s., 1H); LCMS m/z 203.2 (M+H)$^+$.

Intermediate 9E

7-bromo-3-(pyridin-3-ylmethyl)-5H-pyrido[4,3-b]
indol-1-ol

Following the procedure for the preparation of Intermediate 2D using (3-bromophenyl)hydrazine free base (8.32 g, 44.5 mmol) and intermediate 9D (4.50 g, 22.25 mmol) afforded 7-bromo-3-(pyridin-3-ylmethyl)-5H-pyrido[4,3-b] indol-1-ol (7.20 g, 20.33 mmol, 91% yield) as a gray solid containing a mixture of 7-bromo and 9-bromo isomers (2.2:1 ratio). This intermediate was not purified by flash chromatography. LCMS m/z 354.1, 356.1 (M+H)+.

Intermediate 9F

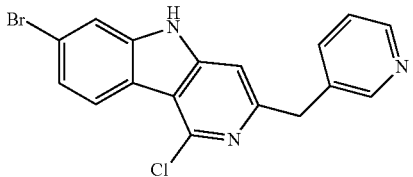 [SMILES: Clc1nc(Cc2cccnc2)cc2[nH]c3cc(Br)ccc3c12]

7-bromo-1-chloro-3-(pyridin-3-ylmethyl)-5H-pyrido
[4,3-b]indole

A mixture of 7-bromo-3-(pyridin-3-ylmethyl)-5H-pyrido [4,3-b]indol-1-ol (2.40 g, 6.78 mmol) in phosphorus oxychloride (18.95 mL, 203 mmol) was heated to 175° C. for 15 minutes in a microwave apparatus. Toluene (100 mL) was added and the mixture concentrated to dryness on rotovap. Water (60.0 mL) was added and the mixture was stirred for 10 minutes. Filtered to remove black solid from the mixture. The flask and solids were washed with Water (20 mL). The combined filtrates were basified to pH 8-10 by adding potassium hydroxide 45% wt. in water (7 mL). Added EtOAc (100 mL) and MeOH (10 mL) and stirred vigorously for 10 minutes. Filtered the solids and rinsed flask and solids with EtOAc (20 mL). Separated the layers in the obtained filtrate. The aqueous layer was extracted with EtOAc (2×100 mL). The combined organic layers were washed with brine (100 mL). The organic layer was dried over anhydrous MgSO4, filtered and concentrated to give 1.63 g as a tan solid. The solid was suspended in 1,4-dioxane (50 mL) and heated to reflux for 30 minutes. Slowly cooled to 20° C. and stirred for 16 hours. The solids were collected on Buchner. The solids were washed with 1,4-dioxane (2×5 mL). The combined filtrates were concentrated to dryness to give 943 mg as a brown solid. The residue was purified on ISCO using a RediSep 80 g column (EtOAc/MeOH) to give 7-bromo-1-chloro-3-(pyridin-3-ylmethyl)-5H-pyrido[4,3-b] indole (450 mg, 1.208 mmol, 17.82% yield) as a tan solid. LCMS m/z 372.1, 374.0 (M+H)+.

Intermediate 9G

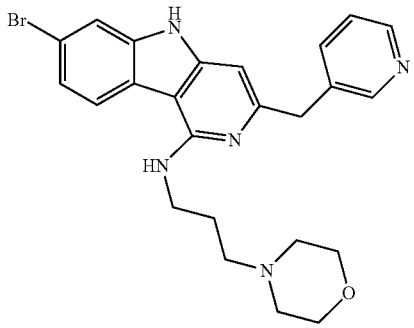 [SMILES: Brc1ccc2c(c1)[nH]c1cc(Cc3cccnc3)nc(NCCCN3CCOCC3)c12]

7-bromo-N-(3-morpholinopropyl)-3-(pyridin-3-ylmethyl)-5H-pyrido[4,3-b]indol-1-amine Following the procedure for the preparation of Intermediate 2F using the Intermediate 9F (100 mg, 0.268 mmol) and 3-morpholinopropan-1-amine (0.588 ml, 4.03 mmol) afforded 7-bromo-N-(3-morpholinopropyl)-3-(pyridin-3-ylmethyl)-5H-pyrido[4,3-b]indol-1-amine (109 mg, 0.227 mmol, 85% yield) as a tan solid. $^1$H NMR (400 MHz, DMSO-d6) δ ppm 1.77 (quin, J=7.04 Hz, 2H) 2.22-2.42 (m, 6H) 3.47-3.63 (m, 6H) 3.98 (s, 2H) 6.44 (t, J=5.67 Hz, 1H) 6.63 (s, 1H) 7.25-7.34 (m, 2H) 7.58 (d, J=1.57 Hz, 1H) 7.74 (dt, J=8.02, 1.66 Hz, 1H) 8.17 (d, J=8.61 Hz, 1H) 8.39 (dd, J=5.09, 1.56 Hz, 1H) 8.58 (d, J=1.96 Hz, 1H) 11.49 (s, 1H); LCMS m/z 480.1, 482.2 (M+H)+.

Example 9

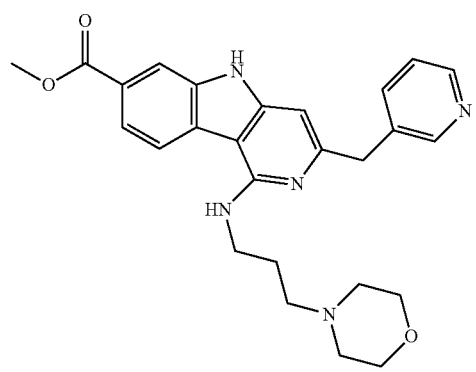 [SMILES: COC(=O)c1ccc2c(c1)[nH]c1cc(Cc3cccnc3)nc(NCCCN3CCOCC3)c12]

methyl 1-((3-morpholinopropyl)amino)-3-(pyridin-3-ylmethyl)-5H-pyrido[4,3-b]indole-7-carboxylate Following the procedure for the preparation of Example 1 using 7-bromo-N-(3-morpholinopropyl)-3-(pyridin-3-ylmethyl)-5H-pyrido[4,3-b]indol-1-amine (100 mg, 0.208 mmol), Pd(OAc)2 (4.67 mg, 0.021 mmol), 4,5-bis(diphenylphosphino)-9,9-dimethylxanthene (24.1 mg, 0.042 mmol), MeOH (337 μl, 8.33 mmol) and triethylamine (1.45 mL, 10.41 mmol) afforded methyl 1-((3-morpholinopropyl)

amino)-3-(pyridin-3-ylmethyl)-5H-pyrido[4,3-b]indole-7-carboxylate (83 mg, 0.181 mmol, 87% yield) as a tan solid. $^1$H NMR (400 MHz, DMSO-d6) δ ppm 1.78 (quin, J=7.04 Hz, 2H) 2.23-2.43 (m, 6H) 3.50-3.64 (m, 6H) 3.88 (s, 3H) 4.00 (s, 2H) 6.61 (t, J=5.67 Hz, 1H) 6.66 (s, 1H) 7.30 (dd, J=7.83, 4.70 Hz, 1H) 7.75 (d, J=7.43 Hz, 1H) 7.78 (d, J=8.22 Hz, 1H) 8.01 (s, 1H) 8.32 (d, J=8.22 Hz, 1H) 8.40 (d, J=4.70 Hz, 1H) 8.59 (d, J=1.57 Hz, 1H) 11.64 (s, 1H); HRMS m/z 460.2354 (M+H)$^+$.

Example 10

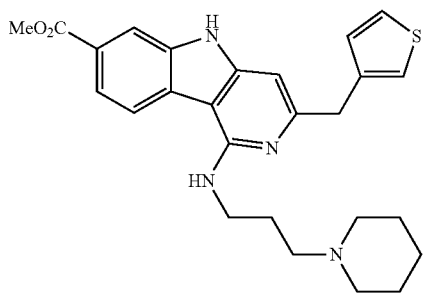 [SMILES: COC(=O)c1ccc2c(c1)[nH]c1cc(Cc3ccsc3)nc(NCCCN3CCCCC3)c12]

methyl 1-((3-(piperidin-1-yl)propyl)amino)-3-(thiophen-3-ylmethyl)-5H-pyrido[4,3-b]indole-7-carboxylate Intermediate 10A

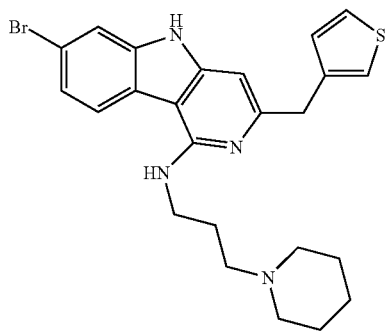 [SMILES: Brc1ccc2c(c1)[nH]c1cc(Cc3ccsc3)nc(NCCCN3CCCCC3)c12]

7-bromo-N-(3-(piperidin-1-yl)propyl)-3-(thiophen-3-ylmethyl)-5H-pyrido[4,3-b]indol-1-amine Following the procedure for the preparation of Intermediate 2F using the Intermediate 8F (300 mg, 0.794 mmol) and 3-(piperidin-1-yl)propan-1-amine (1.894 ml, 11.91 mmol) afforded 7-bromo-N-(3-(piperidin-1-yl)propyl)-3-(thiophen-3-ylmethyl)-5H-pyrido[4,3-b]indol-1-amine (350 mg, 0.724 mmol, 91% yield) as a yellow foam. $^1$H NMR (400 MHz, DMSO-d6) δ ppm 1.33-1.44 (m, 2H) 1.51 (quin, J=5.28 Hz, 4H) 1.83 (quin, J=7.04 Hz, 2H) 2.20-2.46 (m, 6H) 3.60 (q, J=6.52 Hz, 2H) 3.98 (s, 2H) 6.43 (t, J=5.48 Hz, 1H) 6.54 (s, 1H) 7.11 (dd, J=4.89, 0.98 Hz, 1H) 7.26 (m, J=2.00 Hz, 1H) 7.27-7.32 (m, 1H) 7.43 (dd, J=4.70, 3.13 Hz, 1H) 7.57 (d, J=1.96 Hz, 1H) 8.16 (d, J=8.22 Hz, 1H) 11.45 (s, 1H); LCMS m/z 483.1, 485.1 (M+H)$^+$.

Example 10

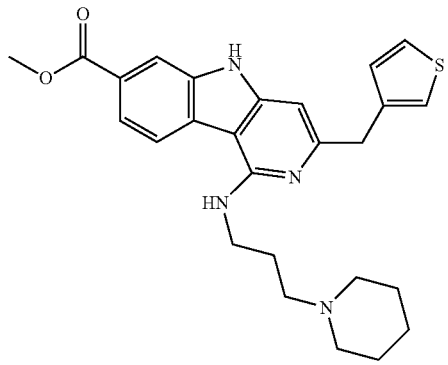 [SMILES: COC(=O)c1ccc2c(c1)[nH]c1cc(Cc3ccsc3)nc(NCCCN3CCCCC3)c12]

methyl 1-((3-(piperidin-1-yl)propyl)amino)-3-(thiophen-3-ylmethyl)-5H-pyrido[4,3-b]indole-7-carboxylate Following the procedure for the preparation of Example 1 using 7-bromo-N-(3-(piperidin-1-yl)propyl)-3-(thiophen-3-ylmethyl)-5H-pyrido[4,3-b]indol-1-amine (200 mg, 0.414 mmol), Pd(OAc)$_2$ (9.29 mg, 0.041 mmol), 4,5-bis(diphenylphosphino)-9,9-dimethylxanthene (47.9 mg, 0.083 mmol), MeOH (669 μl, 16.55 mmol) and triethylamine (2.88 mL, 20.68 mmol) afforded methyl 1-((3-(piperidin-1-yl)propyl)amino)-3-(thiophen-3-ylmethyl)-5H-pyrido[4,3-b]indole-7-carboxylate (164 mg, 0.355 mmol, 86% yield) as an orange foam. $^1$H NMR (400 MHz, DMSO-d6) δ ppm 1.09 (br. s., 2H) 1.43 (br. s., 2H) 1.57 (br. s., 4H) 1.91 (br. s., 2H) 2.33 (br. s., 2H) 2.82 (br. s., 2H) 3.63 (q, J=6.26 Hz, 2H) 3.88 (s, 3H) 4.00 (s, 2H) 6.58 (s, 1H) 6.63 (br. s., 1H) 7.11 (d, J=5.09 Hz, 1H) 7.27 (d, J=2.35 Hz, 1H) 7.44 (dd, J=4.89, 2.93 Hz, 1H) 7.78 (d, J=8.22 Hz, 1H) 8.01 (s, 1H) 8.32 (d, J=8.61 Hz, 1H) 11.62 (s, 1H); HRMS m/z 463.2171 (M+H)$^+$.

Example 11

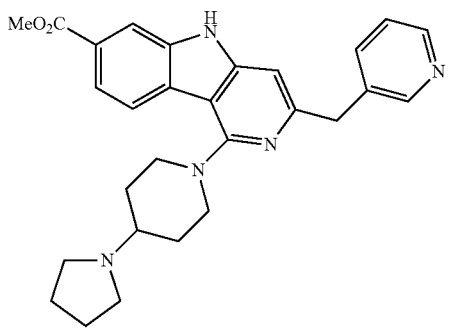 [SMILES: COC(=O)c1ccc2c(c1)[nH]c1cc(Cc3cccnc3)nc(N3CCC(N4CCCC4)CC3)c12]

93 methyl 3-(pyridin-3-ylmethyl)-1-(4-(pyrrolidin-1-yl)piperidin-1-yl)-5H-pyrido[4,3-b]indole-7-carboxylate Intermediate 11A

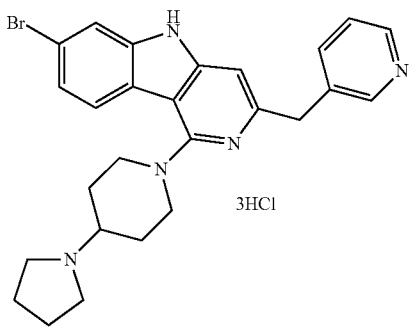 [SMILES: Brc1ccc2c(c1)[nH]c1cc(Cc3cccnc3)nc(N3CCC(N4CCCC4)CC3)c12]

7-bromo-3-(pyridin-3-ylmethyl)-1-(4-(pyrrolidin-1-yl)piperidin-1-yl)-5H-pyrido[4,3-b]indole trihydrochloride Following the procedure for the preparation of Intermediate 2F using the Intermediate 9F (100 mg, 0.268 mmol) and 4-(pyrrolidin-1-yl)piperidine (0.621 g, 4.03 mmol) afforded crude product. The obtained oil was dissolved in MeOH (3 mL). HCl 4M in 1,4-dioxane (0.235 ml, 0.939 mmol) was added followed by slow addition of EtOAc (7.5 mL). The resulting suspension was stirred for 2 hours. The solids were collected on Buchner and washed with MeOH/EtOAc (1:5, 3×0.5 mL). Dried the product at 20° C. under high vacuum until constant weight to give 7-bromo-3-(pyridin-3-ylmethyl)-1-(4-(pyrrolidin-1-yl)piperidin-1-yl)-5H-pyrido[4,3-b]indole trihydrochloride (117 mg, 0.195 mmol, 72.7% yield) as a tan solid. $^1$H NMR (400 MHz, DMSO-d6) δ ppm 1.80-2.10 (m, 6H) 2.13-2.30 (m, 2H) 2.89-3.18 (m, 4H) 3.39 (br. s., 1H) 3.49-3.59 (m, 2H) 3.94 (d, J=11.35 Hz, 2H) 4.37-4.52 (m, 2H) 7.22 (br. s., 1H) 7.47 (d, J=8.22 Hz, 1H) 7.69 (d, J=8.22 Hz, 1H) 7.79 (br. s., 1H) 7.95 (m, J=5.90, 5.90 Hz, 1H) 8.52 (d, J=7.43 Hz, 1H) 8.78 (d, J=5.09 Hz, 1H) 8.97 (s, 1H) 10.97 (br. s., 2H) 12.00 (br. s, 2H); LCMS m/z 490.2, 492.1 (M+H)$^+$.

Example 11

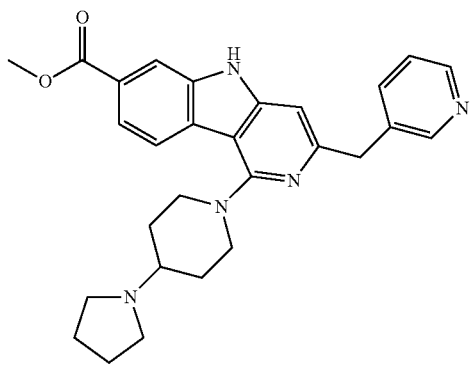 [SMILES: COC(=O)c1ccc2c(c1)[nH]c1cc(Cc3cccnc3)nc(N3CCC(N4CCCC4)CC3)c12]

94 methyl 3-(pyridin-3-ylmethyl)-1-(4-(pyrrolidin-1-yl)piperidin-1-yl)-5H-pyrido[4,3-b]indole-7-carboxylate Following the procedure for the preparation of Example 1 using 7-bromo-3-(pyridin-3-ylmethyl)-1-(4-(pyrrolidin-1-yl)piperidin-1-yl)-5H-pyrido[4,3-b]indole trihydrochloride (100 mg, 0.167 mmol), Pd(OAc)$_2$ (3.74 mg, 0.017 mmol), 4,5-bis(diphenylphosphino)-9,9-dimethylxanthene (19.3 mg, 0.033 mmol), MeOH (270 μl, 6.67 mmol) and triethylamine (1.16 mL, 8.34 mmol) afforded methyl 3-(pyridin-3-ylmethyl)-1-(4-(pyrrolidin-1-yl)piperidin-1-yl)-5H-pyrido[4,3-b]indole-7-carboxylate (64.5 mg, 0.137 mmol, 82% yield) as a white solid. $^1$H NMR (400 MHz, DMSO-d6) δ ppm 1.62-1.79 (m, 6H) 2.04 (d, J=10.17 Hz, 2H) 2.22 (br. s., 1H) 2.56 (br. s., 4H) 2.93 (t, J=11.93 Hz, 2H) 3.78 (d, J=12.91 Hz, 2H) 3.89 (s, 3H) 4.11 (s, 2H) 6.99 (s, 1H) 7.31 (dd, J=7.83, 4.70 Hz, 1H) 7.76 (d, J=7.83 Hz, 1H) 7.82-7.91 (m, 2H) 8.07 (s, 1H) 8.41 (dd, J=4.70, 1.17 Hz, 1H) 8.57-8.64 (m, 1H) 11.83 (s, 1H); HRMS m/z 470.2550 (M+H)$^+$.

Example 12

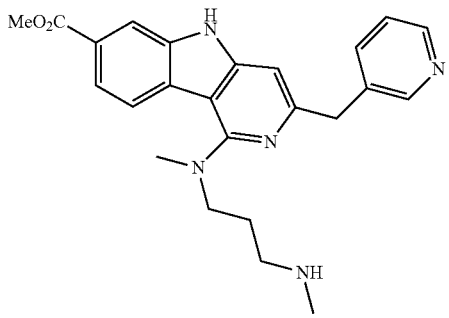 [SMILES: CNCCCN(C)c1nc(Cc2cccnc2)cc2[nH]c3cc(C(=O)OC)ccc3c12]

methyl 1-(methyl(3-(methylamino)propyl)amino)-3-(pyridin-3-ylmethyl)-5H-pyrido[4,3-b]indole-7-carboxylate Intermediate 12A

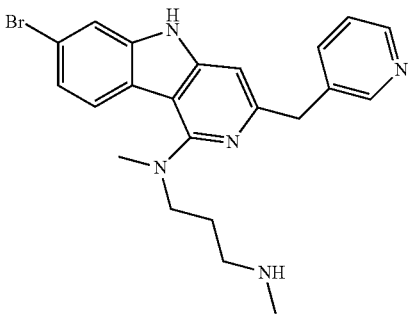 [SMILES: CNCCCN(C)c1nc(Cc2cccnc2)cc2[nH]c3cc(Br)ccc3c12]

$N^1$-(7-bromo-3-(pyridin-3-ylmethyl)-5H-pyrido[4,3-b]indol-1-yl)-$N^1$,$N^3$-dimethylpropane-1,3-diamine Following the procedure for the preparation of Intermediate 2F using the Intermediate 9F (100 mg, 0.268 mmol)

and N¹,N³-dimethylpropane-1,3-diamine (1.007 ml, 8.05 mmol) afforded N¹-(7-bromo-3-(pyridin-3-ylmethyl)-5H-pyrido[4,3-b]indol-1-yl)-N¹,N³-dimethylpropane-1,3-diamine (109 mg, 0.249 mmol, 93% yield) as a tan foam. $^1$H NMR (400 MHz, DMSO-d6) δ ppm 1.69 (quin, J=7.04 Hz, 2H) 2.16 (s, 3H) 2.39 (t, J=7.04 Hz, 2H) 2.97 (s, 3H) 3.40-3.49 (m, 2H) 4.08 (s, 2H) 6.92 (s, 1H) 7.30 (dd, J=7.83, 4.70 Hz, 1H) 7.37 (dd, J=8.41, 1.76 Hz, 1H) 7.65 (d, J=1.96 Hz, 1H) 7.71-7.79 (m, 2H) 8.40 (dd, J=4.70, 1.57 Hz, 1H) 8.60 (d, J=1.96 Hz, 1H) 11.67 (br. s., 2H); LCMS m/z 438.2, 440.1 (M+H)⁺.

Intermediate 12B

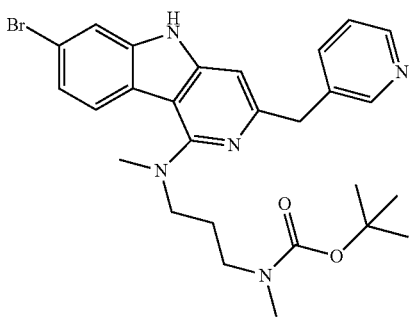 [SMILES: CN(CCCN(C)c1nc(Cc2cccnc2)cc2[nH]c3cc(Br)ccc3c12)C(=O)OC(C)(C)C]

tert-butyl (3-((7-bromo-3-(pyridin-3-ylmethyl)-5H-pyrido[4,3-b]indol-1-yl)(methyl)amino)propyl)(methyl)carbamate Following the procedure for the preparation of Intermediate 8H using N¹-(7-bromo-3-(pyridin-3-ylmethyl)-5H-pyrido[4,3-b]indol-1-yl)-N¹,N³-dimethylpropane-1,3-diamine (0.103 g, 0.235 mmol), triethylamine (0.065 ml, 0.470 mmol), CH₂Cl₂ (5 mL) and a solution of di-tert-butyl dicarbonate (0.076 ml, 0.329 mmol) in CH₂Cl₂ (0.500 ml, 7.78 mmol) afforded tert-butyl (3-((7-bromo-3-(pyridin-3-ylmethyl)-5H-pyrido[4,3-b]indol-1-yl)(methyl)amino)propyl)(methyl)carbamate (109 mg, 0.202 mmol, 86% yield) as a white foam. $^1$H NMR (400 MHz, DMSO-d6) δ ppm 1.12-1.39 (m, 9H) 1.78 (dt, J=13.99, 6.90 Hz, 2H) 2.67 (s, 3H) 2.98 (s, 3H) 3.12 (t, J=6.85 Hz, 2H) 3.37 (br. s., 2H) 4.08 (s, 2H) 6.94 (s, 1H) 7.29 (dd, J=7.63, 4.89 Hz, 1H) 7.35 (d, J=8.61 Hz, 1H) 7.62-7.67 (m, 1H) 7.70-7.79 (m, 2H) 8.40 (dd, J=4.70, 1.57 Hz, 1H) 8.56-8.62 (m, 1H) 11.68 (br. s., 1H); LCMS m/z 538.2, 540.2 (M+H)⁺.

Intermediate 12C

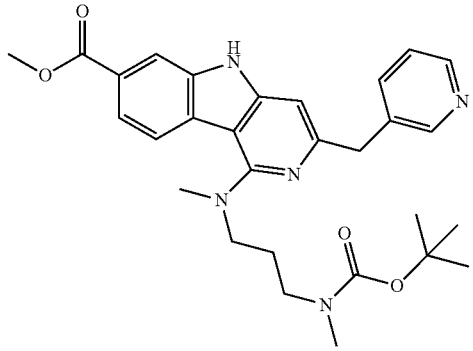 [SMILES: COC(=O)c1ccc2c(c1)[nH]c1cc(Cc3cccnc3)nc(N(C)CCCN(C)C(=O)OC(C)(C)C)c12]

methyl 1-((3-((tert-butoxycarbonyl)(methyl)amino) propyl)(methyl)amino)-3-(pyridin-3-ylmethyl)-5H-pyrido[4,3-b]indole-7-carboxylate Following the procedure for the preparation of Example 1 using tert-butyl (3-((7-bromo-3-(pyridin-3-ylmethyl)-5H-pyrido[4,3-b]indol-1-yl)(methyl)amino)propyl)(methyl)carbamate (94 mg, 0.175 mmol), Pd(OAc)₂ (5.88 mg, 0.026 mmol), 4,5-bis(diphenylphosphino)-9,9-dimethylxanthene (30.3 mg, 0.052 mmol), MeOH (282 µl, 6.98 mmol) and triethylamine (1.22 mL, 8.73 mmol) afforded methyl 1-((3-((tert-butoxycarbonyl)(methyl)amino)propyl)(methyl)amino)-3-(pyridin-3-ylmethyl)-5H-pyrido[4,3-b]indole-7-carboxylate (50 mg, 0.097 mmol, 55.3% yield) as a white foam. $^1$H NMR (400 MHz, DMSO-d6) δ ppm 1.15-1.37 (m, 9H) 1.80 (dt, J=14.09, 7.04 Hz, 2H) 2.68 (br. s., 3H) 3.02 (s, 3H) 3.13 (t, J=6.85 Hz, 2H) 3.42 (br. s., 2H) 3.89 (s, 3H) 4.10 (s, 2H) 6.96 (s, 1H) 7.30 (dd, J=7.63, 4.89 Hz, 1H) 7.75 (d, J=7.43 Hz, 1H) 7.84 (d, J=8.22 Hz, 1H) 7.93 (d, J=8.61 Hz, 1H) 8.06 (s, 1H) 8.40 (d, J=4.70 Hz, 1H) 8.60 (s, 1H) 11.82 (s, 1H); LCMS m/z 518.2 (M+H)⁺.

Example 12

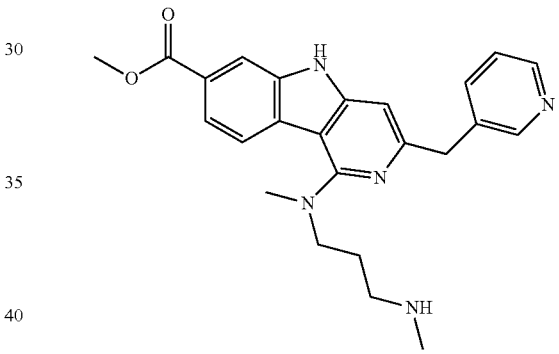

methyl 1-(methyl(3-(methylamino)propyl)amino)-3-(pyridin-3-ylmethyl)-5H-pyrido[4,3-b]indole-7-carboxylate To a mixture of methyl 1-((3-((tert-butoxycarbonyl)-(methyl)amino)propyl)(methyl)amino)-3-(pyridin-3-ylmethyl)-5H-pyrido[4,3-b]indole-7-carboxylate (0.045 g, 0.087 mmol) in CH₂Cl₂ (2 mL) was added trifluoroacetic acid (1.0 mL, 12.98 mmol). Stirred the mixture for 30 minutes and added toluene (2.5 mL). Concentrated the mixture to dryness on rotovap. The residue was purified on ISCO using a RediSep 4 g column (CH₂Cl₂/MeOH/ NH₄OH) to give methyl 1-(methyl(3-(methylamino)propyl) amino)-3-(pyridin-3-ylmethyl)-5H-pyrido[4,3-b]indole-7-carboxylate (35 mg, 0.084 mmol, 96% yield) as a white foam. $^1$H NMR (400 MHz, DMSO-d6) δ ppm 1.72 (dt, J=14.09, 7.04 Hz, 2H) 2.18 (s, 3H) 2.42 (t, J=6.85 Hz, 2H) 3.02 (s, 3H) 3.48 (t, J=7.24 Hz, 2H) 3.89 (s, 3H) 4.09 (s, 2H) 6.94 (s, 1H) 7.31 (dd, J=7.63, 4.89 Hz, 1H) 7.76 (d, J=7.83 Hz, 1H) 7.85 (d, J=8.61 Hz, 1H) 7.93 (d, J=8.22 Hz, 1H) 8.06 (s, 1H) 8.40 (d, J=4.30 Hz, 1H) 8.60 (s, 1H) 11.81 (br. s., 1H); HRMS m/z 418.2246 (M+H)⁺.

Example 13

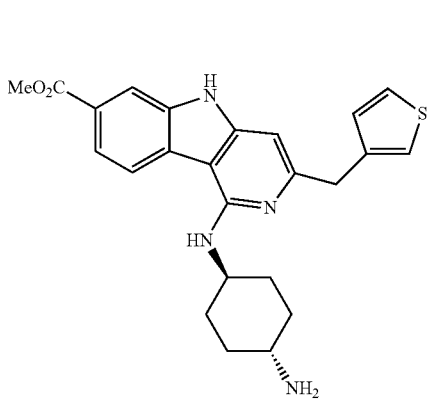 [SMILES: COC(=O)c1ccc2c(c1)[nH]c1cc(Cc3ccsc3)nc(N[C@H]3CC[C@H](N)CC3)c12]

methyl 1-(((1r,4r)-4-aminocyclohexyl)amino)-3-(thiophen-3-ylmethyl)-5H-pyrido[4,3-b]indole-7-carboxylate

Intermediate 13A

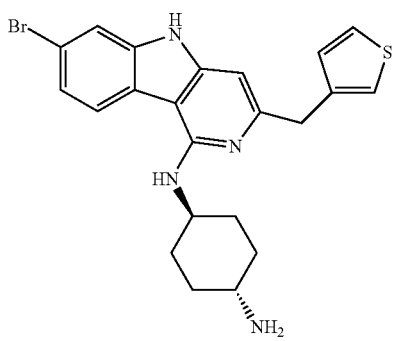 [SMILES: N[C@H]1CC[C@H](Nc2nc(Cc3ccsc3)cc3[nH]c4cc(Br)ccc4c23)CC1]

(1r,4०-N¹-(7-bromo-3-(thiophen-3-ylmethyl)-5H-pyrido[4,3-b]indol-1-yl)cyclohexane-1,4-diamine Following the procedure for the preparation of Intermediate 2F using the Intermediate 8F (100 mg, 0.265 mmol) and (1r,4r)-cyclohexane-1,4-diamine (0.907 g, 7.94 mmol) afforded (1r,4r)-N¹-(7-bromo-3-(thiophen-3-ylmethyl)-5H-pyrido[4,3-b]indol-1-yl)cyclohexane-1,4-diamine (105 mg, 0.231 mmol, 87% yield) as a white solid. $^1$H NMR (400 MHz, DMSO-d6) δ ppm 1.11-1.27 (m, 2H) 1.41-1.66 (m, 4H) 1.82 (m, J=11.70 Hz, 2H) 1.98 (m, J=10.20 Hz, 2H) 2.58 (tt, J=10.96, 3.72 Hz, 1H) 3.98 (s, 2H) 4.17 (m, J=15.40, 7.80, 7.80, 3.90 Hz, 1H) 5.75 (d, J=7.83 Hz, 1H) 6.51-6.57 (m, 1H) 7.09-7.16 (m, 1H) 7.24-7.32 (m, 2H) 7.43 (dd, J=4.70, 3.13 Hz, 1H) 7.54-7.59 (m, 1H) 8.13 (d, J=8.61 Hz, 1H) 11.45 (br. s., 1H); LCMS m/z 455.1, 457.1 (M+H)⁺.

Intermediate 13B

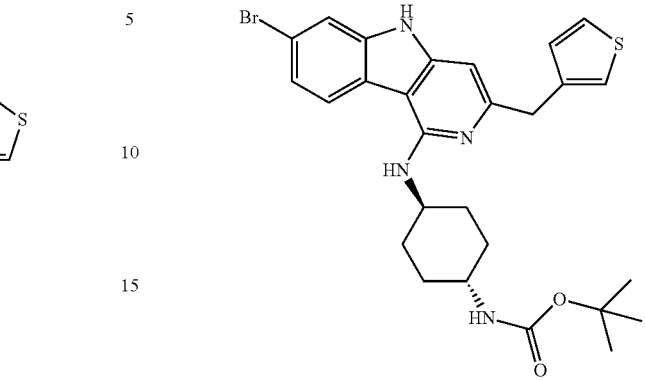

tert-butyl ((1r,4r)-4-((7-bromo-3-(thiophen-3-ylmethyl)-5H-pyrido[4,3-b]indol-1-yl)amino)cyclohexyl)carbamate Following the procedure for the preparation of Intermediate 8H using Intermediate 13A (0.097 g, 0.213 mmol), triethylamine (0.059 ml, 0.426 mmol), —CH₂Cl₂ (4.5 mL), MeOH (1 mL) and a solution of di-tert-butyl dicarbonate (0.081 ml, 0.351 mmol) in CH₂Cl₂ (0.45 mL) afforded tert-butyl ((1r,4r)-4-((7-bromo-3-(thiophen-3-ylmethyl)-5H-pyrido[4,3-b]indol-1-yl)amino)cyclohexyl)carbamate (117 mg, 0.211 mmol, 99% yield) as a white foam. $^1$H NMR (400 MHz, DMSO-d6) δ ppm 1.26-1.45 (m, 11H) 1.46-1.60 (m, 2H) 1.84 (d, J=10.96 Hz, 2H) 1.91-2.07 (m, 2H) 2.20-2.44 (m, 1H) 3.98 (s, 2H) 4.08-4.24 (m, 1H) 5.82 (d, J=7.83 Hz, 1H) 6.54 (s, 1H) 6.75 (d, J=8.22 Hz, 1H) 7.12 (d, J=5.09 Hz, 1H) 7.26 (d, J=2.35 Hz, 1H) 7.29 (dd, J=8.22, 1.56 Hz, 1H) 7.44 (dd, J=4.89, 2.93 Hz, 1H) 7.56 (d, J=1.56 Hz, 1H) 8.14 (d, J=8.61 Hz, 1H) 11.45 (s, 1H); LCMS m/z 555.1, 557.2 (M+H)⁺.

Intermediate 13C

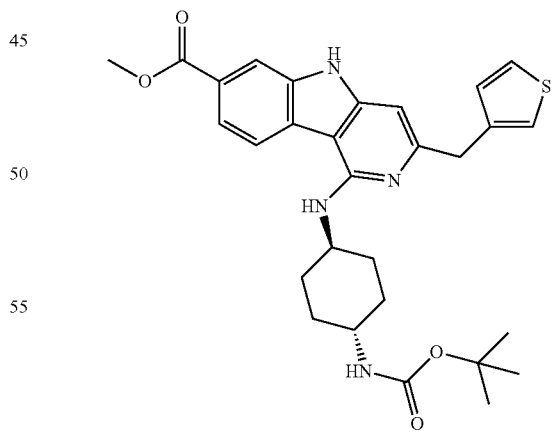

methyl 1-(((1r,4r)-4-((tert-butoxycarbonyl)amino)cyclohexyl)amino)-3-(thiophen-3-ylmethyl)-5H-pyrido[4,3-b]indole-7-carboxylate Following the procedure for the preparation of Example 1 using Intermediate 13B (100 mg, 0.180 mmol), Pd(OAc)₂

(6.06 mg, 0.027 mmol), 4,5-bis(diphenylphosphino)-9,9-dimethylxanthene (31.2 mg, 0.054 mmol), MeOH (291 μl, 7.20 mmol) and triethylamine (1.25 mL, 9.00 mmol) afforded methyl 1-(((1r,4r)-4-((tert-butoxycarbonyl)amino)cyclohexyl)amino)-3-(thiophen-3-ylmethyl)-5H-pyrido[4,3-b]indole-7-carboxylate (90 mg, 0.168 mmol, 94% yield) as a yellow solid. $^1$H NMR (400 MHz, DMSO-d6) δ ppm 1.26-1.37 (m, 2H) 1.40 (s, 9H) 1.48-1.63 (m, 2H) 1.85 (d, J=9.78 Hz, 2H) 2.02 (d, J=10.96 Hz, 2H) 3.25 (m, J=3.52 Hz, 1H) 3.88 (s, 3H) 4.00 (s, 2H) 4.18 (m, J=7.80 Hz, 1H) 5.98 (d, J=7.83 Hz, 1H) 6.57 (s, 1H) 6.76 (d, J=7.83 Hz, 1H) 7.13 (d, J=5.09 Hz, 1H) 7.27 (d, J=2.74 Hz, 1H) 7.45 (dd, J=4.70, 3.13 Hz, 1H) 7.78 (d, J=8.22 Hz, 1H) 7.99 (s, 1H) 8.29 (d, J=8.22 Hz, 1H) 11.60 (s, 1H); LCMS m/z 535.3 (M+H)$^+$.

Intermediate 13D

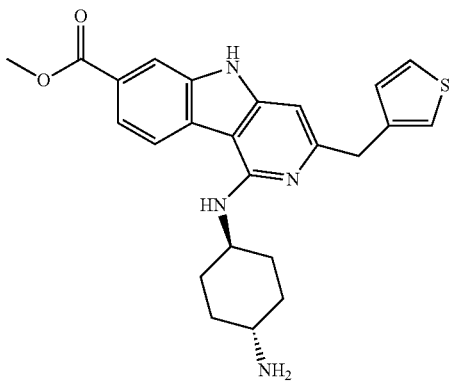 [SMILES: COC(=O)c1ccc2c(c1)[nH]c1cc(Cc3ccsc3)nc(N[C@H]3CC[C@H](N)CC3)c12]

methyl 1-(((1r,4r)-4-aminocyclohexyl)amino)-3-(thiophen-3-ylmethyl)-5H-pyrido[4,3-b]indole-7-carboxylate Following the procedure for the preparation of Example 12 using Intermediate 13O (85 mg, 0.159 mmol), CH$_2$Cl$_2$ (3 mL) and trifluoroacetic acid (1.5 mL) afforded methyl 1-(((1r,4r)-4-aminocyclohexyl)amino)-3-(thiophen-3-ylmethyl)-5H-pyrido[4,3-b]indole-7-carboxylate (69 mg, 0.159 mmol, 100% yield) as a yellow solid. $^1$H NMR (400 MHz, DMSO-d6) δ ppm 1.39-1.66 (m, 4H) 2.00 (d, J=11.35 Hz, 2H) 2.08 (d, J=11.74 Hz, 2H) 3.00 (t, J=11.15 Hz, 1H) 3.88 (s, 3H) 4.01 (s, 2H) 4.20 (m, J=7.40, 3.90 Hz, 1H) 6.03 (d, J=7.83 Hz, 1H) 6.61 (s, 1H) 7.12 (d, J=4.70 Hz, 1H) 7.28 (d, J=2.74 Hz, 1H) 7.38 (br. s., 2H) 7.44 (dd, J=4.70, 3.13 Hz, 1H) 7.78 (d, J=8.61 Hz, 1H) 8.00 (s, 1H) 8.28 (d, J=8.61 Hz, 1H) 11.65 (s, 1H); HRMS m/z 435.1852 (M+H)$^+$.

Example 14

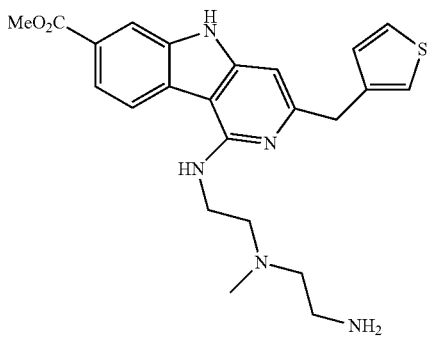 [SMILES: COC(=O)c1ccc2c(c1)[nH]c1cc(Cc3ccsc3)nc(NCCN(C)CCN)c12]

methyl 1-((2-((2-aminoethyl)(methyl)amino)ethyl)amino)-3-(thiophen-3-ylmethyl)-5H-pyrido[4,3-b]indole-7-carboxylate Following the procedure for the preparation of Example 12 using product from Example 8(40 mg, 0.074 mmol), —CH$_2$Cl$_2$ (2 mL) and trifluoroacetic acid (1 mL) afforded methyl 1-((2-((2-aminoethyl)-(methyl)amino)ethyl)amino)-3-(thiophen-3-ylmethyl)-5H-pyrido[4,3-b]indole-7-carboxylate (27 mg, 0.062 mmol, 83% yield) as a tan solid. $^1$H NMR (400 MHz, DMSO-d6) δ ppm 2.27 (s, 3H) 2.43 (t, J=6.46 Hz, 2H) 2.65 (q, J=6.26 Hz, 4H) 3.68 (m, J=5.87 Hz, 2H) 3.88 (s, 3H) 4.01 (s, 2H) 6.45 (t, J=4.30 Hz, 1H) 6.58 (s, 1H) 7.12 (d, J=5.09 Hz, 1H) 7.25-7.30 (m, 1H) 7.44 (dd, J=4.70, 3.13 Hz, 1H) 7.79 (d, J=7.83 Hz, 1H) 8.01 (s, 1H) 8.23 (d, J=8.22 Hz, 1H) 11.62 (br. s., 1H); HRMS m/z 439.1957 (M+H)$^+$.

Example 15

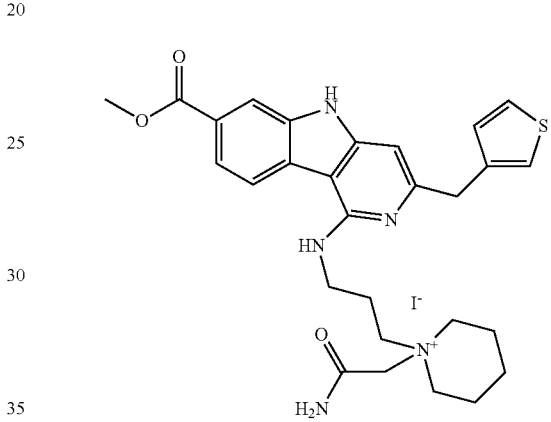

1-(2-amino-2-oxoethyl)-1-(3-((7-(methoxycarbonyl)-3-(thiophen-3-ylmethyl)-5H-pyrido[4,3-b]indol-1-yl)amino)propyl)piperidin-1-ium iodide To a mixture of methyl 1-((3-(piperidin-1-yl)propyl)amino)-3-(thiophen-3-ylmethyl)-5H-pyrido[4,3-b]indole-7-carboxylate (50 mg, 0.108 mmol) in THF (2.45 mL) was added 2-iodoacetamide (23.99 mg, 0.130 mmol). Stirred for 20 hours then added another portion of 2-iodoacetamide (23.99 mg, 0.130 mmol). After another 4 days, added another portion of 2-iodoacetamide (50.0 mg, 0.270 mmol). Continued stirring for another 8 days. Concentrated the mixture to dryness on rotovap. The residue was purified on ISCO using a RediSep 4 g column (CH$_2$Cl$_2$/MeOH) to give 1-(2-amino-2-oxoethyl)-1-(3-((7-(methoxycarbonyl)-3-(thiophen-3-ylmethyl)-5H-pyrido[4,3-b]indol-1-yl)amino)propyl)piperidin-1-ium iodide (31.5 mg, 0.049 mmol, 45.0% yield) as a tan solid. $^1$H NMR (400 MHz, DMSO-d6) δ ppm 1.41-1.64 (m, 2H) 1.76 (br. s., 4H) 2.12 (s, 2H) 3.35-3.46 (m, 2H) 3.54-3.62 (m, 2H) 3.62-3.76 (m, 4H) 3.88 (s, 3H) 3.98-4.10 (m, 4H) 6.63 (s, 1H) 6.72 (t, J=5.48 Hz, 1H) 7.11 (d, J=4.70 Hz, 1H) 7.27 (br. s., 1H) 7.46 (dd, J=4.70, 3.13 Hz, 1H) 7.74 (br. s., 1H) 7.81 (d, J=8.22 Hz, 1H) 7.93 (br. s., 1H) 8.02 (s, 1H) 8.34 (d, J=8.22 Hz, 1H) 11.65 (s, 1H); HRMS m/z 520.2390 (M)$^+$.

Reported HPLC retention time are for reverse-phase HPLC (Agilent, 1200 series) using the following conditions Solvent A: MeOH:H$_2$O:TFA (5:95:0.05); Solvent B: MeOH: H$_2$O:TFA (95:5:0.05); flow: 2.0 mL/min.; gradient 0 to 100% B in 1.5 min; run time: 3.5 min; column: Kinetex C18, 2.6 μm, 100 Å, 4.6×30 mm; wavelength 254 nm.

TABLE 1'
| Compound number | Structure | HPLC $R_T$ (min) analytical | MS m/z $(M + H)^+$ | Biological data $EC_{50}$ |
|---|---|---|---|---|
| 1' | 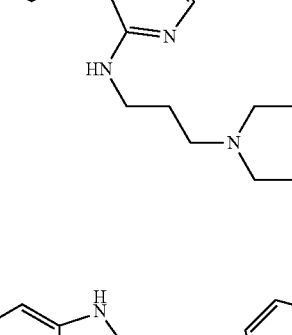 | 1.50 | 367.2 | A |
| 2' | 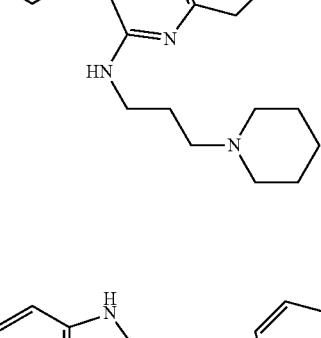 | 1.64 | 457.2 | E |
| 3' | 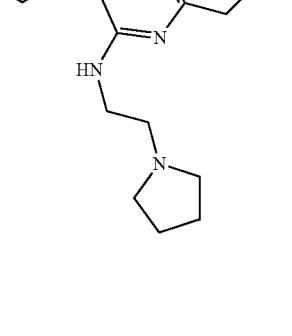 | 1.62 | 429.2 | E |
| 4' | 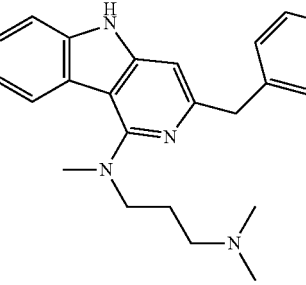 | 1.63 | 431.2 | E |

TABLE 1'-continued
| Compound number | Structure | HPLC R$_T$ (min) analytical | MS m/z (M + H)$^+$ | Biological data EC$_{50}$ |
|---|---|---|---|---|
| 5' | 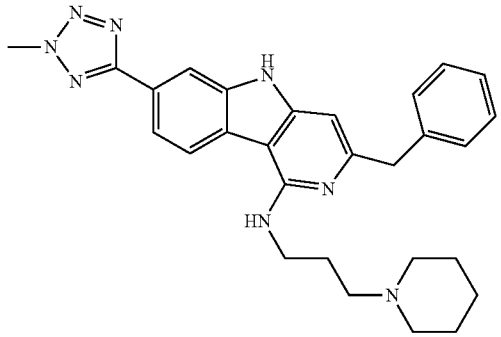 [SMILES: Cn1nnc(-c2ccc3c(c2)[nH]c2cc(Cc4ccccc4)nc(NCCCN4CCCCC4)c23)n1] | 1.63 | 481.4 | D |
| 6' | 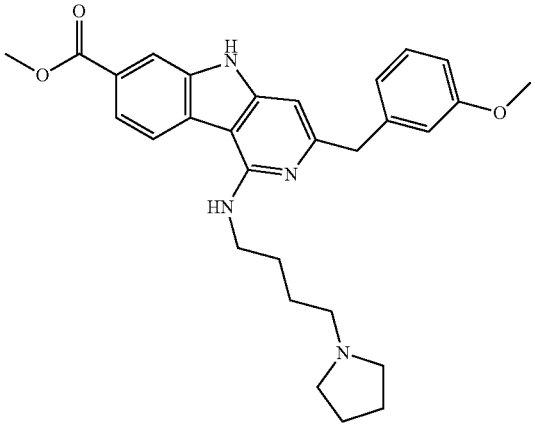 | 1.67 | 487.3 | E |
| 7' | 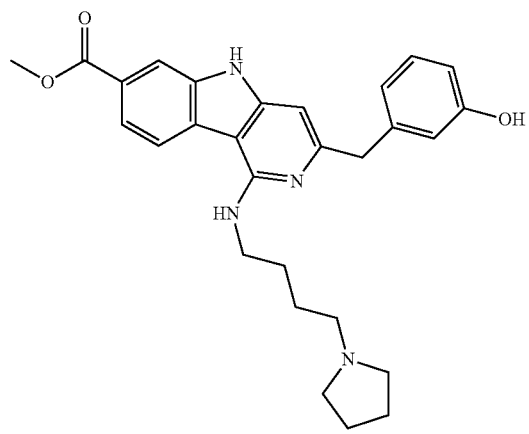 [SMILES: COC(=O)c1ccc2c(c1)[nH]c1cc(Cc3cccc(O)c3)nc(NCCCCN3CCCC3)c12] | 1.76 | 473.3 | E |
| 8' | 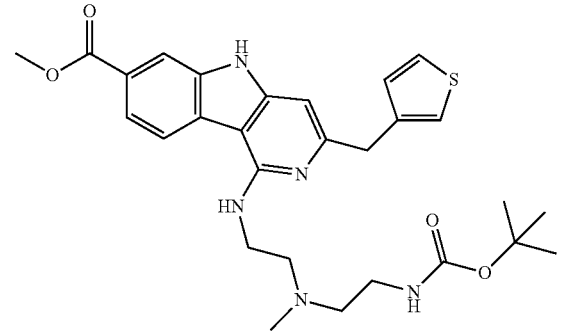 [SMILES: COC(=O)c1ccc2c(c1)[nH]c1cc(Cc3ccsc3)nc(NCCN(C)CCNC(=O)OC(C)(C)C)c12] | 1.72 | 538.2 | A |

TABLE 1'-continued
| Compound number | Structure | HPLC $R_T$ (min) analytical | MS m/z (M + H)$^+$ | Biological data EC$_{50}$ |
|---|---|---|---|---|
| 9' | 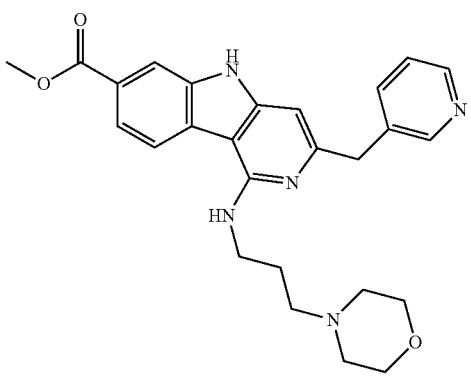 [SMILES: COC(=O)c1ccc2c(c1)[nH]c1cc(Cc3cccnc3)nc(NCCCN3CCOCC3)c12] | 1.12 | 460.3 | B |
| 10' | 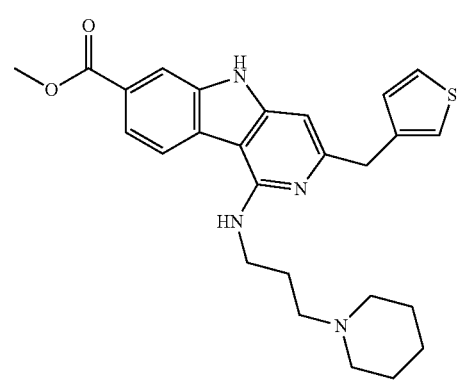 [SMILES: COC(=O)c1ccc2c(c1)[nH]c1cc(Cc3ccsc3)nc(NCCCN3CCCCC3)c12] | 1.58 | 463.2 | D |
| 11' | 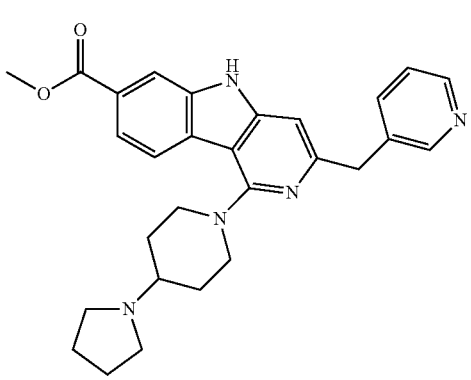 [SMILES: COC(=O)c1ccc2c(c1)[nH]c1cc(Cc3cccnc3)nc(N3CCC(N4CCCC4)CC3)c12] | 1.22 | 470.2 | A |
| 12' | 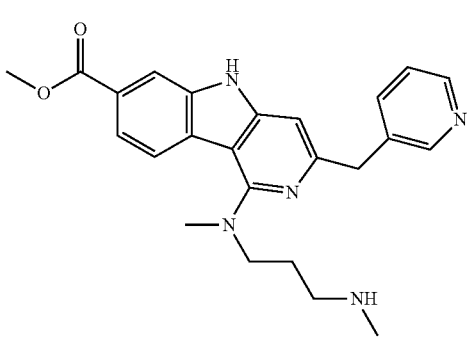 [SMILES: CNCCCN(C)c1nc(Cc2cccnc2)cc2[nH]c3cc(C(=O)OC)ccc3c12] | 1.18 | 418.2 | A |

TABLE 1'-continued
| Compound number | Structure | HPLC R$_T$ (min) analytical | MS m/z (M + H)$^+$ | Biological data EC$_{50}$ |
|---|---|---|---|---|
| 13' | 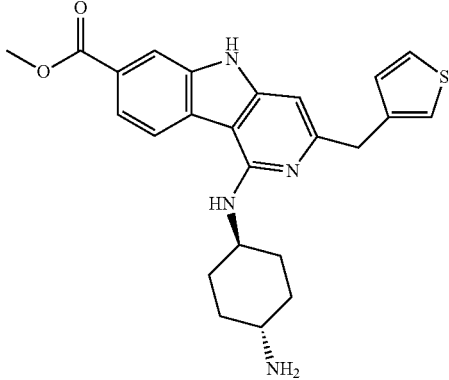 [SMILES: COC(=O)c1ccc2c(c1)[nH]c1cc(Cc3ccsc3)nc(N[C@H]3CC[C@H](N)CC3)c12] | 1.64 | 435.1 | D |
| 14' | 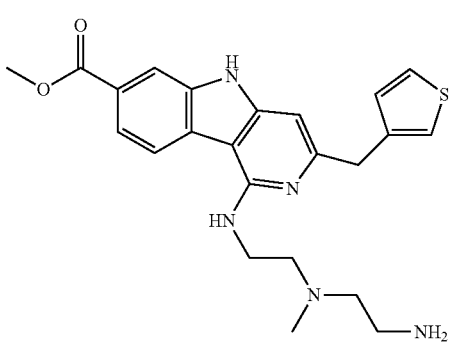 [SMILES: COC(=O)c1ccc2c(c1)[nH]c1cc(Cc3ccsc3)nc(NCCN(C)CCN)c12] | 1.56 | 438.2 | C |
| 15' | 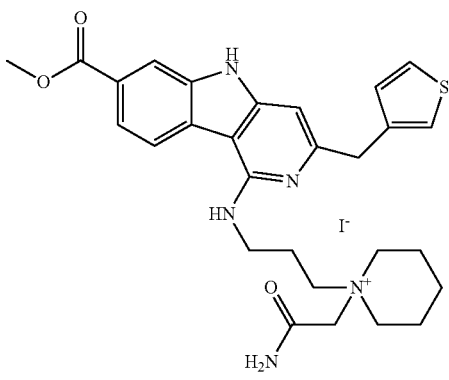 [SMILES: COC(=O)c1ccc2c(c1)[nH]c1cc(Cc3ccsc3)nc(NCCC[N+]3(CC(N)=O)CCCCC3)c12 ; [I-]] | 1.90 | 473.2 | E |
The EC$_{50}$ is defined as the concentration that results in a 50% increase in CD34$^+$CD45RA$^-$ cell count compared to vehicle cultures (DMSO).
* EC$_{50}$:
A >1000 nM;
B: >500-1000 nM;
C: >250-500 nM;
D = 100-250;
E = <100 nM.

It is understood that the examples and embodiments described herein are for illustrative purposes only and that various modifications or changes in light thereof will be suggested to persons skilled in the art and are to be included within the present discovery and scope of the appended claims.

The invention claimed is:
1. A compound of general formula

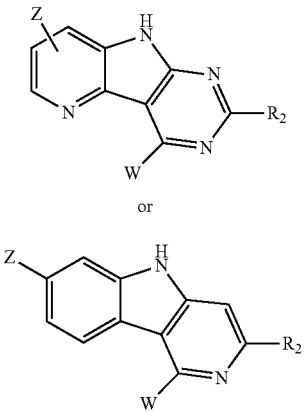

or a salt thereof, wherein:

Z is
1) -P(O) (OR$^1$) (OR$^1$),
2) —C(O)OR$^1$,
3) —C(O)NHR$^1$,
4) —C(O)N(R$^1$)R$^1$,
5) —C(O)R$^1$,
6) —CN,
7) —SR$^1$,
8) —S(O)$_2$NH$_2$,
9) —S(O)$_2$NHR$^1$,
10) —S(O)$_2$N(R$^1$)R$^1$,
11) —S(O)R$^1$,
12) —S(O)$_2$R$^1$,
13) -L,
14) -benzyl optionally substituted with 1, 2 or 3 R$^4$ or R$^1$ substituents,
15) -L-heteroaryl optionally substituted with one or more R$^4$ or R$^1$ substituents attached on either or both the L and the heteroaryl groups,
16) -L-heterocyclyl optionally substituted with one or more R$^4$ or R$^1$ substituents attached on either one or both the L and the heterocyclyl groups,
17) -L-aryl optionally substituted with one or more R$^4$ or R$^1$ substituents attached on either or both the L and the heteroaryl groups,
18) -heteroaryl optionally substituted with one or more R$^4$ or R$^1$ substituents, or
19) -aryl optionally substituted with one or more R$^4$ or R$^1$ substituents,
and wherein each substituent is optionally attached to the L group if it is not already present,
and wherein, when (R$^1$) and R$^1$ are attached to a nitrogen atom, optionally they join together with the nitrogen atom to form a 3 to 7-membered ring which optionally includes one or more other heteroatom selected from N, O and S, optionally the 3 to 7-membered ring is substituted with one or more R$^1$ or R$^4$;

W is
1) —OR$^1$,
2) -L-OH,
3) -L-OR$^1$,
4) —SR$^1$,
5) —CN,
6) —P(O)(OR$^1$)(OR$^1$),
7) —NHR$^1$,
8) —N(R$^1$)R$^1$,
9) -L-NH$_2$,
10) -L-NHR$^1$,
11) -L-N(R$^1$)R$^1$,
12) -L-SR$^1$,
13) -L-S(O)R$^1$,
14) -L-S(O)$_2$R$^1$,
15) -L-P(O)(OR$^1$)(OR$^1$),
16) —C(O)OR$^1$,
17) —C(O)NH$_2$,
18) —C(O)NHR$^1$,
19) —C(O)N(R$^1$)R$^1$,
20) —NHC(O)R$^1$,
21) —NR$^1$C(O)R$^1$,
22) —NHC(O)OR$^1$,
23) —NR$^1$C(O)OR$^1$,
24) —OC(O)NH$_2$,
25) —OC(O)NHR$^1$,
26) —OC(O)N(R$^1$)R$^1$,
27) —OC(O)R$^1$,
28) —C(O)R$^1$,
29) —NHC(O)NH$_2$,
30) —NHC(O)NHR$^1$,
31) —NHC(O)N(R$^1$)R$^1$,
32) —NR$^1$C(O)NH$_2$,
33) —NR$^1$C(O)NHR$^1$,
34) —NR$^1$C(O)N(R$^1$)R$^1$,
35) —NHS(O)$_2$R$^1$,
36) —NR$^1$S(O)$_2$R$^1$,
37) —S(O)$_2$NH$_2$,
38) —S(O)$_2$NHR$^1$,
39) —S(O)$_2$N(R$^1$)R$^1$,
40) —S(O)R$^1$,
41) —S(O)$_2$R$^1$,
42) —OS(O)$_2$R$^1$,
43) —S(O)$_2$OR$^1$,
44) -benzyl optionally substituted with 1, 2 or 3 R$^4$ or R$^1$ substituents,
45) -L-heteroaryl optionally substituted with one or more R$^4$ or R$^1$ substituents attached on either or both the L and the heteroaryl groups,
46) -L-heterocyclyl optionally substituted with one or more R$^4$ or R$^1$ substituents attached on either or both the L and the heterocyclyl groups,
47) -L-aryl optionally substituted with one or more R$^4$ or R$^1$ substituents attached on either or both the L and aryl groups,
48) -L-NR$^1$(R$^1$),
49) -L-)$_2$NR$^1$,
50) -L-(N(R$^1$)-L)$_n$-N(R$^1$)R$^1$,
51) -L-(N(R$^1$)-L)$_n$-(N(R$^1$)R$^1$)$_n$,
52) -L-(N(R$^1$)-L)$_n$-heteroaryl optionally substituted with one or more R$^4$ or R$^1$ substituents attached on either or both the L and heteroaryl groups,
53) -L-(N(R$^1$)-L)$_n$-heterocyclyl optionally substituted with one or more R$^4$ or R$^1$ substituents attached on either or both the L and heterocyclyl groups,
54) -L-(N(R$^1$)-L)$_n$-aryl optionally substituted with one or more R$^4$ or R$^1$ substituents attached on either or both the L and aryl groups, 55) —O-L-N($R^1$)$R^1$,
56) —O-L-heteroaryl optionally substituted with one or more $R^A$ or $R^1$ substituents attached on either or both the L and heteroaryl groups,
57) —O-L-heterocyclyl optionally substituted with one or more $R^A$ or $R^1$ substituents attached on either or both the L and heterocyclyl groups,
58) —O-L-aryl optionally substituted with one or more $R^A$ or $R^1$ substituents attached on either or both the L and aryl groups,
59) —O-L)$_2$-N$R^1$,
60) —O-L-(N($R^1$)-L)$_n$-N($R^1$)$R^1$,
61) —O-L-(N($R^1$)-L)$_n$-(N($R^1$)$R^1$)$_n$,
62) —O-L-(N($R^1$)-L)$_n$-heteroaryl optionally substituted with one or more $R^A$ or $R^1$ substituents attached on either or both the L and heteroaryl groups,
63) —O-L-(N($R^1$)-L)$_n$-heterocyclyl optionally substituted with one or more $R^A$ or $R^1$ substituents attached on either or both the L and heterocyclyl groups,
64) —O-L-(N($R^1$)-L)$_n$-aryl optionally substituted with one or more $R^A$ or $R^1$ substituents,
65) —S-L-heteroaryl optionally substituted with one or more $R^A$ or $R^1$ substituents,
66) —S-L-heterocyclyl optionally substituted with one or more $R^A$ or $R^1$ substituents,
67) —S-L-aryl optionally substituted with one or more $R^A$ or $R^1$ substituents attached on either or both the L and aryl groups,
68) —S-L)$_2$N$R^1$,
69) —S-L-(N($R^1$)-L)$_n$-N($R^1$)$R^1$,
70) —S-L-(N($R^1$)-L)$_n$-(N($R^1$)$R^1$)$_n$,
71) —S-L-(N($R^1$)-L)$_n$-heteroaryl optionally substituted with one or more $R^A$ substituents,
72) —S-L-(N($R^1$)-L)$_n$-heterocyclyl optionally substituted with one or more $R^A$ substituents,
73) —S-L-(N($R^1$)-L)$_n$-aryl optionally substituted with one or more $R^A$ substituents,
74) —N$R^1$($R^1$),
75) —(N($R^1$)-L)$_n$-N($R^1$)$R^1$,
76) —(N($R^1$)-L)$_n$-(N($R^1$)$R^1$)$_n$,
77) —N($R^1$)L)$_2$-N$R^1$,
78) —(N($R^1$)-L)$_n$-N($R^1$)$R^A$,
79) —(N($R^1$)-L)$_n$-heteroaryl optionally substituted with one or more $R^A$ or $R^1$ substituents,
80) —(N($R^1$)-L)$_n$-heterocyclyl optionally substituted with one or more $R^A$ or $R^1$ substituents,
81) —(N($R^1$)-L)$_n$-aryl optionally substituted with one or more $R^A$ or $R^1$ substituents,
82) -heteroaryl optionally substituted with one or more $R^A$ substituents, or
83) -aryl optionally substituted with one or more $R^A$ substituents,
84) —X(C$R^1$C$R^1$)$_m$—C(O)—(C$R^1$C$R^1$)$_n$—X($R^1R^1$)-[L-N($R^1R^1$)]$_p$,
85) —X(C$R^1$C$R^1$)$_m$—C$R^1$(O$R^1$)—(C$R^1$C$R^1$)$_n$—X ($R^1R^1$)-[L-N($R^1R^1$)]$_p$,
86) —X($R^1$)-L-N($R^1$)-(LX)$_n$—$R^A$,
87) —X($R^1$)-L-N($R^1$)-(LX)$_n$—H, and wherein each substituent is optionally attached to the L group if it is not already present,
and wherein when two $R^1$ substituents are present on the same nitrogen atom, then each $R^1$ substituent is independently selected from the list of $R^1$ values described thereafter,
and wherein n and m are each independently an integer equal to either 0, 1, 2, 3, 4, 5 or 6,
and wherein X is C$R^1R^1$, O, N$R^1$ or S,
and wherein, when ($R^1$) and $R^1$ are attached to a nitrogen atom, optionally they join together with the nitrogen atom to form a 3 to 7-membered ring which optionally includes one or more other heteroatom selected from N, O and S, optionally the ring is substituted with one or more $R^1$ or $R^A$;

L is
1) —$C_{1-6}$ alkyl,
2) —$C_{2-6}$ alkenyl,
3) —$C_{2-6}$ alkynyl,
4) —$C_{3-7}$ cycloalkyl,
5) —$C_{3-7}$ cycloalkenyl,
6) heterocyclyl,
7) —$C_{1-6}$ alkyl-$C_{3-7}$ cycloalkyl,
8) —$C_{1-6}$ alkyl-heterocyclyl,
9) aryl, or
10) heteroaryl, and wherein the alkyl, the alkenyl, the alkynyl, the cycloalkyl, the cycloalkenyl, the heterocyclyl, the aryl and the heteroaryl groups are each independently optionally substituted with one or two $R^A$ or $R^1$ substituent;

$R^1$ is
1) —H,
2) —$C_{1-6}$ alkyl,
3) —$C_{2-6}$ alkenyl,
4) —$C_{2-6}$ alkynyl,
5) —$C_{3-7}$ cycloalkyl,
6) —$C_{3-7}$ cycloalkenyl,
7) —$C_{1-5}$ fluorinated including one or more fluorine atoms,
8) -heterocyclyl,
9) -aryl,
10) -heteroaryl,
11) -benzyl, or
12) 5-[(3aS,4S,6aR)-2-oxohexahydro-1H-thieno[3,4-d]imidazol-4-yl]pentanoyl, and wherein the alkyl, the alkenyl, the alkynyl, the cycloalkenyl, the perfluorinated alkyl, the heterocyclyl, the aryl, the heteroaryl and the benzyl groups are each independently optionally substituted with 1, 2 or 3 $R^A$ or $R^1$ substituents and wherein, when ($R^1$) and $R^1$ are attached to a nitrogen atom, optionally they join together with the nitrogen atom to form a 3 to 7-membered ring which optionally includes one or more other heteroatom selected from N, O and S, optionally the ring is substituted with one or more $R^1$ or $R^A$;

$R^2$ is
1) —H,
2) —$C_{1-6}$ alkyl,
3) —S$R^1$,
4) —C(O)$R^1$,
5) —S(O)$R^1$,
6) —S(O)$_2R^1$,
7) -benzyl optionally substituted with 1, 2 or 3 $R^A$ or $R^1$ substituents,
8) -L-heteroaryl optionally substituted with one or more $R^A$ or $R^1$ substituents attached on either one or both the L and the heteroaryl groups,
9) -L-heterocyclyl optionally substituted with one or more $R^A$ or $R^1$ substituents attached on either one or both the L and the heterocyclyl groups,
10) -L-aryl optionally substituted with one or more $R^A$ or $R^1$ substituents attached on either one or both the L and the aryl groups,
11) -heteroaryl optionally substituted with one or more $R^A$ or $R^1$ substituents, or 12) -aryl optionally substituted with one or more $R^4$ or $R^1$ substituents, and wherein each substituent is optionally attached to the L group if it is not already present;

$R^A$ is
1) -halogen,
2) —$CF_3$,
3) —OH,
4) —$OR^1$,
5) -L-OH,
6) -L-$OR^1$,
7) —$OCF_3$,
8) —SH,
9) —SR1,
10) —CN,
11) —$NO_2$,
12) —$NH_2$,
13) —$NHR^1$,
14) —$NR^1R^1$,
15) -L-$NH_2$,
16) -L-$NHR^1$,
17) -L-$NR^1R^1$,
18) -L-$SR^1$,
19) -L-$S(O)R^1$,
20) -L-$S(O)_2R^1$,
21) —C(O)OH,
22) —$C(O)OR^1$,
23) —$C(O)NH_2$,
24) —$C(O)NHR^1$,
25) —$C(O)N(R^1)R^1$,
26) —$NHC(O)R^1$,
27) —$NR^1C(O)R^1$,
28) —$NHC(O)OR^1$,
29) —$NR^1C(O)OR^1$,
30) —$OC(O)NH_2$,
31) —$OC(O)NHR^1$,
32) —$OC(O)N(R^1)R^1$,
33) —$OC(O)R^1$,
34) —$C(O)R^1$,
35) —$NHC(O)NH_2$,
36) —$NHC(O)NHR^1$,
37) —$NHC(O)N(R^1)R^1$,
38) —$NR^1C(O)NH_2$,
39) —$NR^1C(O)NHR^1$,
40) —$NR^1C(O)N(R^1)R^1$,
41) —$NHS(O)_2R^1$,
42) —$NR^1S(O)_2R^1$,
43) —$S(O)_2NH_2$,
44) —$S(O)_2NHR^1$,
45) —$S(O)_2N(R^1)R^1$,
46) —$S(O)R^1$,
47) —$S(O)_2R^1$,
48) —$OS(O)_2R^1$,
49) —$S(O)_2OR^1$,
50) -benzyl,
51) —$N_3$, or
52) —C(—N=N—)($CF_3$), and wherein the benzyl group is optionally substituted with 1, 2 or 3 $R^A$ or $R^1$ substituents, optionally, at least one hydrogen atom in the compound is replaced by a deuterium, optionally, the compound is attached to a solid support which is a resin, a polymer or a cellulose including polystyrene cross-linked, polyamide resin, agarose beads.

2. A compound of claim 1, having the general formula II

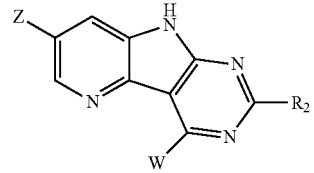

or a salt thereof.

3. The compound of claim 2, wherein

Z is
1) —CN
2) —C(O)OR1,
3) —C(O)N(R1)R3,
4) —C(O)R1, or
5) -heteroaryl optionally substituted with one or more RA or R4 substituents, wherein, when (R1) and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;

W is
1) —CN,
2) —N(R1)R3,
3) —C(O)OR1,
4) —C(O)N(R1)R3,
5) —NR1C(O)R1,
6) —NR1C(O)OR1,
7) —OC(O)N(R1)R3,
8) —OC(O)R1,
9) —C(O)R1,
10) —NR1C(O)N(R1)R3,
11) —$NR1S(O)_2R1$,
12) -benzyl optionally substituted with 1, 2 or 3 RA or R1 substituents,
13) —X-L-(X-L)n-N(R1)R3,
14) —X-L-(X-L)n-heteroaryl optionally substituted with one or more RA or R4 substituents attached on either or both the L and heteroaryl groups,
15) —X-L-(X-L)n-heterocyclyl optionally substituted with one or more RA or R4 substituents attached on either or both the L and heterocyclyl groups,
16) —X-L-(X-L)n-aryl optionally substituted with one or more RA or R4 substituents,
17) —X-L-(X-L)$_n$-NR1RA or
18) —(N(R1)-L)$_n$-N$^+$R1R3R5 R6$^-$ wherein n is an integer equal to either 0, 1, 2, 3, 4, or 5, and wherein, when R1 and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;

each X is independently selected from O, S, and NR1;

each L is independently
1) —$C_{1-6}$ alkylene,
2) —$C_{2-6}$ alkenylene,
3) —$C_{2-6}$ alkynylene,
4) —$C_{3-7}$cycloalkylene, which optionally includes one or more other heteroatom selected from N, O and S or 5) —C3-7 cycloalkenylene, which optionally includes one or more other heteroatom selected from N, O and S wherein the alkylene, the alkenylene, the alkynylene the cycloalkylene and the cycloalkenylene groups are each independently optionally substituted with one or two R4 or RA substituent;

R1 is each independently
1) —H,
2) —$C_{1-6}$ alkyl,
3) —$C_{2-6}$ alkenyl,
4) —$C_{2-6}$ alkynyl,
5) —$C_{3-7}$ cycloalkyl,
6) —$C_{3-7}$ cycloalkenyl,
7) —$C_{1-5}$ perfluorinated,
8) -heterocyclyl,
9) -aryl,
10) -heteroaryl, or
11) -benzyl, wherein the alkyl, the alkenyl, the alkynyl, the cycloalkenyl, the perfluorinated alkyl, the heterocyclyl, the aryl, the heteroaryl and the benzyl groups are each independently optionally substituted with 1, 2 or 3 RA or Rd substituents;

R2 is
1) —H,
2) —$C_{1-6}$ alkyl, optionally substituted with one more RA substituents
3) —C(O)R4,
4) -L-heteroaryl optionally substituted with one or more RA or R4 substituents
5) -L-heterocyclyl optionally substituted with one or more RA or R4, or
6) -L-aryl optionally substituted with one or more RA or R4 substituents;

R3 is each independently
1) —H,
2) —$C_{1-6}$ alkyl,
3) —$C_{2-6}$ alkenyl,
4) —$C_{2-6}$ alkynyl,
5) —$C_{3-7}$ cycloalkyl,
6) —$C_{3-7}$ cycloalkenyl,
7) —$C_{1-5}$ perfluorinated,
8) -heterocyclyl,
9) -aryl,
10) -heteroaryl, or
11) -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

R4 is each independently
1) —H,
2) —$C_{1-6}$ alkyl,
3) —$C_{2-6}$ alkenyl,
4) —$C_{2-6}$ alkynyl,
5) —$C_{3-7}$ cycloalkyl,
6) —$C_{3-7}$ cycloalkenyl,
7) —$C_{1-5}$ perfluorinated,
8) -heterocyclyl,
9) -aryl,
10) -heteroaryl, or
11) -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

R5 is each independently
1) —$C_{1-6}$ alkyl,
2) —$C_{1-6}$ alkylene-$C_{2-6}$alkenyl which optionally includes one or more other heteroatom selected from N, O and S
3) —$C_{1-6}$ alkylene-$C_{2-6}$alkynyl which optionally includes one or more other heteroatom selected from N, O and S
4) -L-aryl which optionally includes one or more RA or R4 substituents
5) -L-heteroaryl which optionally includes one or more RA or R4 substituents
6) —$C_{1-6}$ alkylene-C(O)O—
7) —$C_{1-6}$ alkylene-C(O)OR1
8) —$C_{1-6}$ alkylene-CN
9) —$C_{1-6}$ alkylene-C(O)NR1R3, wherein R1 and R3 optionally they join together with the nitrogen atom to form a 3 to 7-membered ring which optionally includes one or more other heteroatom selected from N, O and S; or
10) —$C_{1-6}$ alkylene-OH;

R6 is
1) halogen
2) OC(O)$CF_3$ or
3) OC(O)R1;

RA is each independently
1) -halogen,
2) —$CF_3$,
3) —OR1,
4) -L-OR1,
5) -O$CF_3$,
6) —SR1,
7) —CN,
8) —$NO_2$,
9) —NR1R3,
10) -L-NR1R1,
11) —C(O)OR1,
12) S(O)$_2$R4
13) —C(O)N(R1)R3,
14) —NR1C(O)R1,
15) —NR1C(O)OR1,
16) —OC(O)N(R1)R3,
17) —OC(O)R1,
18) —C(O)R4,
19) —NHC(O)N(R1)R3,
20) —NR1C(O)N(R1)R3, or
21) —$N_3$; and Rd is each independently
1) —H,
2) —$C_{1-6}$ alkyl,
3) —$C_{2-6}$ alkenyl,
4) —$C_{2-6}$ alkynyl,
5) —$C_{3-7}$ cycloalkyl,
6) —$C_{3-7}$ cycloalkenyl,
7) —$C_{1-5}$ perfluorinated
8) -benzyl or
9) -heterocyclyl.

4. The compound of claim 3 wherein
Z is
1) —CN
2) —C(O)OR1,
3) —C(O)N(R1)R3, or
4) -heteroaryl optionally substituted with one or more RA or R4 substituents, W is
1) —CN,
2) —N(R1)R3,
3) -benzyl optionally substituted with 1, 2 or 3 RA or R1 substituents,
4) —X-L-(X-L)n-N(R1)R3,
5) —X-L-(X-L)$_n$-NR1RA or
6) —(N(R1)-L)$_n$-N$^+$R1R3R5 R6$^-$ wherein n is an integer equal to either 0, 1, 2, or 3
and wherein, when R1 and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;

each X is independently O, S, or NR1,
L is each independently
1) —C$_{1-6}$ alkylene,
2) —C$_{2-6}$ alkenylene,
3) —C$_{2-6}$ alkynylene,
4) —C3-7 cycloalkylene, which optionally includes one or more other heteroatom selected from N, O and S or
5) —C3-7 cycloalkenylene, which optionally includes one or more other heteroatom selected from N, O and S wherein the alkylene, the alkenylene, the alkynylene the cycloalkylene and the cycloalkenylene are each independently optionally substituted with one or two R4 or RA substituent;

R1 is each independently
1) —H,
2) —C$_{1-6}$ alkyl,
3) —C$_{2-6}$ alkenyl,
4) —C$_{2-6}$ alkynyl,
5) —C$_{3-7}$ cycloalkyl,
6) —C$_{3-7}$ cycloalkenyl,
7) —C$_{1-5}$ perfluorinated,
8) -heterocyclyl,
9) -heteroaryl, or
10) -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

R2 is
1) —H,
2) —C$_{1-6}$ alkyl, optionally substituted with one more RA substituents
3) —C(O)R4,
4) -L-heteroaryl optionally substituted with one or more RA or R4 substituents
5) -L-heterocyclyl optionally substituted with one or more RA or R4, or
6) -L-aryl optionally substituted with one or more RA or R4 substituents R3 is each independently
1) —H,
2) —C$_{1-6}$ alkyl,
3) —C$_{2-6}$ alkenyl,
4) —C$_{2-6}$ alkynyl, or
5) —C$_{1-5}$ perfluorinated, wherein the alkyl, the alkenyl, the alkynyl, the perfluorinated alkyl groups are each independently optionally substituted with 1, 2 or 3 RA or Rd substituents;

R4 is each independently
1) —H,
2) —C$_{1-6}$ alkyl,
3) —C$_{2-6}$ alkenyl,
4) —C$_{2-6}$ alkynyl,
5) —C$_{3-7}$ cycloalkyl,
6) —C$_{3-7}$ cycloalkenyl,
7) —C$_{1-5}$ perfluorinated,
8) -heterocyclyl,
9) -aryl,
10) -heteroaryl, or
11) -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

R5 is each independently
1) —C$_{1-6}$ alkyl,
2) -L-aryl which optionally includes one or more RA or R4 substituents
3) -L-heteroaryl which optionally includes one or more RA or R4 substituents
4) —C$_{1-6}$ alkylene-C(O)O—
5) —C$_{1-6}$ alkylene-C(O)OR1
6) —C$_{1-6}$ alkylene-CN
7) —C$_{1-6}$ alkylene-C(O)NR1R3, or
8) —C$_{1-6}$ alkylene-OH;

R6 is
1) halogen
2) OC(O)CF$_3$ or
3) OC(O)R1;

RA is each independently
1) -halogen,
2) —CF$_3$,
3) —OR1,
4) -L-OR1,
5) -OCF$_3$,
6) —SR1,
7) —CN,
8) —NO$_2$,
9) —NR1R3,
10) -L-NR1R1,
11) —C(O)OR1,
12) S(O)$_2$R4
13) —C(O)N(R1)R3,
14) —NR1C(O)R1,
15) —NR1C(O)OR1,
16) —OC(O)N(R1)R3,
17) —OC(O)R1,
18) —C(O)R4,
19) —NHC(O)N(R1)R3,
20) —NR1C(O)N(R1)R3, or
21) —N$_3$;

Rd is each independently
1) —H,
2) —C$_{1-6}$ alkyl,
3) —C$_{2-6}$ alkenyl,
4) —C$_{2-6}$ alkynyl,
5) —C$_{3-7}$ cycloalkyl,
6) —C$_{3-7}$ cycloalkenyl,
7) —C$_{1-5}$ perfluorinated
8) -benzyl or
9) -heterocyclyl.

5. A compound of claim 1, wherein
Z is -heteroaryl optionally substituted with one or more RA or R$^1$ substituents; or —C(O)OR¹, wherein R¹ is -C1-6 alkyl;

W is —(N(R¹)-L)ₙ-N(R¹)R¹, wherein n=1, and L is -C3-7 cycloalkyl or -C1-6 alkyl; or -L-NR¹(R¹) wherein L is heterocyclyl optionally substituted with one or two R⁴ or R¹ substituent, provided that said —NR¹(R¹) is not bound to a heteroatom atom of said heterocyclyl, and wherein each R¹ is independently H, or -C1-6 alkyl, or (R¹) and R¹ join together with the nitrogen atom to form a 3 to 7-membered heterocyclic ring optionally substituted with one or more R¹ or R⁴

(N(R1)-L)ₙ-N⁺R1R3R5 R6⁻ wherein n=1, and L is —C1-6 alkyl;

R2 is

—H;

-L-heteroaryl optionally substituted with one or more RA or R1 substituents on either or both the L and the heteroaryl groups, wherein L is $C_{1-6}$ alkyl, or -L-aryl optionally substituted with one or more RA or R1 substituents on either or both the L and aryl groups, wherein L is $C_{1-6}$ alkyl.

6. A compound of claim 1 having formula IIA or IIA'

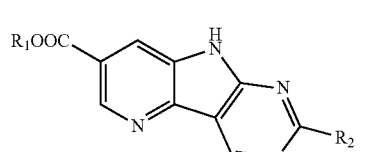

IIA

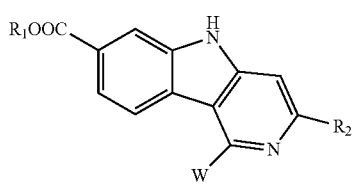

IIA' or a salt thereof.

7. A compound of claim 1 having the formula IIB or IIB'

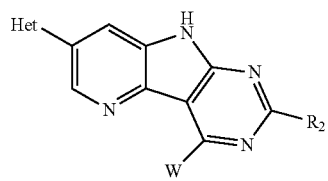

IIB

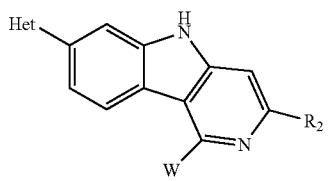

IIB' or a salt thereof, wherein Het is a heteroaryl, optionally substituted with one or more R¹ or R⁴.

8. A compound according to claim 1, wherein:

Z is $CO_2Me$ or 2-methyl-2H-tetrazol-5-yl;

R² is benzyl, 3-thienylmethyl or 3-pyridinyl methyl; and

W is NH-L-N(R¹)R¹ wherein L is $C_{2-4}$ alkyl and R¹ is $C_{1-4}$ alkyl or (R¹) and R¹ join together with the nitrogen atom to which they are attached to form a 3 to 7-membered ring, which optionally includes one or more other heteroatom selected from N, O and S, optionally the ring is substituted with one or more R¹ or R⁴.

9. A compound according to claim 1 which is:

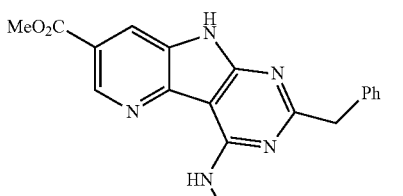

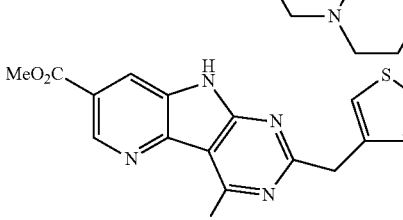

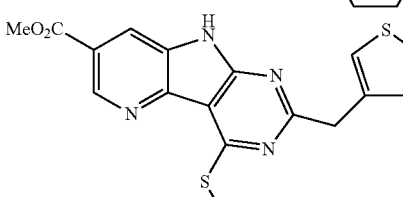

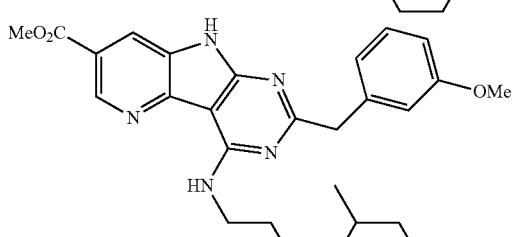

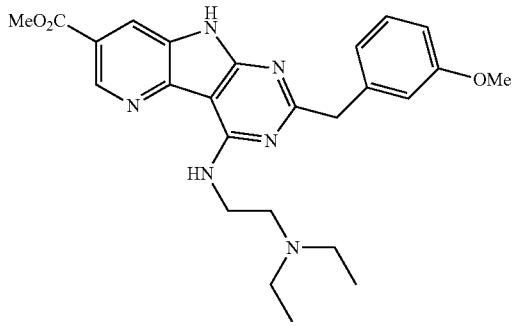

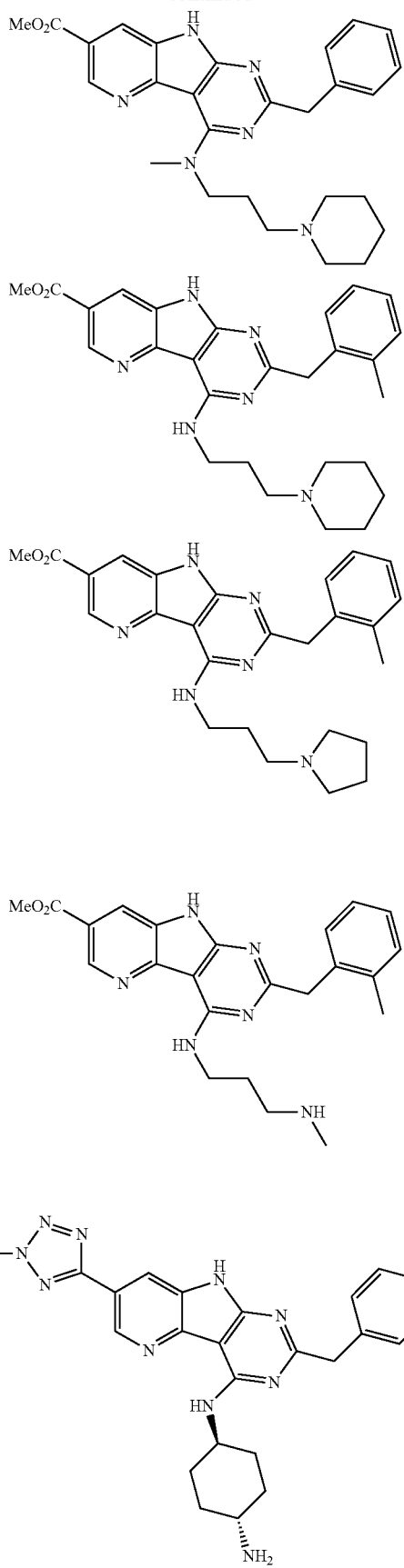
-continued

123
-continued
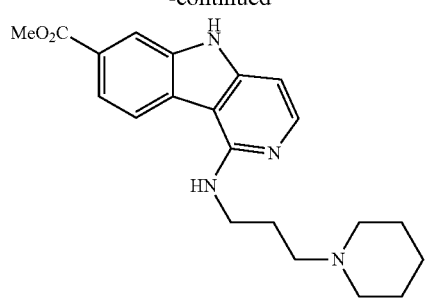
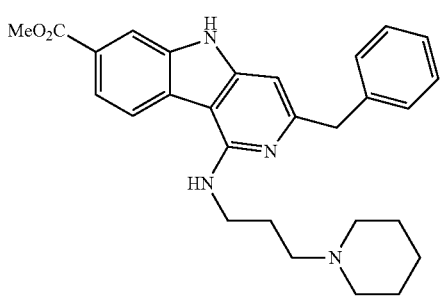
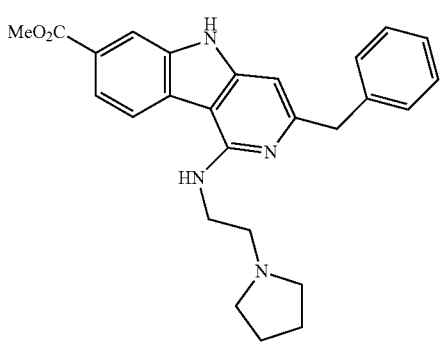
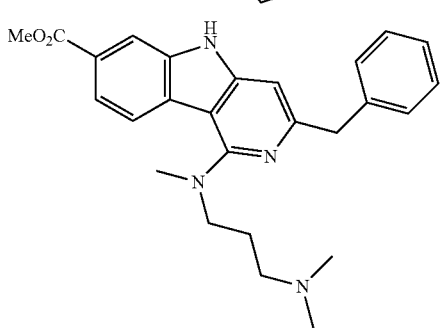
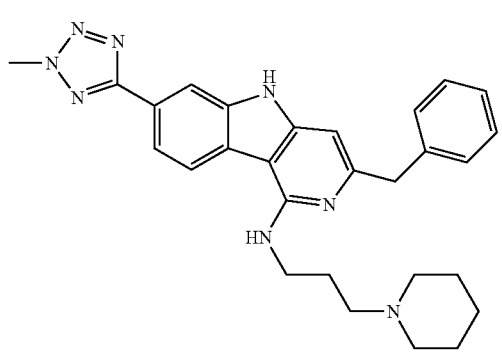
124
-continued
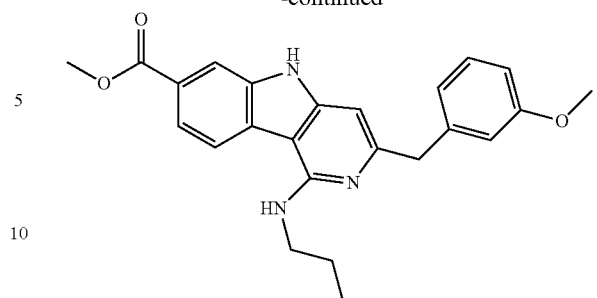
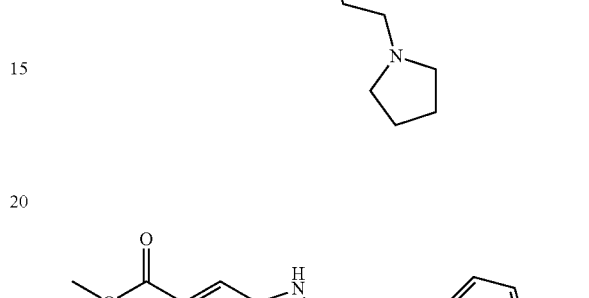
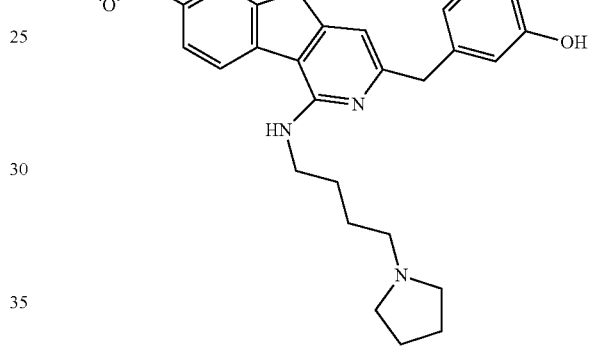
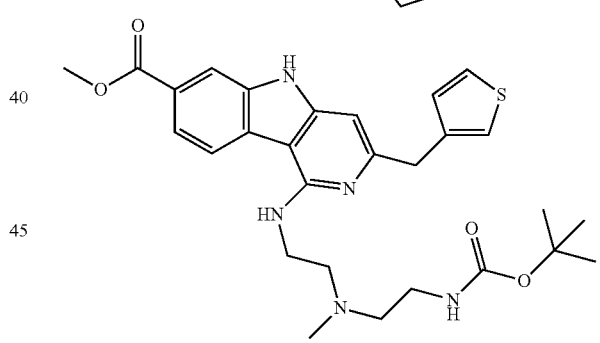
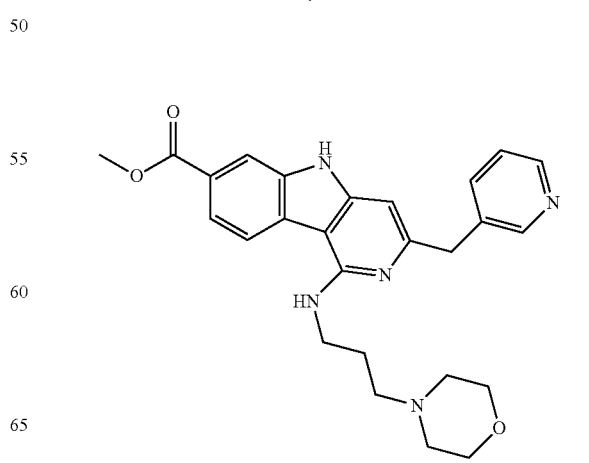

125
-continued

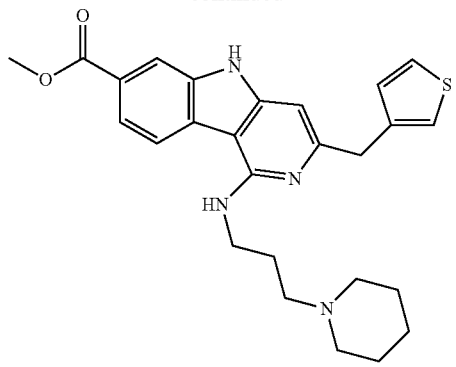

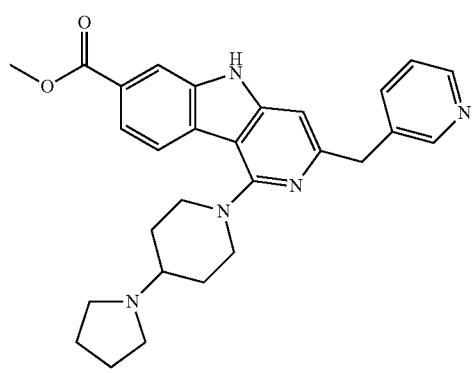

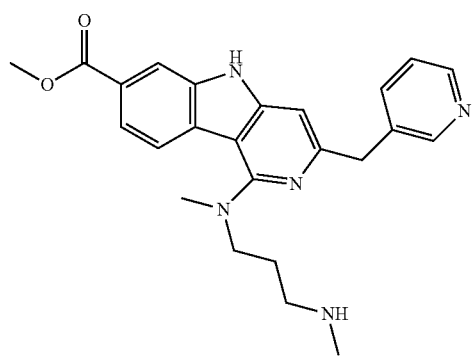

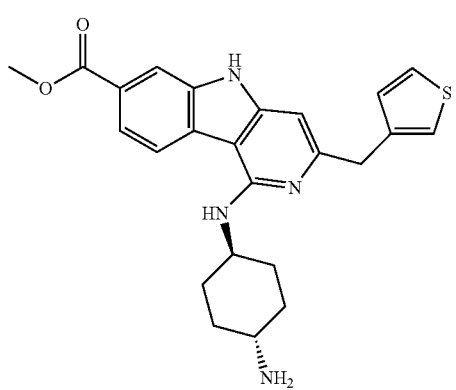

126
-continued

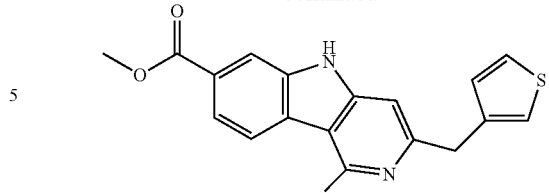

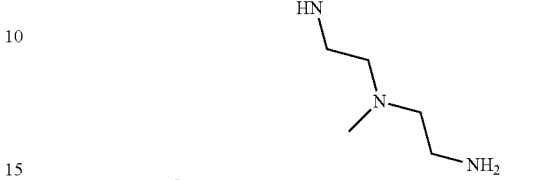

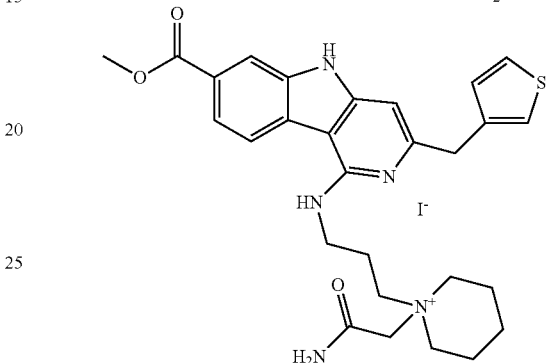

or a salt thereof.

10. A method of expanding hematopoietic stem cells and/or hematopoietic progenitor cells, the method comprising: contacting in vitro or ex vivo a starting cell population comprising hematopoietic stem cells and/or hematopoietic progenitor cells with a compound as defined in claim 1 or a salt thereof.

11. A method according to claim 10, in which the starting cell population includes CD34+ cells harvested from mobilized peripheral blood (mPB), bone marrow (BM) or umbilical cord blood (UCB).

12. A hematopoietic stem cell and/or hematopoietic progenitor cell population as expanded according to a method as defined in claim 10.

13. A method according to claim 10, wherein the starting cell population includes CD34+ cells harvested from umbilical cord blood (UCB).

14. A method according to claim 10, wherein the starting population is contacted together with at least one cell expanding factor which is a biologic or another small molecule.

15. A method according to claim 14, the biologic comprises Interleukin-3 (IL-3), Granulocyte Macrophage Colony-Stimulating Factor (GM-CSF), Thrombopoietin (TPO), FMS-Like Tyrosine Kinase 3 Ligand (FLT3-L), Stem Cell Factor (SCF), Interleukin-6 (IL-6) or a combination thereof.

16. A method according to claim 14, wherein the other small molecule is StemRegenin 1 (SR1).

17. A method according to claim 10, wherein Z is
1) —CN
2) —C(O)OR1,
3) —C(O)N(R1)R3, or
4) -heteroaryl optionally substituted with one or more RA or R4 substituents, W is
1) —CN,
2) —N(R1)R3,
3) -benzyl optionally substituted with 1, 2 or 3 RA or R1 substituents,
4) —X-L-(X-L)n-N(R1)R3,
5) —X-L-(X-L)$_n$-NR1RA or
6) —(N(R1)-L)$_n$-N$^+$R1R3R5 R6$^-$ wherein n is an integer equal to either 0, 1, 2, or 3
and wherein, when R1 and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;
each X is independently O, S, or NR1,
L is each independently
1) —C$_{1-6}$ alkylene,
2) —C$_{2-6}$ alkenylene,
3) —C$_{2-6}$ alkynylene,
4) —C3-7 cycloalkylene, which optionally includes one or more other heteroatom selected from N, O and S or
5) —C3-7 cycloalkenylene, which optionally includes one or more other heteroatom selected from N, O and S wherein the alkylene, the alkenylene, the alkynylene the cycloalkylene and the cycloalkenylene are each independently optionally substituted with one or two R4 or RA substituent;
R1 is each independently
1) —H,
2) —C$_{1-6}$ alkyl,
3) —C$_{2-6}$ alkenyl,
4) —C$_{2-6}$ alkynyl,
5) —C$_{3-7}$ cycloalkyl,
6) —C$_{3-7}$ cycloalkenyl,
7) —C$_{1-5}$ perfluorinated,
8) -heterocyclyl,
9) -heteroaryl, or
10) -benzyl,
wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;
R2 is
1) —H,
2) —C$_{1-6}$ alkyl, optionally substituted with one more RA substituents
3) —C(O)R4,
4) -L-heteroaryl optionally substituted with one or more RA or R4 substituents
5) -L-heterocyclyl optionally substituted with one or more RA or R4, or
6) -L-aryl optionally substituted with one or more RA or R4 substituents
R3 is each independently
1) —H,
2) —C$_{1-6}$ alkyl,
3) —C$_{2-6}$ alkenyl,
4) —C$_{2-6}$ alkynyl, or
5) —C$_{1-5}$ perfluorinated,
wherein the alkyl, the alkenyl, the alkynyl, the perfluorinated alkyl groups are each independently optionally substituted with 1, 2 or 3 RA or Rd substituents;
R4 is each independently
1) —H,
2) —C$_{1-6}$ alkyl,
3) —C$_{2-6}$ alkenyl,
4) —C$_{2-6}$ alkynyl,
5) —C$_{3-7}$ cycloalkyl,
6) —C$_{3-7}$ cycloalkenyl,
7) —C$_{1-5}$ perfluorinated,
8) -heterocyclyl,
9) -aryl,
10) -heteroaryl, or
11) -benzyl,
wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;
R5 is each independently
1) —C$_{1-6}$ alkyl,
2) -L-aryl which optionally includes one or more RA or R4 substituents
3) -L-heteroaryl which optionally includes one or more RA or R4 substituents
4) —C$_{1-6}$ alkylene-C(O)O—
5) —C$_{1-6}$ alkylene-C(O)OR1
6) —C$_{1-6}$ alkylene-CN
7) —C$_{1-6}$ alkylene-C(O)NR1R3, or
8) —C$_{1-6}$ alkylene-OH;
R6 is
1) halogen
2) OC(O)CF$_3$ or
3) OC(O)R1;
RA is each independently
1) -halogen,
2) —CF$_3$,
3) —OR1,
4) -L-OR1,
5) -OCF$_3$,
6) —SR1,
7) —CN,
8) —NO$_2$,
9) —NR1R3,
10) -L-NR1R1,
11) —C(O)OR1,
12) S(O)$_2$R4
13) —C(O)N(R1)R3,
14) —NR1C(O)R1,
15) —NR1C(O)OR1,
16) —OC(O)N(R1)R3,
17) —OC(O)R1,
18) —C(O)R4,
19) —NHC(O)N(R1)R3,
20) —NR1C(O)N(R1)R3, or
21) —N$_3$;
Rd is each independently
1) —H,
2) —C$_{1-6}$ alkyl,
3) —C$_{2-6}$ alkenyl,
4) —C$_{2-6}$ alkynyl,
5) —C$_{3-7}$ cycloalkyl,
6) —C$_{3-7}$ cycloalkenyl,
7) —C$_{1-5}$ perfluorinated
8) -benzyl or
9) -heterocyclyl.

18. A method according to claim 10, wherein the compound is

129
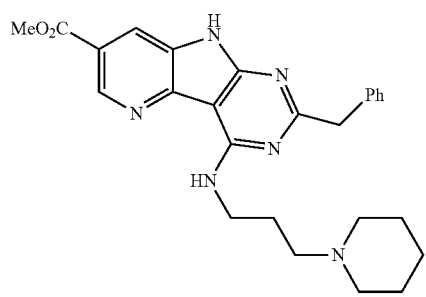
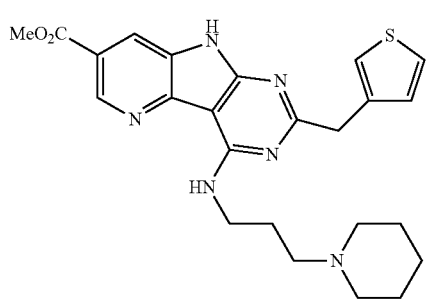
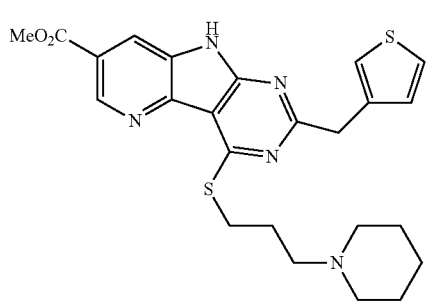
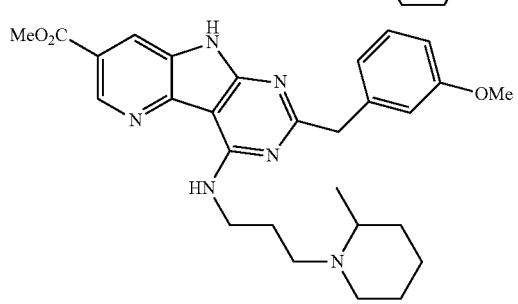
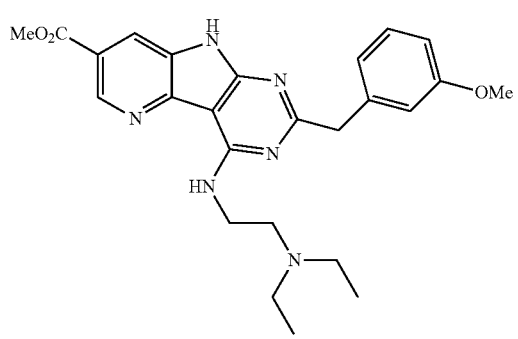
130
-continued
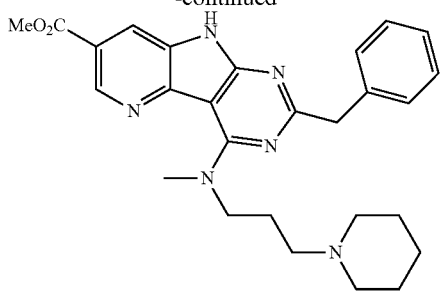
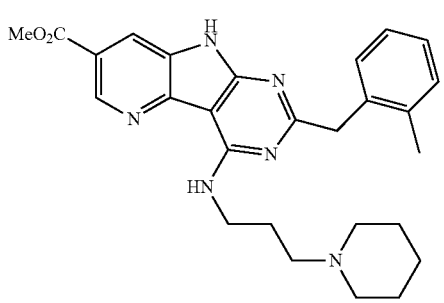
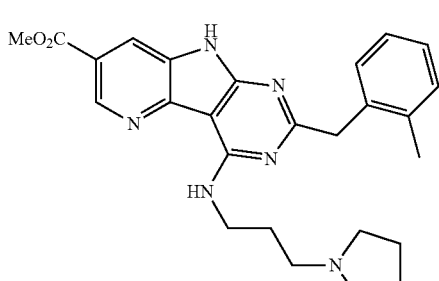
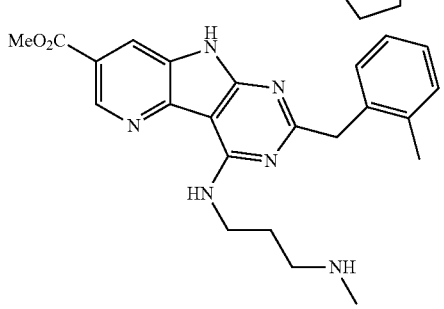
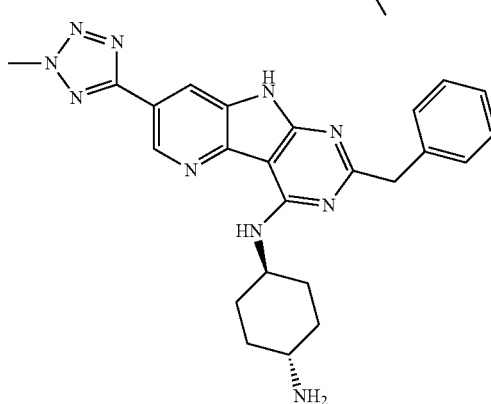

131
-continued
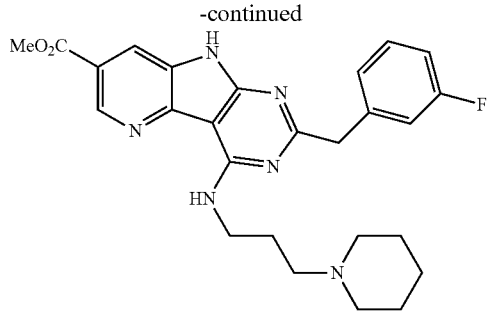
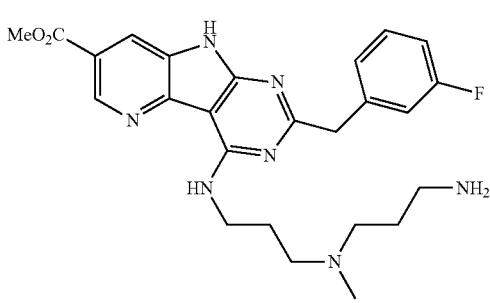
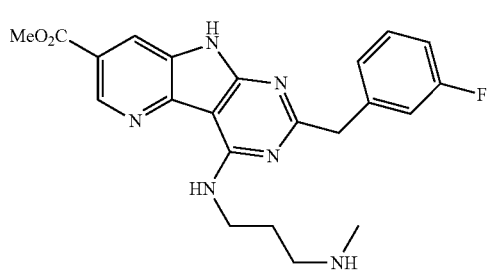
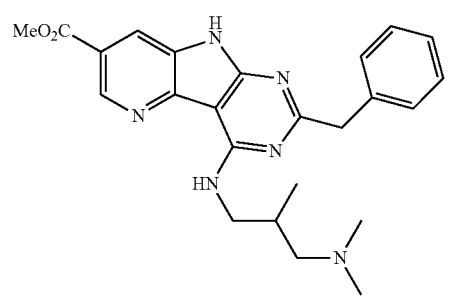
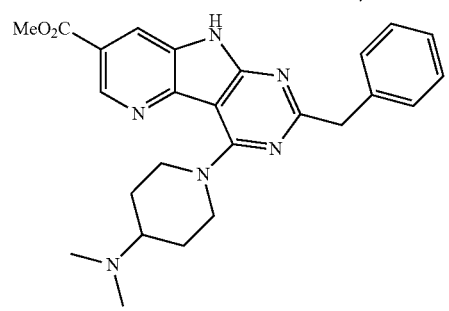
132
-continued
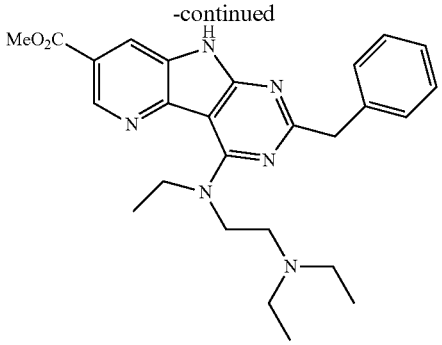
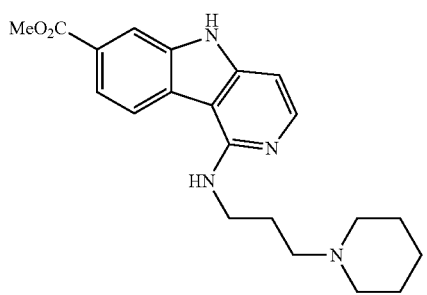
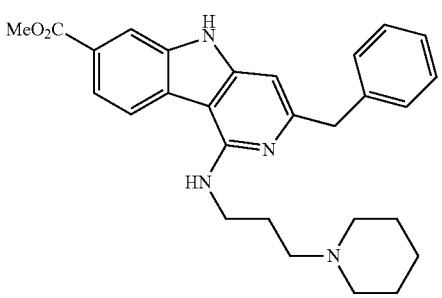
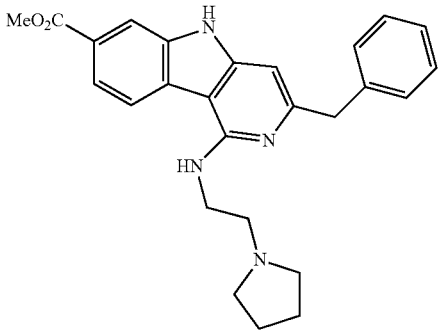
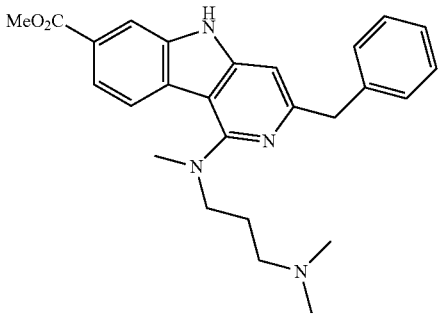

133
-continued
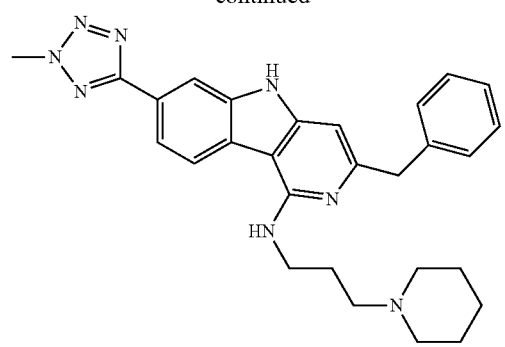
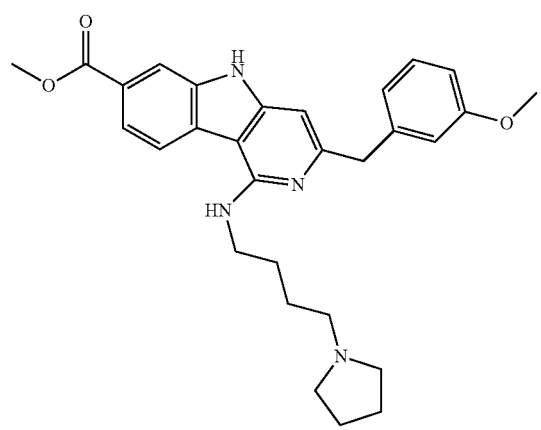
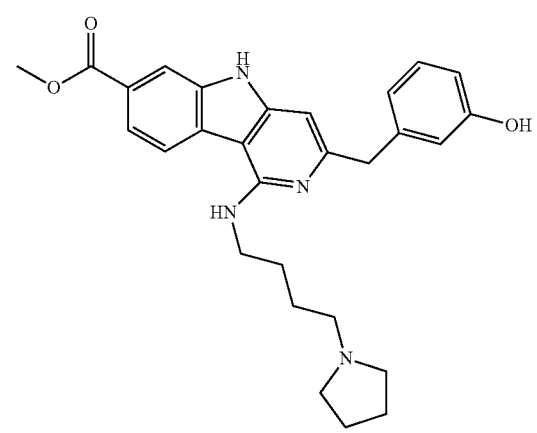
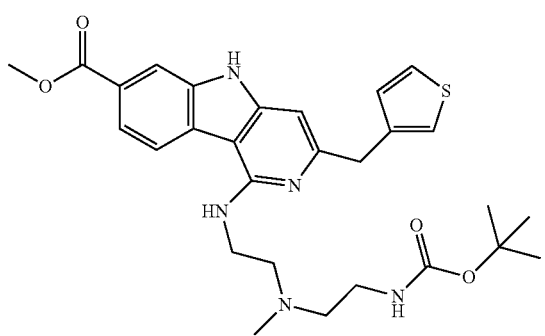
134
-continued
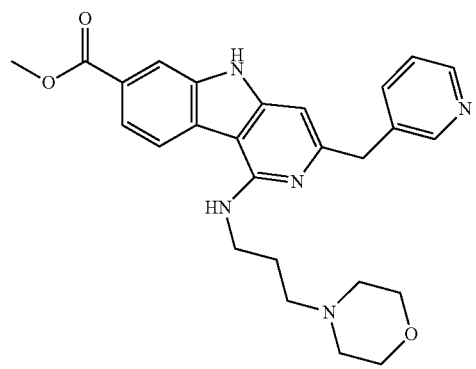
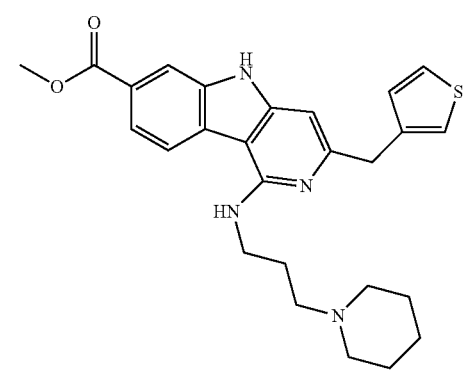
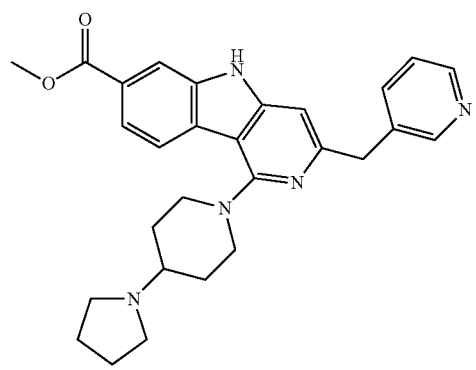

135
-continued
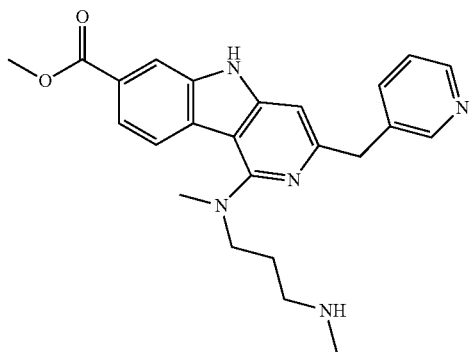
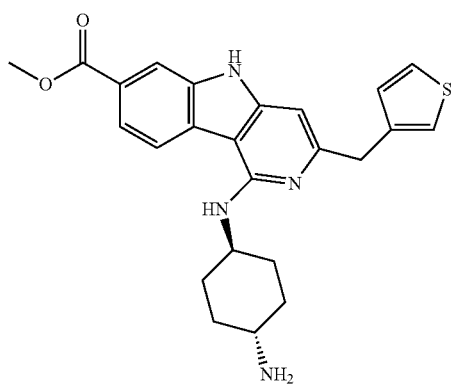
136
-continued
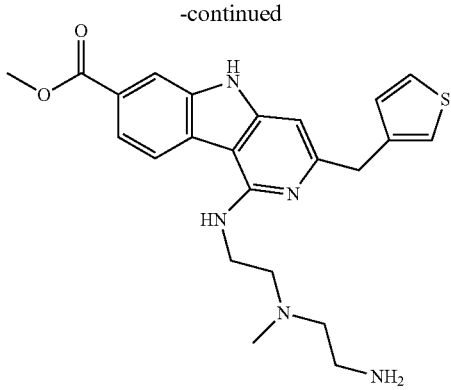
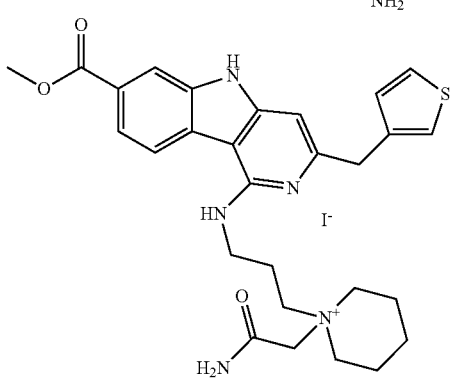
or a salt thereof.
* * * * *